(12) United States Patent
Ryu et al.

(10) Patent No.: US 8,298,775 B2
(45) Date of Patent: Oct. 30, 2012

(54) METHOD FOR DIAGNOSIS OF DISEASE USING QUANTITATIVE MONITORING OF PROTEIN TYROSINE PHOSPHATASE

(75) Inventors: Seong Eon Ryu, Daejeon (KR); Dae Gwin Jeong, Daejeon (KR); Tae Sung Yoon, Seoul (KR); Jeong Hee Moon, Goyang-si (KR); Seok-Il Hong, Seoul (KR); Young Joon Hong, Seoul (KR)

(73) Assignee: Korea Research Institute of Bioscience and Biotechnology, Daejeon (KR)

( * ) Notice: Subject to any disclaimer, the term of this patent is extended or adjusted under 35 U.S.C. 154(b) by 174 days.

(21) Appl. No.: 12/746,425

(22) PCT Filed: Aug. 5, 2008

(86) PCT No.: PCT/KR2008/004541
§ 371 (c)(1),
(2), (4) Date: Jun. 4, 2010

(87) PCT Pub. No.: WO2009/072728
PCT Pub. Date: Jun. 11, 2009

(65) Prior Publication Data
US 2010/0297667 A1    Nov. 25, 2010

(30) Foreign Application Priority Data

Dec. 4, 2007 (KR) .................. 10-2007-0125161

(51) Int. Cl.
*G01N 33/53* (2006.01)
(52) U.S. Cl. ........................ 435/7.1; 436/518
(58) Field of Classification Search ................ None
See application file for complete search history.

(56) References Cited

U.S. PATENT DOCUMENTS

| 7,115,710 B2 | 10/2006 | Plowman et al. |
| 2006/0275794 A1* | 12/2006 | Carrino et al. ............... 435/6 |
| 2010/0261213 A1 | 10/2010 | Ryu et al. |

FOREIGN PATENT DOCUMENTS

| KR | 10-2001-0085287 A | 9/2001 |
| KR | 10-2006-0098528 A | 9/2006 |
| KR | 10-2007-0039704 | 4/2007 |
| WO | WO 00-53801 A1 | 9/2000 |

OTHER PUBLICATIONS

International Search Report of the International Searching Authority, dated Feb. 24, 2009, for corresponding International Application No. PCT/KR2008/004541.

Jeong et al., "Crystal Structure of the Catalytic Domain of Human MAP Kinase Phosphatase 5: Structural Insight into Constitutively Active Phosphatase," *J. Mol. Biol.* 360, 946-955, 2006.

Kim et al., "Crystal Structure of Human TMDP, a Testis-Specific Dual Specificity Protein Phosphatase: Implications for Substrate Specificity," *Proteins* 66:239-245, 2007.

* cited by examiner

*Primary Examiner* — Jacob Cheu
(74) *Attorney, Agent, or Firm* — Klarquist Sparkman, LLP.

(57) ABSTRACT

The present invention relates to a method for quantifying protein tyrosine phosphatase (referred as PTP hereinafter) in biosamples, precisely a diagnostic method for disease by quantifying PTP using mass spectrometry and profiling of comparative PTP levels. By quantifying PTP in biosamples and profiling thereof according to the method of the present invention, disease can be diagnosed and diverse disease conditions and health conditions can be confirmed via profiling.

20 Claims, 11 Drawing Sheets

Fig. 1 a  Sequence of active domain protein

```
> gi|157837067 LMPTP (T46)
  1 AEQATKSVLF VCLGNICRSP IAEAVFRKLV TDQNISENWR VDSAATSGYE
 51 IGNPPDYRGQ SCMKRHGIFM SHVARQITKE DFATFDYILC MDESNLRDLN
101 RKSNQVKTCK AKIELLGSYD PQKQLIIEDP YYGNDSDFET VYQCVRCCR
151 AFLEKAH
```

Observed sequences in tryptic peptides are shown in BOLD.

b

| Start - End | Observed | Mr(expt) | Mr(calc) | Delta | Miss | Peptide Sequence hydrolyzed by trypsin |
|---|---|---|---|---|---|---|
| 1 - 6 | | | 646.3286 | | 0 | AEQATK |
| 7 - 27 | 765.4063 | 2293.1971 | 2293.2074 | -0.0103 | 1 | K.SVLFVCLGNICRSPIAEAVFR.K (Ions score 3) |
| 19 - 28 | 559.3088 | 1116.6030 | 1116.6291 | -0.0260 | 1 | R.SPIAEAVFRK.L (Ions score 58) |
| 28 - 40 | 534.9354 | 1601.7844 | 1601.8161 | -0.0318 | 1 | R.KLVTDQNISENWR.V (Ions score 52) |
| 29 - 40 | 737.8503 | 1473.6860 | 1473.7212 | -0.0351 | 0 | K.LVTDQNISENWR.V (Ions score 89) |
| 41 - 58 | 956.4210 | 1910.8274 | 1910.8646 | -0.0371 | 0 | R.VDSAATSGYEIGNPPDYR.G (Ions score 117) |
| 59 - 64 | | | 652.2673 | | 0 | GQSCMK |
| 65 - 65 | | | 174.1117 | | 0 | R |
| 66 - 75 | 552.7792 | 1103.5438 | 1103.5658 | -0.0219 | 0 | R.HGIPMSHVAR.Q (Ions score 30) |
| 66 - 75 | 560.7872 | 1119.5598 | 1119.5607 | -0.0009 | 0 | R.HGIPMSHVAR.Q Ox.(M) (Ions score 3) |
| 76 - 79 | | | 488.2958 | | 0 | QITK |
| 80 - 97 | 1091.4607 | 2180.9068 | 2180.9394 | -0.0326 | 0 | K.EDFATFDYILCMDESNLR.D (Ions score 95) |
| 80 - 97 | 733.3138 | 2196.9196 | 2196.9343 | -0.0148 | 0 | K.EDFATFDYILCMDESNLR.D Ox.(M) (Ions score 66) |
| 98 - 101 | | | 516.2656 | | 0 | DLNR |
| 102 - 102 | | | 146.1055 | | 0 | K |
| 103 - 107 | | | 574.3075 | | 0 | SNQVK |
| 108 - 110 | | | 350.1624 | | 0 | TCK |
| 111 - 123 | 487.9283 | 1460.7631 | 1460.7874 | -0.0244 | 1 | K.AKIELLGSYDPQK.Q (Ions score 43) |
| 113 - 123 | 631.8241 | 1261.6336 | 1261.6554 | -0.0217 | 0 | K.IELLGSYDPQK.Q (Ions score 79) |
| 124 - 147 | 965.7684 | 2894.2834 | 2894.3068 | -0.0235 | 0 | K.QLIIEDPYYGNDSDFETVYQCVR.C (Ions score 11) |
| 148 - 150 | | | 380.1300 | | 0 | CCR |
| 151 - 155 | | | 606.3377 | | 0 | AFLEK |
| 156 - 157 | | | 226.1066 | | 0 | AH |

# METHOD FOR DIAGNOSIS OF DISEASE USING QUANTITATIVE MONITORING OF PROTEIN TYROSINE PHOSPHATASE

CROSS REFERENCE TO RELATED APPLICATIONS

This is the U.S. National Stage of International Application No. PCT/KR2008/004541, filed Aug. 5, 2008, which was published in English under PCT Article 21(2), which in turn claims the benefit of Korean Patent Application No 10-2007-0125161, filed Dec. 4, 2007.

TECHNICAL FIELD

The present invention relates to a method for quantifying protein tyrosine phosphatase (referred as PTP hereinafter) in biosamples.

BACKGROUND ART

Protein tyrosine phosphorylation-dephosphorylation plays a very important role in intracellular signal transduction system. In particular, protein tyrosine phosphorylation-dephosphorylation is involved in changes of cells such as responses to foreign stimuli, cell growth, differentiation and apoptosis, etc. Therefore, protein tyrosine kinase (PTK; *Curr Pharm Des* 13:2751-65, 2007; *Curr Med Chem* 14:2214-34, 2007) and protein tyrosine phosphatase (PTP) are important target proteins for the treatment of such diseases accompanying the change of cells as cancer, vascular disease, immune disease and nervous disease (Curr Cancer Drug Targets 6:519-532, 2006; Med Res Rev 27:553-73, 2007). Human has approximately 100 kinds of PTPs (Cell 117:699-711, 2004). 20 kinds of these PTPs have been confirmed to be related to disease so that they have been targets of the development of a novel drug. And the remaining 80 kinds of PTPs are presumed to be related to disease as well.

According to the previous reports, PTP levels vary from disease and cell conditions (Crit Rev Oncol/Hemat 52:9-17, 2004; Expert Opin Therapeutic Targets 10:157-177, 2006). However, since there is no tools to measure the level of PTP in cells or blood directly, indirect methods such as measuring intracellular mRNA level by RT-PCR or Western blotting using commercial PTP antibody against limited PTP proteins are being used to quantify PTP. However, quantifying mRNA cannot tell exact amount of PTP. Besides, mRNA measurement is not possible with blood or urine samples. In the case of Western blotting, precise quantification of PTP is still difficult because only 10 PTP antibodies have been known and sensitivity of these antibodies is not very good. Despite PTPs are highly potent as a biomarker, development of a method for diagnosis of disease using these excellent biomarkers is not advanced, yet.

Blood samples, among many biosamples, are excellent test samples for diagnosis of disease using a biomarker, because of easiness in sampling and diversity of materials included in blood. Blood circulates everywhere in human body, during which blood takes cells a bit from each and every part of the body. These cells are broken, so that proteins included in those cells are flowing into blood. So, blood contains such proteins, telling conditions of the body. However, the amounts of such blood proteins are very small, so the presence of blood protein itself is sometimes neglected. In the meantime, large amount of proteins such as albumin and immunoglobulin are included in blood, which make it difficult to analyze minute proteins derived from cell.

To measure those PTPs existing at femto or atto mole level in blood, the present inventors selected standard peptides of PTP active domain facilitating the analysis of 80 kinds of PTPs by using mass spectrometer. So, peptides collected with antibodies binding specifically to the standard peptides are quantified by SISCAPA (Stable Isotope Standards and Capture by Anti-peptide Antibodies) technique that is a method to quantify protein based on mass spectrometry (Mol Cell Proteomics 5:573-588, 2006); Proc Natl Acad Sci USA 100: 6940-6945, 2003). As a result, several PTPs demonstrated different levels between normal individual and cancer patient. The present inventors further completed this invention by confirming that the method of the invention facilitating analysis by PTP panel constructed by using standard peptides and their antibodies can be effectively used for diagnosis of disease.

DISCLOSURE

Technical Problem

It is an object of the present invention to provide a standard peptide derived from protein tyrosine phosphatase (PTP) for quantitative analysis of PTP.

It is another object of the present invention to provide an antibody binding specifically to the standard peptide for quantitative analysis It is also an object of the present invention to provide a method for quantification of PTP in sample using the standard peptide and the antibody.

It is further an object of the present invention to provide a screening method of a cancer related biomarker using the standard peptide and the antibody.

It is also an object of the present invention to provide a screening method of a specific disease related biomarker using the standard peptide and the antibody.

It is also an object of the present invention to provide a method for diagnosis of cancer using the standard peptide and the antibody.

It is also an object of the present invention to provide a diagnostic kit for disease containing an antibody binding specifically to the standard peptide of the biomarker screened by the specific disease related biomarker screening method.

It is also an object of the present invention to provide a use of the synthetic standard peptide for quantification of PTP It is also an object of the present invention to provide a use of the synthetic standard peptide for the screening of a cancer-related biomarker.

It is also an object of the present invention to provide a use of the synthetic standard peptide for the screening of a specific disease related biomarker.

Technical Solution

To achieve the above objects, the present invention provides a standard peptide for quantitative analysis of PTP expressed in the sample which is produced by hydrolysis of protein tyrosine phosphatase (PTP) having PTP active domain comprising the amino acid sequences represented by SEQ. ID. NO: 113-NO: 168 and the amino acid sequences represented by SEQ. ID. NO: 256-NO: 260 and SEQ. ID. NO: 271-NO: 290.

The present invention also provides a synthetic standard peptide for quantitative analysis of PTP expression which has the amino acid sequence selected from the sequences represented by SEQ. ID. NO: 169-NO: 255.

The present invention further provides an antibody binding specifically to the standard peptide or the synthetic standard peptide.

The present invention also provides a method for quantification of PTP comprising the following steps:
1) hydrolyzing a sample separated from a test subject;
2) adding an isotope-substituted synthetic standard peptide to the hydrolyzed sample of step 1);
3) extracting the wild type peptide and the isotope-substituted synthetic standard peptide from the hydrolyzed sample of step 2), followed by quantitative analysis; and
4) comparing the levels of the wild type peptide and the isotope-substituted synthetic standard peptide of step 3) to calculate absolute quantity of the wild type peptide expression.

The present invention also provides a method for quantification of PTP comprising the following steps:
1) concentrating PTP in a sample separated from a test subject;
2) hydrolyzing the concentrated sample of step 1);
3) adding an isotope-substituted synthetic standard peptide to the hydrolyzed sample of step 2); and
4) comparing the levels of the wild type peptide and the isotope-substituted synthetic standard peptide of step 3) to calculate absolute quantity of the wild type peptide expression.

The present invention also provides a screening method of a cancer related biomarker comprising the following steps:
1) hydrolyzing a sample separated from a subject with cancer;
2) adding an isotope-substituted synthetic standard peptide to the hydrolyzed sample of step 1);
3) extracting the wild type peptide and the isotope-substituted synthetic standard peptide from the hydrolyzed sample of step 2), followed by quantitative analysis thereof;
4) comparing the levels of the wild type peptide and the isotope-substituted synthetic standard peptide of step 3) to calculate absolute quantity of the wild type peptide expression; and
5) comparing the absolute quantity of the wild type peptide of step 4) and the absolute quantity of the wild type peptide extracted from a normal subject to confirm the standard peptide demonstrating a significant difference.

The present invention also provides a screening method of a specific disease related biomarker comprising the following steps:
1) hydrolyzing a sample separated from a subject with a specific disease;
2) adding an isotope-substituted synthetic standard peptide to the hydrolyzed sample of step 1);
3) extracting the wild type peptide and the isotope-substituted synthetic standard peptide from the hydrolyzed sample of step 2), followed by quantitative analysis thereof;
4) comparing the levels of the wild type peptide and the isotope-substituted synthetic standard peptide of step 3) to calculate absolute quantity of the wild type peptide expression; and
5) comparing the absolute quantity of the wild type peptide of step 4) and the absolute quantity of the wild type peptide extracted from a normal subject to confirm the standard peptide demonstrating a significant difference.

The present invention also provides a method for diagnosis of cancer comprising the following steps:
1) hydrolyzing a sample separated from a subject with cancer;
2) adding a synthetic standard peptide substituted with an isotope of one or more biomarkers screened by the cancer related biomarker screening method to the hydrolyzed sample of step 1);
3) extracting the wild type peptide and the isotope-substituted synthetic standard peptide from the hydrolyzed sample of step 2), followed by quantitative analysis thereof;
4) comparing the levels of the wild type peptide and the isotope-substituted synthetic standard peptide of step 3) to calculate absolute quantity of the wild type peptide expression; and
5) comparing the absolute quantity of the wild type peptide of step 4) and the absolute quantity of the wild type peptide extracted from a normal subject to confirm the standard peptide demonstrating a significant difference.

The present invention also provides a method for diagnosis of cancer comprising the following steps;
1) concentrating PTP in a sample separated from a test subject;
2) hydrolyzing the concentrated sample of step 1);
3) adding a synthetic standard peptide substituted with an isotope of one or more biomarkers screened by the cancer related biomarker screening method to the hydrolyzed sample of step 2);
4) comparing the levels of the wild type peptide and the isotope-substituted synthetic standard peptide of step 3) to calculate absolute quantity of the wild type peptide expression; and
5) comparing the absolute quantity of the wild type peptide of step 4) and the absolute quantity of the wild type peptide extracted from a normal subject to confirm the standard peptide demonstrating a significant difference.

The present invention also provides a diagnostic kit for disease containing an antibody binding specifically to the standard peptide of the biomarker screened by the specific disease related biomarker screening method.

The present invention also provides a diagnostic kit for disease containing a primary monoclonal antibody binding specifically to a standard peptide of the biomarker screened by the specific disease related biomarker screening method and a secondary monoclonal antibody binding specifically to the overall region except the region where the primary monoclonal antibody is conjugated.

The present invention also provides a use of the synthetic standard peptide for quantification of PTP.

The present invention also provides a use of the synthetic standard peptide for the screening of a cancer-related biomarker.

In addition, the present invention provides a use of the synthetic standard peptide for the screening of a specific disease related biomarker.

Advantageous Effect

Diverse disease conditions and health conditions can be confirmed by measuring and profiling PTP level in a biosample according to the method of the present invention. The method of the present invention can also be effectively used for prediction of prognosis after surgical operation and for determination of treatment strategy. In particular, the method of the present invention facilitates exact PTP quantification even with such a biosample containing a very small amount of PTP like blood, so that it can be effectively used for diagnosis of disease and screening of health condition with samples easily taken.

DESCRIPTION OF DRAWINGS

The application of the preferred embodiments of the present invention is best understood with reference to the accompanying drawings, wherein:

FIG. 1 is a diagram illustrating the selection process of standard peptides of PTP active domain:
  a: sequence of LMPTP active domain protein (residues 2-158 of SEQ ID NO: 164); and,
  b: sequence of trypsin hydrolyzing peptide of LMPTP active domain (residues 2-158 of SEQ ID NO: 164).

FIG. 3: peptide of 41-58; and,
  FIG. 4: peptide of 113-123.

FIG. 5: measurement of PTP T46 in blood of a patient with colon cancer (CL18: colon cancer patient #18);
FIG. 6: measurement of PTP T46 in blood of a patient with liver cancer (LV32: liver cancer patient #32);
FIG. 7: measurement of PTP T46 in blood of a patient with stomach cancer (ST16: stomach cancer patient #16); and,
  FIG. 8: measurement of PTP T46 in blood of a normal subject (SPS01: sigma pooled serum #1; normal serum mixture purchased from Sigma, USA).

FIG. 9: colon cancer patients (CL: colon);
FIG. 10: liver cancer patients (LV: liver); and,
  FIG. 11: stomach cancer patients (ST: stomach).

The Sequence Listing is submitted as an ASCII text file in the form of the file named Sequence_Listing.txt, which was created on May 31, 2010, and is 260,857 bytes, which is incorporated by reference herein.

BEST MODE

Terms used in this invention are described hereinafter.

"Wild type peptide" indicates PTP peptide existing in the hydrolyzed sample of a test subject. In this invention, this peptide is a counter-part of a standard peptide labeled or substituted with a radio-isotope added to the hydrolyzed sample.

Hereinafter, the present invention is described in detail.

The present invention provides a standard peptide for quantitative analysis of PTP expressed in the sample which is produced by hydrolysis of protein tyrosine phosphatase (PTP) having PTP active domain comprising the amino acid sequences represented by SEQ. ID. NO: 113-NO: 168 and the amino acid sequences represented by SEQ. ID. NO: 256-NO: 260 and SEQ. ID. NO: 271-NO: 290.

Figure 2:
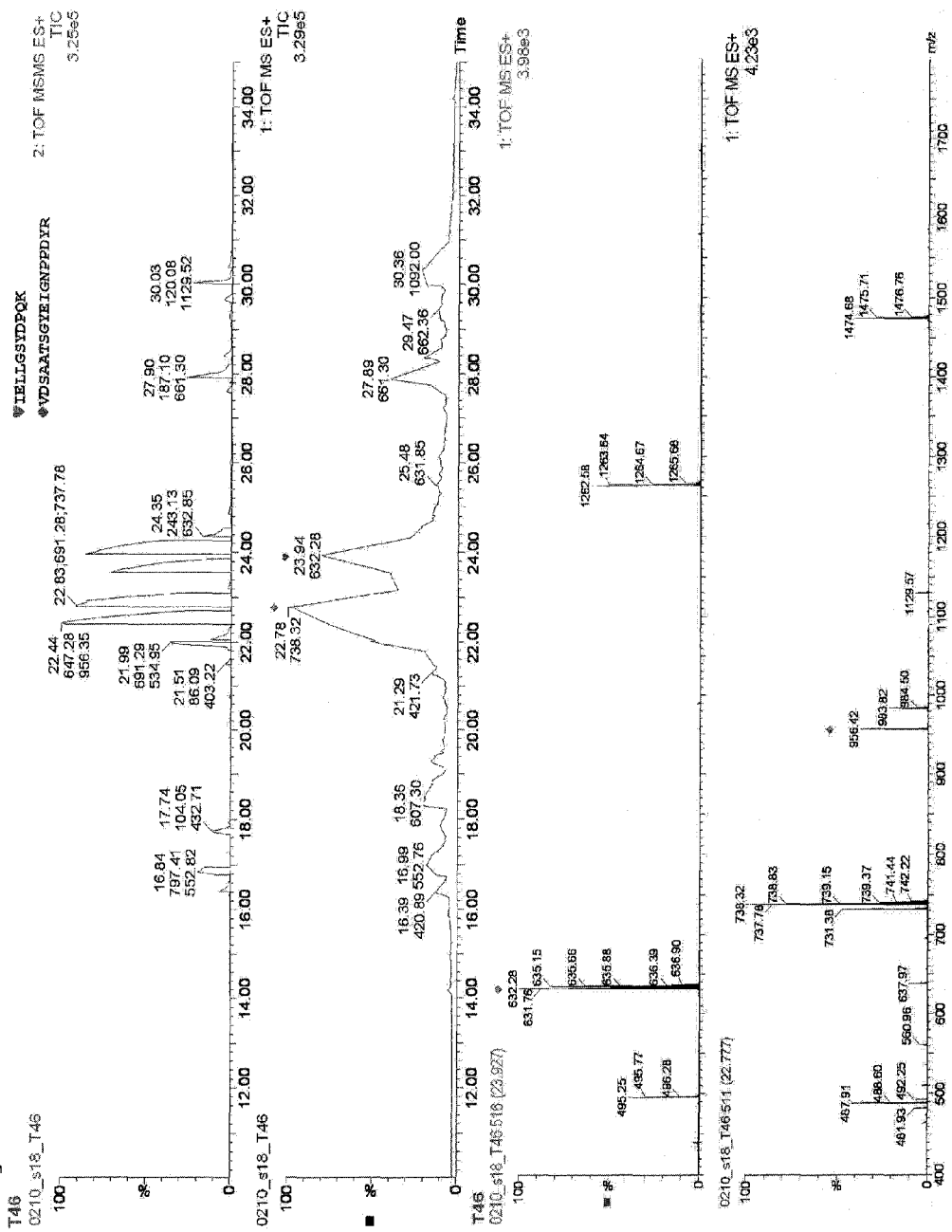
FIG. 2 is a series of diagrams illustrating mass spectrometry chromatograms of PTP T46.
Figure 3:
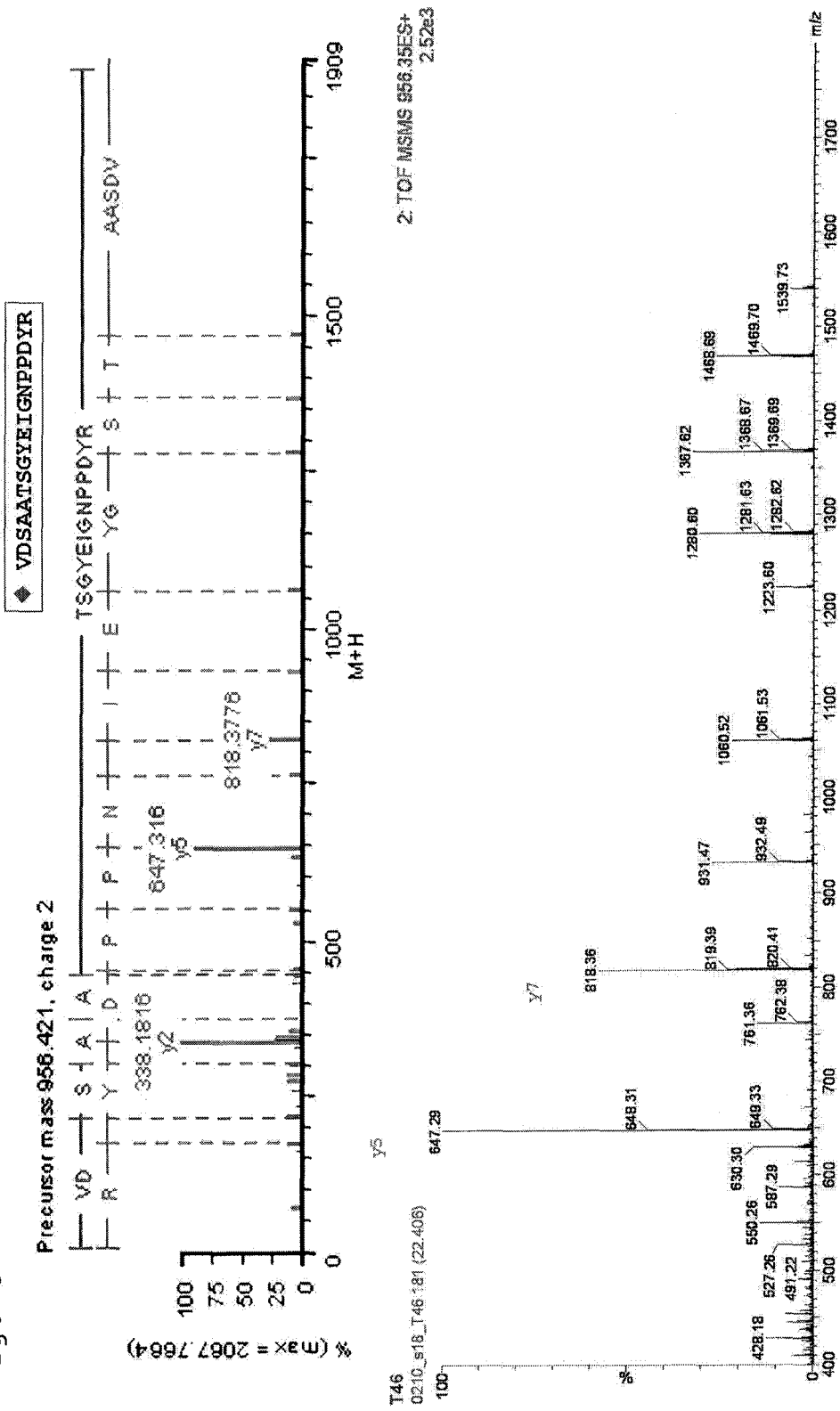
FIG. 3-FIG. 4 are diagrams illustrating the results of sequencing of trypsin hydrolyzing peptide of LMPTP active domain.
Figure 4:
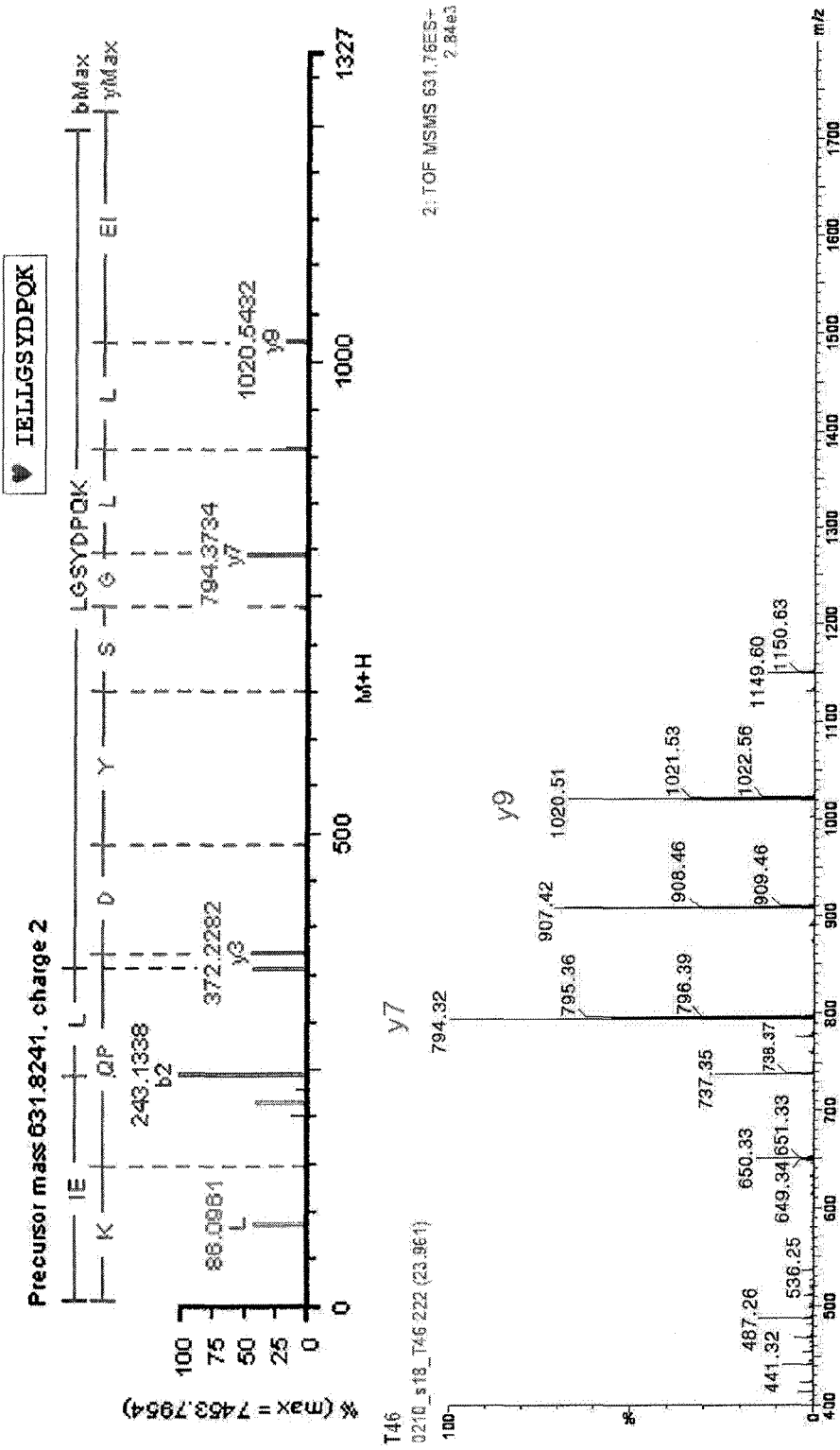
Figure 5:
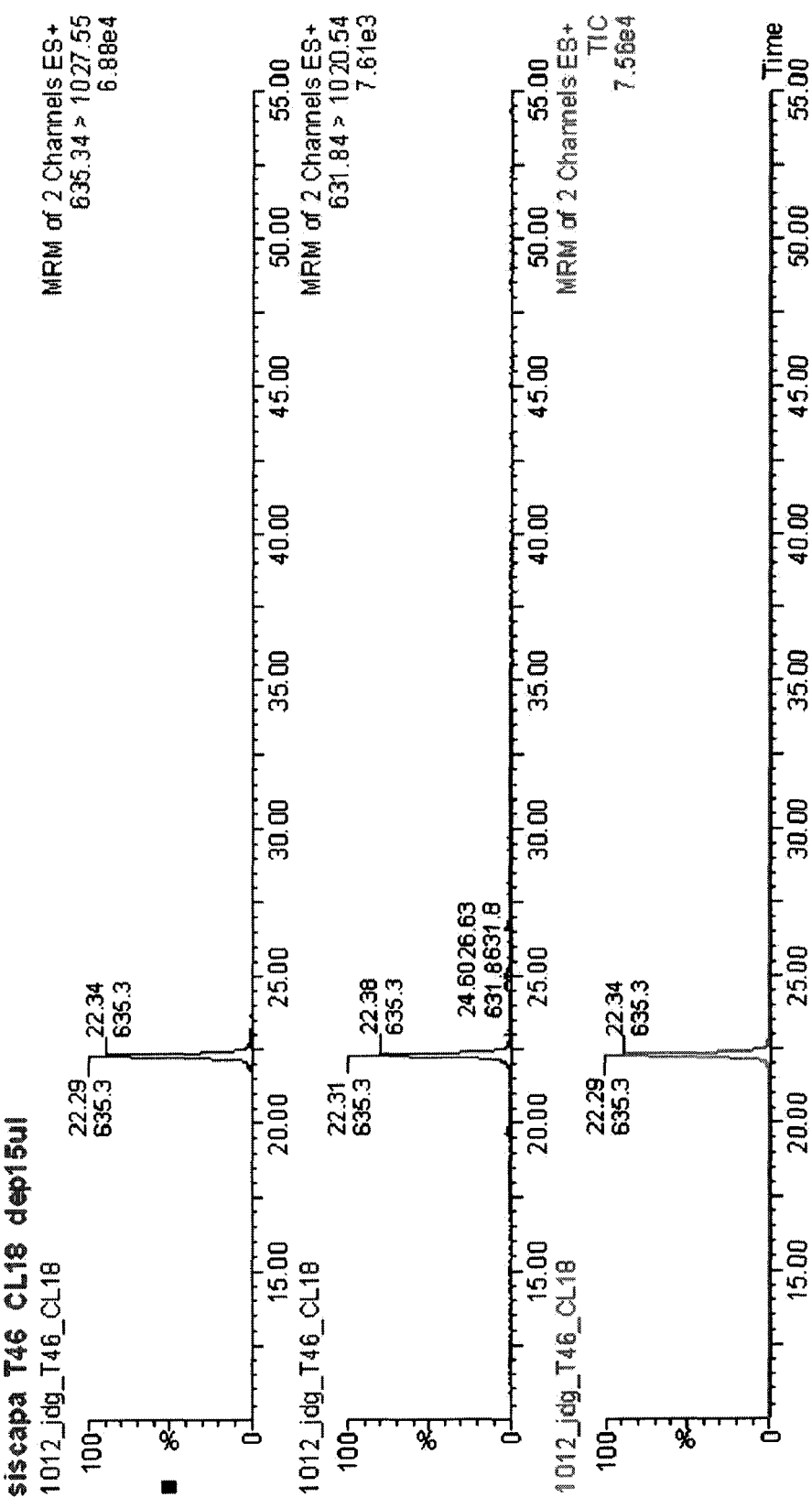
FIGS. 5-8 are diagrams illustrating the results of mass spectrometry chromatogram of PTP of blood sample of a patient:
  SISCAPA (Stable Isotope Standards and Capture by Antipeptide Antibodies): quantitative analysis method of peptides collected with antibodies based on mass spectrometry;
  MRM (Multiple Reaction Monitoring): proteome analysis method using mass spectrometry to analyze complicated proteins and peptides in blood.
Figure 6:
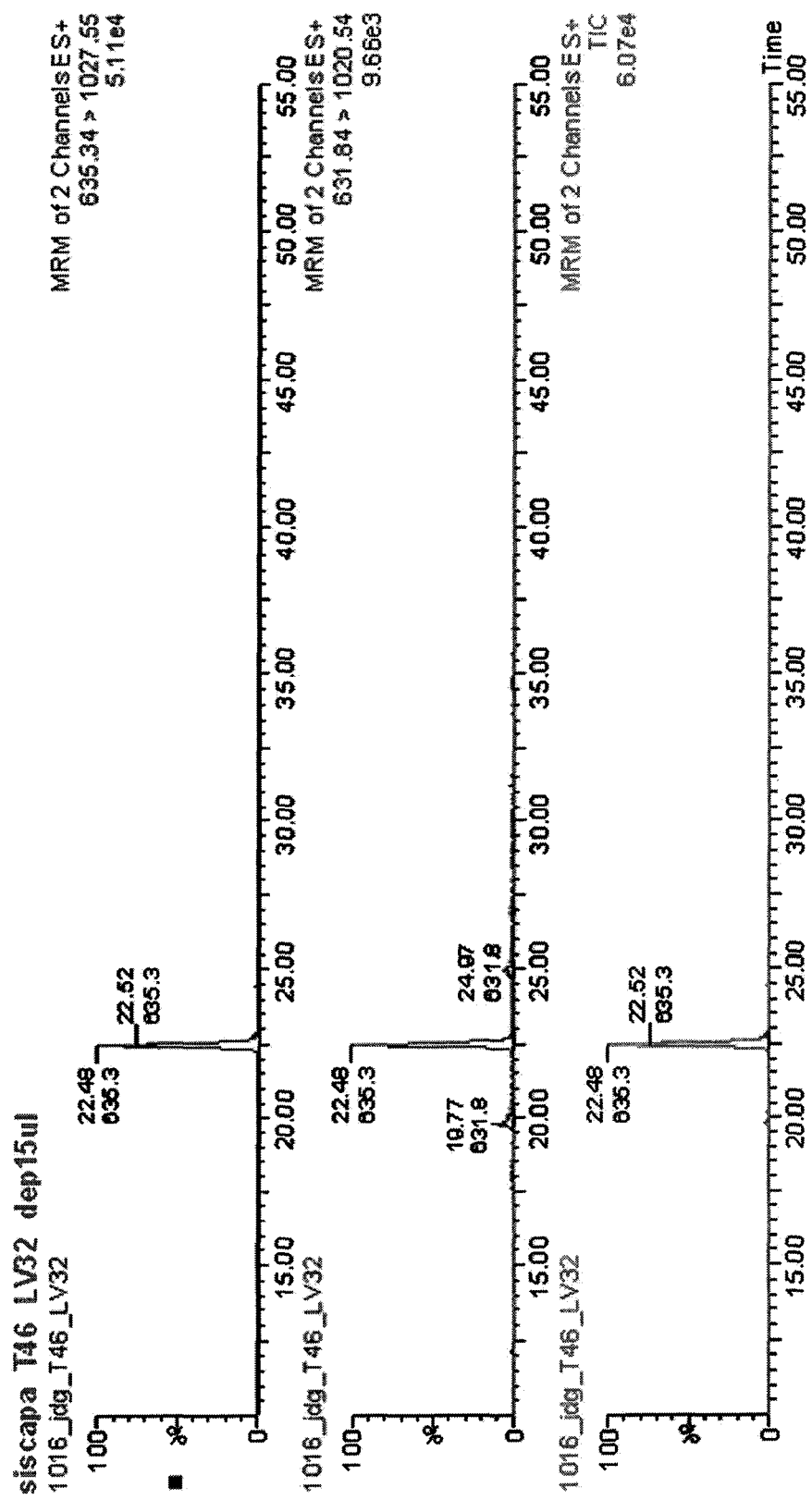
Figure 7:
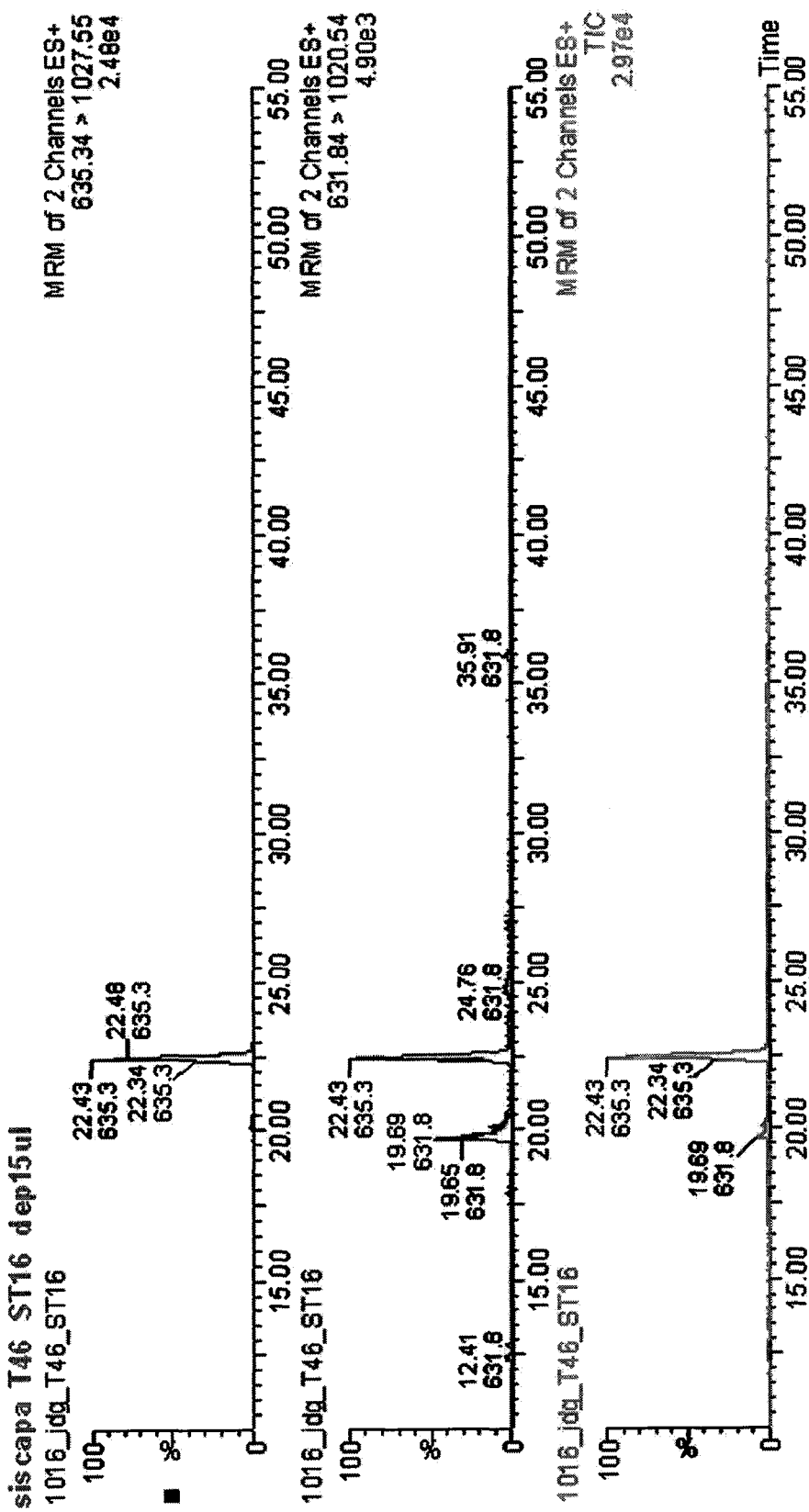

In a preferred embodiment of the present invention, purified PTP active domain was hydrolyzed by trypsin to obtain PTP active domain peptide, followed by tandem mass spectrometry. As a result, 5-10 PTP specific peptides were obtained, among which the peptide that contained a residue replaceable with a stable isotope but not contained cysteine or methionine, the oxidation risk factors, and had high detection strength was selected as standard peptide. That is, considering the said conditions, standard peptide of PTP active domain was selected for quantitative analysis of PTP (see FIG. 1). Sequencing was performed with the peptide having the amino acid sequences represented by SEQ. ID. NO: 169-NO: 255 selected above (see FIG. 2 and FIG. 3), followed by fragmentation according to the standard peptide and ionization. Energy signal of the fragment ion emitting the strongest detection signal was measured. As a result, it was confirmed that the detection strength of each fragment ion increased linearly according to the fragmentation energy. Among the fragment ions, the one demonstrating the strongest detection strength was selected and its energy at the peak of the detection strength curve was determined as the optimum fragmentation energy (see Table 4).

The said standard peptide is composed of protein tyrosine phosphatase (PTP) active domain having the amino acid sequences represented by SEQ. ID. NO: 113-NO: 168 (1-56 of Table 1), PTP protein having the amino acid sequences represented by SEQ. ID. NO: 271-NO: 290 expressed by MBP fusion (described in Korean Patent No. 10-0746993) and a peptide appropriate for optimum ionization generated by hydrolyzing a protein having the amino acid sequences represented by SEQ. ID. NO: 256-NO: 260.

The present invention also provides a synthetic standard peptide for quantitative analysis of PTP expression which has the amino acid sequence selected from the sequences represented by SEQ. ID. NO: 169-NO: 255.

The synthetic standard peptide is composed of those peptides having a residue replaceable with an amino acid having a stable radio-isotope such as leucin or valine but not containing a residue having high risk of oxidation such as cysteine or methionine. The said replacement can be performed by adding an amino acid having a stable isotope during synthesis or labeling a specific amino acid with a functional group having a stable isotope after synthesis. In this invention, the radio-isotope is binding to the standard peptide in order to make mass different from that of the wild type peptide, which makes distinguishment between the two peptides easy. This radio-isotope is not necessarily included in inner-part of the standard peptide but instead it can be bound to OH-terminal of the standard peptide. In the standard peptide, any amino acid except those containing such a residue having risk of oxidation can be substituted with a stable isotope. The said stable isotope is selected from the group consisting of 13C, 15N and 2H. In a preferred embodiment of the present invention, 13C and 15N were used.

The present invention further provides an antibody binding specifically to the standard peptide or the synthetic standard peptide.

The antibody herein includes polyclonal or monoclonal antibody. Polyclonal antibody is used for the extraction of standard peptide from the hydrolyzed sample and quantitative analysis thereof, while monoclonal antibody is used for quantitative analysis of standard peptide in the sample, but not always limited thereto. In a preferred embodiment of the present invention, the polyclonal antibody was used to obtain the wild type standard peptide and the isotope-substituted standard peptide from serums of cancer patients and normal health people added with the isotope-substituted synthetic standard peptide after hydrolysis. Quantitative analysis was performed with the obtained wild type peptide and the isotope-substituted peptide using triple quadrupole analyzer. As a result, the wild type standard peptide of PTP T46 was quantified and absolute quantity of the wild type standard peptide was calculated by comparing with the peak of the isotope-substituted standard peptide (see FIG. 4-FIG. 7).

A polyclonal antibody can be prepared as follows; one of the said standard peptide of PTP active domains is injected into a test animal; blood sample is taken from the animal; and then serum containing antibody is separated to isolate the antibody. Such polyclonal antibody can be purified by any methods known to those in the art and can be produced from host animals which are exemplified by goat, rabbit, sheep, monkey, horse, pig, cow, dog, etc. A monoclonal antibody can be prepared by any method that facilitates the production of antibody molecules via culturing the continuous cell line. The method is exemplified by hybridoma technique, human-B-cell hybridoma technique, and EBV-hybridoma technique, but not always limited thereto (Kohler G et al., *Nature* 256: 495-497, 1975; Kozbor D et al., *J Immunol Methods* 81:31-42, 1985; Cote R J et al., *Proc Natl Acad Sci* 80:2026-2030, 1983; 및 Cole S P et al., *Mol Cell Biol* 62:109-120, 1984). An antibody fragment containing a specific binding site for one of the said standard peptide of PTP active domains can be prepared.

For example, F(ab')2 fragment can be prepared by fractionation of an antibody molecule by using pepsin and Fab fragment can be prepared by reducing disulfide bridge of F(ab')2 fragment, but not always limited thereto. Alternatively it is also possible to identify a monoclonal Fab fragment having desired specificity by constructing Fab expression library (Huse W D et al., *Science* 254: 1275-1281, 1989).

The present invention also provides a method for quantification of PTP comprising the following steps:
1) hydrolyzing a sample separated from a test subject;
2) adding an isotope-substituted synthetic standard peptide to the hydrolyzed sample of step 1);
3) extracting the wild type peptide and the isotope-substituted synthetic standard peptide from the hydrolyzed sample of step 2), followed by quantitative analysis; and
4) comparing the levels of the wild type peptide and the isotope-substituted synthetic standard peptide of step 3) to calculate absolute quantity of the wild type peptide expression.

The sample of step 1) comprise blood, tissue and exudate. For the hydrolysis above, any protease that is capable of recognizing cleavage site of protein included in the sample to digest thereof can be used, and preferably trypsin, chymotrypsin, pepsin, thermolysis and proteinase K are selected. In a preferred embodiment of the present invention, trypsin was used.

The wild type peptide and the isotope-substituted synthetic standard peptide of step 3) are extracted by using a ligand or an antibody binding specifically to the said peptides. The antibody herein can be polyclonal antibody or monoclonal antibody, but polyclonal antibody is preferred to increase yield of extraction. In a preferred embodiment of the present invention, polyclonal antibody conjugated column was used. To obtain the standard peptide, PTP in the sample is hydrolyzed by trypsin and the obtained standard peptide is concentrated. Or, PTP as a protein is concentrated and then hydrolyzed by using trypsin. Particularly, almost every PTP has the same enzyme active site. Even if the structures of the enzyme active sites of different PTPs are a bit different, they have much in common such as active cysteine, etc. So, based on such homology, a low-molecular substance is designed to be conjugated to almost every PTP and then biotin or an analogue thereof is adhered to the low-molecular substance, which is going to be used for PTP concentration.

Quantitative analysis of step 3) is performed by LC/MS mass spectrometry, SELDI (Surface-Enchanced Laser Desorption/Ionization) and sandwich ELISA, but not always limited thereto.

In a preferred embodiment of the present invention, PTP panel composed of the standard peptide of PTP active domain was constructed and used for quantitative analysis of the standard peptide of patients with colon cancer, liver cancer and stomach cancer. As a result, 18 PTPs were detected in total. 10 out of the 18 PTPs were only detected in cancer patients but not in normal healthy people. The rest 8 PTPs were detected in normal healthy people as well but the levels of them in cancer patients were significantly higher, suggesting that they can be used for diagnosis of colon cancer, liver cancer and stomach cancer (see Table 5). Particularly, three PTPs (T46, pk32 and pk3) were able to be quantified. In the case of PTP T46 standard peptide, expression was slightly varied from individuals and types of cancer but regularly detected in general (see FIG. 4-FIG. 10) and the result was consistent with that of examination using PTP panel.

The present invention also provides a method for quantification of PTP comprising the following steps:
1) concentrating PTP in a sample separated from a test subject;
2) hydrolyzing the concentrated sample of step 1);
3) adding an isotope-substituted synthetic standard peptide to the hydrolyzed sample of step 2); and
4) comparing the levels of the wild type peptide and the isotope-substituted synthetic standard peptide of step 3) to calculate absolute quantity of the wild type peptide expression.

If PTP is concentrated in sample before hydrolysis, analysis process can be simplified. PTP concentration in the sample of step 1) is performed by using a compound specifically binding to PTP enzyme active site. Almost every PTP has the same enzyme active site. Even if the structures of the enzyme active sites of different PTPs are a bit different, they have much in common such as active cysteine, etc. So, based on such similarity, a low-molecular substance is designed to be bound to almost every PTP and then biotin or an analogue thereof is adhered to the low-molecular substance, which is going to be used for PTP concentration.

The present invention also provides a screening method of a cancer related biomarker comprising the following steps:
1) hydrolyzing a sample separated from a subject with cancer;
2) adding an isotope-substituted synthetic standard peptide to the hydrolyzed sample of step 1);
3) extracting the wild type peptide and the isotope-substituted synthetic standard peptide from the hydrolyzed sample of step 2), followed by quantitative analysis thereof;
4) comparing the levels of the wild type peptide and the isotope-substituted synthetic standard peptide of step 3) to calculate absolute quantity of the wild type peptide expression; and
5) comparing the absolute quantity of the wild type peptide of step 4) and the absolute quantity of the wild type peptide extracted from a normal subject to confirm the standard peptide demonstrating a significant difference.

The present invention also provides a screening method of a specific disease related biomarker comprising the following steps:
1) hydrolyzing a sample separated from a subject with a specific disease;

2) adding an isotope-substituted synthetic standard peptide to the hydrolyzed sample of step 1);

3) extracting the wild type peptide and the isotope-substituted synthetic standard peptide from the hydrolyzed sample of step 2), followed by quantitative analysis thereof;

4) comparing the levels of the wild type peptide and the isotope-substituted synthetic standard peptide of step 3) to calculate absolute quantity of the wild type peptide expression; and 5) comparing the absolute quantity of the wild type peptide of step 4) and the absolute quantity of the wild type peptide extracted from a normal subject to confirm the standard peptide demonstrating a significant difference.

The present invention also provides a method for diagnosis of cancer comprising the following steps:

1) hydrolyzing a sample separated from a subject with cancer;

2) adding a synthetic standard peptide substituted with an isotope of one or more biomarkers screened by the cancer related biomarker screening method to the hydrolyzed sample of step 1);

3) extracting the wild type peptide and the isotope-substituted synthetic standard peptide from the hydrolyzed sample of step 2), followed by quantitative analysis thereof;

4) comparing the levels of the wild type peptide and the isotope-substituted synthetic standard peptide of step 3) to calculate absolute quantity of the wild type peptide expression; and 5) comparing the absolute quantity of the wild type peptide of step 4) and the absolute quantity of the wild type peptide extracted from a normal subject to confirm the standard peptide demonstrating a significant difference.

The cancer herein is selected from the group consisting of colon cancer, liver cancer and stomach cancer, but not always limited thereto.

The "significant difference" of step 5) indicates that the absolute quantity of the wild type standard peptide of a test subject is either higher or lower than that of a normal subject. Expressions of different standard peptides can vary from types of cancer and conditions thereof. Thus, cancer can be diagnosed by measuring the standard peptide level, either higher or lower. PTP proteins interact in cellular signal transduction pathway. So, unlike the conventional biomarkers, comparative amount of each PTP can be important information of biological functions. Therefore, comparison among expressions of tens of interacting PTPs can be a reliable diagnostic method that cannot be affected by diverse factors such as age, gender, lifestyle, etc.

The present invention also provides a method for diagnosis of cancer comprising the following steps;

1) concentrating PTP in a sample separated from a test subject;

2) hydrolyzing the concentrated sample of step 1);

3) adding a synthetic standard peptide substituted with an isotope of one or more biomarkers screened by the cancer related biomarker screening method to the hydrolyzed sample of step 2);

4) comparing the levels of the wild type peptide and the isotope-substituted synthetic standard peptide of step 3) to calculate absolute quantity of the wild type peptide expression; and 5) comparing the absolute quantity of the wild type peptide of step 4) and the absolute quantity of the wild type peptide extracted from a normal subject to confirm the standard peptide demonstrating a significant difference.

The present invention also provides a diagnostic kit for disease containing an antibody binding specifically to the standard peptide of the biomarker screened by the specific disease related biomarker screening method.

The antibody herein includes polyclonal antibody and monoclonal antibody. The kit herein additionally contains a secondary antibody labeled with an enzyme binding to the said antibody and reacting with a substrate for color development or a secondary antibody labeled with biotin. If a selected secondary antibody is labeled with an enzyme reactive to a substrate for color development, the substrate for color development and reaction buffer are additionally included.

The antibody can be fixed on a solid substrate. The solid substrate herein is selected from the group consisting of magnetic micro-bead, glass plate, bio-degradable organic polymer nano-particle such as PLGA and (micro)well plates.

The present invention also provides a diagnostic kit for disease containing a primary monoclonal antibody binding specifically to a standard peptide of the biomarker screened by the specific disease related biomarker screening method and a secondary monoclonal antibody binding specifically to the overall region except the region where the primary monoclonal antibody is conjugated.

The kit additionally contains a secondary antibody labeled with an enzyme binding to the secondary monoclonal antibody and reactive to a substrate for color development or a secondary antibody labeled with biotin. If a selected secondary antibody is labeled with an enzyme reactive to a substrate for color development, the substrate for color development and reaction buffer are additionally included.

The primary monoclonal antibody can be fixed on a solid substrate. The solid substrate herein is selected from the group consisting of magnetic micro-bead, glass plate, bio-degradable organic polymer nano-particle such as PLGA and (micro)well plates.

The present invention also provides a use of the synthetic standard peptide for quantification of PTP.

The present invention also provides a use of the synthetic standard peptide for the screening of a cancer-related biomarker.

In addition, the present invention provides a use of the synthetic standard peptide for the screening of a specific disease related biomarker.

Mode for Invention

Practical and presently preferred embodiments of the present invention are illustrative as shown in the following Examples.

However, it will be appreciated that those skilled in the art, on consideration of this disclosure, may make modifications and improvements within the spirit and scope of the present invention.

EXAMPLE 1

Large Scale Expression and Purification of PTP Active Domain

<1-1> Cloning of PTP Active Domain

Expression vectors capable of expressing 1-56 PTP active domains which have the amino acid sequences represented by SEQ. ID. NO: 113-NO: 1618 (Table 1) without help of a fusion protein were constructed.

The multiple cloning sites of PET28a (Novagen, USA) contains those restriction enzyme sites not included in DNA sequences of PTP active domains (SEQ. ID. NO: 113-SEQ.

ID. NO: 168; Table 1) most, so that it was used as a backbone vector of the present invention.

As shown in Table 1, to amplify DNA sequences of PTP active domains 1-56 represented by SEQ. ID. NO: 113-SEQ. ID. NO: 168, PCR was performed with primers represented by SEQ. ID. NO: 1-SEQ. ID. NO: 112 using cDNA libraries of brain, muscle and testis purchased from Clontech as template DNAs as follows; at 95° C. for 5 minutes, at 95° C. for 1 minute, at 55-60° C. for 1 minute, at 72° C. for 90 seconds (30 cycles) and at 72° C. for 10 minutes. The amplified PCR products were digested with NdeI, EcoRI or BamHI, which were inserted into pET28a vector (Novagen, USA) and then named respectively pET28a-PTP 1-56.

TABLE 1

Nucleotide sequences of PTP active domain 1-56 and primer sets

| No. | Name | Amino acid location (SEQ. ID. NO) DNA location | Forward primer Reverse primer | SEQ. ID. NO |
|---|---|---|---|---|
| 1 | T4 | 225-793 (113) | CGCGACGCTAGCATGGCAGACGACAATAAGCTCTTC | 1 |
|  |  | 673-2379 | GCTGCGAAGCTTTACTTGAAGTTGGCATAATCTGA | 2 |
| 2 | T7 | 1684-1967 (114) | GGCACCCATATGCTAGTGGCTGTTGTTGCCTTATTG | 3 |
|  |  | 5050-5901 | GCGGGATCCTCAATGCCTTGAATAGACTGGATC | 4 |
| 3 | T48 | 1316-1897 (115) | GCCCCACATATGCGAGACCACCCACCCATCCCC | 5 |
|  |  | 3946-5691 | GGAAGATCTCTACGTTGCATAGTGGTCAAAGCTGCC | 6 |
| 4 | T8 | 821-1089 (116) | GCGCCATATGGCAGACAAGTACCAGCAACTCTCCCTG | 7 |
|  |  | 2461-3267 | GCGCGGATCCCTCGGCTGGGGCCTGGGCTGACTGTTG | 8 |
| 5 | T23 | 1024-1335 (117) | CCGTTACATATGGTGGAGAATTTTGAGGCCTACTTC | 9 |
|  |  | 3070-4005 | CCCGAATTCTTAGGCGATGTAACCATTGGTCTTTC | 10 |
| 6 | T39 | 879-1440 (118) | CACATTGCTAGCATGAAGACATCAGACAGCTATGGG | 11 |
|  |  | 2635-4320 | CGGCTCAAGCTTCTAAGATGATTCCAGGTACTCCAA | 12 |
| 7 | T5 | 848-1452 (119) | GCCCACCATATGGCCAGCGATACCAGCAGCCTG | 13 |
|  |  | 2542-4356 | GCGAGATCTTCAGCCAGAATTCAAGTATTCCAG | 14 |
| 8 | T38 | 709-979 (120) | GACCGGCATATGCTTGCCAAGGAGTGGCAGGCCCTC | 15 |
|  |  | 2125-2935 | CCGGGATCCTCACTGGGGCAGGGCCTTGAGGAT | 16 |
| 9 | T12 | 674-1015 (121) | CGCCAGCATATGGCCACGCGGCCACCAGACCGA | 17 |
|  |  | 2020-3045 | GCGGGATCCTCACTGGGGAAGGGCCTTGAGGAT | 18 |
| 10 | T15 | 851-1216 (122) | GAGCATGCTAGCATGGCTAGGGAGTGTGGAGCTGGT | 19 |
|  |  | 2551-3648 | GCGGGATCCCTAGGACTTGCTAACATTCTCGTATAT | 20 |
| 11 | T10 | 327-650 (123) | CCTTTCCATATGAAGCCCATAGGACTTCAAGAGAAG | 21 |
|  |  | 979-1950 | GACAGTAAGCTTTCAAAGTCTGCTCTCATACAGGCACA | 22 |
| 12 | T22 | 1367-1650 (124) | CGCGAACATATGCTTAGCCACCCGCCAATTCCC | 23 |
|  |  | 4099-4950 | GGCGGATCCTCAGCCCACGGCCTCCAGCAGGGCCTC | 24 |
| 13 | T20 | 890-1180 (125) | TTCGCTAGCGCCATCCGGGTGGCTGACTTG | 25 |
|  |  | 2668-3540 | GCGGGATCCCTAAAAGGAGCTTAAATATTCCAGTGCCA | 26 |
| 14 | PTP1B | 1-299 (126) | ATGGAGATGGAAAAGGAGTTCGAGCAGATC | 27 |
|  |  | 1-897 | GTCAACATGTGCGTGGCTACGGTCCTCACG | 28 |
| 15 | T25 | 1-387 (127) | GCTCCCGCTAGCATGCCCACCATCGAGCGGGAG | 29 |
|  |  | 1-1161 | CGCGGATCCTTAGGTGTCTGTCAATCTTGGCCT | 30 |
| 16 | T41 | 157-537 (128) | TCAGAGCATATGGAGGAGAAGATCGAGGATGAC | 31 |
|  |  | 469-1611 | GTGGACGCTAGCATGAAATATTTGGGCAGTCCCATT | 32 |
| 17 | T18 | 1-595 (129) | GCCCCCATATGGTGAGGTGGTTTCACCGAGAC | 33 |
|  |  | 1-1785 | CCGGAATTCTCACTTCCTCTTGAGGGAACCCTTG | 34 |
| 18 | pk32 | 63-360 (130) | GAACCCCATATGTCTGTGAACACACCCCGGGAGGTC | 35 |
|  |  | 187-1080 | CGGGATCCTCAGGGGCTGGGTTCCTCAGGCAG | 36 |
| 19 | pk28 | 1-526 (131) | CCGCGGCATATGGAACATCACGGGCAATTAAAA | 37 |
|  |  | 1-1578 | CGGGATCCTCACCTGCAGTGCACCACGACCGG | 38 |
| 20 | T32 | 2095-2490 (132) | GCAGTACATATGAATGGGAAGTTATCAGAAGAG | 39 |
|  |  | 6283-7468 | GGCGGATCCTCACTTCAGAAGCTGAGGCTGCTGTTTTT | 40 |
| 21 | T40 | 866-1187 (133) | GAGCAGCATATGGCAGGCCTGGAGGCACAGAAG | 41 |
|  |  | 2596-3561 | CGCGGATCCTTAAATGAGTCTGGAGTTTTGGAG | 42 |

TABLE 1-continued

Nucleotide sequences of PTP active domain 1-56 and primer sets

| No. | Name | Amino acid location (SEQ. ID. NO) DNA location | Forward primer Reverse primer | SEQ. ID. NO |
|---|---|---|---|---|
| 22 | T2 | 839-1174(134)<br>2515-3522 | CTAGGGCATATGAAAAAGACTCGAGTAGATGCA<br>CGCGGATCCTTAGATGAGCCTGGAGCTTTTCAG | 43<br>44 |
| 23 | pk4 | 173-323(135)<br>517-969 | AGGCCGCATATGGTCATGGAAGTGGGCACCCTG<br>GGCGGATCCTCAGCTCCCAGCCTCTGCCGAACAG | 45<br>46 |
| 24 | pk7 | 174-338(136)<br>520-1012 | GTTCATATGAGTGCCACAGAGCCCTTGGAC<br>GCGGGATCCTCAGGACGTGGCCAGCACCTGGGACTC | 47<br>48 |
| 25 | pk8 | 178-321(137)<br>532-962 | GCGGACCATATGGGCCCAGTTGAAATCCTTCCCTTC<br>GCGAGATCTTCACGTGGAGGGCAGGATCTCAGATTCG | 49<br>50 |
| 26 | pk9 | 205-348(138)<br>613-1044 | GGCAGCCATATGTCCTTCCCAGTGGAGATCTTGCCC<br>CGCGGATCCTCAGCTGAGTCCCAGCGTCCTCTCGAA | 51<br>52 |
| 27 | pk10 | 192-338(139)<br>574-1014 | GCTGGCCATATGTTGCGCCGCCTGCGCAAGGGC<br>CGGGATCCTCACGTGGACTCCAGCGTATTGAG | 53<br>54 |
| 28 | T33 | 160-312(140)<br>478-934 | TGCCCCCATATGGCTGGGGACCGGCTCCCGAGG<br>GCGGGATCCTCATGAGGGGGTGCCCGGGTCGCCCTG | 55<br>56 |
| 29 | pk12 | 201-351(141)<br>601-1053 | CGATCGCATATGGAGGGTCTGGGCCGCTCGTG<br>CGGGATCCCTAGGTGGGGGCCAGCTCGAAGG | 57<br>58 |
| 30 | pk13 | 320-467(142)<br>958-1401 | CTGGACCATATGCAGCGGCTGAACATCGGCTAC<br>CGGGATCCTCACACAACCGTCTCCACTCCCATC | 59<br>60 |
| 31 | T27 | 192-339(143)<br>574-1017 | GTTGCCCATATGGGGCCAACCCGAATTCTTC<br>GGATCCTTATGATGCTCCAGTCTGGTTC | 61<br>62 |
| 32 | pk6 | 1-185(144)<br>1-555 | GCCGCCCATATGTCGGGCTCGTTCGAGCTCTCG<br>CGGGATCCCTAGGGTTTCAACTTCCCCTCC | 63<br>64 |
| 33 | pk14 | 27-210(145)<br>79-628 | GCCAAGCATATGGGCGGAAACCACATCCCCGAAAGG<br>GCGGGATCCTCAGGAATTCCAATTCTTTCTGATAGG | 65<br>66 |
| 34 | pk15 | 21-340(146)<br>61-1020 | AGCGCCCATATGGTCAGCTGTGCCGGGCAGATGCTG<br>CGGGATCCTCATATTTTTCCTGTTTGTGATCC | 67<br>68 |
| 35 | pk33 | 1-188(147)<br>1-564 | GGCTGGCATATGGCTGAGACCTCTCTCCCAGAG<br>CGGGATCCTCAGCTCTGGCCGGCACCCCGC | 69<br>70 |
| 36 | p44 | 1-198(148)<br>1-601 | TCCCACCATATGGACTCACTGCAGAAGCAGGAC<br>GCCAAGGGTCAGGGATCCTGGCTG | 71<br>72 |
| 37 | p21 | 1-157(149)<br>1-471 | CCCGGGCATATGGGCAATGGCATGACCAAGGTAC<br>GCGGGATCCTCACTTGCCGCCCTTGCGGGACAG | 73<br>74 |
| 38 | pk35 | 1-188(150)<br>1-564 | GCGGGATCCTCACTTGCCGCCCTTGCGGGACAG<br>CGGGATCCTCACAGTGGAATCATCAAACGGAC | 75<br>76 |
| 39 | NE1 | 1-217(151)<br>1-651 | CCAGGGGCTAGCCGCTAACTGGAAAGAAAA<br>GTCGGATCCTTAGCTTTCTTTGCCCTCTTG | 77<br>78 |
| 40 | p19 | 1-190(152)<br>1-570 | ATGACAGCATCCGCGTCCTCCTTTTC<br>TTACATTGATATCATCATACGTAG | 79<br>80 |
| 41 | pk18 | 1-184(153)<br>1-552 | GCAGCCCATATGGGGAATGGGATGAACAAGATC<br>CGGGATCCTTACAGTCTTCTGAGAAAGGCCCAG | 81<br>82 |
| 42 | p12 | 31-211(154)<br>91-603 | GGGAAGCATATGGGTCGGGCGCACCGGGACTGG<br>GGCACCAAGCTTTCAGAACTCTTTAAGAACATCCAGCT | 83<br>84 |
| 43 | pk17 | 35-211(155)<br>103-633 | CTGGAGCATATGCCAACCGTTCAACATCCTTTCC<br>GCGGGATCCTCATGCTTCCAGACCCTGCCGCAGC | 85<br>86 |
| 44 | p16 | 1-150(156)<br>1-450 | GCGGCGGCTAGCATGGGCGTGCAGCCCCCCAACTTC<br>CGCGCCTCGAGTTTCGTTCGCTGGTAGAACTGGAA | 87<br>88 |
| 45 | T16 | 1-210(157)<br>1-630 | GGCGGCGCTAGCATGGCTCACAACAAGATCCCGCCG<br>TGAGGATCCTTATGATTCCTTCTTTCCATCCTCATC | 89<br>90 |

TABLE 1-continued

Nucleotide sequences of PTP active domain 1-56 and primer sets

| No. | Name | Amino acid location (SEQ. ID. NO) DNA location | Forward primer Reverse primer | SEQ. ID. NO |
|---|---|---|---|---|
| 46 | p18 | 306-450(158) 916-1350 | CCGGGACATATGGACAAGCCCTCCCTTATCTTC GCGGGATCCTCAGCTTGCATCCAAGATGCCTTC | 91 92 |
| 47 | NE3 | 306-350(159) 916-1350 | CTTGGTCATATGGATAGCCCTACACAGATATTTG GCGGGATCCTCACCTTGCCAGCAAGATCCCCTG | 93 94 |
| 48 | pk3 | 4-163(160) 10-489 | GCGGCTCATATGAACCGCCCAGCTCCTGTGGAA GCGGGATCCTCAGGAATCTTTGAAACGCAGCCGCAT | 95 96 |
| 49 | p49 | 14-167(161) 40-501 | CGCCGAGCTAGCATGCGTTTTCTGATAACTCACAAC CGGGATCCCTACTGAACACAGCAATGCCCATTG | 97 98 |
| 50 | p26 | 4-161(162) 10-483 | GCGACCCATATGGCCCCGGTGGAGGTGAGCTACA CGCGGATCCTCAGGTCTTGTGCGTGTGTGGGTCTTTG | 99 100 |
| 51 | T29 | 37-391(163) 109-1173 | GGCGGCCATATGTCGTCGACCTCGCCGGGTGTGAAG GCCGGATCCTTATTTGGAGAAGGCTGCTCTGTGTTGTC | 101 102 |
| 52 | T46 | 1-157(164) 1-471 | ATGGCGGAACAGGCTACCAAGTCCGTG TCAGTGGGCCTTCTCCAAGAACGCTCTGC | 103 104 |
| 53 | pk1 | 336-523(165) 1006-1569 | GCTCTAGACTTATAGGAGACTTCTCCAAGGG GCCCTAGGTCAGAGCTTCTTCAGACGACTGTAC | 105 106 |
| 54 | T47 | 378-566(166) 1132-1701 | GACCACCATATGCTGATTGGAGATTACTCTAAGGCC CCGGGATCCTCACTGGTCCTGCAGCCGGCTACA | 107 108 |
| 55 | T45 | 207-400(167) 619-1200 | GATTCTGCTAGCGGGCACCTGATTGGTGATTTTCC CCGGGATCCTCATGGGCTCATGTCCTTCACCAG | 109 110 |
| 56 | Eya2 | 244-514(168) 730-1542 | GACAATCATATGGAGCGTGTGTTCGTGTGGGAC GAATTCTTATAAATACTCCAGCTCCAGGGCGTG | 111 112 |

<1-2> Expression Vector for PTP Expressed by MBP Fusion

Vectors pET28a-MBP-PTP 1-5 for the expression of 5 PTPs via MBP fusion which have the amino acid sequences represented by SEQ. ID. NO: 256-NO: 260 (1-5 of Table 2) were constructed by the similar method to that described in Korean Patent No. 10-0746933. The primer sets used for the construction are shown in Table 2.

<1-3> Conditions for Large Scale Expression with Maintaining Activity and Stability

*E. coli* was transfected respectively with the 56 vectors constructed in Example <1-1> and 5 vector constructed in Example <1-2> according to the method of Hanahan (Hanahan D, *DNA Cloning* vol. 109-135, IRS press 1985).

TABLE 2

Sequences of PTP 1-5 expressed as MBP fusion protein and primer sets

| No | Name | Amino acid location (SEQ. ID. NO) DNA location | Forward primer Reverse primer | SEQ. ID. NO |
|---|---|---|---|---|
| 1 | p45 | 1-295(256) 1-885 | ATGAGGAGAACTTCCGGAGCAACC CTATAGGCACGATGATACAAAATATAA | 261 262 |
| 2 | p46 | 149-420(257) 445-1260 | CCTCTAGCTAGCGATACGCGCAAAATTGTT GGATCCTTAATCCAAAGTCAGAAGTTTCC | 263 264 |
| 3 | p47 | 1-242(258) 1-726 | CGCCCACATATGACAGCCATCATCAAAGAGAT CGGGATCCTCAAAGTACATGAACTTGTCTTCC | 265 266 |
| 4 | T21 | 166-500(259) 496-1500 | CTTGCACATATGGGCTTTGACGTGCAGAACG CCGAGATCTTCATTGCACCAGTTTTACCAGGAA | 267 268 |
| 5 | T53 | 1-223(260) 1-669 | TCGGCCCATATGCCTGGTTTGCTTTTATGTGAA CGGAATTCTCAGTAGAGCGGATCCATGATG | 269 270 |

Particularly, *E. coli* BL21-DE3-RIL treated with $CaCl_2$ was transfected with vectors constructed in Example <2-1> by heat-shock method. Then, the cells were cultured in medium containing kanamycin (Sigma, USA). Colonies having kanamycin resistance were selected. These colonies were cultured in LB medium for overnight and then some of the seed culture solution was inoculated in LB medium containing 30 μg/ml of kanamycin, followed by culture until stationary phase. The culture solution was diluted at the ratio of 1:100 and inoculated in fresh LB medium (400 ml/flask). Temperature was lowered slowly from 37° C. to 17° C. during 2-3 hour culture. Then, culture was continued at 17° C. at 200 rpm. When $OD_{600}$ of the culture solution reached 0.5, IPTG was added at the lowest concentration (0.05-0.1 mM), followed by further culture for 20 or 16-18 hours to induce expression of PTP active domain.

<1-4> Conditions for Purification and Storage with Maintaining Activity and Stability

*E. coli* cultured in Example <1-3> was centrifuged at 4° C. at 6,000 rpm for 5 minutes. The cell precipitate was recovered, which was resuspended in 5 ml of cell lysis buffer (10 mM Tris-HCl buffer, pH 7.5, 10 mM EDTA). The cells were lysed using ultrasonicator at 4° C. Centrifugation was performed at 4° C. at 13,000 rpm for 10 minutes to separate supernatant and insoluble aggregate. Protein was eluted from the supernatant by linear density gradient using Ni—NTA resin (Qiagen, USA) at 4° C. for about 3 hours from low concentration buffer [20 mM Tris-HCl buffer, pH 7.5, 0.2 M NaCl, 1.0 mM PMSF, 4 mM β-mercaptoethanol (Sigma, USA)] to high concentration buffer [0.5 M imidazole (Sigma, USA) was added to the low concentration buffer]. The histidine tag of N-terminal of the eluted protein was eliminated by treating thrombin (protease) (Sigma, USA) by 1 unit/100 μg protein. The protein was purified by ion exchange chromatography (GE Healthcare, USA) and gel filtration chromatography (GE Healthcare, USA).

During the purification of PTP active domain, 10 mM β-mercaptoethanol (Sigma, USA) or DTT (Promega, USA) was added to the buffer and pH of the buffer was regulated to 6.5-8.0. The purified PTP active domain was stored at 4° C. with the addition of 10% glycerol in protein solution [10% glycerol solution prepared by adding 100-250 mM NaCl, 10 mM reducing agent (β-mercaptoethanol or DTT) and 0.5~2 μg/ml protease inhibitor (Sigma, USA) to pH 7.5-8.0 Tris buffer].

EXAMPLE 2

Construction of Standard Peptide of PTP Active Domain

<2-1> Hydrolysis of PTP Active Domain Using Trypsin

56 PTP active domains obtained by the method described in Example 1, 5 proteins expressed by MBP fusion and 20 proteins expressed by MBP fusion described in Korean Patent No. 10-0746933 and shown in Table 3 were hydrolyzed by using trypsin (Sequencing Grade Modified Trypsin; Promega, USA) protease. Particularly, denaturation of PTP active domains purified at the concentration of 1 mg/ml was performed with 50 mM Ammonium Bicarbonate 0.1% (w/v) Rapigest reagent (Waters, USA)/20 μl PTP active domain for 30 minutes at 60° C. After cooling at room temperature, 1 μg of trypsin was added thereto, followed by hydrolysis at 37° C. 2 hours later, the reaction was terminated by adding 0.5% (final conc.) TFA (trifluoroacetic acid; Burdick & Jackson Brand, USA). After incubation for 30 minutes at 37° C., the reaction mixture was centrifuged for 10 minutes at 13,000 rpm. Precipitate was eliminated and only hydrolyzed peptide solution was obtained. LC-MS/MS analysis was performed with the hydrolyzed peptide solution. For denaturation of the domain, urea, guanidine-HCL, etc can be used as a denaturant in addition to the Rapigest and heat treatment (90° C.) can also be accepted. Sample was loaded by on-line using trap column Symmetry $C_{18}$ (Waters, USA) for nanoAcquity HPLC before analysis using Q-Tof premier mass spectrometer (Waters, USA). After loading, salts were eliminated, followed by drying under vacuum condition to give the sample for mass spectrometry.

TABLE 3

20 proteins expressed by MBP fusion described in Korean Patent No. 10-9746993

| No. | Name | Protein | Unitprot accession no, | Amino acid location | SEQ. ID. NO |
|---|---|---|---|---|---|
| 1 | p13 | MTMR8 | Q96EF0 | 122-704 | 271 |
| 2 | p20 | VHP(DUSP26) | Q05923 | 1-176 | 272 |
| 3 | p24 | TENC1 | Q2NL80 | 125-320 | 273 |
| 4 | pk16 | MTMR7 | Q9Y216 | 1-334 | 274 |
| 5 | pk19 | Laforin(EPM2A) | O95278 | 1-331 | 275 |
| 6 | pk30 | MKP6(DUSP14) | O95147 | 1-198 | 276 |
| 7 | pk36 | SSH3 | Q8TE77 | 11-150 | 277 |
| 8 | pk38 | MK-STYX | Q9Y6J8 | 1-313 | 278 |
| 9 | pk5 | PAC-1(DUSP2) | Q05923 | 1-314 | 279 |
| 10 | T1 | PTP-PEST(PTPN12) | Q05209 | 1-324 | 280 |
| 11 | T17 | CD45(PTPRC) | Q5T5R0 | 465-1143 | 281 |
| 12 | T19 | MTMR3 | Q13615 | 137-530 | 282 |
| 13 | T24 | MTMR1 | Q13613 | 1-571 | 283 |
| 14 | T26 | RPTP δ (PTPRD) | P23468 | 1331-1912 | 284 |
| 15 | T30 | HD-PTP(PTPN23) | Q9H3S7 | 1060-1636 | 285 |
| 16 | T3 | PTP-HSCF(PTPN18) | Q99952 | 1-300 | 286 |
| 17 | T31 | PTPJ(PTPRU) | Q92729 | 817-1436 | 287 |
| 18 | T35 | LYP(PTPN22) | Q9Y2R2 | 1-326 | 288 |
| 19 | T37 | RPTP(PTPRE) | P23469 | 100-700 | 289 |
| 20 | T6 | RPTP γ (PTPRG) | P23470 | 825-1414 | 290 |

<2-2> Hydrolyzed Peptide Pattern and Ionization Pattern of Hydrolyzed PTP Active Domain To determine peptide sequence of the hydrolyzed PTP active domain prepared in Example <2-1> and to record ionization pattern, Q-TOF premier/nanoAcquity (Waters, USA) system was used.

Peptides were separated from the proteins obtained in Example <2-1> by retention time on Atlantis C18 nanoAcquity column (Waters, USA) using density gradient method with solution A [0.1% formic acid (Fluka, Japan) deionized water] and solution B [0.1% formic acid acetonitrile (Fluka, Germany)] for 40 minutes at flow rate of 300 n2/min. At this time, ESI Source temperature was 80° C., and Capillary Voltage was maintained at 3.8 kV. MS spectrum of peptide detected on-line was analyzed, followed by MS/MS assay for maximum 10 seconds with peptide ions having +2 and +3 charges. MassLynx version 4.1 (Waters, USA) was used for MS/MS spectrum analysis. ProteinLynx v2.2 (Waters, USA) and Mascot release 2.1 (Matrix Science, USA) were used for peptide sequencing and hydrolyzed peptide analysis. By which, hydrolyzed peptide pattern and ionization tendency of each PTP active domain were analyzed.

<2-3> Selection and Synthesis of Standard Peptide of PTP Active Domain

Among the peptides confirmed to be efficiently ionized in Example <2-2>, the peptides which do not contain a residue having risk of oxidation such as cysteine or methionine but contain a residue replaceable with a stable isotope such as leucine or valine were selected. And each of those peptides was synthesized to 1-3 mg and to be replaced with an isotope.

Particularly, hydrolysis by trypsin resulted in cleavage of the region behind of Arg and Lys unless Pro is there, suggesting that the resultant peptide always includes C-terminal which is composed of Arg or Lys (FIG. 1). Such peptide that was hard to be separated on LC because it was highly hydrophilic or highly hydrophobic or that was impossible to be detected by MS because its mass was too big or too small or demonstrated too low MS/MS ionization efficiency was excluded. Those peptides which were apt to be modified because of high reactivity, such as Trp, Met, Cys, etc, were also excluded. Shorter peptides were preferably selected by BLAST search as long as they were long enough to represent specific proteins and had similar ionization strength.

4 different FMOC amino acids (Cambridge Isotope Laboratories; CIL, USA), L-arginine-N—FMOC—$^{13}C_6,^{15}N_4$ (+10Da), L-lysine-α-N—FMOC—$^{13}C_6,^{15}N_2$ (+8Da), L-leucine-N—FMOC—$^{13}C_6,^{15}N$(+7Da) and L-valine-N—FMOC—$^{13}C_5,^{15}N$(+6Da), labeled with $^{13}C$ and $^{15}N$ were used to synthesize 1~3 mg of isotope-substituted peptides according to Fmoc solid-phase synthesis method. Every trypsin hydrolase can be labeled with Arg or Lys of C-terminal, but when peptides contained Leu and Val in addition to C-terminal, those FMOC amino acids labeled with a stable isotope on Leu and Val were first selected because they were less expensive.

As a result, the peptide (or ion) having the amino acid sequences represented by SEQ. ID. NO: 169-NO: 255 generated by hydrolysis of PTP active domain was selected. Particularly, as shown in FIG. 1a, 12 different peptides were detected from LC-MS/MS analysis of hydrolyzed LMPTP (T46; #52 of Table 1), from which 2 peptides were selected (diamond mark of FIG. 1b: 41-58, 113-123) after eliminating peptides which were incompletely hydrolyzed or modified or had possibility of modification. Upon completion of sequencing of the selected peptides (FIG. 2 and FIG. 3), real ionization strength of daughter ion on raw-spectrum was examined (Ion value is presented in parentheses in "Native" line of Table 4). Each PTP active domain was analyzed by the same manner. At last, among those peptides generating daughter ion which could optimize MRM (multiple reaction monitoring) signal, the peptide appropriate for synthesis was firstly synthesized. Purity of the peptide was confirmed to be 92-99% by HPLC-MS. The amino acids marked by * in the standard peptide sequence are the region labeled with a stable isotope amino acid purchased from CIL (presented in the "Sequence" line shown in Table 4).

TABLE 4

20 proteins expressed by MBP fusion described in Korean Patent No. 10-9746993
Sequence of standard peptide; Mass and Energy value of optimal fragments

| lab ID | Name | Sequence | Native |
| --- | --- | --- | --- |
| Eya2-1 | Eya2 | AVYVVIGDGVEEEQGAK* | 881.95(+2)->weak |
| NE1-1 | DUSP17, SKRP1 | THILNVAYGVENAFLSDFTYK* | pep err |
| NE3-1 | SSH2, slingshot2 | EIDNFFPGV*FEYHNIR | 666.32(+3)->616.32(+2) |
| p12-1 | MOSP, DUSP23 | IDPTVLLGALPL*R | 689.43(+2)->852.57(+1) |
| p13-1 | MTMR8 | VPVLSYL*YK | 361.22(+3)->weak |
| p16-R* | VHZ, DUSP25 | FVQIVDEANAR* | 631.33(+2)->774.37(+1) |
| p18-1 | SSH1, slingshot1 | EIDNFFPGL*FAYHNIR | 651.66(+3)->594.32(+2) |
| p19-1 | LMW-DSP21, DUSP21 | SLFLSNGVAANDK* | 668.35(+2)->875.42(+1) |
| p20-1 | VHP | AAGAEEQL*AR | 508.26(+2)->873.44(+1) |
| p21-1 | VHY, DUSP15 | DLDQL*GR | 408.71(+2)->588.31(+1) |
| p24-1 | C1-TEN | VATELQPSQR* | 564.80(+2)->487.26(+1) |
| p44-1 | TMDP, DUSP13B | QLQVL*DNR | 493.28(+2)->517.27(+1) |
| p45-1 | TENSIN | VLEFGWPDLHTPAL*EK | 617.99(+3)->820.41(+2) |
| p46-1 | TypPTP | VFLENYQILQYFIIR* | 653.70(+3)->839.48(+1) |
| p47-1 | PTEN | AQEALDFYGEV*R | 466.56(+3) weak |
| pk10-1 | PYST2, DUSP7 | DSTNLDVL*GK | 531.28(+2)->758.44(+1) |
| pk1-1 | CDC25A | GYLFHTVAGK* | 546.80(+2)->759.42(+1) |
| pk12-1 | MKP-4, DUSP9 | DSANLESL*AK | 524.27(+2)->774.44(+1) |
| pk13-1 | MKP-5, DUSP10 | LNIGYVINVTTHLPL*YHYEK | 796.43(+3)->1024.04(+2) |
| pk14-1 | PIR1, DUSP11 | IFTVGHQVPDDETIFK* | 615.98(+3)->793.40(+2) |
| pk15-1 | HYVH1, DUSP12 | SSSIL*DHR | 457.74(+2)->540.29(+1) |
| pk16-1 | MTMR7 | GYENEDNYSNIK* | 482.54(+3)->weak |

TABLE 4-continued 20 proteins expressed by MBP fusion described in
Korean Patent No. 10-9746993
Sequence of standard peptide; Mass and Energy value of optimal fragments

| | | | |
|---|---|---|---|
| pk17-1 | MGC1136 | GTPEAYEGL*GIR | 631.82(+2)->878.47(+1) |
| pk18-1 | VHX, DUSP22 | EEYGESPL*QDAEEAK | 847.87(+2)->1000.50(+1) |
| pk19-1 | Laforin, EPM2A | EPGGELSWEGNGPHHDR* | 625.28(+3)->702.82(+2) |
| pk2-1 | KAP, CDKN3 | LAAHL*SSR | 285.50(+3)->462.27(+1) |
| pk28-1 | SHP2, PTPN11 | FDSLTDLVEHYK* | 489.58(+3)->602.81(+2) |
| pk30-1 | MKP6, DUSP14 | MVQTPYGIVPDV*YEK | 580.30(+3)->750.36(+1) |
| pk32-1 | HePTP, PTPN7 | IPSNFVSPEDLDIPGHASK* | 675.01(+3)->596.32(+1) |
| pk33-1 | BEDP, DUSP13A | VDEVWPNL*FIGDAATANNR | 701.35(+3)->737.38(+2) |
| pk35-1 | DUSP20, LMW-DSP20 | QPSVSGL*SQITK | 622.85(+2)->613.84(+2) |
| pk36-1 | SSH3, slingshot3 | FTYHNV*R | 312.83(+3)->388.23(+1) |
| pk38-1 | STYX | IEDSPEAQILPFL*R | 543.30(+3)->532.32(+1) |
| pk4-1 | MKP-1, 3CH134 | LDEAFEFV*K | 549.28(+2)->869.44(+1) |
| pk5-1 | PAC-1 | LDEAFDFV*K | 361.85(+3)->weak |
| pk6-2 | VHR, T-DSP11 | LGITHVLNAAEGR* | 450.92(+3)->730.38(+1) |
| pk7-1 | MKP-2, hVH2/TYP1 | LEEAFEFV*K | 556.29(+2)->869.44(+1) |
| pk8-1LK | hVH3/B23 | LKEAFDYIK* | 376.21(+3)->538.29(+1) |
| pk9-1 | PYST1, MKP-3/rVH6 | DSTNLDVL*EEFGIK | 790.40(+2)->1049.55(+1) |
| PRL1-*KK | PRL1 | FIEEL*KK | 453.77(+2)->646.38(+1) |
| PRL12-R* | PRL1/2 | YEDAVQFIR* | 570.79(+2)->848.46(+1) |
| PRL2-*KK | PRL2 | FTEEL*KK | 447.75(+2)->646.38(+1) |
| PRL3-F*KK | PRL3 | FLITHNIPTNATLSTFIEDL*KK | 601.58(+4)->715.05(+3) |
| PRL3-R* | PRL3 | YEDAIQFIR* | 577.80(+2)->862.48(+1) |
| PTP1B-1 | PTP1B | LHQEDNDYINASLIK* | 591.63(+3)->645.39(+1) |
| PTPRT1 | PTPRT | VTLIETEPLAEYV*IR | 582.66(+3)->480.78(+2) |
| PTPRT2 | PTPRT | GASTQNSNTV*EPEK | 731.35(+2)->npp |
| SHP1-1 | SHP1 | DLSGLDAETL*LK | 637.85(+2)->1046.57(+1) |
| SHP1-2 | SHP1 | GEPWTFL*VR | 552.80(+2)->459.76(+2) |
| SHP1-3 | SHP1 | NQLL*GPDENAK | 599.81(+2)->843.42(+1) |
| T10-1 | PTP-SL, PCPTP | TILPNPL*SR | 505.80(+2)->683.38(+1) |
| T1-1 | PTP-PEST, PTP-P19 | EQYELV*HR | 358.52(+3)->408.72(+2) |
| T12-1 | PTPRP, IA-2beta | SLAVL*TYDHSR | 421.22(+3)->531.27(+2) |
| T15-1 | GLEPP1, PTP-U2 | FSLQFEEL*K | 570.80(+2)->665.35(+1) |
| T16-R* | mRNA capping enzyme | YDSQVAEENR* | 605.77(+2)->618.28(+1) |
| T17-1 | CD45, LCA | YIAAQGPR* | 438.24(+2)->599.33(+1) |
| T19-1 | MTMR3, FYVE-DSP1 | NADDEHLVQSV*AK | 475.90(+3)->620.81(+2) |
| T2-1 | PTPD1, PTP2E | HNTVTYGR* | 316.50(+3)->weak |
| T21-1 | MTRM4, FYVE-DSP2 | SYTAAV*ANR | 476.75(+2)->702.39(+1) |
| T22-1 | RPTPsigma | TVDVYGHVTL*MR | 464.24(+3)->weak |

TABLE 4-continued 20 proteins expressed by MBP fusion described in
Korean Patent No. 10-9746993
Sequence of standard peptide; Mass and Energy value of optimal fragments

| | | | |
|---|---|---|---|
| T23-1 | DEP1, CD148 | NIQTSESHPL*R | 427.89(+3)->385.26(+1) |
| T24-1 | MTMR1 | VYDPV*SEYK | 367.18(+3)->weak |
| T25-1 | TCPTP, MPTP | EFEEL*DTQR | 583.77(+2)->632.34(+1) |
| T26-1 | RPTPdelta | PSDTTKYLLEQL*EK | 555.63(+3)->759.43(+1) |
| T27-1 | MKP-7, MKP-M | ILPNLYL*GCQR | 430.57(+3)->weak |
| T29-1 | CDC14B | NHNV*TTIIR | 534.30(+2)->816.49(+1) |
| T30-1 | HD-PTP, PTP-TD1 | VLSL*QFR | 288.18(+2)->npp |
| T3-1 | PTP-HSCF, PTP20 | YKDVLPYDQTR* | 466.57(+3)->519.25(+1) |
| T31-1 | PTPJ, PTP-U1 | VADLLQHINQMK* | 470.59(+3)->620.33(+2) |
| T32-1 | PTP-BAS, FAP-1 | VPLGDEGGYINASFIK* | 560.63(+3)->679.38(+1) |
| T33-1 | hVH5, M3/6, HB5 | ILPHLYL*GSQK | 423.58(+3)->521.79(+2) |
| T35-1 | LYP, PEP | DGIIPENFSVFSL*IR | 569.64(+3)->npp |
| T37-1 | RPTP | DFLVTL*NQPQAR | 467.92(+3)->nmatch |
| T38-1 | IA-2 | EIDIAATL*EHVR | 456.25(+3)->562.81(+2) |
| T39-1 | RPTPkappa | QNVVDVFHAV*K | 419.23(+3)->601.35(+1) |
| T40-1 | PTP36, PEZ, PTPD2 | ANGIFSTAAL*PENAER | 830.92(+2)->899.46(+1) |
| T4-1 | RPTPalpha | AEGILDVFQTV*K | 660.36(+2)->949.54(+1) |
| T41-1 | STEP | APPLLHLV*R | 339.22(+3)->424.28(+2) |
| T45-1 | CDC25C | YVNPETVAALL*SGK | 731.40(+2)->1085.62(+1) |
| T46-1 | LMPTP | IELL*GSYDPQK | 631.84(+2)->1020.54(+1) |
| T47-1 | CDC25B | AFLLQTVDGK* | 364.54(+3)->437.26(+2) |
| T48-1 | LAR | NLYAHIQK* | 493.78(+2)->759.42(+1) |
| T5-1 | RPTPmu | TVDVFHAV*K | 508.28(+2)->815.44(+1) |
| T53-1 | STYX | SLSVHSGTTGSL*K | 425.23(+3)->537.28(+2) |
| T6-1 | RPTPgamma | HSDYINANYVDGYNK* | 591.60(+3)->nmatch |
| T7-1 | RPTPbeta | DSVDIYGAVHDL*R | 487.24(+3)->579.80(+2) |
| T8-1 | SAP1 | TGTLIALDVLL*R | 642.90(+2)->799.50(+1) |

| lab ID | SIS | QTOF | Quat |
|---|---|---|---|
| Eya2-1 | 885.95(+2) | | |
| NE1-1 | | | |
| NE3-1 | 668.33(+3)->619.32(+2) | CE: 20V | CE: 22V |
| p12-1 | 692.94(+2)->859.58(+1) | CE: 20V | CE: 26V |
| p13-1 | 363.55(+3) | | |
| p16-R* | 636.34(+2)->784.38(+1) | CE: 20V | CE: 24V |
| p18-1 | 654.00(+3)->597.83(+2) | CE: 18V | CE: 20V |
| p19-1 | 672.36(+2)->883.44(+1) | CE: 21V | CE: 22V |
| p20-1 | 511.77(+2)->880.46(+1) | CE: 17V | CE: 18V |
| p21-1 | 412.22(+2)->595.33(+1) | CE: 13V | CE: 15V |

TABLE 4-continued 20 proteins expressed by MBP fusion described in
Korean Patent No. 10-9746993
Sequence of standard peptide; Mass and Energy value of optimal fragments

| | | |
|---|---|---|
| p24-1 | 569.81(+2)->497.27(+1) | CE: 18V CE: 22V |
| p44-1 | 496.78(+2)->524.29(+1) | CE: 17V CE: 19V |
| p45-1 | 620.33(+3)->823.92(+2) | CE: 16V CE: 18V |
| p46-1 | 657.03(+3)->849.49(+1) | CE: 18V weak |
| p47-1 | 468.57(+3) | |
| pk10-1 | 534.79(+2)->765.46(+1) | CE: 17V CE: 20V |
| pk1-1 | 550.80(+2)->767.43(+1) | CE: 19V CE: 21V |
| pk12-1 | 527.78(+2)->781.45(+1) | CE: 15V CE: 18V |
| pk13-1 | 798.77(+3)->1027.55(+2) | CE: 24V weak |
| pk14-1 | 618.66(+3)->797.40(+2) | CE: 16V CE: 17V |
| pk15-1 | 461.25(+2)->547.31(+1) | CE: 16V CE: 19V |
| pk16-1 | 485.22(+3)-> | |
| pk17-1 | 635.33(+2)->885.49(+1) | CE: 26V CE: 28V |
| pk18-1 | 851.38(+2)->1007.51(+1) | CE: 28V CE: 29V |
| pk19-1 | 628.62(+3)->707.83(+2) | CE: 18V weak |
| pk2-1 | 287.84(+3)->469.28(+1) | CE: 12V CE: 14V |
| pk28-1 | 492.25(+3)->606.82(+2) | CE: 13V CE: 15V |
| pk30-1 | 582.30(+3)->756.38(+1) | CE: 14V CE: 16V |
| pk32-1 | 677.68(+3)->604.33(+1) | CE: 22V CE: 22V |
| pk33-1 | 703.69(+3)->740.89(+2) | CE: 16V CE: 16V |
| pk35-1 | 626.36(+2)->617.35(+2) | CE: 21V CE: 20V |
| pk36-1 | 314.83(+3)->394.24(+1) | CE: 14V CE: 15V |
| pk38-1 | 545.63(+3)->539.34(+1) | CE: 14V CE: 16V |
| pk4-1 | 552.29(+2)->875.45(+1) | CE: 15V CE: 18V |
| pk5-1 | 363.86(+3)-> | |
| pk6-2 | 454.26(+3)->740.39(+1) | CE: 18V CE: 20V |
| pk7-1 | 559.29(+2)->875.45(+1) | CE: 16V CE: 18V |
| pk8-1LK | 378.88(+3)->546.30(+1) | CE: 12V CE: 13V |
| pk9-1 | 793.91(+2)->1056.57(+1) | CE: 25V weak |
| PRL1-*KK | 457.28(+2)->653.39(+1) | CE: 15V CE: 18V |
| PRL12-R* | 575.79(+2)->858.47(+1) | CE: 19V CE: 21V |
| PRL2-*KK | 451.26(+2)->653.39(+1) | CE: 15V CE: 18V |
| PRL3-F*KK | 603.33(+4)->717.39(+3) | CE: 20V CE: 16V |
| PRL3-R* | 582.80(+2)->872.49(+1) | CE: 18V CE: 21V |
| PTP1B-1 | 594.30(+3)->653.41(+1) | CE: 14V CE: 18V |
| PTPRT1 | 584.67(+3)->483.78(+2) | CE: 14V CE: 15V |
| PTPRT2 | 734.35(+2) | |
| SHP1-1 | 641.35(+2)->1053.59(+1) | CE: 18V CE: 22V |

TABLE 4-continued 20 proteins expressed by MBP fusion described in
Korean Patent No. 10-9746993
Sequence of standard peptide; Mass and Energy value of optimal fragments

| | | | |
|---|---|---|---|
| SHP1-2 | 556.30(+2)->463.27(+2) | CE: 14V | CE: 17V |
| SHP1-3 | 603.32(+2)->850.44(+1) | CE: 17V | CE: 21V |
| T10-1 | 509.31(+2)->690.40(+1) | CE: 15V | CE: 20V |
| T1-1 | 360.52(+3)->411.73(+2) | CE: 9V | CE: 12V |
| T12-1 | 423.56(+3)->534.78(+2) | CE: 9V | CE: 12V |
| T15-1 | 574.31(+2)->672.37(+1) | CE: 19V | CE: 22V |
| T16-R* | 610.78(+2)->628.29(+1) | CE: 19V | CE: 22V |
| T17-1 | 443.25(+2)->609.33(+1) | CE: 12V | CE: 16V |
| T19-1 | 477.91(+3)->623.82(+2) | CE: 12V | CE: 14V |
| T2-1 | 319.83(+3) | | |
| T21-1 | 479.75(+2)->708.47(+1) | CE: 14V | CE: 16V |
| T22-1 | 466.58(+3) | | |
| T23-1 | 403.23(+3)->392.27(+1) | | weak |
| T24-1 | 369.19(+3) | | |
| T25-1 | 587.28(+2)->639.35(+1) | CE: 17V | CE: 20V |
| T26-1 | 557.97(+3)->766.44(+1) | CE: 20V | CE: 22V |
| T27-1 | 432.91(+3) | | |
| T29-1 | 537.31(+2)->822.51(+1) | CE: 20V | CE: 23V |
| T30-1 | 290.52(+2) | | |
| T3-1 | 469.91(+3)->529.26(+1) | CE: 16V | CE: 18V |
| T31-1 | 473.26(+3)->624.34(+2) | CE: 13V | CE: 15V |
| T32-1 | 563.30(+3)->687.39(+1) | CE: 12V | CE: 15V |
| T33-1 | 425.92(+3)->525.30(+2) | CE: 10V | CE: 12V |
| T35-1 | 571.98(+3) | | |
| T37-1 | 470.26(+3) | | |
| T38-1 | 458.59(+3)->566.32(+2) | CE: 11V | CE: 13V |
| T39-1 | 421.24(+3)->607.36(+1) | CE: 14V | CE: 18V |
| T40-1 | 834.43(+2)->906.48(+1) | CE: 27V | CE: 29V |
| T4-1 | 663.37(+2)->955.55(+1) | CE: 20V | CE: 24V |
| T41-1 | 341.22(+3)->427.29(+2) | CE: 9V | CE: 12V |
| T45-1 | 734.91(+2)->1092.64(+1) | CE: 22V | CE: 24V |
| T46-1 | 635.34(+2)->1027.55(+1) | CE: 19V | CE: 22V |
| T47-1 | 367.21(+3)->441.26(+2) | CE: 8V | CE: 10V |
| T48-1 | 497.78(+2)->767.43(+1) | CE: 16V | CE: 19V |
| T5-1 | 511.29(+2)->821.46(+1) | CE: 16V | CE: 19V |
| T53-1 | 427.57(+3)->540.79(+2) | | CE: 14V |
| T6-1 | 594.27(+3) | | |

TABLE 4-continued 20 proteins expressed by MBP fusion described in
Korean Patent No. 10-9746993
Sequence of standard peptide; Mass and Energy value of optimal fragments

| | | |
|---|---|---|
| T7-1 | 489.58(+3)->583.31(+2) | CE: 11V CE: 14V |
| T8-1 | 646.41(+2)->806.52(+1) | CE: 21V CE: 28V |

EXAMPLE 3

Measuring Optimum Ionization Energy of Standard Peptide

Energy value of synthetic standard peptide having substitution with an isotope prepared in Example 2 was measured. The synthetic standard peptide has the strongest detection signal, because it preceeded to optimal fragmentation and ionization on tandem mass spectrometer.

2 μl of a mixed sample containing 100 femto mole of each of 87 isotope-substituted synthetic standard peptides (Table 4) was loaded in Q-Tof mass spectrometer (Waters, USA) connected to nanoAquity HPLC, followed by recording the fragmentation pattern with changing energy from 4-30 V by 2 V each time according to Full scan MS/MS method. MS/MS spectrum of each peptide obtained over energy changes was sorted to analyze increase or decrease of fragmented ions. The daughter ion demonstrating the strongest ionic strength and fragmentation energy at that time were recorded. And We confirmed whether theoretically predicted fragmented ion, charge number and mass were consistent If they were consistent, they were finally determined to optimum daughter ion and fragmentation energy of corresponding isotope-substituted standard peptide. The wild type standard peptide had the same molecules and ionic properties with the isotope-substituted synthetic standard peptide. So, fragmentation energy corresponding to ion of the wild type standard peptide corresponding to fragmented ion determined by the isotope-substituted synthetic standard peptide was used.

Mass of the isotope-substituted synthetic standard peptide was presented in "SIS" line of Table 4. Optimum fragmentation energy measured by Q-Tof and Quattro mass spectrometer was presented in "QTOF" and "Quat" lines of Table 4 peptide by peptide. Standard peptide mass and ion number (numbers in parentheses) of the wild type standard peptide (Native) and the isotope-substituted synthetic standard peptide (SIS) were presented in "Native" and "SIS" lines. Mass and ion number of the optimum daughter ion (optimum fragmented peptide) determined by the above method were also presented in "Native" and "SIS" lines. For example, in A(AN)->B(Bn) of "Native" and "SIS" lines of Table 4, A indicates mass of the standard peptide, An indicates ion number of the standard peptide, B indicates mass of the optimum daughter ion generated by the standard peptide and Bn indicates ion number of the optimum daughter ion generated by the standard peptide. "Weak" means weak signal which indicates that no-corresponding value was determined.

EXAMPLE 4

Construction of Antibody Binding to Standard Peptide

Polyclonal antibody binding to the standard peptide was constructed to concentrate the wild type and isotope-substituted standard peptides in sample.

First, a peptide for antigen production was prepared by adding cysteine residue for the purification of an antibody to N-terminal or C-terminal of the standard peptide sequence obtained in Example 2 (Peptron Inc., Korea). Polyclonal antibody binding to the standard peptide was produced by AbFrontier Co., Ltd., Korea using the said standard peptide as an antigen. Particularly, a rabbit was immunized with the above antigen. Three months later, serum of the rabbit was obtained. The standard peptide was loaded on SulfoLink (Pierce, USA) containing iodo-acethyl residue via acetylation of terminal cysteine.

After equilibrium of 1 ml column using equilibrium solution (25 mM Tris-HCl pH8.3, 250 mM NaCl, 0.05% sodium azide; Sigma, USA), 10 ml in of the serum obtained in Example <4-2> was added, followed by antigen-antibody reaction at room temperature with stirring for 2 hours, resulting in anti-standard peptide antibody was conjugated on the column. The column was washed with washing solution (25 mM Tris-HCl pH8.3, 1.0 M NaCl, 0.05% sodium azide) four times, followed by equilibrium again with equilibrium solution. At last, the antibody was eluted using 2.5 and of elution solution (0.2 M glycine, pH 2.5, Sigma, USA).

EXAMPLE 5

Extraction of PTP from Sample

<5-1> Hydrolysis of Microprotein in Blood

Blood Samples were Provided by 50 Patients Diagnosed with colon cancer, liver cancer and stomach cancer, from which serums were separated. As a normal blood sample, a commercial normal serum mixture (Sigma, USA) was used. The blood samples were centrifuged at 2,000 rpm for 10 minutes. The supernatant serum was stored at −70° C. Proteins (albumin, globulin, etc) dominant in the serum were eliminated by using multiple affinity removal cartridge, Hu-7 kit (Agilent, USA) according to the manufacturer's instruction.

The purified serum was diluted with 0.1 M ammonium bicarbonate, leading to the substitution for trypsin hydrolysis. The serum was then treated with heat or/and denaturant (urea, guanidine-HCl, detergent such as rapigest, etc). Particularly, the sample was treated at 95° C. for 10 minutes or treated with 6-8 M urea or guanidine-HCl and added with RapiGes (final conc: 0.1%), followed by reaction at 60° C. for 2 hours. Then, trypsin was added to the reaction solution at the amount of 1/50-100 plasma protein, followed by reaction at 37° C. for 16 hours. Peptide mixture was obtained by hydrolyzing micro proteins in blood plasma.

<5-2> Extraction of Standard Peptide Using Antibody Column 10-50 femto mole of the isotope-substituted synthetic standard peptide obtained in Example 2 was added to 15 μl of the hydrolyzed peptide mixture in blood plasma obtained in Example <5-1>, followed by incubation at room temperature for 2 hours.

After biotinylation, the anti-standard peptide polyclonal antibody prepared in Example 4 was conjugated to immobilized streptavidin (Pierce, USA). Biotinylation was performed by the following processes; dissolving Sulfo-NHS-LC-Biotin (Pierce, USA) in ultra pure distilled water at the final concentration of 10 mM; mixing target antibody with biotin at the molar ratio of 1:20; and reacting at room temperature for one hour with stirring. Non-reacted biotin was eliminated by dilution with PBS (phosphate buffered saline).

Standard peptide was mixed with the polyclonal antibody conjugated column prepared above, followed by reaction at room temperature for 2 hours. The column was washed with washing solution and 0.1 M ammonium bicarbonate solution 4 times, followed by elution of target peptide using 2% formic acid.

<5-3> Extraction of Standard Peptide Using Antibody Mixture Solution

Antibody mixture solution was used for simultaneous analysis and profiling of multiple standard peptides.

Particularly, 1-10 µg of each antibody against 2-80 standard peptides (rabbit serum or purified antibody) was mixed with peptide mixture (50 mM Tris HCl pH 8.1, 250 mM NaCl) hydrolyzed with trypsin. Reaction was induced at 4° C. for overnight, and then the standard peptide conjugated antibody was concentrated using protein G beads (GE Healthcare, USA). Antibody conjugated beads were washed twice with washing solution, once with 1 M NaCl, and three times with ddH$_2$O, which was mixed with 500 µl of ddH$_2$O, followed by heating at 85° C. for 10 minutes, leading to solubilization of the antibody and peptide from the beads. Standard peptide dissolved in the solution was filtered by using microcon YM10 (Millipore, USA). Standard peptide in flow-through was dried by cold trap type speedvac. Then, the standard peptide was dissolved in 0.1% formic acid, followed by analysis using mass spectrometer.

EXAMPLE 6

Measurement of Standard Peptide by Quantitative Analysis

<6-1> Preparation of Sample for Mass Spectrometry

Desalting from the isotope-substituted synthetic standard peptide obtained in Example 2, the wild type standard peptide obtained in Example <5-2>, and the peptide mixture obtained in Example <5-3> was performed using small rotary column (Waters, USA) filled with C$_{18}$ column. The peptides were dried by using cold trap type speedvac at 25° C. to −85° C. for 2 and half hours with the pressure of 0.2 torr, which were then dissolved again in 0.1% formic acid solution, leading to analysis using NanoAquity HPLC linked Quattro Premier mass spectrometer (Waters, USA) or the same HPLC linked Q-Tof Premier mass spectrometer. The Quattro Premier mass spectrometer or the Q-Tof Premier mass spectrometer is tandem mass spectrometer, which was used for LC-tandem spectrometry by connecting to NanoAquity HPLC. In particular, Quattro Premier is Triple Quadrupole Mass Spectrometer, which has a high sensitivity, so that it has been largely used for quantitative analysis of peptides in samples. In the meantime, Q-Tof Premier mass spectrometer combining Quadrupole and TOF has also high accuracy in mass analysis and has been largely used for precise measurement of peptide to select standard peptide.

<6-2> Quantitative Analysis Using Tandem Mass Spectrometer

Quantitative analysis was performed with the wild type peptide and the isotope-substituted standard peptide prepared in Example <6-1> for mass analysis by using Quadrupole mass spectrometer which is nanoAQUITY HPLC linked to Quattro Premiere mass spectrometer (Waters, USA). For nanoAQUITY HPLC, BEH300 column (particle size 1.7 µm, ID 75 µm, length 100 mm) was used. The HPLC was operated by density gradient by mixing solution A (0.1% formic acid deionized water) and solution B (0.1% formic acid acetonitrile) with the flow velocity of 300 mL/min for 40 minutes. Capillary voltage of the mass spectrometer was 3.2 kV. For mass spectrometry data collection, MRM (multiple reaction monitoring) routine provided by MassLynx software (Waters, USA) was used. Optimum fragmentation energy of each target standard peptide was used (Table 4) and every isotope-substituted synthetic standard peptide was scanned under the same conditions to analyze exact amount of each peptide. Considering the number of standard peptides to be analyzed at a time, dwell time was adjusted to 0.05-0.02 seconds and interscan time was adjusted to 0.02-0.007 seconds. Absolute quantity of the wild type standard peptide in a sample was determined by comparing chromatogram peaks generated by the isotope-substituted standard peptide whose exact amount added was already known.

As a result, as shown in FIG. 4-FIG. 7, the wild type standard peptide corresponding to PTP T46 was quantified, suggesting that absolute quantity of the wild type standard peptide can be calculated by comparing the peak of the isotope-substituted standard peptide.

EXAMPLE 7

Diagnosis of Disease Using PTP Panel

<7-1> Composition of PTP Panel

A mixed solution was prepared by mixing 10-50 femto mole of each isotope-substituted synthetic standard peptide prepared in Example 2.

<7-2> Diagnosis of Disease Using PTP Panel

Serums taken from 20-30 cancer patients and normal health people obtained in Example <5-1> were mixed to prepare a mixed serum disease by disease. The mixed serum was treated with trypsin for hydrolysis by the same manner as described in Example <5-1> to obtain a peptide mixture. 10-50 femto mole of the isotope-substituted synthetic standard peptide mixed solution prepared in Example <7-1> was added to 15 µl of the peptide mixture. The wild type standard peptide and the isotope-substituted synthetic standard peptide were concentrated using the standard peptide specific antibody column or the antibody solution mixture by the same manner as described in Example <5-2> or Example <5-3>, followed by desalting by the same manner as described in Example <6-1> and drying in speedvac. The resultant sample was dissolved in 0.1% formic acid, followed by quantification of standard peptide using Quadrupole mass spectrometer which is nanoAquity UPLC linked to Quattro Premiere mass spectrometer, the triple quadrupole mass spectrometer, by the same manner as described in Example <6-2>. Absolute quantity of the wild type standard peptide in a sample was determined by comparing spectrum peaks generated by the isotope-substituted synthetic standard peptide whose exact amount added was already known.

As a result, 18 PTPs were detected from samples of colon cancer, liver cancer and stomach cancer patients in total (Table 5). 12 out of 18 PTPs were only detected in cancer patient samples. 6 PTPs were detected in normal samples as well as in cancer patient samples, but the levels were much higher in cancer patient samples, indicating they can be used for diagnosis of cancer (Table 5). Particularly, three PTPs (T46, pk32 and pk3) were able to be quantified.

TABLE 5

PTP standard peptide found in cancer patient serum (unit: femto mole)

| No. | Name | colon cancer | liver cancer | stomach cancer | normal health people |
|-----|------|--------------|--------------|----------------|----------------------|
| 1   | T18  | 0.8          | 1.4          | 1.0            | x                    |
| 2   | pk3  | 1.0          | 0.9          | x              | x                    |
| 3   | T46  | 3.3          | 3.4          | 3.3            | x                    |
| 4   | T4   | 2.5          | 0.6          | x              | x                    |
| 5   | pk17 | 2.7          | 2.5          | 2.6            | 1.2                  |
| 6   | pk32 | 3.8          | 2.3          | 1.4            | x                    |
| 7   | T1   | 4.0          | 4.4          | 5.6            | 3.1                  |
| 8   | T19  | 2.4          | 1.6          | 3.1            | 1.2                  |
| 9   | T3   | 10.7         | 14.3         | 7.6            | ns                   |
| 10  | T41  | 9.1          | 7.7          | 15.6           | 10.8                 |
| 11  | pk4  | ns           | ns           | 4.2            | ns                   |
| 12  | T25  | ns           | ns           | 28.8           | 11.1                 |
| 13  | pk12 | 2.5          | 0.7          | 1.3            | ns                   |
| 14  | p12  | 2.4          | ns           | x              | ns                   |
| 15  | p16  | 1.9          | 1.0          | ns             | x                    |
| 16  | p19  | x            | 34.5         | ns             | ns                   |
| 17  | pk15 | x            | ns           | 1.5            | x                    |
| 18  | T32  | 2.2          | 10.9         | ns             | 5.3                  |

(x, not detected; ns, data is too weak to interpret.)

<7-3> Quantitative Analysis of PTP T46 Standard Peptide

Quantitave analysis was performed with T46 detected in cancer patients but not detected in normal people confirmed in Example <7-2> using serums separated from each disease.

50 femto mole of the isotope-substituted synthetic standard peptide T46 prepared in Example 2 was added to the entire peptide mixture prepared by disease in Example <7-2>. The wild type peptide and the isotope-substituted synthetic standard peptide were concentrated using T46 standard peptide specific antibody and dried by the same manner as described in Example <7-2>. Then, the wild type standard peptide was quantified.

Figure 8:
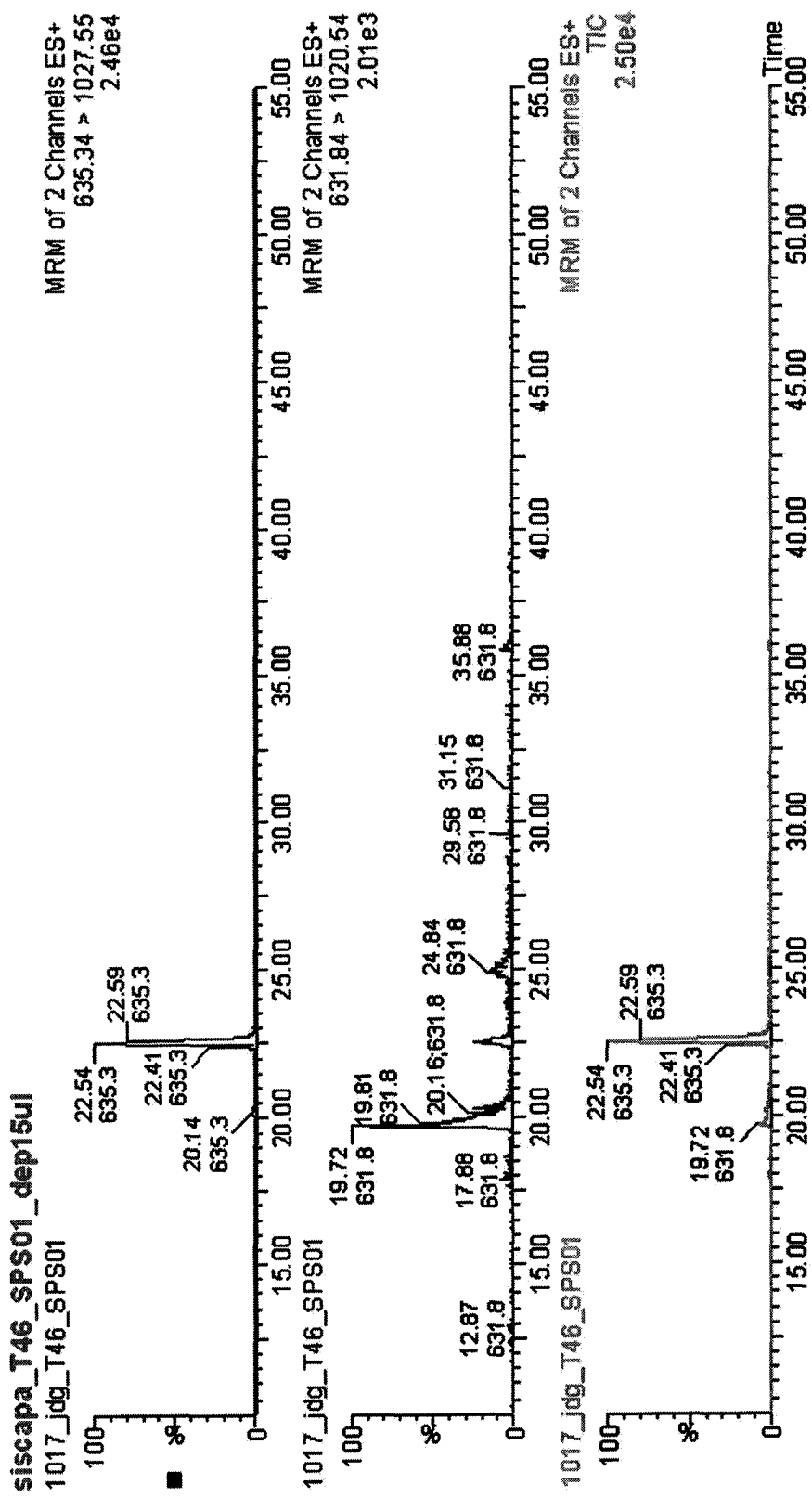
Figure 9:
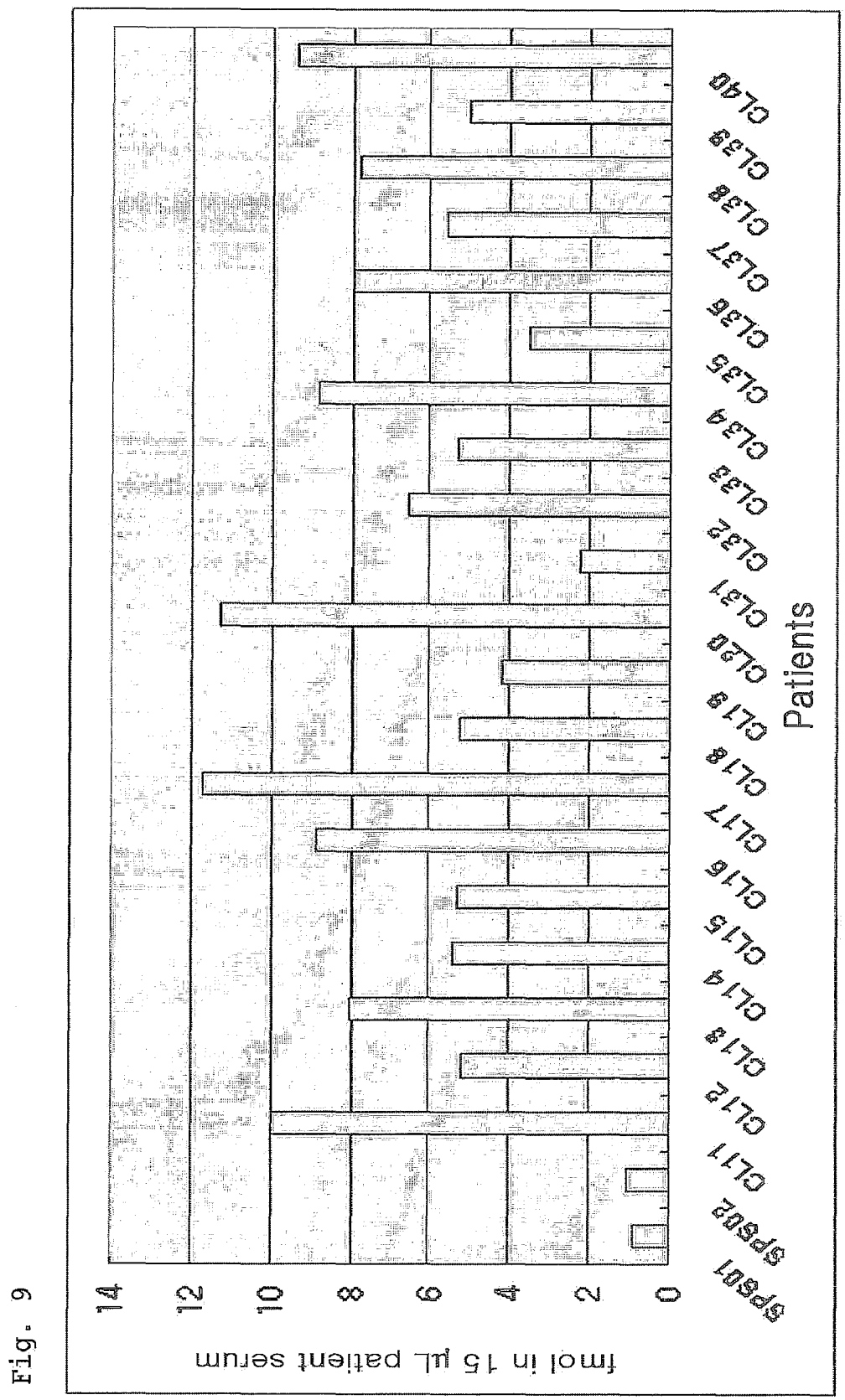
FIGS. 9-11 are diagrams illustrating the absolute quantity of PTP in blood samples of cancer patients (20 of each colon cancer, liver cancer and stomach cancer patients) (levels of LV34, LV35 and ST20 were so low because of test error)
Figure 10:
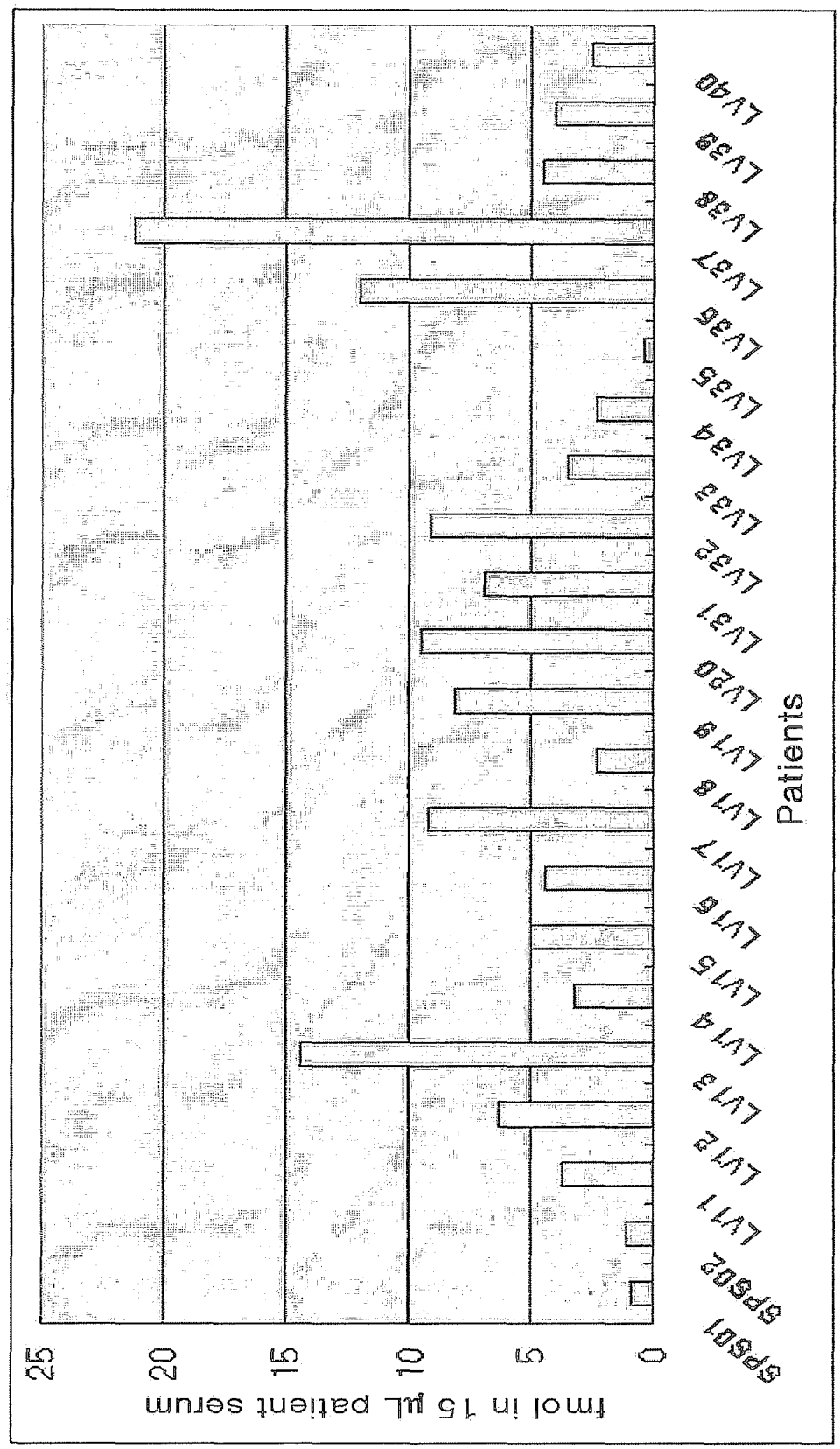
Figure 11:
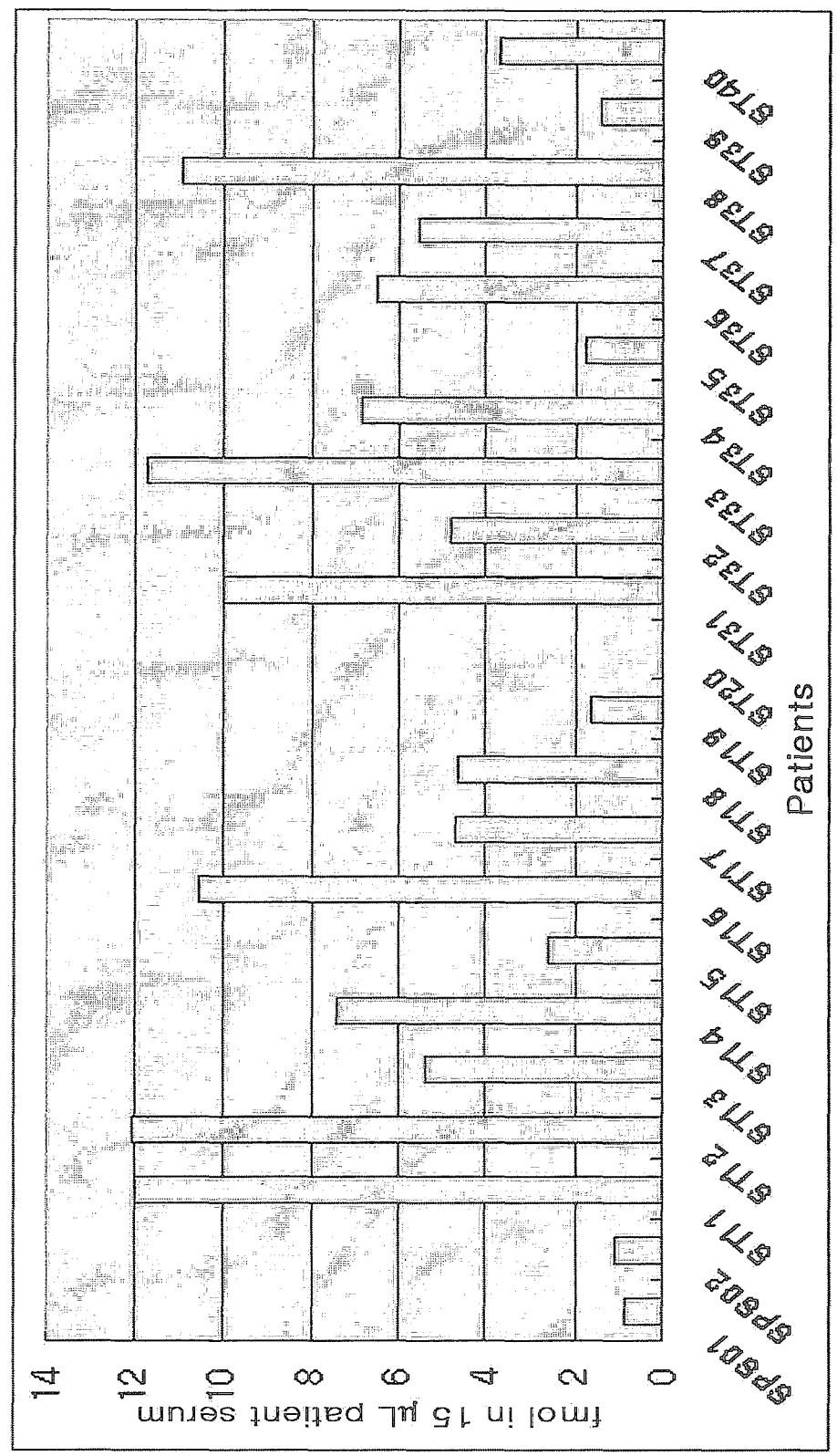

As a result, as shown in FIG. 8-FIG. 10, T46 was commonly detected in each patient and in each disease, even if there was a slight difference in expression level.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

The invention claimed is:

1. A method for quantification of protein tyrosine phosphatase (PTP) comprising the following steps:
   1) hydrolyzing a sample separated from a test subject;
   2) adding a known amount of an isotope-substituted synthetic standard peptide to the hydrolyzed sample of step 1), wherein the synthetic standard peptide is selected from SEQ ID NOs:191, 220, 225, 236, 246, 202, 231, 186, 172, 176 and 238;
   3) extracting wild type peptide and the isotope-substituted synthetic standard peptide from the hydrolyzed sample of step 2), followed by quantitative analysis; and
   4) comparing the levels of the wild type peptide and the isotope-substituted synthetic standard peptide of step 3) to calculate a quantity of the wild type peptide expression.

2. The method according to claim 1, wherein the sample of step 1) is selected from the group consisting of blood, tissue and exudate.

3. The method according to claim 1, wherein the hydrolysis of step 1) is performed by using an enzyme selected from the group consisting of trypsin, chymotrypsin, pepsin, thermolysin and proteinase K.

4. The method according to claim 1, wherein the extraction of the standard peptide of step 3) is performed by using an antibody or a ligand specifically binding to the peptide.

5. The method according to claim 4, wherein the antibody is polyclonal antibody or monoclonal antibody.

6. The method according to claim 1, wherein the quantitative analysis of step 3) is performed by a method selected from the group consisting of LC/MS mass spectrometry, SELDI (Surface-Enhanced Laser Desorption/Ionization) and sandwich ELISA.

7. A method for quantification of protein tyrosine phosphatase (PTP) comprising the following steps:
   1) concentrating PTP in a sample separated from a test subject;
   2) hydrolyzing the concentrated sample of step 1);
   3) adding a known amount of an isotope-substituted synthetic standard peptide to the hydrolyzed sample of step 2), wherein the synthetic standard peptide is selected from SEQ ID NOs:191, 220, 225, 236, 246, 202, 231, 186, 172, 176 and 238; and
   4) comparing the levels of wild type peptide and the isotope-substituted synthetic standard peptide of step 3) to calculate a quantity of the wild type peptide expression.

8. The method according to claim 7, wherein the concentration of PTP in step 1) is performed by using a compound specifically binding to PTP enzyme active site.

9. A screening method of a colon cancer, liver cancer, or lung cancer related biomarker comprising the following steps:
   1) hydrolyzing a sample separated from a subject with colon cancer, liver cancer, or lung cancer;
   2) adding a known amount of an isotope-substituted synthetic standard peptide to the hydrolyzed sample of step 1), wherein the synthetic standard peptide is selected from SEQ ID NOs:191, 220, 225, 236, 246, 202, 231, 186, 172, 176 and 238;
   3) extracting the wild type peptide and the isotope-substituted synthetic standard peptide from the hydrolyzed sample of step 2), followed by quantitative analysis thereof;
   4) comparing the levels of a wild type peptide and the isotope-substituted synthetic standard peptide of step 3) to calculate a quantity of the wild type peptide expression; and
   5) comparing the quantity of the wild type peptide of step 4) and the quantity of the wild type peptide extracted from a normal subject to confirm the standard peptide demonstrating a significant difference.

10. The method of claim 1, wherein an amino acid in the synthetic standard peptide is substituted with a stable isotope-containing amino acid, wherein an amino acid having risk of oxidation is not substituted.

11. The method of claim 10, wherein the amino acid in the synthetic standard peptide is substituted with an amino acid having a stable isotope during synthesis of the peptide or by labeling a specific amino acid with a functional group having a stable isotope after synthesis of the peptide.

12. The method of claim 10, wherein the amino acid having risk of oxidation comprises cysteine or methionine.

13. The method of claim 10, wherein the stable isotope is selected from the group consisting of $^{13}C$, $^{15}N$, and $^{2}H$.

14. The method of claim 9, wherein an amino acid in the synthetic standard peptide is substituted with a stable isotope-containing amino acid, wherein an amino acid having risk of oxidation is not substituted.

15. The method of claim 14, wherein the amino acid in the synthetic standard peptide is substituted with an amino acid having a stable isotope during synthesis of the peptide or by labeling a specific amino acid with a functional group having a stable isotope after synthesis of the peptide.

16. The method of claim 14, wherein the amino acid having risk of oxidation comprises cysteine or methionine.

17. The method of claim 14, wherein the stable isotope is selected from the group consisting of $^{13}C$, $^{15}N$, and $^{2}H$.

18. The method of claim 12, wherein the known amount of an isotope-substituted synthetic standard peptide is 10-50 femtomoles.

19. The method of claim 7, wherein the known amount of an isotope-substituted synthetic standard peptide is 10-50 femtomoles.

20. The method of claim 9, wherein the known amount of an isotope-substituted synthetic standard peptide is 10-50 femtomoles.

* * * * *

SEQUENCE LISTING

<160> NUMBER OF SEQ ID NOS: 290

<210> SEQ ID NO 1
<211> LENGTH: 36
<212> TYPE: DNA
<213> ORGANISM: Artificial Sequence
<220> FEATURE:
<223> OTHER INFORMATION: T4 Forward primer

<400> SEQUENCE: 1
cgcgacgcta gcatggcaga cgacaataag ctcttc                              36

<210> SEQ ID NO 2
<211> LENGTH: 35
<212> TYPE: DNA
<213> ORGANISM: Artificial Sequence
<220> FEATURE:
<223> OTHER INFORMATION: T4 Reverse primer

<400> SEQUENCE: 2
gctgcgaagc tttacttgaa gttggcataa tctga                               35

<210> SEQ ID NO 3
<211> LENGTH: 36
<212> TYPE: DNA
<213> ORGANISM: Artificial Sequence
<220> FEATURE:
<223> OTHER INFORMATION: T7 Forward primer

<400> SEQUENCE: 3
ggcacccata tgctagtggc tgttgttgcc ttattg                              36

<210> SEQ ID NO 4
<211> LENGTH: 33
<212> TYPE: DNA
<213> ORGANISM: Artificial Sequence
<220> FEATURE:

```
<223> OTHER INFORMATION: T7 Reverse primer

<400> SEQUENCE: 4
gcgggatcct caatgccttg aatagactgg atc                                33

<210> SEQ ID NO 5
<211> LENGTH: 33
<212> TYPE: DNA
<213> ORGANISM: Artificial Sequence
<220> FEATURE:
<223> OTHER INFORMATION: T48 Forward primer

<400> SEQUENCE: 5
gccccacata tgcgagacca cccacccatc ccc                                33

<210> SEQ ID NO 6
<211> LENGTH: 36
<212> TYPE: DNA
<213> ORGANISM: Artificial Sequence
<220> FEATURE:
<223> OTHER INFORMATION: T48 Reverse primer

<400> SEQUENCE: 6
ggaagatctc tacgttgcat agtggtcaaa gctgcc                             36

<210> SEQ ID NO 7
<211> LENGTH: 37
<212> TYPE: DNA
<213> ORGANISM: Artificial Sequence
<220> FEATURE:
<223> OTHER INFORMATION: T8 Forward primer

<400> SEQUENCE: 7
gcgccatatg gcagacaagt accagcaact ctccctg                            37

<210> SEQ ID NO 8
<211> LENGTH: 37
<212> TYPE: DNA
<213> ORGANISM: Artificial Sequence
<220> FEATURE:
<223> OTHER INFORMATION: T8 Reverse primer

<400> SEQUENCE: 8
gcgcggatcc ctcggctggg gcctgggctg actgttg                            37

<210> SEQ ID NO 9
<211> LENGTH: 36
<212> TYPE: DNA
<213> ORGANISM: Artificial Sequence
<220> FEATURE:
<223> OTHER INFORMATION: T23 Forward primer

<400> SEQUENCE: 9
ccgttacata tggtggagaa ttttgaggcc tacttc                             36

<210> SEQ ID NO 10
<211> LENGTH: 35
<212> TYPE: DNA
<213> ORGANISM: Artificial Sequence
<220> FEATURE:
<223> OTHER INFORMATION: T23 Reverse primer

<400> SEQUENCE: 10
cccgaattct taggcgatgt aaccattggt ctttc                              35

<210> SEQ ID NO 11
```

```
<211> LENGTH: 36
<212> TYPE: DNA
<213> ORGANISM: Artificial Sequence
<220> FEATURE:
<223> OTHER INFORMATION: T39 Forward primer

<400> SEQUENCE: 11
cacattgcta gcatgaagac atcagacagc tatggg                                    36

<210> SEQ ID NO 12
<211> LENGTH: 36
<212> TYPE: DNA
<213> ORGANISM: Artificial Sequence
<220> FEATURE:
<223> OTHER INFORMATION: T39 Reverse primer

<400> SEQUENCE: 12
cggctcaagc ttctaagatg attccaggta ctccaa                                    36

<210> SEQ ID NO 13
<211> LENGTH: 33
<212> TYPE: DNA
<213> ORGANISM: Artificial Sequence
<220> FEATURE:
<223> OTHER INFORMATION: T5 Forward primer

<400> SEQUENCE: 13
gcccaccata tggccagcga taccagcagc ctg                                       33

<210> SEQ ID NO 14
<211> LENGTH: 33
<212> TYPE: DNA
<213> ORGANISM: Artificial Sequence
<220> FEATURE:
<223> OTHER INFORMATION: T5 Reverse primer

<400> SEQUENCE: 14
gcgagatctt cagccagaat tcaagtattc cag                                       33

<210> SEQ ID NO 15
<211> LENGTH: 36
<212> TYPE: DNA
<213> ORGANISM: Artificial Sequence
<220> FEATURE:
<223> OTHER INFORMATION: T38 Forward primer

<400> SEQUENCE: 15
gaccggcata tgcttgccaa ggagtggcag gccctc                                    36

<210> SEQ ID NO 16
<211> LENGTH: 33
<212> TYPE: DNA
<213> ORGANISM: Artificial Sequence
<220> FEATURE:
<223> OTHER INFORMATION: T38 Reverse primer

<400> SEQUENCE: 16
ccgggatcct cactggggca gggccttgag gat                                       33

<210> SEQ ID NO 17
<211> LENGTH: 33
<212> TYPE: DNA
<213> ORGANISM: Artificial Sequence
<220> FEATURE:
<223> OTHER INFORMATION: T12 Forward primer

<400> SEQUENCE: 17
```
cgccagcata tggccacgcg gccaccagac cga                                      33

<210> SEQ ID NO 18
<211> LENGTH: 33
<212> TYPE: DNA
<213> ORGANISM: Artificial Sequence
<220> FEATURE:
<223> OTHER INFORMATION: T12 Reverse primer

<400> SEQUENCE: 18
gcgggatcct cactggggaa gggccttgag gat                                      33

<210> SEQ ID NO 19
<211> LENGTH: 36
<212> TYPE: DNA
<213> ORGANISM: Artificial Sequence
<220> FEATURE:
<223> OTHER INFORMATION: T15 Forward primer

<400> SEQUENCE: 19
gagcatgcta gcatggctag ggagtgtgga gctggt                                   36

<210> SEQ ID NO 20
<211> LENGTH: 36
<212> TYPE: DNA
<213> ORGANISM: Artificial Sequence
<220> FEATURE:
<223> OTHER INFORMATION: T15 Reverse primer

<400> SEQUENCE: 20
gcgggatccc taggacttgc taacattctc gtatat                                   36

<210> SEQ ID NO 21
<211> LENGTH: 38
<212> TYPE: DNA
<213> ORGANISM: Artificial Sequence
<220> FEATURE:
<223> OTHER INFORMATION: T10 Forward primer

<400> SEQUENCE: 21
cctttccata tgaagcccat aggacttcaa gagagaag                                 38

<210> SEQ ID NO 22
<211> LENGTH: 38
<212> TYPE: DNA
<213> ORGANISM: Artificial Sequence
<220> FEATURE:
<223> OTHER INFORMATION: T10 Reverse primer

<400> SEQUENCE: 22
gacagtaagc tttcaaagtc tgctctcata caggcaca                                 38

<210> SEQ ID NO 23
<211> LENGTH: 33
<212> TYPE: DNA
<213> ORGANISM: Artificial Sequence
<220> FEATURE:
<223> OTHER INFORMATION: T22 Forward primer

<400> SEQUENCE: 23
cgcgaacata tgcttagcca cccgccaatt ccc                                      33

<210> SEQ ID NO 24
<211> LENGTH: 36
<212> TYPE: DNA
<213> ORGANISM: Artificial Sequence
<220> FEATURE:

<223> OTHER INFORMATION: T22 Reverse primer

<400> SEQUENCE: 24
ggcggatcct cagcccacgg cctccagcag ggcctc         36

<210> SEQ ID NO 25
<211> LENGTH: 30
<212> TYPE: DNA
<213> ORGANISM: Artificial Sequence
<220> FEATURE:
<223> OTHER INFORMATION: T20 Forward primer

<400> SEQUENCE: 25
ttcgctagcg ccatccgggt ggctgacttg         30

<210> SEQ ID NO 26
<211> LENGTH: 38
<212> TYPE: DNA
<213> ORGANISM: Artificial Sequence
<220> FEATURE:
<223> OTHER INFORMATION: T20 Reverse primer

<400> SEQUENCE: 26
gcgggatccc taaaaggagc ttaaatattc cagtgcca         38

<210> SEQ ID NO 27
<211> LENGTH: 30
<212> TYPE: DNA
<213> ORGANISM: Artificial Sequence
<220> FEATURE:
<223> OTHER INFORMATION: PTP1B Forward primer

<400> SEQUENCE: 27
atggagatgg aaaaggagtt cgagcagatc         30

<210> SEQ ID NO 28
<211> LENGTH: 30
<212> TYPE: DNA
<213> ORGANISM: Artificial Sequence
<220> FEATURE:
<223> OTHER INFORMATION: PTP1B Reverse primer

<400> SEQUENCE: 28
gtcaacatgt gcgtggctac ggtcctcacg         30

<210> SEQ ID NO 29
<211> LENGTH: 33
<212> TYPE: DNA
<213> ORGANISM: Artificial Sequence
<220> FEATURE:
<223> OTHER INFORMATION: T25 Forward primer

<400> SEQUENCE: 29
gctcccgcta gcatgcccac catcgagcgg gag         33

<210> SEQ ID NO 30
<211> LENGTH: 33
<212> TYPE: DNA
<213> ORGANISM: Artificial Sequence
<220> FEATURE:
<223> OTHER INFORMATION: T25 Reverse primer

<400> SEQUENCE: 30
cgcggatcct taggtgtctg tcaatcttgg cct         33

<210> SEQ ID NO 31

<211> LENGTH: 33
<212> TYPE: DNA
<213> ORGANISM: Artificial Sequence
<220> FEATURE:
<223> OTHER INFORMATION: T41 Forward primer

<400> SEQUENCE: 31
tcagagcata tggaggagaa gatcgaggat gac                    33

<210> SEQ ID NO 32
<211> LENGTH: 36
<212> TYPE: DNA
<213> ORGANISM: Artificial Sequence
<220> FEATURE:
<223> OTHER INFORMATION: T41 Reverse primer

<400> SEQUENCE: 32
gtggacgcta gcatgaaata tttgggcagt cccatt                 36

<210> SEQ ID NO 33
<211> LENGTH: 33
<212> TYPE: DNA
<213> ORGANISM: Artificial Sequence
<220> FEATURE:
<223> OTHER INFORMATION: T18 Forward primer

<400> SEQUENCE: 33 gcccccata tggtgaggtg gtttcaccga gac                     33

<210> SEQ ID NO 34
<211> LENGTH: 34
<212> TYPE: DNA
<213> ORGANISM: Artificial Sequence
<220> FEATURE:
<223> OTHER INFORMATION: T18 Reverse primer

<400> SEQUENCE: 34
ccggaattct cacttcctct tgagggaacc cttg                   34

<210> SEQ ID NO 35
<211> LENGTH: 36
<212> TYPE: DNA
<213> ORGANISM: Artificial Sequence
<220> FEATURE:
<223> OTHER INFORMATION: pk32 Forward primer

<400> SEQUENCE: 35
gaaccccata tgtctgtgaa cacaccccgg gaggtc                 36

<210> SEQ ID NO 36
<211> LENGTH: 32
<212> TYPE: DNA
<213> ORGANISM: Artificial Sequence
<220> FEATURE:
<223> OTHER INFORMATION: pk32 Reverse primer

<400> SEQUENCE: 36
cgggatcctc aggggctggg ttcctcaggc ag                     32

<210> SEQ ID NO 37
<211> LENGTH: 33
<212> TYPE: DNA
<213> ORGANISM: Artificial Sequence
<220> FEATURE:
<223> OTHER INFORMATION: pk28 Forward primer

<400> SEQUENCE: 37

```
ccgcggcata tggaacatca cgggcaatta aaa                              33
```

<210> SEQ ID NO 38
<211> LENGTH: 32
<212> TYPE: DNA
<213> ORGANISM: Artificial Sequence
<220> FEATURE:
<223> OTHER INFORMATION: pk28 Reverse primer

<400> SEQUENCE: 38

```
cgggatcctc acctgcagtg caccacgacc gg                               32
```

<210> SEQ ID NO 39
<211> LENGTH: 33
<212> TYPE: DNA
<213> ORGANISM: Artificial Sequence
<220> FEATURE:
<223> OTHER INFORMATION: T32 Forward primer

<400> SEQUENCE: 39

```
gcagtacata tgaatgggaa gttatcagaa gag                              33
```

<210> SEQ ID NO 40
<211> LENGTH: 38
<212> TYPE: DNA
<213> ORGANISM: Artificial Sequence
<220> FEATURE:
<223> OTHER INFORMATION: T32 Reverse primer

<400> SEQUENCE: 40

```
ggcggatcct cacttcagaa gctgaggctg ctgttttt                         38
```

<210> SEQ ID NO 41
<211> LENGTH: 33
<212> TYPE: DNA
<213> ORGANISM: Artificial Sequence
<220> FEATURE:
<223> OTHER INFORMATION: T40 Forward primer

<400> SEQUENCE: 41

```
gagcagcata tggcaggcct ggaggcacag aag                              33
```

<210> SEQ ID NO 42
<211> LENGTH: 33
<212> TYPE: DNA
<213> ORGANISM: Artificial Sequence
<220> FEATURE:
<223> OTHER INFORMATION: T40 Reverse primer

<400> SEQUENCE: 42

```
cgcggatcct taaatgagtc tggagttttg gag                              33
```

<210> SEQ ID NO 43
<211> LENGTH: 33
<212> TYPE: DNA
<213> ORGANISM: Artificial Sequence
<220> FEATURE:
<223> OTHER INFORMATION: T2 Forward primer

<400> SEQUENCE: 43

```
ctagggcata tgaaaaagac tcgagtagat gca                              33
```

<210> SEQ ID NO 44
<211> LENGTH: 33
<212> TYPE: DNA
<213> ORGANISM: Artificial Sequence
<220> FEATURE:

<223> OTHER INFORMATION: T2 Reverse primer

<400> SEQUENCE: 44
cgcggatcct tagatgagcc tggagctttt cag                                    33

<210> SEQ ID NO 45
<211> LENGTH: 33
<212> TYPE: DNA
<213> ORGANISM: Artificial Sequence
<220> FEATURE:
<223> OTHER INFORMATION: pk4 Forward primer

<400> SEQUENCE: 45
aggccgcata tggtcatgga agtgggcacc ctg                                    33

<210> SEQ ID NO 46
<211> LENGTH: 34
<212> TYPE: DNA
<213> ORGANISM: Artificial Sequence
<220> FEATURE:
<223> OTHER INFORMATION: pk4 Reverse primer

<400> SEQUENCE: 46
ggcggatcct cagctcccag cctctgccga acag                                   34

<210> SEQ ID NO 47
<211> LENGTH: 30
<212> TYPE: DNA
<213> ORGANISM: Artificial Sequence
<220> FEATURE:
<223> OTHER INFORMATION: pk7 Forward primer

<400> SEQUENCE: 47
gttcatatga gtgccacaga gcccttggac                                        30

<210> SEQ ID NO 48
<211> LENGTH: 36
<212> TYPE: DNA
<213> ORGANISM: Artificial Sequence
<220> FEATURE:
<223> OTHER INFORMATION: pk7 Reverse primer

<400> SEQUENCE: 48
gcgggatcct caggacgtgg ccagcacctg ggactc                                 36

<210> SEQ ID NO 49
<211> LENGTH: 36
<212> TYPE: DNA
<213> ORGANISM: Artificial Sequence
<220> FEATURE:
<223> OTHER INFORMATION: pk8 Forward primer

<400> SEQUENCE: 49
gcggaccata tgggcccagt tgaaatcctt cccttc                                 36

<210> SEQ ID NO 50
<211> LENGTH: 37
<212> TYPE: DNA
<213> ORGANISM: Artificial Sequence
<220> FEATURE:
<223> OTHER INFORMATION: pk8 Reverse primer

<400> SEQUENCE: 50
gcgagatctt cacgtggagg gcaggatctc agattcg                                37

<210> SEQ ID NO 51

```
<211> LENGTH: 36
<212> TYPE: DNA
<213> ORGANISM: Artificial Sequence
<220> FEATURE:
<223> OTHER INFORMATION: pk9 Forward primer

<400> SEQUENCE: 51
ggcagccata tgtccttccc agtggagatc ttgccc                              36

<210> SEQ ID NO 52
<211> LENGTH: 36
<212> TYPE: DNA
<213> ORGANISM: Artificial Sequence
<220> FEATURE:
<223> OTHER INFORMATION: pk9 Reverse primer

<400> SEQUENCE: 52
cgcggatcct cagctgagtc ccagcgtcct ctcgaa                              36

<210> SEQ ID NO 53
<211> LENGTH: 33
<212> TYPE: DNA
<213> ORGANISM: Artificial Sequence
<220> FEATURE:
<223> OTHER INFORMATION: pk10 Forward primer

<400> SEQUENCE: 53
gctggccata tgttgcgccg cctgcgcaag ggc                                 33

<210> SEQ ID NO 54
<211> LENGTH: 32
<212> TYPE: DNA
<213> ORGANISM: Artificial Sequence
<220> FEATURE:
<223> OTHER INFORMATION: pk10 Reverse primer

<400> SEQUENCE: 54
cgggatcctc acgtggactc cagcgtattg ag                                  32

<210> SEQ ID NO 55
<211> LENGTH: 33
<212> TYPE: DNA
<213> ORGANISM: Artificial Sequence
<220> FEATURE:
<223> OTHER INFORMATION: T33 Forward primer

<400> SEQUENCE: 55
tgcccccata tggctgggga ccggctcccg agg                                 33

<210> SEQ ID NO 56
<211> LENGTH: 36
<212> TYPE: DNA
<213> ORGANISM: Artificial Sequence
<220> FEATURE:
<223> OTHER INFORMATION: T33 Reverse primer

<400> SEQUENCE: 56
gcgggatcct catgaggggg tgcccgggtc gccctg                              36

<210> SEQ ID NO 57
<211> LENGTH: 32
<212> TYPE: DNA
<213> ORGANISM: Artificial Sequence
<220> FEATURE:
<223> OTHER INFORMATION: pk12 Forward primer

<400> SEQUENCE: 57
```

```
cgatcgcata tggagggtct gggccgctcg tg                                    32

<210> SEQ ID NO 58
<211> LENGTH: 31
<212> TYPE: DNA
<213> ORGANISM: Artificial Sequence
<220> FEATURE:
<223> OTHER INFORMATION: pk12 Reverse primer

<400> SEQUENCE: 58
cgggatccct aggtgggggc cagctcgaag g                                     31

<210> SEQ ID NO 59
<211> LENGTH: 33
<212> TYPE: DNA
<213> ORGANISM: Artificial Sequence
<220> FEATURE:
<223> OTHER INFORMATION: pk13 Forward primer

<400> SEQUENCE: 59
ctggaccata tgcagcggct gaacatcggc tac                                   33

<210> SEQ ID NO 60
<211> LENGTH: 33
<212> TYPE: DNA
<213> ORGANISM: Artificial Sequence
<220> FEATURE:
<223> OTHER INFORMATION: pk13 Reverse primer

<400> SEQUENCE: 60
cgggatcctc acacaaccgt ctccactccc atc                                   33

<210> SEQ ID NO 61
<211> LENGTH: 31
<212> TYPE: DNA
<213> ORGANISM: Artificial Sequence
<220> FEATURE:
<223> OTHER INFORMATION: T27 Forward primer

<400> SEQUENCE: 61
gttgcccata tggggccaac ccgaattctt c                                     31

<210> SEQ ID NO 62
<211> LENGTH: 28
<212> TYPE: DNA
<213> ORGANISM: Artificial Sequence
<220> FEATURE:
<223> OTHER INFORMATION: T27 Reverse primer

<400> SEQUENCE: 62
ggatccttat gatgctccag tctggttc                                         28

<210> SEQ ID NO 63
<211> LENGTH: 33
<212> TYPE: DNA
<213> ORGANISM: Artificial Sequence
<220> FEATURE:
<223> OTHER INFORMATION: pk6 Forward primer

<400> SEQUENCE: 63
gccgcccata tgtcgggctc gttcgagctc tcg                                   33

<210> SEQ ID NO 64
<211> LENGTH: 30
<212> TYPE: DNA
<213> ORGANISM: Artificial Sequence
<220> FEATURE:
```

<223> OTHER INFORMATION: pk6 Reverse primer

<400> SEQUENCE: 64
cgggatccct agggtttcaa cttcccctcc                                    30

<210> SEQ ID NO 65
<211> LENGTH: 36
<212> TYPE: DNA
<213> ORGANISM: Artificial Sequence
<220> FEATURE:
<223> OTHER INFORMATION: pk14 Forward primer

<400> SEQUENCE: 65
gccaagcata tgggcggaaa ccacatcccc gaaagg                             36

<210> SEQ ID NO 66
<211> LENGTH: 36
<212> TYPE: DNA
<213> ORGANISM: Artificial Sequence
<220> FEATURE:
<223> OTHER INFORMATION: pk14 Reverse primer

<400> SEQUENCE: 66
gcgggatcct caggaattcc aattctttct gatagg                             36

<210> SEQ ID NO 67
<211> LENGTH: 36
<212> TYPE: DNA
<213> ORGANISM: Artificial Sequence
<220> FEATURE:
<223> OTHER INFORMATION: pk15 Forward primer

<400> SEQUENCE: 67
agcgcccata tggtcagctg tgccgggcag atgctg                             36

<210> SEQ ID NO 68
<211> LENGTH: 32
<212> TYPE: DNA
<213> ORGANISM: Artificial Sequence
<220> FEATURE:
<223> OTHER INFORMATION: pk15 Reverse primer

<400> SEQUENCE: 68
cgggatcctc atattttcc tgtttgtgat cc                                  32

<210> SEQ ID NO 69
<211> LENGTH: 33
<212> TYPE: DNA
<213> ORGANISM: Artificial Sequence
<220> FEATURE:
<223> OTHER INFORMATION: pk33 Forward primer

<400> SEQUENCE: 69
ggctggcata tggctgagac ctctctccca gag                                33

<210> SEQ ID NO 70
<211> LENGTH: 30
<212> TYPE: DNA
<213> ORGANISM: Artificial Sequence
<220> FEATURE:
<223> OTHER INFORMATION: pk33 Reverse primer

<400> SEQUENCE: 70
cgggatcctc agctctggcc ggcaccccgc                                    30

<210> SEQ ID NO 71

```
<211> LENGTH: 33
<212> TYPE: DNA
<213> ORGANISM: Artificial Sequence
<220> FEATURE:
<223> OTHER INFORMATION: p44 Forward primer

<400> SEQUENCE: 71
tcccaccata tggactcact gcagaagcag gac                                    33

<210> SEQ ID NO 72
<211> LENGTH: 24
<212> TYPE: DNA
<213> ORGANISM: Artificial Sequence
<220> FEATURE:
<223> OTHER INFORMATION: p44 Reverse primer

<400> SEQUENCE: 72
gccaagggtc agggatcctg gctg                                              24

<210> SEQ ID NO 73
<211> LENGTH: 34
<212> TYPE: DNA
<213> ORGANISM: Artificial Sequence
<220> FEATURE:
<223> OTHER INFORMATION: p21 Forward primer

<400> SEQUENCE: 73
cccgggcata tgggcaatgg catgaccaag gtac                                   34

<210> SEQ ID NO 74
<211> LENGTH: 33
<212> TYPE: DNA
<213> ORGANISM: Artificial Sequence
<220> FEATURE:
<223> OTHER INFORMATION: p21 Reverse primer

<400> SEQUENCE: 74
gcgggatcct cacttgccgc ccttgcggga cag                                    33

<210> SEQ ID NO 75
<211> LENGTH: 33
<212> TYPE: DNA
<213> ORGANISM: Artificial Sequence
<220> FEATURE:
<223> OTHER INFORMATION: pk35 Forward primer

<400> SEQUENCE: 75
gcgggatcct cacttgccgc ccttgcggga cag                                    33

<210> SEQ ID NO 76
<211> LENGTH: 32
<212> TYPE: DNA
<213> ORGANISM: Artificial Sequence
<220> FEATURE:
<223> OTHER INFORMATION: pk35 Reverse primer

<400> SEQUENCE: 76
cgggatcctc acagtggaat catcaaacgg ac                                     32

<210> SEQ ID NO 77
<211> LENGTH: 30
<212> TYPE: DNA
<213> ORGANISM: Artificial Sequence
<220> FEATURE:
<223> OTHER INFORMATION: NE1 Forward primer

<400> SEQUENCE: 77
```

```
ccaggggcta gccgctaact ggaaagaaaa                                      30
```

<210> SEQ ID NO 78
<211> LENGTH: 30
<212> TYPE: DNA
<213> ORGANISM: Artificial Sequence
<220> FEATURE:
<223> OTHER INFORMATION: NE1 Reverse primer

<400> SEQUENCE: 78

```
gtcggatcct tagctttctt tgccctcttg                                      30
```

<210> SEQ ID NO 79
<211> LENGTH: 26
<212> TYPE: DNA
<213> ORGANISM: Artificial Sequence
<220> FEATURE:
<223> OTHER INFORMATION: p19 Forward primer

<400> SEQUENCE: 79

```
atgacagcat ccgcgtcctc cttttc                                          26
```

<210> SEQ ID NO 80
<211> LENGTH: 24
<212> TYPE: DNA
<213> ORGANISM: Artificial Sequence
<220> FEATURE:
<223> OTHER INFORMATION: p19 Reverse primer

<400> SEQUENCE: 80

```
ttacattgat atcatcatac gtag                                            24
```

<210> SEQ ID NO 81
<211> LENGTH: 33
<212> TYPE: DNA
<213> ORGANISM: Artificial Sequence
<220> FEATURE:
<223> OTHER INFORMATION: pk18 Forward primer

<400> SEQUENCE: 81

```
gcagcccata tggggaatgg gatgaacaag atc                                  33
```

<210> SEQ ID NO 82
<211> LENGTH: 33
<212> TYPE: DNA
<213> ORGANISM: Artificial Sequence
<220> FEATURE:
<223> OTHER INFORMATION: pk18 Reverse primer

<400> SEQUENCE: 82

```
cgggatcctt acagtcttct gagaaaggcc cag                                  33
```

<210> SEQ ID NO 83
<211> LENGTH: 33
<212> TYPE: DNA
<213> ORGANISM: Artificial Sequence
<220> FEATURE:
<223> OTHER INFORMATION: p12 Forward primer

<400> SEQUENCE: 83

```
gggaagcata tgggtcgggc gcaccgggac tgg                                  33
```

<210> SEQ ID NO 84
<211> LENGTH: 38
<212> TYPE: DNA
<213> ORGANISM: Artificial Sequence
<220> FEATURE:

```
<223> OTHER INFORMATION: p12 Reverse primer

<400> SEQUENCE: 84
ggcaccaagc tttcagaact ctttaagaac atccagct                              38

<210> SEQ ID NO 85
<211> LENGTH: 34
<212> TYPE: DNA
<213> ORGANISM: Artificial Sequence
<220> FEATURE:
<223> OTHER INFORMATION: pk17 Forward primer

<400> SEQUENCE: 85
ctggagcata tgccaaccgt tcaacatcct ttcc                                  34

<210> SEQ ID NO 86
<211> LENGTH: 34
<212> TYPE: DNA
<213> ORGANISM: Artificial Sequence
<220> FEATURE:
<223> OTHER INFORMATION: pk17 Reverse primer

<400> SEQUENCE: 86
gcgggatcct catgcttcca gaccctgccg cagc                                  34

<210> SEQ ID NO 87
<211> LENGTH: 36
<212> TYPE: DNA
<213> ORGANISM: Artificial Sequence
<220> FEATURE:
<223> OTHER INFORMATION: p16 Forward primer

<400> SEQUENCE: 87
gcggcggcta gcatgggcgt gcagccccccc aacttc                               36

<210> SEQ ID NO 88
<211> LENGTH: 35
<212> TYPE: DNA
<213> ORGANISM: Artificial Sequence
<220> FEATURE:
<223> OTHER INFORMATION: p16 Reverse primer

<400> SEQUENCE: 88
cgcgcctcga gtttcgttcg ctggtagaac tggaa                                 35

<210> SEQ ID NO 89
<211> LENGTH: 36
<212> TYPE: DNA
<213> ORGANISM: Artificial Sequence
<220> FEATURE:
<223> OTHER INFORMATION: T16 Forward primer

<400> SEQUENCE: 89
ggcggcgcta gcatggctca caacaagatc ccgccg                                36

<210> SEQ ID NO 90
<211> LENGTH: 36
<212> TYPE: DNA
<213> ORGANISM: Artificial Sequence
<220> FEATURE:
<223> OTHER INFORMATION: T16 Reverse primer

<400> SEQUENCE: 90
tgaggatcct tatgattcct tctttccatc ctcatc                                36

<210> SEQ ID NO 91
```

```
<211> LENGTH: 33
<212> TYPE: DNA
<213> ORGANISM: Artificial Sequence
<220> FEATURE:
<223> OTHER INFORMATION: p18 Forward primer

<400> SEQUENCE: 91
ccgggacata tggacaagcc ctcccttatc ttc                                33

<210> SEQ ID NO 92
<211> LENGTH: 33
<212> TYPE: DNA
<213> ORGANISM: Artificial Sequence
<220> FEATURE:
<223> OTHER INFORMATION: p18 Reverse primer

<400> SEQUENCE: 92
gcgggatcct cagcttgcat ccaagatgcc ttc                                33

<210> SEQ ID NO 93
<211> LENGTH: 34
<212> TYPE: DNA
<213> ORGANISM: Artificial Sequence
<220> FEATURE:
<223> OTHER INFORMATION: NE3 Forward primer

<400> SEQUENCE: 93
cttggtcata tggatagccc tacacagata tttg                               34

<210> SEQ ID NO 94
<211> LENGTH: 33
<212> TYPE: DNA
<213> ORGANISM: Artificial Sequence
<220> FEATURE:
<223> OTHER INFORMATION: NE3 Reverse primer

<400> SEQUENCE: 94
gcgggatcct caccttgcca gcaagatccc ctg                                33

<210> SEQ ID NO 95
<211> LENGTH: 33
<212> TYPE: DNA
<213> ORGANISM: Artificial Sequence
<220> FEATURE:
<223> OTHER INFORMATION: pk3 Forward primer

<400> SEQUENCE: 95
gcggctcata tgaaccgccc agctcctgtg gaa                                33

<210> SEQ ID NO 96
<211> LENGTH: 36
<212> TYPE: DNA
<213> ORGANISM: Artificial Sequence
<220> FEATURE:
<223> OTHER INFORMATION: pk3 Reverse primer

<400> SEQUENCE: 96
gcgggatcct caggaatctt tgaaacgcag ccgcat                             36

<210> SEQ ID NO 97
<211> LENGTH: 36
<212> TYPE: DNA
<213> ORGANISM: Artificial Sequence
<220> FEATURE:
<223> OTHER INFORMATION: p49 Forward primer

<400> SEQUENCE: 97
```

```
cgccgagcta gcatgcgttt tctgataact cacaac                                    36
```

<210> SEQ ID NO 98
<211> LENGTH: 33
<212> TYPE: DNA
<213> ORGANISM: Artificial Sequence
<220> FEATURE:
<223> OTHER INFORMATION: p49 Reverse primer

<400> SEQUENCE: 98

```
cgggatccct actgaacaca gcaatgccca ttg                                       33
```

<210> SEQ ID NO 99
<211> LENGTH: 34
<212> TYPE: DNA
<213> ORGANISM: Artificial Sequence
<220> FEATURE:
<223> OTHER INFORMATION: p26 Forward primer

<400> SEQUENCE: 99

```
gcgacccata tggccccggt ggaggtgagc taca                                      34
```

<210> SEQ ID NO 100
<211> LENGTH: 37
<212> TYPE: DNA
<213> ORGANISM: Artificial Sequence
<220> FEATURE:
<223> OTHER INFORMATION: p26 Reverse primer

<400> SEQUENCE: 100

```
cgcggatcct caggtcttgt gcgtgtgtgg gtctttg                                   37
```

<210> SEQ ID NO 101
<211> LENGTH: 36
<212> TYPE: DNA
<213> ORGANISM: Artificial Sequence
<220> FEATURE:
<223> OTHER INFORMATION: T29 Forward primer

<400> SEQUENCE: 101

```
ggcggccata tgtcgtcgac ctcgccgggt gtgaag                                    36
```

<210> SEQ ID NO 102
<211> LENGTH: 38
<212> TYPE: DNA
<213> ORGANISM: Artificial Sequence
<220> FEATURE:
<223> OTHER INFORMATION: T29 Reverse primer

<400> SEQUENCE: 102

```
gccggatcct tatttggaga aggctgctct gtgttgtc                                  38
```

<210> SEQ ID NO 103
<211> LENGTH: 27
<212> TYPE: DNA
<213> ORGANISM: Artificial Sequence
<220> FEATURE:
<223> OTHER INFORMATION: T46 Forward primer

<400> SEQUENCE: 103

```
atggcggaac aggctaccaa gtccgtg                                              27
```

<210> SEQ ID NO 104
<211> LENGTH: 29
<212> TYPE: DNA
<213> ORGANISM: Artificial Sequence
<220> FEATURE:

-continued

<223> OTHER INFORMATION: T46 Reverse primer

<400> SEQUENCE: 104
tcagtgggcc ttctccaaga acgctctgc         29

<210> SEQ ID NO 105
<211> LENGTH: 31
<212> TYPE: DNA
<213> ORGANISM: Artificial Sequence
<220> FEATURE:
<223> OTHER INFORMATION: pk1 Forward primer

<400> SEQUENCE: 105
gctctagact tataggagac ttctccaagg g         31

<210> SEQ ID NO 106
<211> LENGTH: 33
<212> TYPE: DNA
<213> ORGANISM: Artificial Sequence
<220> FEATURE:
<223> OTHER INFORMATION: pk1 Reverse primer

<400> SEQUENCE: 106
gccctaggtc agagcttctt cagacgactg tac         33

<210> SEQ ID NO 107
<211> LENGTH: 36
<212> TYPE: DNA
<213> ORGANISM: Artificial Sequence
<220> FEATURE:
<223> OTHER INFORMATION: T47 Forward primer

<400> SEQUENCE: 107
gaccaccata tgctgattgg agattactct aaggcc         36

<210> SEQ ID NO 108
<211> LENGTH: 33
<212> TYPE: DNA
<213> ORGANISM: Artificial Sequence
<220> FEATURE:
<223> OTHER INFORMATION: T47 Reverse primer

<400> SEQUENCE: 108
ccgggatcct cactggtcct gcagccggct aca         33

<210> SEQ ID NO 109
<211> LENGTH: 36
<212> TYPE: DNA
<213> ORGANISM: Artificial Sequence
<220> FEATURE:
<223> OTHER INFORMATION: T45 Forward primer

<400> SEQUENCE: 109
gattctgcta gcgggcacct gattggtgat ttttcc         36

<210> SEQ ID NO 110
<211> LENGTH: 33
<212> TYPE: DNA
<213> ORGANISM: Artificial Sequence
<220> FEATURE:
<223> OTHER INFORMATION: T45 Reverse primer

<400> SEQUENCE: 110
ccgggatcct catgggctca tgtccttcac cag         33

<210> SEQ ID NO 111

```
<211> LENGTH: 33
<212> TYPE: DNA
<213> ORGANISM: Artificial Sequence
<220> FEATURE:
<223> OTHER INFORMATION: Eya2 Forward primer

<400> SEQUENCE: 111
gacaatcata tggagcgtgt gttcgtgtgg gac                                  33

<210> SEQ ID NO 112
<211> LENGTH: 33
<212> TYPE: DNA
<213> ORGANISM: Artificial Sequence
<220> FEATURE:
<223> OTHER INFORMATION: Eya2 Reverse primer

<400> SEQUENCE: 112
gaattcttat aaatactcca gctccagggc gtg                                  33

<210> SEQ ID NO 113
<211> LENGTH: 569
<212> TYPE: PRT
<213> ORGANISM: Artificial Sequence
<220> FEATURE:
<223> OTHER INFORMATION: Amino acid sequence of PTP active domain T4

<400> SEQUENCE: 113

Met Ala Asp Asp Asn Lys Leu Phe Arg Glu Glu Phe Asn Ala Leu Pro
1               5                   10                  15

Ala Cys Pro Ile Gln Ala Thr Cys Glu Ala Ala Ser Lys Glu Glu Asn
            20                  25                  30

Lys Glu Lys Asn Arg Tyr Val Asn Ile Leu Pro Tyr Asp His Ser Arg
        35                  40                  45

Val His Leu Thr Pro Val Glu Gly Val Pro Asp Ser Asp Tyr Ile Asn
    50                  55                  60

Ala Ser Phe Ile Asn Gly Tyr Gln Glu Lys Asn Lys Phe Ile Ala Ala
65                  70                  75                  80

Gln Gly Pro Lys Glu Glu Thr Val Asn Asp Phe Trp Arg Met Ile Trp
                85                  90                  95

Glu Gln Asn Thr Ala Thr Ile Val Met Val Thr Asn Leu Lys Glu Arg
            100                 105                 110

Lys Glu Cys Lys Cys Ala Gln Tyr Trp Pro Asp Gln Gly Cys Trp Thr
        115                 120                 125

Tyr Gly Asn Ile Arg Val Ser Val Glu Asp Val Thr Val Leu Val Asp
    130                 135                 140

Tyr Thr Val Arg Lys Phe Cys Ile Gln Gln Val Gly Asp Met Thr Asn
145                 150                 155                 160

Arg Lys Pro Gln Arg Leu Ile Thr Gln Phe His Phe Thr Ser Trp Pro
                165                 170                 175

Asp Phe Gly Val Pro Phe Thr Pro Ile Gly Met Leu Lys Phe Leu Lys
            180                 185                 190

Lys Val Lys Ala Cys Asn Pro Gln Tyr Ala Gly Ala Ile Val Val His
        195                 200                 205

Cys Ser Ala Gly Val Gly Arg Thr Gly Thr Phe Val Val Ile Asp Ala
    210                 215                 220

Met Leu Asp Met Met His Thr Glu Arg Lys Val Asp Val Tyr Gly Phe
225                 230                 235                 240

Val Ser Arg Ile Arg Ala Gln Arg Cys Gln Met Val Gln Thr Asp Met
                245                 250                 255
```

Gln Tyr Val Phe Ile Tyr Gln Ala Leu Leu Glu His Tyr Leu Tyr Gly
            260                 265                 270

Asp Thr Glu Leu Glu Val Thr Ser Leu Glu Thr His Leu Gln Lys Ile
        275                 280                 285

Tyr Asn Lys Ile Pro Gly Thr Ser Asn Gly Leu Glu Glu Phe
    290                 295                 300

Lys Lys Leu Thr Ser Ile Lys Ile Gln Asn Asp Lys Met Arg Thr Gly
305                 310                 315                 320

Asn Leu Pro Ala Asn Met Lys Lys Asn Arg Val Leu Gln Ile Ile Pro
                325                 330                 335

Tyr Glu Phe Asn Arg Val Ile Ile Pro Val Lys Arg Gly Glu Glu Asn
            340                 345                 350

Thr Asp Tyr Val Asn Ala Ser Phe Ile Asp Gly Tyr Arg Gln Lys Asp
        355                 360                 365

Ser Tyr Ile Ala Ser Gln Gly Pro Leu Leu His Thr Ile Glu Asp Phe
    370                 375                 380

Trp Arg Met Ile Trp Glu Trp Lys Ser Cys Ser Ile Val Met Leu Thr
385                 390                 395                 400

Glu Leu Glu Glu Arg Gly Gln Glu Lys Cys Ala Gln Tyr Trp Pro Ser
                405                 410                 415

Asp Gly Leu Val Ser Tyr Gly Asp Ile Thr Val Glu Leu Lys Lys Glu
            420                 425                 430

Glu Glu Cys Glu Ser Tyr Thr Val Arg Asp Leu Leu Val Thr Asn Thr
        435                 440                 445

Arg Glu Asn Lys Ser Arg Gln Ile Arg Gln Phe His Phe His Gly Trp
    450                 455                 460

Pro Glu Val Gly Ile Pro Ser Asp Gly Lys Gly Met Ile Ser Ile Ile
465                 470                 475                 480

Ala Ala Val Gln Lys Gln Gln Gln Ser Gly Asn His Pro Ile Thr
                485                 490                 495

Val His Cys Ser Ala Gly Ala Gly Arg Thr Gly Thr Phe Cys Ala Leu
            500                 505                 510

Ser Thr Val Leu Glu Arg Val Lys Ala Glu Gly Ile Leu Asp Val Phe
        515                 520                 525

Gln Thr Val Lys Ser Leu Arg Leu Gln Arg Pro His Met Val Gln Thr
    530                 535                 540

Leu Glu Gln Tyr Glu Phe Cys Tyr Lys Val Val Gln Glu Tyr Ile Asp
545                 550                 555                 560

Ala Phe Ser Asp Tyr Ala Asn Phe Lys
                565

<210> SEQ ID NO 114
<211> LENGTH: 284
<212> TYPE: PRT
<213> ORGANISM: Artificial Sequence
<220> FEATURE:
<223> OTHER INFORMATION: Amino acid sequence of PTP active domain T7

<400> SEQUENCE: 114

Lys Ile Asn Gln Phe Glu Gly His Phe Met Lys Leu Gln Ala Asp Ser
1               5                   10                  15

Asn Tyr Leu Leu Ser Lys Glu Tyr Glu Glu Leu Lys Asp Val Gly Arg
            20                  25                  30

Asn Gln Ser Cys Asp Ile Ala Leu Leu Pro Glu Asn Arg Gly Lys Asn
        35                  40                  45

Arg Tyr Asn Asn Ile Leu Pro Tyr Asp Ala Thr Arg Val Lys Leu Ser

```
                50                  55                  60
Asn Val Asp Asp Asp Pro Cys Ser Asp Tyr Ile Asn Ala Ser Tyr Ile
 65                  70                  75                  80

Pro Gly Asn Asn Phe Arg Arg Glu Tyr Ile Val Thr Gln Gly Pro Leu
                 85                  90                  95

Pro Gly Thr Lys Asp Asp Phe Trp Lys Met Val Trp Glu Gln Asn Val
            100                 105                 110

His Asn Ile Val Met Val Thr Gln Cys Val Glu Lys Gly Arg Val Lys
        115                 120                 125

Cys Asp His Tyr Trp Pro Ala Asp Gln Asp Ser Leu Tyr Tyr Gly Asp
    130                 135                 140

Leu Ile Leu Gln Met Leu Ser Glu Ser Val Leu Pro Glu Trp Thr Ile
145                 150                 155                 160

Arg Glu Phe Lys Ile Cys Gly Glu Glu Gln Leu Asp Ala His Arg Leu
                165                 170                 175

Ile Arg His Phe His Tyr Thr Val Trp Pro Asp His Gly Val Pro Glu
            180                 185                 190

Thr Thr Gln Ser Leu Ile Gln Phe Val Arg Thr Val Arg Asp Tyr Ile
        195                 200                 205

Asn Arg Ser Pro Gly Ala Gly Pro Thr Val Val His Cys Ser Ala Gly
    210                 215                 220

Val Gly Arg Thr Gly Thr Phe Ile Ala Leu Asp Arg Ile Leu Gln Gln
225                 230                 235                 240

Leu Asp Ser Lys Asp Ser Val Asp Ile Tyr Gly Ala Val His Asp Leu
                245                 250                 255

Arg Leu His Arg Val His Met Val Gln Thr Glu Cys Gln Tyr Val Tyr
            260                 265                 270

Leu His Gln Cys Val Arg Asp Val Leu Arg Ala Arg
        275                 280

<210> SEQ ID NO 115
<211> LENGTH: 582
<212> TYPE: PRT
<213> ORGANISM: Artificial Sequence
<220> FEATURE:
<223> OTHER INFORMATION: Amino acid sequence of PTP active domain T48

<400> SEQUENCE: 115

Gly Arg Ile Val Tyr Gly Leu Arg Pro Gly Arg Ser Tyr Gln Phe Asn
 1               5                  10                  15

Val Lys Thr Val Ser Gly Asp Ser Trp Lys Thr Tyr Ser Lys Pro Ile
             20                  25                  30

Phe Gly Ser Val Arg Thr Lys Pro Asp Lys Ile Gln Asn Leu His Cys
         35                  40                  45

Arg Pro Gln Asn Ser Thr Ala Ile Ala Cys Ser Trp Ile Pro Pro Asp
    50                  55                  60

Ser Asp Phe Asp Gly Tyr Ser Ile Glu Cys Arg Lys Met Asp Thr Gln
 65                  70                  75                  80

Glu Val Glu Phe Ser Arg Lys Leu Glu Lys Glu Lys Ser Leu Leu Asn
                 85                  90                  95

Ile Met Met Leu Val Pro His Lys Arg Tyr Leu Val Ser Ile Lys Val
            100                 105                 110

Gln Ser Ala Gly Met Thr Ser Glu Val Val Glu Asp Ser Thr Ile Thr
        115                 120                 125

Met Ile Asp Arg Pro Pro Pro Pro Pro His Ile Arg Val Asn Glu
    130                 135                 140
```

```
Lys Asp Val Leu Ile Ser Lys Ser Ser Ile Asn Phe Thr Val Asn Cys
145                 150                 155                 160

Ser Trp Phe Ser Asp Thr Asn Gly Ala Val Lys Tyr Phe Thr Val Val
                165                 170                 175

Val Arg Glu Ala Asp Gly Ser Asp Glu Leu Lys Pro Glu Gln Gln His
            180                 185                 190

Pro Leu Pro Ser Tyr Leu Glu Tyr Arg His Asn Ala Ser Ile Arg Val
        195                 200                 205

Tyr Gln Thr Asn Tyr Phe Ala Ser Lys Cys Ala Glu Asn Pro Asn Ser
    210                 215                 220

Asn Ser Lys Ser Phe Asn Ile Lys Leu Gly Ala Glu Met Glu Ser Leu
225                 230                 235                 240

Gly Gly Lys Arg Asp Pro Thr Gln Gln Lys Phe Cys Asp Gly Pro Leu
                245                 250                 255

Lys Pro His Thr Ala Tyr Arg Ile Ser Ile Arg Ala Phe Thr Gln Leu
            260                 265                 270

Phe Asp Glu Asp Leu Lys Glu Phe Thr Lys Pro Leu Tyr Ser Asp Thr
        275                 280                 285

Phe Phe Ser Leu Pro Ile Thr Thr Glu Ser Glu Pro Leu Phe Gly Ala
    290                 295                 300

Ile Glu Gly Val Ser Ala Gly Leu Phe Leu Ile Gly Met Leu Val Ala
305                 310                 315                 320

Val Val Ala Leu Leu Ile Cys Arg Gln Lys Val Ser His Gly Arg Glu
                325                 330                 335

Arg Pro Ser Ala Arg Leu Ser Ile Arg Arg Asp Arg Pro Leu Ser Val
            340                 345                 350

His Leu Asn Leu Gly Gln Lys Gly Asn Arg Lys Thr Ser Cys Pro Ile
        355                 360                 365

Lys Ile Asn Gln Phe Glu Gly His Phe Met Lys Leu Gln Ala Asp Ser
    370                 375                 380

Asn Tyr Leu Leu Ser Lys Glu Tyr Glu Glu Leu Lys Asp Val Gly Arg
385                 390                 395                 400

Asn Gln Ser Cys Asp Ile Ala Leu Leu Pro Glu Asn Arg Gly Lys Asn
                405                 410                 415

Arg Tyr Asn Asn Ile Leu Pro Tyr Asp Ala Thr Arg Val Lys Leu Ser
            420                 425                 430

Asn Val Asp Asp Asp Pro Cys Ser Asp Tyr Ile Asn Ala Ser Tyr Ile
        435                 440                 445

Pro Gly Asn Asn Phe Arg Arg Glu Tyr Ile Val Thr Gln Gly Pro Leu
    450                 455                 460

Pro Gly Thr Lys Asp Asp Phe Trp Lys Met Val Trp Glu Gln Asn Val
465                 470                 475                 480

His Asn Ile Val Met Val Thr Gln Cys Val Glu Lys Gly Arg Val Lys
                485                 490                 495

Cys Asp His Tyr Trp Pro Ala Asp Gln Asp Ser Leu Tyr Tyr Gly Asp
            500                 505                 510

Leu Ile Leu Gln Met Leu Ser Glu Ser Val Leu Pro Glu Trp Thr Ile
        515                 520                 525

Arg Glu Phe Lys Ile Cys Gly Glu Glu Gln Leu Asp Ala His Arg Leu
    530                 535                 540

Ile Arg His Phe His Tyr Thr Val Trp Pro Asp His Gly Val Pro Glu
545                 550                 555                 560

Thr Thr Gln Ser Leu Ile Gln Phe Val Arg Thr Val Arg Asp Tyr Ile
```

```
                565                 570                 575

Asn Arg Ser Pro Gly Ala
            580

<210> SEQ ID NO 116
<211> LENGTH: 269
<212> TYPE: PRT
<213> ORGANISM: Artificial Sequence
<220> FEATURE:
<223> OTHER INFORMATION: Amino acid sequence of PTP active domain T8

<400> SEQUENCE: 116

Pro Val Lys Asp Leu Thr Leu Arg Asn Arg Ser Thr Glu Asp Leu His
1               5                   10                  15

Val Thr Trp Ser Gly Ala Asn Gly Asp Val Asp Gln Tyr Glu Ile Gln
            20                  25                  30

Leu Leu Phe Asn Asp Met Lys Val Phe Pro Phe His Leu Val Asn
        35                  40                  45

Thr Ala Thr Glu Tyr Arg Phe Thr Ser Leu Thr Pro Gly Arg Gln Tyr
    50                  55                  60

Lys Ile Leu Val Leu Thr Ile Ser Gly Asp Val Gln Gln Ser Ala Phe
65                  70                  75                  80

Ile Glu Gly Phe Thr Val Pro Ser Ala Val Lys Asn Ile His Ile Ser
                85                  90                  95

Pro Asn Gly Ala Thr Asp Ser Leu Thr Val Asn Trp Thr Pro Gly Gly
            100                 105                 110

Gly Asp Val Asp Ser Tyr Thr Val Ser Ala Phe Arg His Ser Gln Lys
        115                 120                 125

Val Asp Ser Gln Thr Ile Pro Lys His Val Phe Glu His Thr Phe His
    130                 135                 140

Arg Leu Glu Ala Gly Glu Gln Tyr Gln Ile Met Ile Ala Ser Val Ser
145                 150                 155                 160

Gly Ser Leu Lys Asn Gln Ile Asn Val Val Gly Arg Thr Val Pro Ala
                165                 170                 175

Ser Val Gln Gly Val Ile Ala Asp Asn Ala Tyr Ser Ser Tyr Ser Leu
            180                 185                 190

Ile Val Ser Trp Gln Lys Ala Ala Gly Val Ala Glu Arg Tyr Asp Ile
        195                 200                 205

Leu Leu Leu Thr Glu Asn Gly Ile Leu Leu Arg Asn Thr Ser Glu Pro
    210                 215                 220

Ala Thr Thr Lys Gln His Lys Phe Glu Asp Leu Thr Pro Gly Lys Lys
225                 230                 235                 240

Tyr Lys Ile Gln Ile Leu Thr Val Ser Gly Gly Leu Phe Ser Lys Glu
                245                 250                 255

Ala Gln Thr Glu Gly Arg Thr Val Pro Ala Ala Val Thr
            260                 265

<210> SEQ ID NO 117
<211> LENGTH: 312
<212> TYPE: PRT
<213> ORGANISM: Artificial Sequence
<220> FEATURE:
<223> OTHER INFORMATION: Amino acid sequence of PTP active domain T23

<400> SEQUENCE: 117

Glu Asn Phe Glu Ala Tyr Phe Lys Lys Gln Gln Ala Asp Ser Asn Cys
1               5                   10                  15

Gly Phe Ala Glu Glu Tyr Glu Asp Leu Lys Leu Val Gly Ile Ser Gln
```

```
                    20                  25                  30
Pro Lys Tyr Ala Ala Glu Leu Ala Glu Asn Arg Gly Lys Asn Arg Tyr
                35                  40                  45
Asn Asn Val Leu Pro Tyr Asp Ile Ser Arg Val Lys Leu Ser Val Gln
     50                  55                  60
Thr His Ser Thr Asp Asp Tyr Ile Asn Ala Asn Tyr Met Pro Gly Tyr
65                  70                  75                  80
His Ser Lys Lys Asp Phe Ile Ala Thr Gln Gly Pro Leu Pro Asn Thr
                85                  90                  95
Leu Lys Asp Phe Trp Arg Met Val Trp Glu Lys Asn Val Tyr Ala Ile
            100                 105                 110
Ile Met Leu Thr Lys Cys Val Glu Gln Gly Arg Thr Lys Cys Glu Glu
            115                 120                 125
Tyr Trp Pro Ser Lys Gln Ala Gln Asp Tyr Gly Asp Ile Thr Val Ala
            130                 135                 140
Met Thr Ser Glu Ile Val Leu Pro Glu Trp Thr Ile Arg Asp Phe Thr
145                 150                 155                 160
Val Lys Asn Ile Gln Thr Ser Glu Ser His Pro Leu Arg Gln Phe His
                165                 170                 175
Phe Thr Ser Trp Pro Asp His Gly Val Pro Asp Thr Thr Asp Leu Leu
            180                 185                 190
Ile Asn Phe Arg Tyr Leu Val Arg Asp Tyr Met Lys Gln Ser Pro Pro
            195                 200                 205
Glu Ser Pro Ile Leu Val His Cys Ser Ala Gly Val Gly Arg Thr Gly
            210                 215                 220
Thr Phe Ile Ala Ile Asp Arg Leu Ile Tyr Gln Ile Glu Asn Glu Asn
225                 230                 235                 240
Thr Val Asp Val Tyr Gly Ile Val Tyr Asp Leu Arg Met His Arg Pro
                245                 250                 255
Leu Met Val Gln Thr Glu Asp Gln Tyr Val Phe Leu Asn Gln Cys Val
            260                 265                 270
Leu Asp Ile Val Arg Ser Gln Lys Asp Ser Lys Val Asp Leu Ile Tyr
            275                 280                 285
Gln Asn Thr Thr Ala Met Thr Ile Tyr Glu Asn Leu Ala Pro Val Thr
            290                 295                 300
Thr Phe Gly Lys Thr Asn Gly Tyr
305                 310

<210> SEQ ID NO 118
<211> LENGTH: 561
<212> TYPE: PRT
<213> ORGANISM: Artificial Sequence
<220> FEATURE:
<223> OTHER INFORMATION: Amino acid sequence of PTP active domain T39

<400> SEQUENCE: 118

Met Lys Thr Ser Asp Ser Tyr Gly Phe Lys Glu Glu Tyr Glu Ser Phe
1               5                   10                  15
Phe Glu Gly Gln Ser Ala Ser Trp Asp Val Ala Lys Lys Asp Gln Asn
                20                  25                  30
Arg Ala Lys Asn Arg Tyr Gly Asn Ile Ile Ala Tyr Asp His Ser Arg
            35                  40                  45
Val Ile Leu Gln Pro Val Glu Asp Pro Ser Ser Asp Tyr Ile Asn
     50                  55                  60
Ala Asn Tyr Ile Asp Gly Tyr Gln Arg Pro Ser His Tyr Ile Ala Thr
65                  70                  75                  80
```

```
Gln Gly Pro Val His Glu Thr Val Tyr Asp Phe Trp Arg Met Ile Trp
                85                  90                  95

Gln Glu Gln Ser Ala Cys Ile Val Met Val Thr Asn Leu Val Glu Val
            100                 105                 110

Gly Arg Val Lys Cys Tyr Lys Tyr Trp Pro Asp Thr Glu Val Tyr
        115                 120                 125

Gly Asp Phe Lys Val Thr Cys Val Glu Met Glu Pro Leu Ala Glu Tyr
130                 135                 140

Val Val Arg Thr Phe Thr Leu Glu Arg Arg Gly Tyr Asn Glu Ile Arg
145                 150                 155                 160

Glu Val Lys Gln Phe His Phe Thr Gly Trp Pro Asp His Gly Val Pro
                165                 170                 175

Tyr His Ala Thr Gly Leu Leu Ser Phe Ile Arg Arg Val Lys Leu Ser
                180                 185                 190

Asn Pro Pro Ser Ala Gly Pro Ile Val Val His Cys Ser Ala Gly Ala
                195                 200                 205

Gly Arg Thr Gly Cys Tyr Ile Val Ile Asp Ile Met Leu Asp Met Ala
210                 215                 220

Glu Arg Glu Gly Val Val Asp Ile Tyr Asn Cys Val Lys Ala Leu Arg
225                 230                 235                 240

Ser Arg Arg Ile Asn Met Val Gln Thr Glu Glu Gln Tyr Ile Phe Ile
                245                 250                 255

His Asp Ala Ile Leu Glu Ala Cys Leu Cys Gly Glu Thr Ala Ile Pro
                260                 265                 270

Val Cys Glu Phe Lys Ala Ala Tyr Phe Asp Met Ile Arg Ile Asp Ser
                275                 280                 285

Gln Thr Asn Ser Ser His Leu Lys Asp Glu Phe Gln Thr Leu Asn Ser
                290                 295                 300

Val Thr Pro Arg Leu Gln Ala Glu Asp Cys Ser Ile Ala Cys Leu Pro
305                 310                 315                 320

Arg Asn His Asp Lys Asn Arg Phe Met Asp Met Leu Pro Pro Asp Arg
                325                 330                 335

Cys Leu Pro Phe Leu Ile Thr Ile Asp Gly Glu Ser Ser Asn Tyr Ile
                340                 345                 350

Asn Ala Ala Leu Met Asp Ser Tyr Arg Gln Pro Ala Ala Phe Ile Val
                355                 360                 365

Thr Gln Tyr Pro Leu Pro Asn Thr Val Lys Asp Phe Trp Arg Leu Val
    370                 375                 380

Tyr Asp Tyr Gly Cys Thr Ser Ile Val Met Leu Asn Glu Val Asp Leu
385                 390                 395                 400

Ser Gln Gly Cys Pro Gln Tyr Trp Pro Glu Glu Gly Met Leu Arg Tyr
                405                 410                 415

Gly Pro Ile Gln Val Glu Cys Met Ser Cys Ser Met Asp Cys Asp Val
                420                 425                 430

Ile Asn Arg Ile Phe Arg Ile Cys Asn Leu Thr Arg Pro Gln Glu Gly
            435                 440                 445

Tyr Leu Met Val Gln Gln Phe Gln Tyr Leu Gly Trp Ala Ser His Arg
    450                 455                 460

Glu Val Pro Gly Ser Lys Arg Ser Phe Leu Lys Leu Ile Leu Gln Val
465                 470                 475                 480

Glu Lys Trp Gln Glu Glu Cys Glu Glu Gly Glu Gly Arg Thr Ile Ile
                485                 490                 495

His Cys Leu Asn Gly Gly Gly Arg Ser Gly Met Phe Cys Ala Ile Gly
```

```
                       500                 505                 510
Ile Val Val Glu Met Val Lys Arg Gln Asn Val Asp Val Phe His
            515                 520                 525
Ala Val Lys Thr Leu Arg Asn Ser Lys Pro Asn Met Val Glu Ala Pro
530                 535                 540
Gln Tyr Arg Phe Cys Tyr Asp Val Ala Leu Glu Tyr Leu Glu Ser
545                 550                 555                 560
Ser

<210> SEQ ID NO 119
<211> LENGTH: 605
<212> TYPE: PRT
<213> ORGANISM: Artificial Sequence
<220> FEATURE:
<223> OTHER INFORMATION: Amino acid sequence of PTP active domain T5

<400> SEQUENCE: 119

Met Ala Ser Asp Thr Ser Ser Leu Val Gln Ser His Thr Tyr Lys Lys
1               5                   10                  15
Arg Glu Pro Ala Asp Val Pro Tyr Gln Thr Gly Gln Leu His Pro Ala
            20                  25                  30
Ile Arg Val Ala Asp Leu Leu Gln His Ile Thr Gln Met Lys Cys Ala
        35                  40                  45
Glu Gly Tyr Gly Phe Lys Glu Glu Tyr Glu Ser Phe Phe Glu Gly Gln
    50                  55                  60
Ser Ala Pro Trp Asp Ser Ala Lys Lys Asp Glu Asn Arg Met Lys Asn
65                  70                  75                  80
Arg Tyr Gly Asn Ile Ile Ala Tyr Asp His Ser Arg Val Arg Leu Gln
                85                  90                  95
Thr Ile Glu Gly Asp Thr Asn Ser Asp Tyr Ile Asn Gly Asn Tyr Ile
            100                 105                 110
Asp Gly Tyr His Arg Pro Asn His Tyr Ile Ala Thr Gln Gly Pro Met
        115                 120                 125
Gln Glu Thr Ile Tyr Asp Phe Trp Arg Met Val Trp His Glu Asn Thr
130                 135                 140
Ala Ser Ile Ile Met Val Thr Asn Leu Val Glu Val Gly Arg Val Lys
145                 150                 155                 160
Cys Cys Lys Tyr Trp Pro Asp Asp Thr Glu Ile Tyr Lys Asp Ile Lys
                165                 170                 175
Val Thr Leu Ile Glu Thr Glu Leu Leu Ala Glu Tyr Val Ile Arg Thr
            180                 185                 190
Phe Ala Val Glu Lys Arg Gly Val His Glu Ile Arg Glu Ile Arg Gln
        195                 200                 205
Phe His Phe Thr Gly Trp Pro Asp His Gly Val Pro Tyr His Ala Thr
210                 215                 220
Gly Leu Leu Gly Phe Val Arg Gln Val Lys Ser Lys Ser Pro Pro Ser
225                 230                 235                 240
Ala Gly Pro Leu Val Val His Cys Ser Ala Gly Ala Gly Arg Thr Gly
                245                 250                 255
Cys Phe Ile Val Ile Asp Ile Met Leu Asp Met Ala Glu Arg Glu Gly
            260                 265                 270
Val Val Asp Ile Tyr Asn Cys Val Arg Glu Leu Arg Ser Arg Arg Val
        275                 280                 285
Asn Met Val Gln Thr Glu Glu Gln Tyr Val Phe Ile His Asp Ala Ile
    290                 295                 300
```

```
Leu Glu Ala Cys Leu Cys Gly Asp Thr Ser Val Pro Ala Ser Gln Val
305                 310                 315                 320

Arg Ser Leu Tyr Tyr Asp Met Asn Lys Leu Asp Pro Gln Thr Asn Ser
            325                 330                 335

Ser Gln Ile Lys Glu Glu Phe Arg Thr Leu Asn Met Val Thr Pro Thr
        340                 345                 350

Leu Arg Val Glu Asp Cys Ser Ile Ala Leu Leu Pro Arg Asn His Glu
            355                 360                 365

Lys Asn Arg Cys Met Asp Ile Leu Pro Pro Asp Arg Cys Leu Pro Phe
    370                 375                 380

Leu Ile Thr Ile Asp Gly Glu Ser Ser Asn Tyr Ile Asn Ala Ala Leu
385                 390                 395                 400

Met Asp Ser Tyr Lys Gln Pro Ser Ala Phe Ile Val Thr Gln His Pro
            405                 410                 415

Leu Pro Asn Thr Val Lys Asp Phe Trp Arg Leu Val Leu Asp Tyr His
        420                 425                 430

Cys Thr Ser Val Val Met Leu Asn Asp Val Asp Pro Ala Gln Leu Cys
            435                 440                 445

Pro Gln Tyr Trp Pro Glu Asn Gly Val His Arg His Gly Pro Ile Gln
    450                 455                 460

Val Glu Phe Val Ser Ala Asp Leu Glu Glu Asp Ile Ile Ser Arg Ile
465                 470                 475                 480

Phe Arg Ile Tyr Asn Ala Ala Arg Pro Gln Asp Gly Tyr Arg Met Val
            485                 490                 495

Gln Gln Phe Gln Phe Leu Gly Trp Pro Met Tyr Arg Asp Thr Pro Val
        500                 505                 510

Ser Lys Arg Ser Phe Leu Lys Leu Ile Arg Gln Val Asp Lys Trp Gln
            515                 520                 525

Glu Glu Tyr Asn Gly Gly Glu Gly Pro Thr Val Val His Cys Leu Asn
    530                 535                 540

Gly Gly Gly Arg Ser Gly Thr Phe Cys Ala Ile Ser Ile Val Cys Glu
545                 550                 555                 560

Met Leu Arg His Gln Arg Thr Val Asp Val Phe His Ala Val Lys Thr
            565                 570                 575

Leu Arg Asn Asn Lys Pro Asn Met Val Asp Leu Leu Asp Gln Tyr Lys
        580                 585                 590

Phe Cys Tyr Glu Val Ala Leu Glu Tyr Leu Asn Ser Gly
            595                 600                 605

<210> SEQ ID NO 120
<211> LENGTH: 270
<212> TYPE: PRT
<213> ORGANISM: Artificial Sequence
<220> FEATURE:
<223> OTHER INFORMATION: Amino acid sequence of PTP active domain T38

<400> SEQUENCE: 120

Leu Ala Lys Glu Trp Gln Ala Leu Cys Ala Tyr Gln Ala Glu Pro Asn
1               5                   10                  15

Thr Cys Ala Thr Ala Gln Gly Glu Gly Asn Ile Lys Lys Asn Arg His
            20                  25                  30

Pro Asp Phe Leu Pro Tyr Asp His Ala Arg Ile Lys Leu Lys Val Glu
        35                  40                  45

Ser Ser Pro Ser Arg Ser Asp Tyr Ile Asn Ala Ser Pro Ile Ile Glu
    50                  55                  60

His Asp Pro Arg Met Pro Ala Tyr Ile Ala Thr Gln Gly Pro Leu Ser
```

```
                65                  70                  75                  80
His Thr Ile Ala Asp Phe Trp Gln Met Val Trp Glu Ser Gly Cys Thr
                85                  90                  95

Val Ile Val Met Leu Thr Pro Leu Val Glu Asp Gly Val Lys Gln Cys
                100                 105                 110

Asp Arg Tyr Trp Pro Asp Glu Gly Ala Ser Leu Tyr His Val Tyr Glu
                115                 120                 125

Val Asn Leu Val Ser Glu His Ile Trp Cys Glu Asp Phe Leu Val Arg
            130                 135                 140

Ser Phe Tyr Leu Lys Asn Val Gln Thr Gln Glu Thr Arg Thr Leu Thr
145                 150                 155                 160

Gln Phe His Phe Leu Ser Trp Pro Ala Glu Gly Thr Pro Ala Ser Thr
                165                 170                 175

Arg Pro Leu Leu Asp Phe Arg Arg Lys Val Asn Lys Cys Tyr Arg Gly
                180                 185                 190

Arg Ser Cys Pro Ile Ile Val His Cys Ser Asp Gly Ala Gly Arg Thr
            195                 200                 205

Gly Thr Tyr Ile Leu Ile Asp Met Val Leu Asn Arg Met Ala Lys Gly
        210                 215                 220

Val Lys Glu Ile Asp Ile Ala Ala Thr Leu Glu His Val Arg Asp Gln
225                 230                 235                 240

Arg Pro Gly Leu Val Arg Ser Lys Asp Gln Phe Glu Phe Ala Leu Thr
                245                 250                 255

Ala Val Ala Glu Glu Val Asn Ala Ile Leu Lys Ala Leu Pro
                260                 265                 270

<210> SEQ ID NO 121
<211> LENGTH: 342
<212> TYPE: PRT
<213> ORGANISM: Artificial Sequence
<220> FEATURE:
<223> OTHER INFORMATION: Amino acid sequence of PTP active domain T12

<400> SEQUENCE: 121

Met Ala Thr Arg Pro Pro Asp Arg Pro Glu Gly Pro His Thr Ser Arg
1               5                   10                  15

Ile Ser Ser Val Ser Ser Gln Phe Ser Asp Gly Pro Ile Pro Ser Pro
                20                  25                  30

Ser Ala Arg Ser Ser Ala Ser Ser Trp Ser Glu Glu Pro Val Gln Ser
            35                  40                  45

Asn Met Asp Ile Ser Thr Gly His Met Ile Leu Ser Tyr Met Glu Asp
    50                  55                  60

His Leu Lys Asn Lys Asn Arg Leu Glu Lys Glu Trp Glu Ala Leu Cys
65                  70                  75                  80

Ala Tyr Gln Ala Glu Pro Asn Ser Ser Phe Val Ala Gln Arg Glu Glu
                85                  90                  95

Asn Val Pro Lys Asn Arg Ser Leu Ala Val Leu Thr Tyr Asp His Ser
                100                 105                 110

Arg Val Leu Leu Lys Ala Glu Asn Ser His Ser His Ser Asp Tyr Ile
            115                 120                 125

Asn Ala Ser Pro Ile Met Asp His Asp Pro Arg Asn Pro Ala Tyr Ile
        130                 135                 140

Ala Thr Gln Gly Pro Leu Pro Ala Thr Val Ala Asp Phe Trp Gln Met
145                 150                 155                 160

Val Trp Glu Ser Gly Cys Val Val Ile Val Met Leu Thr Pro Leu Ala
                165                 170                 175
```

Glu Asn Gly Val Arg Gln Cys Tyr His Tyr Trp Pro Asp Glu Gly Ser
            180                 185                 190

Asn Leu Tyr His Ile Tyr Glu Val Asn Leu Val Ser Glu His Ile Trp
            195                 200                 205

Cys Glu Asp Phe Leu Val Arg Ser Phe Tyr Leu Lys Asn Leu Gln Thr
            210                 215                 220

Asn Glu Thr Arg Thr Val Thr Gln Phe His Phe Leu Ser Trp Tyr Asp
225                 230                 235                 240

Arg Gly Val Pro Ser Ser Arg Ser Leu Leu Asp Phe Arg Arg Lys
            245                 250                 255

Val Asn Lys Cys Tyr Arg Gly Arg Ser Cys Pro Ile Ile Val His Cys
            260                 265                 270

Ser Asp Gly Ala Gly Arg Ser Gly Thr Tyr Val Leu Ile Asp Met Val
            275                 280                 285

Leu Asn Lys Met Ala Lys Gly Ala Lys Glu Ile Asp Ile Ala Ala Thr
            290                 295                 300

Leu Glu His Leu Arg Asp Gln Arg Pro Gly Met Val Gln Thr Lys Glu
305                 310                 315                 320

Gln Phe Glu Phe Ala Leu Thr Ala Val Ala Glu Glu Val Asn Ala Ile
            325                 330                 335

Leu Lys Ala Leu Pro Gln
            340

<210> SEQ ID NO 122
<211> LENGTH: 366
<212> TYPE: PRT
<213> ORGANISM: Artificial Sequence
<220> FEATURE:
<223> OTHER INFORMATION: Amino acid sequence of PTP active domain T15

<400> SEQUENCE: 122

Met Ala Arg Glu Cys Gly Ala Gly Thr Phe Val Asn Phe Ala Ser Leu
1               5                   10                  15

Glu Arg Asp Gly Lys Leu Pro Tyr Asn Trp Arg Arg Ser Ile Phe Ala
            20                  25                  30

Phe Leu Thr Leu Leu Pro Ser Cys Leu Trp Thr Asp Tyr Leu Leu Ala
            35                  40                  45

Phe Tyr Ile Asn Pro Trp Ser Lys Asn Gly Leu Lys Lys Arg Lys Leu
            50                  55                  60

Thr Asn Pro Val Gln Leu Asp Asp Phe Asp Ala Tyr Ile Lys Asp Met
65                  70                  75                  80

Ala Lys Asp Ser Asp Tyr Lys Phe Ser Leu Gln Phe Glu Glu Leu Lys
            85                  90                  95

Leu Ile Gly Leu Asp Ile Pro His Phe Ala Ala Asp Leu Pro Leu Asn
            100                 105                 110

Arg Cys Lys Asn Arg Tyr Thr Asn Ile Leu Pro Tyr Asp Phe Ser Arg
            115                 120                 125

Val Arg Leu Val Ser Met Asn Glu Glu Glu Gly Ala Asp Tyr Ile Asn
            130                 135                 140

Ala Asn Tyr Ile Pro Gly Tyr Asn Ser Pro Gln Glu Tyr Ile Ala Thr
145                 150                 155                 160

Gln Gly Pro Leu Pro Glu Thr Arg Asn Asp Phe Trp Lys Met Val Leu
            165                 170                 175

Gln Gln Lys Ser Gln Ile Ile Val Met Leu Thr Gln Cys Asn Glu Lys
            180                 185                 190

```
Arg Arg Val Lys Cys Asp His Tyr Trp Pro Phe Thr Glu Glu Pro Ile
        195                 200                 205

Ala Tyr Gly Asp Ile Thr Val Glu Met Ile Ser Glu Glu Gln Asp
    210                 215                 220

Asp Trp Ala Cys Arg His Phe Arg Ile Asn Tyr Ala Asp Glu Met Gln
225                 230                 235                 240

Asp Val Met His Phe Asn Tyr Thr Ala Trp Pro Asp His Gly Val Pro
            245                 250                 255

Thr Ala Asn Ala Ala Glu Ser Ile Leu Gln Phe Val His Met Val Arg
                260                 265                 270

Gln Gln Ala Thr Lys Ser Lys Gly Pro Met Ile Ile His Cys Ser Ala
                275                 280                 285

Gly Val Gly Arg Thr Gly Thr Phe Ile Ala Leu Asp Arg Leu Leu Gln
    290                 295                 300

His Ile Arg Asp His Glu Phe Val Asp Ile Leu Gly Leu Val Ser Glu
305                 310                 315                 320

Met Arg Ser Tyr Arg Met Ser Met Val Gln Thr Glu Glu Gln Tyr Ile
                325                 330                 335

Phe Ile His Gln Cys Val Gln Leu Met Trp Met Lys Lys Gln Gln
            340                 345                 350

Phe Cys Ile Ser Asp Val Ile Tyr Glu Asn Val Ser Lys Ser
            355                 360                 365

<210> SEQ ID NO 123
<211> LENGTH: 322
<212> TYPE: PRT
<213> ORGANISM: Artificial Sequence
<220> FEATURE:
<223> OTHER INFORMATION: Amino acid sequence of PTP active domain T10

<400> SEQUENCE: 123

Met Lys Pro Ile Gly Leu Gln Glu Arg Arg Gly Ser Asn Val Ser Leu
1               5                   10                  15

Thr Leu Asp Met Ser Ser Leu Gly Asn Ile Glu Pro Phe Val Ser Ile
            20                  25                  30

Pro Thr Pro Arg Glu Lys Val Ala Met Glu Tyr Leu Gln Ser Ala Ser
        35                  40                  45

Arg Ile Leu Thr Arg Ser Gln Leu Arg Asp Val Val Ala Ser Ser His
    50                  55                  60

Leu Leu Gln Ser Glu Phe Met Glu Ile Pro Met Asn Phe Val Asp Pro
65                  70                  75                  80

Lys Glu Ile Asp Ile Pro Arg His Gly Thr Lys Asn Arg Tyr Lys Thr
                85                  90                  95

Ile Leu Pro Asn Pro Leu Ser Arg Val Cys Leu Arg Pro Lys Asn Val
            100                 105                 110

Thr Asp Ser Leu Ser Thr Tyr Ile Asn Ala Asn Tyr Ile Arg Gly Tyr
        115                 120                 125

Ser Gly Lys Glu Lys Ala Phe Ile Ala Thr Gln Gly Pro Met Ile Asn
    130                 135                 140

Thr Val Asp Asp Phe Trp Gln Met Val Trp Gln Glu Asp Ser Pro Val
145                 150                 155                 160

Ile Val Met Ile Thr Lys Leu Lys Glu Lys Asn Glu Lys Cys Val Leu
                165                 170                 175

Tyr Trp Pro Glu Lys Arg Gly Ile Tyr Gly Lys Val Glu Val Leu Val
            180                 185                 190

Ile Ser Val Asn Glu Cys Asp Asn Tyr Thr Ile Arg Asn Leu Val Leu
```

```
              195                 200                 205
Lys Gln Gly Ser His Thr Gln His Val Lys His Tyr Trp Tyr Thr Ser
    210                 215                 220

Trp Pro Asp His Lys Thr Pro Asp Ser Ala Gln Pro Leu Leu Gln Leu
225                 230                 235                 240

Met Leu Asp Val Glu Glu Asp Arg Leu Ala Ser Gln Gly Arg Gly Pro
                245                 250                 255

Val Val Val His Cys Ser Ala Gly Ile Gly Arg Thr Gly Cys Phe Ile
                260                 265                 270

Ala Thr Ser Ile Gly Cys Gln Gln Leu Lys Glu Glu Gly Val Val Asp
            275                 280                 285

Ala Leu Ser Ile Val Cys Gln Leu Arg Met Asp Arg Gly Gly Met Val
            290                 295                 300

Gln Thr Ser Glu Gln Tyr Glu Phe Val His His Ala Leu Cys Leu Tyr
305                 310                 315                 320

Glu Ser

<210> SEQ ID NO 124
<211> LENGTH: 284
<212> TYPE: PRT
<213> ORGANISM: Artificial Sequence
<220> FEATURE:
<223> OTHER INFORMATION: Amino acid sequence of PTP active domain T22

<400> SEQUENCE: 124

Met Leu Ser His Pro Pro Ile Pro Ile Ala Asp Met Ala Glu His Thr
1               5                   10                  15

Glu Arg Leu Lys Ala Asn Asp Ser Leu Lys Leu Ser Gln Glu Tyr Glu
                20                  25                  30

Ser Ile Asp Pro Gly Gln Gln Phe Thr Trp Glu His Ser Asn Leu Glu
            35                  40                  45

Val Asn Lys Pro Lys Asn Arg Tyr Ala Asn Val Ile Ala Tyr Asp His
        50                  55                  60

Ser Arg Val Ile Leu Gln Pro Ile Glu Gly Ile Met Gly Ser Asp Tyr
65                  70                  75                  80

Ile Asn Ala Asn Tyr Val Asp Gly Tyr Arg Arg Gln Asn Ala Tyr Ile
                85                  90                  95

Ala Thr Gln Gly Pro Leu Pro Glu Thr Phe Gly Asp Phe Trp Arg Met
            100                 105                 110

Val Trp Glu Gln Arg Ser Ala Thr Ile Val Met Met Thr Arg Leu Glu
        115                 120                 125

Glu Lys Ser Arg Ile Lys Cys Asp Gln Tyr Trp Pro Asn Arg Gly Thr
130                 135                 140

Glu Thr Tyr Gly Phe Ile Gln Val Thr Leu Leu Asp Thr Ile Glu Leu
145                 150                 155                 160

Ala Thr Phe Cys Val Arg Thr Phe Ser Leu His Lys Asn Gly Ser Ser
                165                 170                 175

Glu Lys Arg Glu Val Arg Gln Phe Gln Phe Thr Ala Trp Pro Asp His
            180                 185                 190

Gly Val Pro Glu Tyr Pro Thr Pro Phe Leu Ala Phe Leu Arg Arg Val
        195                 200                 205

Lys Thr Cys Asn Pro Pro Asp Ala Gly Pro Ile Val Val His Cys Ser
    210                 215                 220

Ala Gly Val Gly Arg Thr Gly Cys Phe Ile Val Ile Asp Ala Met Leu
225                 230                 235                 240
```

```
Glu Arg Ile Lys Pro Glu Lys Thr Val Asp Val Tyr Gly His Val Thr
                245                 250                 255

Leu Met Arg Ser Gln Arg Asn Tyr Met Val Gln Thr Glu Asp Gln Tyr
            260                 265                 270

Ser Phe Ile His Glu Ala Leu Leu Glu Ala Val Gly
        275                 280
```

<210> SEQ ID NO 125
<211> LENGTH: 291
<212> TYPE: PRT
<213> ORGANISM: Artificial Sequence
<220> FEATURE:
<223> OTHER INFORMATION: Amino acid sequence of PTP active domain T20

<400> SEQUENCE: 125

```
Ala Ile Arg Val Ala Asp Leu Leu Gln His Ile Thr Gln Met Lys Arg
1               5                   10                  15

Gly Gln Gly Tyr Gly Phe Lys Glu Glu Tyr Glu Ala Leu Pro Glu Gly
            20                  25                  30

Gln Thr Ala Ser Trp Asp Thr Ala Lys Glu Asp Glu Asn Arg Asn Lys
        35                  40                  45

Asn Arg Tyr Gly Asn Ile Ile Ser Tyr Asp His Ser Arg Val Arg Leu
50                  55                  60

Leu Val Leu Asp Gly Asp Pro His Ser Asp Tyr Ile Asn Ala Asn Tyr
65                  70                  75                  80

Ile Asp Gly Tyr His Arg Pro Arg His Tyr Ile Ala Thr Gln Gly Pro
                85                  90                  95

Met Gln Glu Thr Val Lys Asp Phe Trp Arg Met Ile Trp Gln Glu Asn
            100                 105                 110

Ser Ala Ser Ile Val Met Val Thr Asn Leu Val Glu Val Gly Arg Val
        115                 120                 125

Lys Cys Val Arg Tyr Trp Pro Asp Asp Thr Glu Val Tyr Gly Asp Ile
130                 135                 140

Lys Val Thr Leu Ile Glu Thr Glu Pro Leu Ala Glu Tyr Val Ile Arg
145                 150                 155                 160

Thr Phe Thr Val Gln Lys Lys Gly Tyr His Glu Ile Arg Glu Leu Arg
                165                 170                 175

Leu Phe His Phe Thr Ser Trp Pro Asp His Gly Val Pro Cys Tyr Ala
            180                 185                 190

Thr Gly Leu Leu Gly Phe Val Arg Gln Val Lys Phe Leu Asn Pro Pro
        195                 200                 205

Glu Ala Gly Pro Ile Val Val His Cys Ser Ala Gly Ala Gly Arg Thr
210                 215                 220

Gly Cys Phe Ile Ala Ile Asp Thr Met Leu Asp Met Ala Glu Asn Glu
225                 230                 235                 240

Gly Val Val Asp Ile Phe Asn Cys Val Arg Glu Leu Arg Ala Gln Arg
                245                 250                 255

Val Asn Leu Val Gln Thr Glu Glu Gln Tyr Val Phe Val His Asp Ala
            260                 265                 270

Ile Leu Glu Ala Cys Leu Cys Gly Asn Thr Ala Ile Pro Val Cys Glu
        275                 280                 285

Phe Arg Ser
    290
```

<210> SEQ ID NO 126
<211> LENGTH: 299
<212> TYPE: PRT

<213> ORGANISM: Artificial Sequence
<220> FEATURE:
<223> OTHER INFORMATION: Amino acid sequence of PTP active domain PTP1B

<400> SEQUENCE: 126

Met Glu Met Glu Lys Glu Phe Glu Gln Ile Asp Lys Ser Gly Ser Trp
1               5                   10                  15

Ala Ala Ile Tyr Gln Asp Ile Arg His Glu Ala Ser Asp Phe Pro Cys
            20                  25                  30

Arg Val Ala Lys Leu Pro Lys Asn Lys Asn Arg Asn Arg Tyr Arg Asp
        35                  40                  45

Val Ser Pro Phe Asp His Ser Arg Ile Lys Leu His Gln Glu Asp Asn
    50                  55                  60

Asp Tyr Ile Asn Ala Ser Leu Ile Lys Met Glu Glu Ala Gln Arg Ser
65                  70                  75                  80

Tyr Ile Leu Thr Gln Gly Pro Leu Pro Asn Thr Cys Gly His Phe Trp
                85                  90                  95

Glu Met Val Trp Glu Gln Lys Ser Arg Gly Val Val Met Leu Asn Arg
            100                 105                 110

Val Met Glu Lys Gly Ser Leu Lys Cys Ala Gln Tyr Trp Pro Gln Lys
        115                 120                 125

Glu Glu Lys Glu Met Ile Phe Glu Asp Thr Asn Leu Lys Leu Thr Leu
    130                 135                 140

Ile Ser Glu Asp Ile Lys Ser Tyr Tyr Thr Val Arg Gln Leu Glu Leu
145                 150                 155                 160

Glu Asn Leu Thr Thr Gln Glu Thr Arg Glu Ile Leu His Phe His Tyr
                165                 170                 175

Thr Thr Trp Pro Asp Phe Gly Val Pro Glu Ser Pro Ala Ser Phe Leu
            180                 185                 190

Asn Phe Leu Phe Lys Val Arg Glu Ser Gly Ser Leu Ser Pro Glu His
        195                 200                 205

Gly Pro Val Val Val His Cys Ser Ala Gly Ile Gly Arg Ser Gly Thr
    210                 215                 220

Phe Cys Leu Ala Asp Thr Cys Leu Leu Leu Met Asp Lys Arg Lys Asp
225                 230                 235                 240

Pro Ser Ser Val Asp Ile Lys Lys Val Leu Leu Glu Met Arg Lys Phe
                245                 250                 255

Arg Met Gly Leu Ile Gln Thr Ala Asp Gln Leu Arg Phe Ser Tyr Leu
            260                 265                 270

Ala Val Ile Glu Gly Ala Lys Phe Ile Met Gly Asp Ser Ser Val Gln
        275                 280                 285

Asp Gln Trp Lys Glu Leu Ser His Glu Asp Leu
    290                 295

<210> SEQ ID NO 127
<211> LENGTH: 387
<212> TYPE: PRT
<213> ORGANISM: Artificial Sequence
<220> FEATURE:
<223> OTHER INFORMATION: Amino acid sequence of PTP active domain T25

<400> SEQUENCE: 127

Met Pro Thr Thr Ile Glu Arg Glu Phe Glu Glu Leu Asp Thr Gln Arg
1               5                   10                  15

Arg Trp Gln Pro Leu Tyr Leu Glu Ile Arg Asn Glu Ser His Asp Tyr
            20                  25                  30

Pro His Arg Val Ala Lys Phe Pro Glu Asn Arg Asn Arg Asn Arg Tyr

-continued

```
                35                  40                  45
Arg Asp Val Ser Pro Tyr Asp His Ser Arg Val Lys Leu Gln Asn Ala
 50                  55                  60
Glu Asn Asp Tyr Ile Asn Ala Ser Leu Val Asp Ile Glu Glu Ala Gln
 65                  70                  75                  80
Arg Ser Tyr Ile Leu Thr Gln Gly Pro Leu Pro Asn Thr Cys Cys His
                 85                  90                  95
Phe Trp Leu Met Val Trp Gln Gln Lys Thr Lys Ala Val Val Met Leu
                100                 105                 110
Asn Arg Ile Val Glu Lys Glu Ser Val Lys Cys Ala Gln Tyr Trp Pro
                115                 120                 125
Thr Asp Asp Gln Glu Met Leu Phe Lys Glu Thr Gly Phe Ser Val Lys
130                 135                 140
Leu Leu Ser Glu Asp Val Lys Ser Tyr Tyr Thr Val His Leu Leu Gln
145                 150                 155                 160
Leu Glu Asn Ile Asn Ser Gly Glu Thr Arg Thr Ile Ser His Phe His
                165                 170                 175
Tyr Thr Thr Trp Pro Asp Phe Gly Val Pro Glu Ser Pro Ala Ser Phe
                180                 185                 190
Leu Asn Phe Leu Phe Lys Val Arg Glu Ser Gly Ser Leu Asn Pro Asp
                195                 200                 205
His Gly Pro Ala Val Ile His Cys Ser Ala Gly Ile Gly Arg Ser Gly
                210                 215                 220
Thr Phe Ser Leu Val Asp Thr Cys Leu Val Leu Met Glu Lys Gly Asp
225                 230                 235                 240
Asp Ile Asn Ile Lys Gln Val Leu Leu Asn Met Arg Lys Tyr Arg Met
                245                 250                 255
Gly Leu Ile Gln Thr Pro Asp Gln Leu Arg Phe Ser Tyr Met Ala Ile
                260                 265                 270
Ile Glu Gly Ala Lys Cys Ile Lys Gly Asp Ser Ser Ile Gln Lys Arg
                275                 280                 285
Trp Lys Glu Leu Ser Lys Glu Asp Leu Ser Pro Ala Phe Asp His Ser
                290                 295                 300
Pro Asn Lys Ile Met Thr Glu Lys Tyr Asn Gly Asn Arg Ile Gly Leu
305                 310                 315                 320
Glu Glu Glu Lys Leu Thr Gly Asp Arg Cys Thr Gly Leu Ser Ser Lys
                325                 330                 335
Met Gln Asp Thr Met Glu Glu Asn Ser Glu Ser Ala Leu Arg Lys Arg
                340                 345                 350
Ile Arg Glu Asp Arg Lys Ala Thr Thr Ala Gln Lys Val Gln Gln Met
                355                 360                 365
Lys Gln Arg Leu Asn Glu Asn Glu Arg Lys Arg Lys Arg Pro Arg Leu
                370                 375                 380
Thr Asp Thr
385

<210> SEQ ID NO 128
<211> LENGTH: 381
<212> TYPE: PRT
<213> ORGANISM: Artificial Sequence
<220> FEATURE:
<223> OTHER INFORMATION: Amino acid sequence of PTP active domain T41

<400> SEQUENCE: 128

Val Ser Arg Gln Pro Ser Phe Thr Tyr Ser Glu Trp Met Glu Glu Lys
 1               5                  10                  15
```

```
Ile Glu Asp Asp Phe Leu Asp Leu Asp Pro Val Pro Glu Thr Pro Val
             20                  25                  30

Phe Asp Cys Val Met Asp Ile Lys Pro Glu Ala Asp Pro Thr Ser Leu
             35                  40                  45

Thr Val Lys Ser Met Gly Leu Gln Glu Arg Arg Gly Ser Asn Val Ser
 50                  55                  60

Leu Thr Leu Asp Met Cys Thr Pro Gly Cys Asn Glu Glu Gly Phe Gly
 65                  70                  75                  80

Tyr Leu Met Ser Pro Arg Glu Glu Ser Ala Arg Glu Tyr Leu Leu Ser
                 85                  90                  95

Ala Ser Arg Val Leu Gln Ala Glu Glu Leu His Glu Lys Ala Leu Asp
                100                 105                 110

Pro Phe Leu Leu Gln Ala Glu Phe Phe Glu Ile Pro Met Asn Phe Val
            115                 120                 125

Val Pro Lys Glu Tyr Asp Ile Pro Gly Arg Cys Arg Lys Asn Arg Tyr
130                 135                 140

Lys Thr Ile Leu Pro Asn Pro His Ser Arg Val Cys Leu Thr Ser Pro
145                 150                 155                 160

Asp Pro Asp Asp Pro Leu Ser Ser Tyr Ile Asn Ala Asn Tyr Ile Arg
                165                 170                 175

Gly Tyr Gly Gly Glu Glu Lys Val Tyr Ile Ala Thr Gln Gly Pro Ile
            180                 185                 190

Val Ser Thr Val Ala Asp Phe Trp Arg Met Val Trp Gln Glu His Thr
            195                 200                 205

Pro Ile Ile Val Met Ile Thr Asn Ile Glu Glu Met Asn Glu Lys Cys
210                 215                 220

Thr Glu Tyr Trp Pro Glu Glu Gln Val Ala Tyr Asp Gly Val Glu Ile
225                 230                 235                 240

Thr Val Gln Lys Val Ile His Thr Glu Asp Tyr Arg Leu Arg Leu Ile
                245                 250                 255

Ser Leu Lys Ser Gly Thr Glu Glu Arg Gly Leu Lys His Tyr Trp Phe
            260                 265                 270

Thr Ser Trp Pro Asp Gln Lys Thr Pro Asp Arg Ala Pro Pro Leu Leu
            275                 280                 285

His Leu Val Arg Glu Val Glu Glu Ala Ala Gln Gln Glu Gly Pro His
290                 295                 300

Cys Ala Pro Ile Ile Val His Cys Ser Ala Gly Ile Gly Arg Thr Gly
305                 310                 315                 320

Cys Phe Ile Ala Thr Ser Ile Cys Cys Gln Gln Leu Arg Gln Glu Gly
                325                 330                 335

Val Val Asp Ile Leu Lys Thr Thr Cys Gln Leu Arg Gln Asp Arg Gly
            340                 345                 350

Gly Met Ile Gln His Cys Glu Gln Tyr Gln Phe Val His His Val Met
            355                 360                 365

Ser Leu Tyr Glu Lys Gln Leu Ser His Gln Ser Pro Glu
    370                 375                 380

<210> SEQ ID NO 129
<211> LENGTH: 595
<212> TYPE: PRT
<213> ORGANISM: Artificial Sequence
<220> FEATURE:
<223> OTHER INFORMATION: Amino acid sequence of PTP active domain T18

<400> SEQUENCE: 129
```

-continued

```
Met Val Arg Trp Phe His Arg Asp Leu Ser Gly Leu Asp Ala Glu Thr
1               5                   10                  15

Leu Leu Lys Gly Arg Gly Val His Gly Ser Phe Leu Ala Arg Pro Ser
            20                  25                  30

Arg Lys Asn Gln Gly Asp Phe Ser Leu Ser Val Arg Val Gly Asp Gln
        35                  40                  45

Val Thr His Ile Arg Ile Gln Asn Ser Gly Asp Phe Tyr Asp Leu Tyr
    50                  55                  60

Gly Gly Glu Lys Phe Ala Thr Leu Thr Glu Leu Val Glu Tyr Tyr Thr
65                  70                  75                  80

Gln Gln Gln Gly Val Leu Gln Asp Arg Asp Gly Thr Ile Ile His Leu
                85                  90                  95

Lys Tyr Pro Leu Asn Cys Ser Asp Pro Thr Ser Glu Arg Trp Tyr His
                100                 105                 110

Gly His Met Ser Gly Gly Gln Ala Glu Thr Leu Leu Gln Ala Lys Gly
            115                 120                 125

Glu Pro Trp Thr Phe Leu Val Arg Glu Ser Leu Ser Gln Pro Gly Asp
        130                 135                 140

Phe Val Leu Ser Val Leu Ser Asp Gln Pro Lys Ala Gly Pro Gly Ser
145                 150                 155                 160

Pro Leu Arg Val Thr His Ile Lys Val Met Cys Glu Gly Gly Arg Tyr
                165                 170                 175

Thr Val Gly Gly Leu Glu Thr Phe Asp Ser Leu Thr Asp Leu Val Glu
            180                 185                 190

His Phe Lys Lys Thr Gly Ile Glu Glu Ala Ser Gly Ala Phe Val Tyr
        195                 200                 205

Leu Arg Gln Pro Tyr Tyr Ala Thr Arg Val Asn Ala Ala Asp Ile Glu
    210                 215                 220

Asn Arg Val Leu Glu Leu Asn Lys Lys Gln Glu Ser Glu Asp Thr Ala
225                 230                 235                 240

Lys Ala Gly Phe Trp Glu Glu Phe Glu Ser Leu Gln Lys Gln Glu Val
                245                 250                 255

Lys Asn Leu His Gln Arg Leu Glu Gly Gln Arg Pro Asp Asn Lys Gly
            260                 265                 270

Lys Asn Arg Tyr Lys Asn Ile Leu Pro Phe Asp His Ser Arg Val Ile
        275                 280                 285

Leu Gln Gly Arg Asp Ser Asn Ile Pro Gly Ser Asp Tyr Ile Asn Ala
    290                 295                 300

Asn Tyr Ile Lys Asn Gln Leu Leu Gly Pro Asp Glu Asn Ala Lys Thr
305                 310                 315                 320

Tyr Ile Ala Ser Gln Gly Cys Leu Glu Ala Thr Val Asn Asp Phe Trp
                325                 330                 335

Gln Met Ala Trp Gln Glu Asn Ser Arg Val Ile Val Met Thr Thr Arg
            340                 345                 350

Glu Val Glu Lys Gly Arg Asn Lys Cys Val Pro Tyr Trp Pro Glu Val
        355                 360                 365

Gly Met Gln Arg Ala Tyr Gly Pro Tyr Ser Val Thr Asn Cys Gly Glu
    370                 375                 380

His Asp Thr Thr Glu Tyr Lys Leu Arg Thr Leu Gln Val Ser Pro Leu
385                 390                 395                 400

Asp Asn Gly Asp Leu Ile Arg Glu Ile Trp His Tyr Gln Tyr Leu Ser
                405                 410                 415

Trp Pro Asp His Gly Val Pro Ser Glu Pro Gly Gly Val Leu Ser Phe
            420                 425                 430
```

```
Leu Asp Gln Ile Asn Gln Arg Gln Glu Ser Leu Pro His Ala Gly Pro
            435                 440                 445

Ile Ile Val His Cys Ser Ala Gly Ile Gly Arg Thr Gly Thr Ile Ile
    450                 455                 460

Val Ile Asp Met Leu Met Glu Asn Ile Ser Thr Lys Gly Leu Asp Cys
465                 470                 475                 480

Asp Ile Asp Ile Gln Lys Thr Ile Gln Met Val Arg Ala Gln Arg Ser
                485                 490                 495

Gly Met Val Gln Thr Glu Ala Gln Tyr Lys Phe Ile Tyr Val Ala Ile
                500                 505                 510

Ala Gln Phe Ile Glu Thr Thr Lys Lys Leu Glu Val Leu Gln Ser
            515                 520                 525

Gln Lys Gly Gln Glu Ser Glu Tyr Gly Asn Ile Thr Tyr Pro Pro Ala
            530                 535                 540

Met Lys Asn Ala His Ala Lys Ala Ser Arg Thr Ser Ser Lys His Lys
545                 550                 555                 560

Glu Asp Val Tyr Glu Asn Leu His Thr Lys Asn Lys Arg Glu Glu Lys
                565                 570                 575

Val Lys Lys Gln Arg Ser Ala Asp Lys Glu Lys Ser Lys Gly Ser Leu
            580                 585                 590

Lys Arg Lys
    595
```

<210> SEQ ID NO 130
<211> LENGTH: 298
<212> TYPE: PRT
<213> ORGANISM: Artificial Sequence
<220> FEATURE:
<223> OTHER INFORMATION: Amino acid sequence of PTP active domain pk32

<400> SEQUENCE: 130

```
Gln Pro Pro Pro Glu Lys Thr Pro Ala Lys His Val Arg Leu Gln
1               5                   10                  15

Glu Arg Arg Gly Ser Asn Val Ala Leu Met Leu Asp Val Arg Ser Leu
                20                  25                  30

Gly Ala Val Glu Pro Ile Cys Ser Val Asn Thr Pro Arg Glu Val Thr
            35                  40                  45

Leu His Phe Leu Arg Thr Ala Gly His Pro Leu Thr Arg Trp Ala Leu
    50                  55                  60

Gln Arg Gln Pro Pro Ser Pro Lys Gln Leu Glu Glu Phe Leu Lys
65                  70                  75                  80

Ile Pro Ser Asn Phe Val Ser Pro Glu Asp Leu Asp Ile Pro Gly His
                85                  90                  95

Ala Ser Lys Asp Arg Tyr Lys Thr Ile Leu Pro Asn Pro Gln Ser Arg
                100                 105                 110

Val Cys Leu Gly Arg Ala Gln Ser Gln Glu Asp Gly Asp Tyr Ile Asn
            115                 120                 125

Ala Asn Tyr Ile Arg Gly Tyr Asp Gly Lys Glu Lys Val Tyr Ile Ala
    130                 135                 140

Thr Gln Gly Pro Met Pro Asn Thr Val Ser Asp Phe Trp Glu Met Val
145                 150                 155                 160

Trp Gln Glu Glu Val Ser Leu Ile Val Met Leu Thr Gln Leu Arg Glu
                165                 170                 175

Gly Lys Glu Lys Cys Val His Tyr Trp Pro Thr Glu Glu Thr Tyr
            180                 185                 190
```

```
Gly Pro Phe Gln Ile Arg Ile Gln Asp Met Lys Glu Cys Pro Glu Tyr
            195                 200                 205

Thr Val Arg Gln Leu Thr Ile Gln Tyr Gln Glu Glu Arg Arg Ser Val
    210                 215                 220

Lys His Ile Leu Phe Ser Ala Trp Pro Asp His Gln Thr Pro Glu Ser
225                 230                 235                 240

Ala Gly Pro Leu Leu Arg Leu Val Ala Glu Val Glu Glu Ser Pro Glu
                245                 250                 255

Thr Ala Ala His Pro Gly Pro Ile Val Val His Cys Ser Ala Gly Ile
                260                 265                 270

Gly Arg Thr Gly Cys Phe Ile Ala Thr Arg Ile Gly Cys Gln Gln Leu
            275                 280                 285

Lys Ala Arg Gly Glu Val Asp Ile Leu Gly
    290                 295

<210> SEQ ID NO 131
<211> LENGTH: 526
<212> TYPE: PRT
<213> ORGANISM: Artificial Sequence
<220> FEATURE:
<223> OTHER INFORMATION: Amino acid sequence of PTP active domain pk28

<400> SEQUENCE: 131

Met Thr Ser Arg Arg Trp Phe His Pro Asn Ile Thr Gly Val Glu Ala
1               5                   10                  15

Glu Asn Leu Leu Leu Thr Arg Gly Val Asp Gly Ser Phe Leu Ala Arg
                20                  25                  30

Pro Ser Lys Ser Asn Pro Gly Asp Phe Thr Leu Ser Val Arg Arg Asn
            35                  40                  45

Gly Ala Val Thr His Ile Lys Ile Gln Asn Thr Gly Asp Tyr Tyr Asp
    50                  55                  60

Leu Tyr Gly Gly Glu Lys Phe Ala Thr Leu Ala Glu Leu Val Gln Tyr
65                  70                  75                  80

Tyr Met Glu His His Gly Gln Leu Lys Glu Lys Asn Gly Asp Val Ile
                85                  90                  95

Glu Leu Lys Tyr Pro Leu Asn Cys Ala Asp Pro Thr Ser Glu Arg Trp
            100                 105                 110

Phe His Gly His Leu Ser Gly Lys Glu Ala Glu Lys Leu Leu Thr Glu
        115                 120                 125

Lys Gly Lys His Gly Ser Phe Leu Val Arg Glu Ser Gln Ser His Pro
130                 135                 140

Gly Asp Phe Val Leu Ser Val Arg Thr Gly Asp Asp Lys Gly Glu Ser
145                 150                 155                 160

Asn Asp Gly Lys Ser Lys Val Thr His Val Met Ile Arg Cys Gln Glu
                165                 170                 175

Leu Lys Tyr Asp Val Gly Gly Gly Glu Arg Phe Asp Ser Leu Thr Asp
            180                 185                 190

Leu Val Glu His Tyr Lys Lys Asn Pro Met Val Glu Thr Leu Gly Thr
        195                 200                 205

Val Leu Gln Leu Lys Gln Pro Leu Asn Thr Thr Arg Ile Asn Ala Ala
    210                 215                 220

Glu Ile Glu Ser Arg Val Arg Glu Leu Ser Lys Leu Ala Glu Thr Thr
225                 230                 235                 240

Asp Lys Val Lys Gln Gly Phe Trp Glu Glu Phe Glu Thr Leu Gln Gln
                245                 250                 255

Gln Glu Cys Lys Leu Leu Tyr Ser Arg Lys Glu Gly Gln Arg Gln Glu
```

```
                   260                 265                 270
Asn Lys Asn Lys Asn Arg Tyr Lys Asn Ile Leu Pro Phe Asp His Thr
            275                 280                 285

Arg Val Val Leu His Asp Gly Asp Pro Asn Glu Pro Val Ser Asp Tyr
        290                 295                 300

Ile Asn Ala Asn Ile Ile Met Pro Glu Phe Glu Thr Lys Cys Asn Asn
305                 310                 315                 320

Ser Lys Pro Lys Lys Ser Tyr Ile Ala Thr Gln Gly Cys Leu Gln Asn
            325                 330                 335

Thr Val Asn Asp Phe Trp Arg Met Val Phe Gln Glu Asn Ser Arg Val
        340                 345                 350

Ile Val Met Thr Thr Lys Glu Val Glu Arg Gly Lys Ser Lys Cys Val
            355                 360                 365

Lys Tyr Trp Pro Asp Glu Tyr Ala Leu Lys Glu Tyr Gly Val Met Arg
        370                 375                 380

Val Arg Asn Val Lys Glu Ser Ala Ala His Asp Tyr Thr Leu Arg Glu
385                 390                 395                 400

Leu Lys Leu Ser Lys Val Gly Gln Gly Asn Thr Glu Arg Thr Val Trp
            405                 410                 415

Gln Tyr His Phe Arg Thr Trp Pro Asp His Gly Val Pro Ser Asp Pro
        420                 425                 430

Gly Gly Val Leu Asp Phe Leu Glu Glu Val His His Lys Gln Glu Ser
            435                 440                 445

Ile Met Asp Ala Gly Pro Val Val His Cys Ser Ala Gly Ile Gly
        450                 455                 460

Arg Thr Gly Thr Phe Ile Val Ile Asp Ile Leu Ile Asp Ile Ile Arg
465                 470                 475                 480

Glu Lys Gly Val Asp Cys Asp Ile Asp Val Pro Lys Thr Ile Gln Met
            485                 490                 495

Val Arg Ser Gln Arg Ser Gly Met Val Gln Thr Glu Ala Gln Tyr Arg
        500                 505                 510

Phe Ile Tyr Met Ala Val Gln His Tyr Ile Glu Thr Leu Gln
        515                 520                 525

<210> SEQ ID NO 132
<211> LENGTH: 396
<212> TYPE: PRT
<213> ORGANISM: Artificial Sequence
<220> FEATURE:
<223> OTHER INFORMATION: Amino acid sequence of PTP active domain T32

<400> SEQUENCE: 132

Met Asn Gly Lys Leu Ser Glu Glu Arg Thr Glu Asp Thr Asp Cys Asp
1               5                   10                  15

Gly Ser Pro Leu Pro Glu Tyr Phe Thr Glu Ala Thr Lys Met Asn Gly
            20                  25                  30

Cys Glu Glu Tyr Cys Glu Glu Lys Val Lys Ser Glu Ser Leu Ile Gln
        35                  40                  45

Lys Pro Gln Glu Lys Lys Thr Asp Asp Glu Ile Thr Trp Gly Asn
    50                  55                  60

Asp Glu Leu Pro Ile Glu Arg Thr Asn His Glu Asp Ser Asp Lys Asp
65                  70                  75                  80

His Ser Phe Leu Thr Asn Asp Glu Leu Ala Val Leu Pro Val Val Lys
                85                  90                  95

Val Leu Pro Ser Gly Lys Tyr Thr Gly Ala Asn Leu Lys Ser Val Ile
            100                 105                 110
```

```
Arg Val Leu Arg Gly Leu Leu Asp Gln Gly Ile Pro Ser Lys Glu Leu
        115                 120                 125

Glu Asn Leu Gln Glu Leu Lys Pro Leu Asp Gln Cys Leu Ile Gly Gln
        130                 135                 140

Thr Lys Glu Asn Arg Arg Lys Asn Arg Tyr Lys Asn Ile Leu Pro Tyr
145                 150                 155                 160

Asp Ala Thr Arg Val Pro Leu Gly Asp Glu Gly Gly Tyr Ile Asn Ala
                165                 170                 175

Ser Phe Ile Lys Ile Pro Val Gly Lys Glu Glu Phe Val Tyr Ile Ala
                180                 185                 190

Cys Gln Gly Pro Leu Pro Thr Thr Val Gly Asp Phe Trp Gln Met Ile
        195                 200                 205

Trp Glu Gln Lys Ser Thr Val Ile Ala Met Met Thr Gln Glu Val Glu
        210                 215                 220

Gly Glu Lys Ile Lys Cys Gln Arg Tyr Trp Pro Asn Ile Leu Gly Lys
225                 230                 235                 240

Thr Thr Met Val Ser Asn Arg Leu Arg Leu Ala Leu Val Arg Met Gln
                245                 250                 255

Gln Leu Lys Gly Phe Val Val Arg Ala Met Thr Leu Glu Asp Ile Gln
        260                 265                 270

Thr Arg Glu Val Arg His Ile Ser His Leu Asn Phe Thr Ala Trp Pro
        275                 280                 285

Asp His Asp Thr Pro Ser Gln Pro Asp Asp Leu Leu Thr Phe Ile Ser
        290                 295                 300

Tyr Met Arg His Ile His Arg Ser Gly Pro Ile Ile Thr His Cys Ser
305                 310                 315                 320

Ala Gly Ile Gly Arg Ser Gly Thr Leu Ile Cys Ile Asp Val Val Leu
                325                 330                 335

Gly Leu Ile Ser Gln Asp Leu Asp Phe Asp Ile Ser Asp Leu Val Arg
        340                 345                 350

Cys Met Arg Leu Gln Arg His Gly Met Val Gln Thr Glu Asp Gln Tyr
        355                 360                 365

Ile Phe Cys Tyr Gln Val Ile Leu Tyr Val Leu Thr Arg Leu Gln Ala
        370                 375                 380

Glu Glu Glu Gln Lys Gln Gln Pro Gln Leu Leu Lys
385                 390                 395

<210> SEQ ID NO 133
<211> LENGTH: 322
<212> TYPE: PRT
<213> ORGANISM: Artificial Sequence
<220> FEATURE:
<223> OTHER INFORMATION: Amino acid sequence of PTP active domain T40

<400> SEQUENCE: 133

Met Leu Ala Ala Leu Asn Gly Leu Ser Val Ala Arg Val Ser Gly Arg
1               5                   10                  15

Glu Glu Asn Arg Val Asp Ala Thr Arg Val Pro Met Asp Glu Arg Phe
                20                  25                  30

Arg Thr Leu Lys Lys Lys Leu Glu Glu Gly Met Val Phe Thr Glu Tyr
        35                  40                  45

Glu Gln Ile Pro Lys Lys Lys Ala Asn Gly Ile Phe Ser Thr Ala Ala
        50                  55                  60

Leu Pro Glu Asn Ala Glu Arg Ser Arg Ile Arg Glu Val Val Pro Tyr
65                  70                  75                  80
```

```
Glu Glu Asn Arg Val Glu Leu Ile Pro Thr Lys Glu Asn Asn Thr Gly
            85                  90                  95

Tyr Ile Asn Ala Ser His Ile Lys Val Val Gly Ala Glu Trp
            100                 105                 110

His Tyr Ile Ala Thr Gln Gly Pro Leu Pro His Thr Cys His Asp Phe
            115                 120                 125

Trp Gln Met Val Trp Glu Gln Gly Val Asn Val Ile Ala Met Val Thr
        130                 135                 140

Ala Glu Glu Glu Gly Gly Arg Thr Lys Ser His Arg Tyr Trp Pro Lys
145                 150                 155                 160

Leu Gly Ser Lys His Ser Ser Ala Thr Tyr Gly Lys Phe Lys Val Thr
                165                 170                 175

Thr Lys Phe Arg Thr Asp Ser Val Cys Tyr Ala Thr Thr Gly Leu Lys
            180                 185                 190

Val Lys His Leu Leu Ser Gly Gln Glu Arg Thr Val Trp His Leu Gln
            195                 200                 205

Tyr Thr Asp Trp Pro Asp His Gly Cys Pro Glu Asp Val Gln Gly Phe
        210                 215                 220

Leu Ser Tyr Leu Glu Glu Ile Gln Ser Val Arg Arg His Thr Asn Ser
225                 230                 235                 240

Met Leu Glu Gly Thr Lys Asn Arg His Pro Pro Ile Val Val His Cys
            245                 250                 255

Ser Ala Gly Val Gly Arg Thr Gly Val Leu Ile Leu Ser Glu Leu Met
            260                 265                 270

Ile Tyr Cys Leu Glu His Asn Glu Lys Val Glu Val Pro Met Met Leu
            275                 280                 285

Arg Leu Leu Arg Glu Gln Arg Met Phe Met Ile Gln Thr Ile Ala Gln
290                 295                 300

Tyr Lys Phe Val Tyr Gln Val Leu Ile Gln Phe Leu Gln Asn Ser Arg
305                 310                 315                 320

Leu Ile

<210> SEQ ID NO 134
<211> LENGTH: 336
<212> TYPE: PRT
<213> ORGANISM: Artificial Sequence
<220> FEATURE:
<223> OTHER INFORMATION: Amino acid sequence of PTP active domain T2

<400> SEQUENCE: 134

Met Lys Lys Thr Arg Val Asp Ala Lys Lys Ile Gly Pro Leu Lys Leu
1               5                   10                  15

Ala Ala Leu Asn Gly Leu Ser Leu Ser Arg Val Pro Leu Pro Asp Glu
            20                  25                  30

Gly Lys Glu Val Ala Thr Arg Ala Thr Asn Asp Glu Arg Cys Lys Ile
            35                  40                  45

Leu Glu Gln Arg Leu Glu Gln Gly Met Val Phe Thr Glu Tyr Glu Arg
        50                  55                  60

Ile Leu Lys Lys Arg Leu Val Asp Gly Glu Cys Ser Thr Ala Arg Leu
65                  70                  75                  80

Pro Glu Asn Ala Glu Arg Asn Arg Phe Gln Asp Val Leu Pro Tyr Asp
            85                  90                  95

Asp Val Arg Val Glu Leu Val Pro Thr Lys Glu Asn Asn Thr Gly Tyr
            100                 105                 110

Ile Asn Ala Ser His Ile Lys Val Ser Val Ser Gly Ile Glu Trp Asp
            115                 120                 125
```

```
Tyr Ile Ala Thr Gln Gly Pro Leu Gln Asn Thr Cys Gln Asp Phe Trp
        130                 135                 140

Gln Met Val Trp Glu Gln Gly Ile Ala Ile Ala Met Val Thr Ala
145                 150                 155                 160

Glu Glu Glu Gly Gly Arg Glu Lys Ser Phe Arg Tyr Trp Pro Arg Leu
                165                 170                 175

Gly Ser Arg His Asn Thr Val Thr Tyr Gly Arg Phe Lys Ile Thr Thr
            180                 185                 190

Arg Phe Arg Thr Asp Ser Gly Cys Tyr Ala Thr Thr Gly Leu Lys Met
        195                 200                 205

Lys His Leu Leu Thr Gly Gln Glu Arg Thr Val Trp His Leu Gln Tyr
210                 215                 220

Thr Asp Trp Pro Glu His Gly Cys Pro Glu Asp Leu Lys Gly Phe Leu
225                 230                 235                 240

Ser Tyr Leu Glu Glu Ile Gln Ser Val Arg Arg His Thr Asn Ser Thr
                245                 250                 255

Ser Asp Pro Gln Ser Pro Asn Pro Pro Leu Leu Val His Cys Ser Ala
                260                 265                 270

Gly Val Gly Arg Thr Gly Val Val Ile Leu Ser Glu Ile Met Ile Ala
                275                 280                 285

Cys Leu Glu His Asn Glu Val Leu Asp Ile Pro Arg Val Leu Asp Met
290                 295                 300

Leu Arg Gln Gln Arg Met Met Leu Val Gln Thr Leu Cys Gln Tyr Thr
305                 310                 315                 320

Phe Val Tyr Arg Val Leu Ile Gln Phe Leu Lys Ser Ser Arg Leu Ile
                325                 330                 335

<210> SEQ ID NO 135
<211> LENGTH: 151
<212> TYPE: PRT
<213> ORGANISM: Artificial Sequence
<220> FEATURE:
<223> OTHER INFORMATION: Amino acid sequence of PTP active domain pk4

<400> SEQUENCE: 135

Gly Pro Val Glu Ile Leu Pro Phe Leu Tyr Leu Gly Ser Ala Tyr His
1               5                   10                  15

Ala Ser Arg Lys Asp Met Leu Asp Ala Leu Gly Ile Thr Ala Leu Ile
                20                  25                  30

Asn Val Ser Ala Asn Cys Pro Asn His Phe Glu Gly His Tyr Gln Tyr
            35                  40                  45

Lys Ser Ile Pro Val Glu Asp Asn His Lys Ala Asp Ile Ser Ser Trp
50                  55                  60

Phe Asn Glu Ala Ile Asp Phe Ile Asp Ser Ile Lys Asn Ala Gly Gly
65                  70                  75                  80

Arg Val Phe Val His Cys Gln Ala Gly Ile Ser Arg Ser Ala Thr Ile
                85                  90                  95

Cys Leu Ala Tyr Leu Met Arg Thr Asn Arg Val Lys Leu Asp Glu Ala
                100                 105                 110

Phe Glu Phe Val Lys Gln Arg Arg Ser Ile Ile Ser Pro Asn Phe Ser
            115                 120                 125

Phe Met Gly Gln Leu Leu Gln Phe Glu Ser Gln Val Leu Ala Pro His
        130                 135                 140

Cys Ser Ala Glu Ala Gly Ser
145                 150
```

<210> SEQ ID NO 136
<211> LENGTH: 165
<212> TYPE: PRT
<213> ORGANISM: Artificial Sequence
<220> FEATURE:
<223> OTHER INFORMATION: Amino acid sequence of PTP active domain pk7

<400> SEQUENCE: 136

```
Ser Ala Thr Glu Pro Leu Asp Leu Gly Cys Ser Ser Cys Gly Thr Pro
1               5                   10                  15

Leu His Asp Gln Gly Gly Pro Val Glu Ile Leu Pro Phe Leu Tyr Leu
            20                  25                  30

Gly Ser Ala Tyr His Ala Ala Arg Arg Asp Met Leu Asp Ala Leu Gly
        35                  40                  45

Ile Thr Ala Leu Leu Asn Val Ser Ser Asp Cys Pro Asn His Phe Glu
    50                  55                  60

Gly His Tyr Gln Tyr Lys Cys Ile Pro Val Glu Asp Asn His Lys Ala
65                  70                  75                  80

Asp Ile Ser Ser Trp Phe Met Glu Ala Ile Glu Tyr Ile Asp Ala Val
                85                  90                  95

Lys Asp Cys Arg Gly Arg Val Leu Val His Cys Gln Ala Gly Ile Ser
            100                 105                 110

Arg Ser Ala Thr Ile Cys Leu Ala Tyr Leu Met Met Lys Lys Arg Val
        115                 120                 125

Arg Leu Glu Glu Ala Phe Glu Phe Val Lys Gln Arg Arg Ser Ile Ile
    130                 135                 140

Ser Pro Asn Phe Ser Phe Met Gly Gln Leu Leu Gln Phe Glu Ser Gln
145                 150                 155                 160

Val Leu Ala Thr Ser
            165
```

<210> SEQ ID NO 137
<211> LENGTH: 144
<212> TYPE: PRT
<213> ORGANISM: Artificial Sequence
<220> FEATURE:
<223> OTHER INFORMATION: Amino acid sequence of PTP active domain pk8

<400> SEQUENCE: 137

```
Gly Pro Val Glu Ile Leu Pro Phe Leu Tyr Leu Gly Ser Ala Tyr His
1               5                   10                  15

Ala Ser Lys Cys Glu Phe Leu Ala Asn Leu His Ile Thr Ala Leu Leu
            20                  25                  30

Asn Val Ser Arg Arg Thr Ser Glu Ala Cys Ala Thr His Leu His Tyr
        35                  40                  45

Lys Trp Ile Pro Val Glu Asp Ser His Thr Ala Asp Ile Ser Ser His
    50                  55                  60

Phe Gln Glu Ala Ile Asp Phe Ile Asp Cys Val Arg Glu Lys Gly Gly
65                  70                  75                  80

Lys Val Leu Val His Cys Glu Ala Gly Ile Ser Arg Ser Pro Thr Ile
                85                  90                  95

Cys Met Ala Tyr Leu Met Lys Thr Lys Gln Phe Arg Leu Lys Glu Ala
            100                 105                 110

Phe Asp Tyr Ile Lys Gln Arg Arg Ser Met Val Ser Pro Asn Phe Gly
        115                 120                 125

Phe Met Gly Gln Leu Leu Gln Tyr Glu Ser Glu Ile Leu Pro Ser Thr
    130                 135                 140
```

<210> SEQ ID NO 138
<211> LENGTH: 144
<212> TYPE: PRT
<213> ORGANISM: Artificial Sequence
<220> FEATURE:
<223> OTHER INFORMATION: Amino acid sequence of PTP active domain pk9

<400> SEQUENCE: 138

```
Ser Phe Pro Val Glu Ile Leu Pro Phe Tyr Leu Gly Cys Ala Lys
1               5                   10                  15

Asp Ser Thr Asn Leu Asp Val Leu Glu Glu Phe Gly Ile Lys Tyr Ile
            20                  25                  30

Leu Asn Val Thr Pro Asn Leu Pro Asn Leu Phe Glu Asn Ala Gly Glu
        35                  40                  45

Phe Lys Tyr Lys Gln Ile Pro Ile Ser Asp His Trp Ser Gln Asn Leu
    50                  55                  60

Ser Gln Phe Phe Pro Glu Ala Ile Ser Phe Ile Asp Glu Ala Arg Gly
65                  70                  75                  80

Lys Asn Cys Gly Val Leu Val His Cys Leu Ala Gly Ile Ser Arg Ser
                85                  90                  95

Val Thr Val Thr Val Ala Tyr Leu Met Gln Lys Leu Asn Leu Ser Met
            100                 105                 110

Asn Asp Ala Tyr Asp Ile Val Lys Met Lys Ser Asn Ile Ser Pro
        115                 120                 125

Asn Phe Asn Phe Met Gly Gln Leu Leu Asp Phe Glu Arg Thr Leu Gly
    130                 135                 140
```

<210> SEQ ID NO 139
<211> LENGTH: 147
<212> TYPE: PRT
<213> ORGANISM: Artificial Sequence
<220> FEATURE:
<223> OTHER INFORMATION: Amino acid sequence of PTP active domain pk10

<400> SEQUENCE: 139

```
Ala Phe Pro Val Gln Ile Leu Pro Tyr Leu Tyr Leu Gly Cys Ala Lys
1               5                   10                  15

Asp Ser Thr Asn Leu Asp Val Leu Gly Lys Tyr Gly Ile Lys Tyr Ile
            20                  25                  30

Leu Asn Val Thr Pro Asn Leu Pro Asn Ala Phe Glu His Gly Gly Glu
        35                  40                  45

Phe Thr Tyr Lys Gln Ile Pro Ile Ser Asp His Trp Ser Gln Asn Leu
    50                  55                  60

Ser Gln Phe Phe Pro Glu Ala Ile Ser Phe Ile Asp Glu Ala Arg Ser
65                  70                  75                  80

Lys Lys Cys Gly Val Leu Val His Cys Leu Ala Gly Ile Ser Arg Ser
                85                  90                  95

Val Thr Val Thr Val Ala Tyr Leu Met Gln Lys Met Asn Leu Ser Leu
            100                 105                 110

Asn Asp Ala Tyr Asp Phe Val Lys Arg Lys Lys Ser Asn Ile Ser Pro
        115                 120                 125

Asn Phe Asn Phe Met Gly Gln Leu Leu Asp Phe Glu Arg Thr Leu Gly
    130                 135                 140

Leu Ser Ser
145
```

<210> SEQ ID NO 140
<211> LENGTH: 153

```
<212> TYPE: PRT
<213> ORGANISM: Artificial Sequence
<220> FEATURE:
<223> OTHER INFORMATION: Amino acid sequence of PTP active domain T33

<400> SEQUENCE: 140

Gly Leu Thr Arg Ile Leu Pro His Leu Tyr Leu Gly Ser Gln Lys Asp
1               5                   10                  15

Val Leu Asn Lys Asp Leu Met Thr Gln Asn Gly Ile Ser Tyr Val Leu
            20                  25                  30

Asn Ala Ser Asn Ser Cys Pro Lys Pro Asp Phe Ile Cys Glu Ser Arg
        35                  40                  45

Phe Met Arg Val Pro Ile Asn Asp Asn Tyr Cys Glu Lys Leu Leu Pro
50                  55                  60

Trp Leu Asp Lys Ser Ile Glu Phe Ile Asp Lys Ala Lys Leu Ser Ser
65                  70                  75                  80

Cys Gln Val Ile Val His Cys Leu Ala Gly Ile Ser Arg Ser Ala Thr
                85                  90                  95

Ile Ala Ile Ala Tyr Ile Met Lys Thr Met Gly Met Ser Ser Asp Asp
                100                 105                 110

Ala Tyr Arg Phe Val Lys Asp Arg Arg Pro Ser Ile Ser Pro Asn Phe
            115                 120                 125

Asn Phe Leu Gly Gln Leu Leu Glu Tyr Glu Arg Thr Leu Lys Leu Leu
130                 135                 140

Ala Ala Leu Gln Gly Asp Pro Gly Thr
145                 150

<210> SEQ ID NO 141
<211> LENGTH: 151
<212> TYPE: PRT
<213> ORGANISM: Artificial Sequence
<220> FEATURE:
<223> OTHER INFORMATION: Amino acid sequence of PTP active domain pk12

<400> SEQUENCE: 141

Ala Ser Phe Pro Val Gln Ile Leu Pro Asn Leu Tyr Leu Gly Ser Ala
1               5                   10                  15

Arg Asp Ser Ala Asn Leu Glu Ser Leu Ala Lys Leu Gly Ile Arg Tyr
            20                  25                  30

Ile Leu Asn Val Thr Pro Asn Leu Pro Asn Phe Phe Glu Lys Asn Gly
        35                  40                  45

Asp Phe His Tyr Lys Gln Ile Pro Ile Ser Asp His Trp Ser Gln Asn
50                  55                  60

Leu Ser Arg Phe Phe Pro Glu Ala Ile Glu Phe Ile Asp Glu Ala Leu
65                  70                  75                  80

Ser Gln Asn Cys Gly Val Leu Val His Cys Leu Ala Gly Val Ser Arg
                85                  90                  95

Ser Val Thr Val Thr Val Ala Tyr Leu Met Gln Lys Leu His Leu Ser
                100                 105                 110

Leu Asn Asp Ala Tyr Asp Leu Val Lys Arg Lys Lys Ser Asn Ile Ser
            115                 120                 125

Pro Asn Phe Asn Phe Met Gly Gln Leu Leu Asp Phe Glu Arg Ser Leu
130                 135                 140

Arg Leu Glu Glu Arg His Ser
145                 150

<210> SEQ ID NO 142
<211> LENGTH: 148
```

```
<212> TYPE: PRT
<213> ORGANISM: Artificial Sequence
<220> FEATURE:
<223> OTHER INFORMATION: Amino acid sequence of PTP active domain pk13

<400> SEQUENCE: 142

Ala Glu Leu Thr Pro Ile Leu Pro Phe Leu Phe Leu Gly Asn Glu Gln
1               5                   10                  15

Asp Ala Gln Asp Leu Asp Thr Met Gln Arg Leu Asn Ile Gly Tyr Val
            20                  25                  30

Ile Asn Val Thr Thr His Leu Pro Leu Tyr His Tyr Glu Lys Gly Leu
        35                  40                  45

Phe Asn Tyr Lys Arg Leu Pro Ala Thr Asp Ser Asn Lys Gln Asn Leu
    50                  55                  60

Arg Gln Tyr Phe Glu Glu Ala Phe Glu Phe Ile Glu Glu Ala His Gln
65                  70                  75                  80

Cys Gly Lys Gly Leu Leu Ile His Cys Gln Ala Gly Val Ser Arg Ser
                85                  90                  95

Ala Thr Ile Val Ile Ala Tyr Leu Met Lys His Thr Arg Met Thr Met
            100                 105                 110

Thr Asp Ala Tyr Lys Phe Val Lys Gly Lys Arg Pro Ile Ile Ser Pro
        115                 120                 125

Asn Leu Asn Phe Met Gly Gln Leu Leu Glu Phe Glu Glu Asp Leu Asn
    130                 135                 140

Asn Gly Val Thr
145

<210> SEQ ID NO 143
<211> LENGTH: 148
<212> TYPE: PRT
<213> ORGANISM: Artificial Sequence
<220> FEATURE:
<223> OTHER INFORMATION: Amino acid sequence of PTP active domain T27

<400> SEQUENCE: 143

Gly Pro Thr Arg Ile Leu Pro Asn Leu Tyr Leu Gly Cys Gln Arg Asp
1               5                   10                  15

Val Leu Asn Lys Glu Leu Met Gln Gln Asn Gly Ile Gly Tyr Val Leu
            20                  25                  30

Asn Ala Ser Asn Thr Cys Pro Lys Pro Asp Phe Ile Pro Glu Ser His
        35                  40                  45

Phe Leu Arg Val Pro Val Asn Asp Ser Phe Cys Glu Lys Ile Leu Pro
    50                  55                  60

Trp Leu Asp Lys Ser Val Asp Phe Ile Glu Lys Ala Lys Ala Ser Asn
65                  70                  75                  80

Gly Cys Val Leu Val His Cys Leu Ala Gly Ile Ser Arg Ser Ala Thr
                85                  90                  95

Ile Ala Ile Ala Tyr Ile Met Lys Arg Met Asp Met Ser Leu Asp Glu
            100                 105                 110

Ala Tyr Arg Phe Val Lys Glu Lys Arg Pro Thr Ile Ser Pro Asn Phe
        115                 120                 125

Asn Phe Leu Gly Gln Leu Leu Asp Tyr Glu Lys Lys Ile Lys Asn Gln
    130                 135                 140

Thr Gly Ala Ser
145

<210> SEQ ID NO 144
<211> LENGTH: 185
```

```
<212> TYPE: PRT
<213> ORGANISM: Artificial Sequence
<220> FEATURE:
<223> OTHER INFORMATION: Amino acid sequence of PTP active domain pk6

<400> SEQUENCE: 144

Met Ser Gly Ser Phe Glu Leu Ser Val Gln Asp Leu Asn Asp Leu Leu
1               5                   10                  15

Ser Asp Gly Ser Gly Cys Tyr Ser Leu Pro Ser Gln Pro Cys Asn Glu
            20                  25                  30

Val Thr Pro Arg Ile Tyr Val Gly Asn Ala Ser Val Ala Gln Asp Ile
        35                  40                  45

Pro Lys Leu Gln Lys Leu Gly Ile Thr His Val Leu Asn Ala Ala Glu
    50                  55                  60

Gly Arg Ser Phe Met His Val Asn Thr Asn Ala Asn Phe Tyr Lys Asp
65                  70                  75                  80

Ser Gly Ile Thr Tyr Leu Gly Ile Lys Ala Asn Asp Thr Gln Glu Phe
                85                  90                  95

Asn Leu Ser Ala Tyr Phe Glu Arg Ala Ala Asp Phe Ile Asp Gln Ala
            100                 105                 110

Leu Ala Gln Lys Asn Gly Arg Val Leu Val His Cys Arg Glu Gly Tyr
        115                 120                 125

Ser Arg Ser Pro Thr Leu Val Ile Ala Tyr Leu Met Met Arg Gln Lys
    130                 135                 140

Met Asp Val Lys Ser Ala Leu Ser Ile Val Arg Gln Asn Arg Glu Ile
145                 150                 155                 160

Gly Pro Asn Asp Gly Phe Leu Ala Gln Leu Cys Gln Leu Asn Asp Arg
                165                 170                 175

Leu Ala Lys Glu Gly Lys Leu Lys Pro
            180                 185

<210> SEQ ID NO 145
<211> LENGTH: 184
<212> TYPE: PRT
<213> ORGANISM: Artificial Sequence
<220> FEATURE:
<223> OTHER INFORMATION: Amino acid sequence of PTP active domain pk14

<400> SEQUENCE: 145

Gly Gly Asn His Ile Pro Glu Arg Trp Lys Asp Tyr Leu Pro Val Gly
1               5                   10                  15

Gln Arg Met Pro Gly Thr Arg Phe Ile Ala Phe Lys Val Pro Leu Gln
            20                  25                  30

Lys Ser Phe Glu Lys Lys Leu Ala Pro Glu Glu Cys Phe Ser Pro Leu
        35                  40                  45

Asp Leu Phe Asn Lys Ile Arg Glu Gln Asn Glu Glu Leu Gly Leu Ile
    50                  55                  60

Ile Asp Leu Thr Tyr Thr Gln Arg Tyr Tyr Lys Pro Glu Asp Leu Pro
65                  70                  75                  80

Glu Thr Val Pro Tyr Leu Lys Ile Phe Thr Val Gly His Gln Val Pro
                85                  90                  95

Asp Asp Glu Thr Ile Phe Lys Phe Lys His Ala Val Asn Gly Phe Leu
            100                 105                 110

Lys Glu Asn Lys Asp Asn Asp Lys Leu Ile Gly Val His Cys Thr His
        115                 120                 125

Gly Leu Asn Arg Thr Gly Tyr Leu Ile Cys Arg Tyr Leu Ile Asp Val
    130                 135                 140
```

```
Glu Gly Val Arg Pro Asp Asp Ala Ile Glu Leu Phe Asn Arg Cys Arg
145                 150                 155                 160

Gly His Cys Leu Glu Arg Gln Asn Tyr Ile Glu Asp Leu Gln Asn Gly
                165                 170                 175

Pro Ile Arg Lys Asn Trp Asn Ser
            180
```

<210> SEQ ID NO 146
<211> LENGTH: 320
<212> TYPE: PRT
<213> ORGANISM: Artificial Sequence
<220> FEATURE:
<223> OTHER INFORMATION: Amino acid sequence of PTP active domain pk15

<400> SEQUENCE: 146

```
Val Ser Cys Ala Gly Gln Met Leu Glu Val Gln Pro Gly Leu Tyr Phe
1               5                   10                  15

Gly Gly Ala Ala Ala Val Ala Glu Pro Asp His Leu Arg Glu Ala Gly
                20                  25                  30

Ile Thr Ala Val Leu Thr Val Asp Ser Glu Glu Pro Ser Phe Lys Ala
            35                  40                  45

Gly Pro Gly Val Glu Asp Leu Trp Arg Leu Phe Val Pro Ala Leu Asp
50                  55                  60

Lys Pro Glu Thr Asp Leu Leu Ser His Leu Asp Arg Cys Val Ala Phe
65                  70                  75                  80

Ile Gly Gln Ala Arg Ala Glu Gly Arg Ala Val Leu Val His Cys His
                85                  90                  95

Ala Gly Val Ser Arg Ser Val Ala Ile Ile Thr Ala Phe Leu Met Lys
                100                 105                 110

Thr Asp Gln Leu Pro Phe Glu Lys Ala Tyr Glu Lys Leu Gln Ile Leu
            115                 120                 125

Lys Pro Glu Ala Lys Met Asn Glu Gly Phe Glu Trp Gln Leu Lys Leu
130                 135                 140

Tyr Gln Ala Met Gly Tyr Glu Val Asp Thr Ser Ser Ala Ile Tyr Lys
145                 150                 155                 160

Gln Tyr Arg Leu Gln Lys Val Thr Glu Lys Tyr Pro Glu Leu Gln Asn
                165                 170                 175

Leu Pro Gln Glu Leu Phe Ala Val Asp Pro Thr Thr Val Ser Gln Gly
            180                 185                 190

Leu Lys Asp Glu Val Leu Tyr Lys Cys Arg Lys Cys Arg Arg Ser Leu
            195                 200                 205

Phe Arg Ser Ser Ser Ile Leu Asp His Arg Glu Gly Ser Gly Pro Ile
210                 215                 220

Ala Phe Ala His Lys Arg Met Thr Pro Ser Ser Met Leu Thr Thr Gly
225                 230                 235                 240

Arg Gln Ala Gln Cys Thr Ser Tyr Phe Ile Glu Pro Val Gln Trp Met
                245                 250                 255

Glu Ser Ala Leu Leu Gly Val Met Asp Gly Gln Leu Leu Cys Pro Lys
            260                 265                 270

Cys Ser Ala Lys Leu Gly Ser Phe Asn Trp Tyr Gly Glu Gln Cys Ser
            275                 280                 285

Cys Gly Arg Trp Ile Thr Pro Ala Phe Gln Ile His Lys Asn Arg Val
            290                 295                 300

Asp Glu Met Lys Ile Leu Pro Val Leu Gly Ser Gln Thr Gly Lys Ile
305                 310                 315                 320
```

<210> SEQ ID NO 147
<211> LENGTH: 188
<212> TYPE: PRT
<213> ORGANISM: Artificial Sequence
<220> FEATURE:
<223> OTHER INFORMATION: Amino acid sequence of PTP active domain pk33

<400> SEQUENCE: 147

```
Met Ala Glu Thr Ser Leu Pro Glu Leu Gly Gly Glu Asp Lys Ala Thr
1               5                   10                  15

Pro Cys Pro Ser Ile Leu Glu Leu Glu Glu Leu Leu Arg Ala Gly Lys
            20                  25                  30

Ser Ser Cys Ser Arg Val Asp Glu Val Trp Pro Asn Leu Phe Ile Gly
        35                  40                  45

Asp Ala Ala Thr Ala Asn Asn Arg Phe Glu Leu Trp Lys Leu Gly Ile
    50                  55                  60

Thr His Val Leu Asn Ala Ala His Arg Gly Leu Tyr Cys Gln Gly Gly
65                  70                  75                  80

Pro Asp Phe Tyr Gly Ser Ser Val Ser Tyr Leu Gly Val Pro Ala His
                85                  90                  95

Asp Leu Pro Asp Phe Asp Ile Ser Ala Tyr Phe Ser Ser Ala Ala Asp
            100                 105                 110

Phe Ile His Arg Ala Leu Asn Thr Pro Gly Ala Lys Val Leu Val His
        115                 120                 125

Cys Val Val Gly Val Ser Arg Ser Ala Thr Leu Val Leu Ala Tyr Leu
    130                 135                 140

Met Leu His Gln Arg Leu Ser Leu Arg Gln Ala Val Ile Thr Val Arg
145                 150                 155                 160

Gln His Arg Trp Val Phe Pro Asn Arg Gly Phe Leu His Gln Leu Cys
                165                 170                 175

Arg Leu Asp Gln Gln Leu Arg Gly Ala Gly Gln Ser
            180                 185
```

<210> SEQ ID NO 148
<211> LENGTH: 198
<212> TYPE: PRT
<213> ORGANISM: Artificial Sequence
<220> FEATURE:
<223> OTHER INFORMATION: Amino acid sequence of PTP active domain p44

<400> SEQUENCE: 148

```
Met Asp Ser Leu Gln Lys Gln Asp Leu Arg Arg Pro Lys Ile His Gly
1               5                   10                  15

Ala Val Gln Ala Ser Pro Tyr Gln Pro Pro Thr Leu Ala Ser Leu Gln
            20                  25                  30

Arg Leu Leu Trp Val Arg Gln Ala Ala Thr Leu Asn His Ile Asp Glu
        35                  40                  45

Val Trp Pro Ser Leu Phe Leu Gly Asp Ala Tyr Ala Ala Arg Asp Lys
    50                  55                  60

Ser Lys Leu Ile Gln Leu Gly Ile Thr His Val Val Asn Ala Ala Ala
65                  70                  75                  80

Gly Lys Phe Gln Val Asp Thr Gly Ala Lys Phe Tyr Arg Gly Met Ser
                85                  90                  95

Leu Glu Tyr Tyr Gly Ile Glu Ala Asp Asp Asn Pro Phe Phe Asp Leu
            100                 105                 110

Ser Val Tyr Phe Leu Pro Val Ala Arg Tyr Ile Arg Ala Ala Leu Ser
        115                 120                 125

Val Pro Gln Gly Arg Val Leu Val His Cys Ala Met Gly Val Ser Arg
```

```
                130               135               140
Ser Ala Thr Leu Val Leu Ala Phe Leu Met Ile Tyr Glu Asn Met Thr
145                 150                 155                 160

Leu Val Glu Ala Ile Gln Thr Val Gln Ala His Arg Asn Ile Cys Pro
                165                 170                 175

Asn Ser Gly Phe Leu Arg Gln Leu Gln Val Leu Asp Asn Arg Leu Gly
            180                 185                 190

Arg Glu Thr Gly Arg Phe
            195

<210> SEQ ID NO 149
<211> LENGTH: 157
<212> TYPE: PRT
<213> ORGANISM: Artificial Sequence
<220> FEATURE:
<223> OTHER INFORMATION: Amino acid sequence of PTP active domain p21

<400> SEQUENCE: 149

Met Gly Asn Gly Met Thr Lys Val Leu Pro Gly Leu Tyr Leu Gly Asn
1               5                   10                  15

Phe Ile Asp Ala Lys Asp Leu Asp Gln Leu Gly Arg Asn Lys Ile Thr
                20                  25                  30

His Ile Ile Ser Ile His Glu Ser Pro Gln Pro Leu Leu Gln Asp Ile
            35                  40                  45

Thr Tyr Leu Arg Ile Pro Val Ala Asp Thr Pro Glu Val Pro Ile Lys
50                  55                  60

Lys His Phe Lys Glu Cys Ile Asn Phe Ile His Cys Cys Arg Leu Asn
65                  70                  75                  80

Gly Gly Asn Cys Leu Val His Cys Phe Ala Gly Ile Ser Arg Ser Thr
                85                  90                  95

Thr Ile Val Thr Ala Tyr Val Met Thr Val Thr Gly Leu Gly Trp Arg
            100                 105                 110

Asp Val Leu Glu Ala Ile Lys Ala Thr Arg Pro Ile Ala Asn Pro Asn
        115                 120                 125

Pro Gly Phe Arg Gln Gln Leu Glu Glu Phe Gly Trp Ala Ser Ser Gln
    130                 135                 140

Lys Leu Arg Arg Gln Leu Glu Glu Arg Phe Gly Glu Ser
145                 150                 155

<210> SEQ ID NO 150
<211> LENGTH: 188
<212> TYPE: PRT
<213> ORGANISM: Artificial Sequence
<220> FEATURE:
<223> OTHER INFORMATION: Amino acid sequence of PTP active domain pk35

<400> SEQUENCE: 150

Met Thr Ala Pro Ser Cys Ala Phe Pro Val Gln Phe Arg Gln Pro Ser
1               5                   10                  15

Val Ser Gly Leu Ser Gln Ile Thr Lys Ser Leu Tyr Ile Ser Asn Gly
                20                  25                  30

Val Ala Ala Asn Asn Lys Leu Met Leu Ser Asn Gln Ile Thr Met
            35                  40                  45

Val Ile Asn Val Ser Val Glu Val Val Asn Thr Leu Tyr Glu Asp Ile
        50                  55                  60

Gln Tyr Met Gln Val Pro Val Ala Asp Ser Pro Asn Ser Arg Leu Cys
65                  70                  75                  80

Asp Phe Phe Asp Pro Ile Ala Asp His Ile His Ser Val Glu Met Lys
```

-continued

```
                        85                  90                  95
Gln Gly Arg Thr Leu Leu His Cys Ala Ala Gly Val Ser Arg Ser Ala
                100                 105                 110

Ala Leu Cys Leu Ala Tyr Leu Met Lys Tyr His Ala Met Ser Leu Leu
        115                 120                 125

Asp Ala His Thr Trp Thr Lys Ser Cys Arg Pro Ile Ile Arg Pro Asn
    130                 135                 140

Ser Gly Phe Trp Glu Gln Leu Ile His Tyr Glu Phe Gln Leu Phe Gly
145                 150                 155                 160

Lys Asn Thr Val His Met Val Ser Ser Pro Val Gly Met Ile Pro Asp
                165                 170                 175

Ile Tyr Glu Lys Glu Val Arg Leu Met Ile Pro Leu
                180                 185

<210> SEQ ID NO 151
<211> LENGTH: 217
<212> TYPE: PRT
<213> ORGANISM: Artificial Sequence
<220> FEATURE:
<223> OTHER INFORMATION: Amino acid sequence of PTP active domain NE1

<400> SEQUENCE: 151

Met Tyr Ser Leu Asn Gln Glu Ile Lys Ala Phe Ser Arg Asn Asn Leu
1               5                   10                  15

Arg Lys Gln Cys Thr Arg Val Thr Thr Leu Thr Gly Lys Lys Ile Ile
            20                  25                  30

Glu Thr Trp Lys Asp Ala Arg Ile His Val Val Glu Val Glu Pro
        35                  40                  45

Ser Ser Gly Gly Gly Cys Gly Tyr Val Gln Asp Leu Ser Ser Asp Leu
    50                  55                  60

Gln Val Gly Val Ile Lys Pro Trp Leu Leu Leu Gly Ser Gln Asp Ala
65                  70                  75                  80

Ala His Asp Leu Asp Thr Leu Lys Lys Asn Lys Val Thr His Ile Leu
                85                  90                  95

Asn Val Ala Tyr Gly Val Glu Asn Ala Phe Leu Ser Asp Phe Thr Tyr
                100                 105                 110

Lys Ser Ile Ser Ile Leu Asp Leu Pro Glu Thr Asn Ile Leu Ser Tyr
            115                 120                 125

Phe Pro Glu Cys Phe Glu Phe Ile Glu Glu Ala Lys Arg Lys Asp Gly
        130                 135                 140

Val Val Leu Val His Cys Asn Ala Gly Val Ser Arg Ala Ala Ala Ile
145                 150                 155                 160

Val Ile Gly Phe Leu Met Asn Ser Glu Gln Thr Ser Phe Thr Ser Ala
                165                 170                 175

Phe Ser Leu Val Lys Asn Ala Arg Pro Ser Ile Cys Pro Asn Ser Gly
            180                 185                 190

Phe Met Glu Gln Leu Arg Thr Tyr Gln Glu Gly Lys Glu Ser Asn Lys
        195                 200                 205

Cys Asp Arg Ile Gln Glu Asn Ser Ser
    210                 215

<210> SEQ ID NO 152
<211> LENGTH: 190
<212> TYPE: PRT
<213> ORGANISM: Artificial Sequence
<220> FEATURE:
<223> OTHER INFORMATION: Amino acid sequence of PTP active domain p19
```

<400> SEQUENCE: 152

Met Thr Ala Ser Ala Ser Ser Phe Ser Ser Gln Gly Val Gln Gln
1               5                   10                  15

Pro Ser Ile Tyr Ser Phe Ser Gln Ile Thr Arg Ser Leu Phe Leu Ser
            20                  25                  30

Asn Gly Val Ala Ala Asn Asp Lys Leu Leu Leu Ser Ser Asn Arg Ile
        35                  40                  45

Thr Ala Ile Val Asn Ala Ser Val Glu Val Val Asn Val Phe Phe Glu
    50                  55                  60

Gly Ile Gln Tyr Ile Lys Val Pro Val Thr Asp Ala Arg Asp Ser Arg
65                  70                  75                  80

Leu Tyr Asp Phe Phe Asp Pro Ile Ala Asp Leu Ile His Thr Ile Asp
                85                  90                  95

Met Arg Gln Gly Arg Thr Leu Leu His Cys Met Ala Gly Val Ser Arg
            100                 105                 110

Ser Ala Ser Leu Cys Leu Ala Tyr Leu Met Lys Tyr His Ser Met Ser
        115                 120                 125

Leu Leu Asp Ala His Thr Trp Thr Lys Ser Arg Arg Pro Ile Ile Arg
130                 135                 140

Pro Asn Asn Gly Phe Trp Glu Gln Leu Ile Asn Tyr Glu Phe Lys Leu
145                 150                 155                 160

Phe Asn Asn Thr Val Arg Met Ile Asn Ser Pro Val Gly Asn Ile
                165                 170                 175

Pro Asp Ile Tyr Glu Lys Asp Leu Arg Met Met Ile Ser Met
            180                 185                 190

<210> SEQ ID NO 153
<211> LENGTH: 184
<212> TYPE: PRT
<213> ORGANISM: Artificial Sequence
<220> FEATURE:
<223> OTHER INFORMATION: Amino acid sequence of PTP active domain pk18
<220> FEATURE:
<221> NAME/KEY: misc_feature
<222> LOCATION: (40)..(46)
<223> OTHER INFORMATION: Xaa can be any naturally occurring amino acid

<400> SEQUENCE: 153

Met Gly Asn Gly Met Asn Lys Ile Leu Pro Gly Leu Tyr Ile Gly Asn
1               5                   10                  15

Phe Lys Asp Ala Arg Asp Ala Gly Gln Leu Ser Arg Asn Lys Val Thr
            20                  25                  30

His Ile Leu Ser Val His Asp Xaa Xaa Xaa Xaa Xaa Xaa Xaa Gly Val
        35                  40                  45

Lys Tyr Leu Cys Ile Pro Ala Ala Asp Ser Pro Ser Gln Asn Leu Thr
    50                  55                  60

Arg His Phe Lys Glu Ser Ile Lys Phe Ile His Glu Cys Arg Leu Arg
65                  70                  75                  80

Gly Glu Ser Cys Leu Val His Cys Leu Ala Gly Val Ser Arg Ser Val
                85                  90                  95

Thr Leu Val Ile Ala Tyr Ile Met Thr Val Thr Asp Phe Gly Trp Glu
            100                 105                 110

Asp Ala Leu His Thr Val Arg Ala Gly Arg Ser Cys Ala Asn Pro Asn
        115                 120                 125

Val Gly Phe Gln Arg Gln Leu Gln Glu Phe Glu Lys His Glu Val His
    130                 135                 140

Gln Tyr Arg Gln Trp Leu Lys Glu Glu Tyr Gly Glu Ser Pro Leu Gln

```
               145                 150                 155                 160
Asp Ala Glu Glu Ala Lys Asn Ile Leu Ala Ala Pro Gly Ile Met Lys
                   165                 170                 175

Phe Trp Ala Phe Leu Arg Arg Leu
               180

<210> SEQ ID NO 154
<211> LENGTH: 171
<212> TYPE: PRT
<213> ORGANISM: Artificial Sequence
<220> FEATURE:
<223> OTHER INFORMATION: Amino acid sequence of PTP active domain p12

<400> SEQUENCE: 154

Gly Arg Ala His Arg Asp Trp Tyr His Arg Ile Asp Pro Thr Val Leu
1               5                   10                  15

Leu Gly Ala Leu Pro Leu Arg Ser Leu Thr Arg Gln Leu Val Gln Asp
            20                  25                  30

Glu Asn Val Arg Gly Val Ile Thr Met Asn Glu Glu Tyr Glu Thr Arg
        35                  40                  45

Phe Leu Cys Asn Ser Ser Gln Glu Trp Lys Arg Leu Gly Val Glu Gln
    50                  55                  60

Leu Arg Leu Ser Thr Val Asp Met Thr Gly Ile Pro Thr Leu Asp Asn
65                  70                  75                  80

Leu Gln Lys Gly Val Gln Phe Ala Leu Lys Tyr Gln Ser Leu Gly Gln
                85                  90                  95

Cys Val Tyr Val His Cys Lys Ala Gly Arg Ser Arg Ser Ala Thr Met
            100                 105                 110

Val Ala Ala Tyr Leu Ile Gln Val His Lys Trp Ser Pro Glu Glu Ala
        115                 120                 125

Val Arg Ala Ile Ala Lys Ile Arg Ser Tyr Ile His Ile Arg Pro Gly
    130                 135                 140

Gln Leu Asp Val Leu Lys Glu Phe His Lys Gln Ile Thr Ala Arg Ala
145                 150                 155                 160

Thr Lys Asp Gly Thr Phe Val Ile Ser Lys Thr
                165                 170

<210> SEQ ID NO 155
<211> LENGTH: 177
<212> TYPE: PRT
<213> ORGANISM: Artificial Sequence
<220> FEATURE:
<223> OTHER INFORMATION: Amino acid sequence of PTP active domain pk17

<400> SEQUENCE: 155

Met Pro Thr Val Gln His Pro Phe Leu Asn Val Phe Glu Leu Glu Arg
1               5                   10                  15

Leu Leu Tyr Thr Gly Lys Thr Ala Cys Asn His Ala Asp Glu Val Trp
            20                  25                  30

Pro Gly Leu Tyr Leu Gly Asp Gln Asp Met Ala Asn Asn Arg Arg Glu
        35                  40                  45

Leu Arg Arg Leu Gly Ile Thr His Val Leu Asn Ala Ser His Ser Arg
    50                  55                  60

Trp Arg Gly Thr Pro Glu Ala Tyr Glu Gly Leu Gly Ile Arg Tyr Leu
65                  70                  75                  80

Gly Val Glu Ala His Asp Ser Pro Ala Phe Asp Met Ser Ile His Phe
                85                  90                  95

Gln Thr Ala Ala Asp Phe Ile His Arg Ala Leu Ser Gln Pro Gly Gly
```

```
                100                 105                 110
Lys Ile Leu Val His Cys Ala Val Gly Val Ser Arg Ser Ala Thr Leu
        115                 120                 125

Val Leu Ala Tyr Leu Met Leu Tyr His His Leu Thr Leu Val Glu Ala
        130                 135                 140

Ile Lys Lys Val Lys Asp His Arg Gly Ile Ile Pro Asn Arg Gly Phe
145                 150                 155                 160

Leu Arg Gln Leu Leu Ala Leu Asp Arg Arg Leu Arg Gln Gly Leu Glu
                165                 170                 175

Ala

<210> SEQ ID NO 156
<211> LENGTH: 150
<212> TYPE: PRT
<213> ORGANISM: Artificial Sequence
<220> FEATURE:
<223> OTHER INFORMATION: Amino acid sequence of PTP active domain p16

<400> SEQUENCE: 156

Met Gly Val Gln Pro Pro Asn Phe Ser Trp Val Leu Pro Gly Arg Leu
1               5                   10                  15

Ala Gly Leu Ala Leu Pro Arg Leu Pro Ala His Tyr Gln Phe Leu Leu
                20                  25                  30

Asp Leu Gly Val Arg His Leu Val Ser Leu Thr Glu Arg Gly Pro Pro
            35                  40                  45

His Ser Asp Ser Cys Pro Gly Leu Thr Leu His Arg Leu Arg Ile Pro
        50                  55                  60

Asp Phe Cys Pro Pro Ala Pro Asp Gln Ile Asp Arg Phe Val Gln Ile
65                  70                  75                  80

Val Asp Glu Ala Asn Ala Arg Gly Glu Ala Val Gly Val His Cys Ala
                85                  90                  95

Leu Gly Phe Gly Arg Thr Gly Thr Met Leu Ala Cys Tyr Leu Val Lys
            100                 105                 110

Glu Arg Gly Leu Ala Ala Gly Asp Ala Ile Ala Glu Ile Arg Arg Leu
        115                 120                 125

Arg Pro Gly Ser Ile Glu Thr Tyr Glu Gln Glu Lys Ala Val Phe Gln
    130                 135                 140

Phe Tyr Gln Arg Thr Lys
145                 150

<210> SEQ ID NO 157
<211> LENGTH: 210
<212> TYPE: PRT
<213> ORGANISM: Artificial Sequence
<220> FEATURE:
<223> OTHER INFORMATION: Amino acid sequence of PTP active domain T16

<400> SEQUENCE: 157

Met Ala His Asn Lys Ile Pro Pro Arg Trp Leu Asn Cys Pro Arg Arg
1               5                   10                  15

Gly Gln Pro Val Ala Gly Arg Phe Leu Pro Leu Lys Thr Met Leu Gly
                20                  25                  30

Pro Arg Tyr Asp Ser Gln Val Ala Glu Glu Asn Arg Phe His Pro Ser
            35                  40                  45

Met Leu Ser Asn Tyr Leu Lys Ser Leu Lys Val Lys Met Gly Leu Leu
        50                  55                  60

Val Asp Leu Thr Asn Thr Ser Arg Phe Tyr Asp Arg Asn Asp Ile Glu
65                  70                  75                  80
```

```
Lys Glu Gly Ile Lys Tyr Ile Lys Leu Gln Cys Lys Gly His Gly Glu
                85                  90                  95

Cys Pro Thr Thr Glu Asn Thr Glu Thr Phe Ile Arg Leu Cys Glu Arg
            100                 105                 110

Phe Asn Glu Arg Asn Pro Pro Glu Leu Ile Gly Val His Cys Thr His
        115                 120                 125

Gly Phe Asn Arg Thr Gly Phe Leu Ile Cys Ala Phe Leu Val Glu Lys
    130                 135                 140

Met Asp Trp Ser Ile Glu Ala Ala Val Ala Thr Phe Ala Gln Ala Arg
145                 150                 155                 160

Pro Pro Gly Ile Tyr Lys Gly Asp Tyr Leu Lys Glu Leu Phe Arg Arg
                165                 170                 175

Tyr Gly Asp Ile Glu Glu Ala Pro Pro Pro Leu Leu Pro Asp Trp
            180                 185                 190

Cys Phe Glu Asp Asp Glu Asp Glu Asp Glu Asp Gly Lys Lys
        195                 200                 205

Glu Ser
    210

<210> SEQ ID NO 158
<211> LENGTH: 152
<212> TYPE: PRT
<213> ORGANISM: Artificial Sequence
<220> FEATURE:
<223> OTHER INFORMATION: Amino acid sequence of PTP active domain p18

<400> SEQUENCE: 158

Met Leu Leu Ile Leu Gly Gln Met Asp Lys Pro Ser Leu Ile Phe Asp
1               5                   10                  15

His Leu Tyr Leu Gly Ser Glu Trp Asn Ala Ser Asn Leu Glu Glu Leu
                20                  25                  30

Gln Gly Ser Gly Val Asp Tyr Ile Leu Asn Val Thr Arg Glu Ile Asp
            35                  40                  45

Asn Phe Phe Pro Gly Leu Phe Ala Tyr His Asn Ile Arg Val Tyr Asp
        50                  55                  60

Glu Glu Thr Thr Asp Leu Leu Ala His Trp Asn Glu Ala Tyr His Phe
65                  70                  75                  80

Ile Asn Lys Ala Lys Arg Asn His Ser Lys Cys Leu Val His Cys Lys
                85                  90                  95

Met Gly Val Ser Arg Ser Ala Ser Thr Val Ile Ala Tyr Ala Met Lys
            100                 105                 110

Glu Phe Gly Trp Pro Leu Glu Lys Ala Tyr Asn Tyr Val Lys Gln Lys
        115                 120                 125

Arg Ser Ile Thr Arg Pro Asn Ala Gly Phe Met Arg Gln Leu Ser Glu
    130                 135                 140

Tyr Glu Gly Ile Leu Asp Ala Ser
145                 150

<210> SEQ ID NO 159
<211> LENGTH: 145
<212> TYPE: PRT
<213> ORGANISM: Artificial Sequence
<220> FEATURE:
<223> OTHER INFORMATION: Amino acid sequence of PTP active domain NE3

<400> SEQUENCE: 159

Met Asp Ser Pro Thr Gln Ile Phe Glu His Val Phe Leu Gly Ser Glu
1               5                   10                  15
```

-continued

```
Trp Asn Ala Ser Asn Leu Glu Asp Leu Gln Asn Arg Gly Val Arg Tyr
             20                  25                  30

Ile Leu Asn Val Thr Arg Glu Ile Asp Asn Phe Phe Pro Gly Val Phe
         35                  40                  45

Glu Tyr His Asn Ile Arg Val Tyr Asp Glu Glu Ala Thr Asp Leu Leu
     50                  55                  60

Ala Tyr Trp Asn Asp Thr Tyr Lys Phe Ile Ser Lys Ala Lys Lys His
 65                  70                  75                  80

Gly Ser Lys Cys Leu Val His Cys Lys Met Gly Val Ser Arg Ser Ala
                 85                  90                  95

Ser Thr Val Ile Ala Tyr Ala Met Lys Glu Tyr Gly Trp Asn Leu Asp
            100                 105                 110

Arg Ala Tyr Asp Tyr Val Lys Glu Arg Arg Thr Val Thr Lys Pro Asn
        115                 120                 125

Pro Ser Phe Met Arg Gln Leu Glu Glu Tyr Gln Gly Ile Leu Leu Ala
    130                 135                 140

Arg
145

<210> SEQ ID NO 160
<211> LENGTH: 160
<212> TYPE: PRT
<213> ORGANISM: Artificial Sequence
<220> FEATURE:
<223> OTHER INFORMATION: Amino acid sequence of PTP active domain pk3

<400> SEQUENCE: 160

Met Asn Arg Pro Ala Pro Val Glu Val Thr Tyr Lys Asn Met Arg Phe
 1               5                  10                  15

Leu Ile Thr His Asn Pro Thr Asn Ala Thr Leu Asn Lys Phe Ile Glu
             20                  25                  30

Glu Leu Lys Lys Tyr Gly Val Thr Thr Ile Val Arg Val Cys Glu Ala
         35                  40                  45

Thr Tyr Asp Thr Thr Leu Val Glu Lys Glu Gly Ile His Val Leu Asp
     50                  55                  60

Trp Pro Phe Asp Asp Gly Ala Pro Pro Ser Asn Gln Ile Val Asp Asp
 65                  70                  75                  80

Trp Leu Ser Leu Val Lys Ile Lys Phe Arg Glu Glu Pro Gly Cys Cys
                 85                  90                  95

Ile Ala Val His Cys Val Ala Gly Leu Gly Arg Ala Pro Val Leu Val
            100                 105                 110

Ala Leu Ala Leu Ile Glu Gly Gly Met Lys Tyr Glu Asp Ala Val Gln
        115                 120                 125

Phe Ile Arg Gln Lys Arg Arg Gly Ala Phe Asn Ser Lys Gln Leu Leu
    130                 135                 140

Tyr Leu Glu Lys Tyr Arg Pro Lys Met Arg Leu Arg Phe Lys Asp Ser
145                 150                 155                 160

<210> SEQ ID NO 161
<211> LENGTH: 154
<212> TYPE: PRT
<213> ORGANISM: Artificial Sequence
<220> FEATURE:
<223> OTHER INFORMATION: Amino acid sequence of PTP active domain p49

<400> SEQUENCE: 161

Met Arg Phe Leu Ile Thr His Asn Pro Thr Asn Ala Thr Leu Asn Lys
 1               5                  10                  15
```

Phe Thr Glu Glu Leu Lys Lys Tyr Gly Val Thr Thr Leu Val Arg Val
            20                  25                  30

Cys Asp Ala Thr Tyr Asp Lys Ala Pro Val Glu Lys Glu Gly Ile His
            35                  40                  45

Val Leu Asp Trp Pro Phe Asp Asp Gly Ala Pro Pro Asn Gln Ile
 50                  55                  60

Val Asp Asp Trp Leu Asn Leu Leu Lys Thr Lys Phe Arg Glu Pro
 65                  70                  75                  80

Gly Cys Cys Val Ala Val His Cys Val Ala Gly Leu Gly Arg Ala Pro
                 85                  90                  95

Val Leu Val Ala Leu Ala Leu Ile Glu Cys Gly Met Lys Tyr Glu Asp
            100                 105                 110

Ala Val Gln Phe Ile Arg Gln Lys Arg Gly Ala Phe Asn Ser Lys
            115                 120                 125

Gln Leu Leu Tyr Leu Glu Lys Tyr Arg Pro Lys Met Arg Leu Arg Phe
 130                 135                 140

Arg Asp Thr Asn Gly His Cys Cys Val Gln
 145                 150

<210> SEQ ID NO 162
<211> LENGTH: 158
<212> TYPE: PRT
<213> ORGANISM: Artificial Sequence
<220> FEATURE:
<223> OTHER INFORMATION: Amino acid sequence of PTP active domain p26

<400> SEQUENCE: 162

Met Asn Arg Pro Ala Pro Val Glu Val Ser Tyr Lys His Met Arg Phe
 1               5                  10                  15

Leu Ile Thr His Asn Pro Thr Asn Ala Thr Leu Ser Thr Phe Ile Glu
            20                  25                  30

Asp Leu Lys Lys Tyr Gly Ala Thr Thr Val Val Arg Val Cys Glu Val
            35                  40                  45

Thr Tyr Asp Lys Thr Pro Leu Glu Lys Asp Gly Ile Thr Val Val Asp
 50                  55                  60

Trp Pro Phe Asp Asp Gly Ala Pro Pro Gly Lys Val Val Glu Asp
 65                  70                  75                  80

Trp Leu Ser Leu Val Lys Ala Lys Phe Cys Glu Ala Pro Gly Ser Cys
                 85                  90                  95

Val Ala Val His Cys Val Ala Gly Leu Gly Arg Ala Pro Val Leu Val
            100                 105                 110

Ala Leu Ala Leu Ile Glu Ser Gly Met Lys Tyr Glu Asp Ala Ile Gln
            115                 120                 125

Phe Ile Arg Gln Lys Arg Arg Gly Ala Ile Asn Ser Lys Gln Leu Thr
 130                 135                 140

Tyr Leu Glu Lys Tyr Arg Pro Lys Gln Arg Leu Arg Phe Lys
 145                 150                 155

<210> SEQ ID NO 163
<211> LENGTH: 355
<212> TYPE: PRT
<213> ORGANISM: Artificial Sequence
<220> FEATURE:
<223> OTHER INFORMATION: Amino acid sequence of PTP active domain T29

<400> SEQUENCE: 163

Gln Asp Pro Arg Arg Arg Asp Pro Gln Asp Asp Val Tyr Leu Asp Ile
 1               5                  10                  15

Thr Asp Arg Leu Cys Phe Ala Ile Leu Tyr Ser Arg Pro Lys Ser Ala
                20                  25                  30

Ser Asn Val His Tyr Phe Ser Ile Asp Asn Glu Leu Glu Tyr Glu Asn
                35                  40                  45

Phe Tyr Ala Asp Phe Gly Pro Leu Asn Leu Ala Met Val Tyr Arg Tyr
 50                  55                  60

Cys Cys Lys Ile Asn Lys Leu Lys Ser Ile Thr Met Leu Arg Lys
 65                  70                  75                  80

Lys Ile Val His Phe Thr Gly Ser Asp Gln Arg Lys Gln Ala Asn Ala
                85                  90                  95

Ala Phe Leu Val Gly Cys Tyr Met Val Ile Tyr Leu Gly Arg Thr Pro
                100                 105                 110

Glu Glu Ala Tyr Arg Ile Leu Ile Phe Gly Glu Thr Ser Tyr Ile Pro
                115                 120                 125

Phe Arg Asp Ala Ala Tyr Gly Ser Cys Asn Phe Tyr Ile Thr Leu Leu
                130                 135                 140

Asp Cys Phe His Ala Val Lys Lys Ala Met Gln Tyr Gly Phe Leu Asn
145                 150                 155                 160

Phe Asn Ser Phe Asn Leu Asp Glu Tyr Glu His Tyr Glu Lys Ala Glu
                165                 170                 175

Asn Gly Asp Leu Asn Trp Ile Ile Pro Asp Arg Phe Ile Ala Phe Cys
                180                 185                 190

Gly Pro His Ser Arg Ala Arg Leu Glu Ser Gly Tyr His Gln His Ser
                195                 200                 205

Pro Glu Thr Tyr Ile Gln Tyr Phe Lys Asn His Asn Val Thr Thr Ile
                210                 215                 220

Ile Arg Leu Asn Lys Arg Met Tyr Asp Ala Lys Arg Phe Thr Asp Ala
225                 230                 235                 240

Gly Phe Asp His His Asp Leu Phe Phe Ala Asp Gly Ser Thr Pro Thr
                245                 250                 255

Asp Ala Ile Val Lys Glu Phe Leu Asp Ile Cys Glu Asn Ala Glu Gly
                260                 265                 270

Ala Ile Ala Val His Cys Lys Ala Gly Leu Gly Arg Thr Gly Thr Leu
                275                 280                 285

Ile Ala Cys Tyr Ile Met Lys His Tyr Arg Met Thr Ala Ala Glu Thr
                290                 295                 300

Ile Ala Trp Val Arg Ile Cys Arg Pro Gly Ser Val Ile Gly Pro Gln
305                 310                 315                 320

Gln Gln Phe Leu Val Met Lys Gln Thr Asn Leu Trp Leu Glu Gly Asp
                325                 330                 335

Tyr Phe Arg Gln Lys Leu Lys Gly Gln Glu Asn Gly Gln His Arg Ala
                340                 345                 350

Ala Phe Ser
        355

<210> SEQ ID NO 164
<211> LENGTH: 158
<212> TYPE: PRT
<213> ORGANISM: Artificial Sequence
<220> FEATURE:
<223> OTHER INFORMATION: Amino acid sequence of PTP active domain T46

<400> SEQUENCE: 164

Met Ala Glu Gln Ala Thr Lys Ser Val Leu Phe Val Cys Leu Gly Asn
1               5                   10                  15

```
Ile Cys Arg Ser Pro Ile Ala Glu Ala Val Phe Arg Lys Leu Val Thr
            20                  25                  30

Asp Gln Asn Ile Ser Glu Asn Trp Val Ile Asp Ser Gly Ala Val Ser
                35                  40                  45

Asp Trp Asn Val Gly Arg Ser Pro Asp Pro Arg Ala Val Ser Cys Leu
50                          55                  60

Arg Asn His Gly Ile His Thr Ala His Lys Ala Arg Gln Ile Thr Lys
65                  70                  75                  80

Glu Asp Phe Ala Thr Phe Asp Tyr Ile Leu Cys Met Asp Glu Ser Asn
                    85                  90                  95

Leu Arg Asp Leu Asn Arg Lys Ser Asn Gln Val Lys Thr Cys Lys Ala
            100                 105                 110

Lys Ile Glu Leu Leu Gly Ser Tyr Asp Pro Gln Lys Gln Leu Ile Ile
                115                 120                 125

Glu Asp Pro Tyr Tyr Gly Asn Asp Ser Asp Phe Glu Thr Val Tyr Gln
            130                 135                 140

Gln Cys Val Arg Cys Arg Ala Phe Leu Glu Lys Ala His
145                 150                 155
```

<210> SEQ ID NO 165
<211> LENGTH: 188
<212> TYPE: PRT
<213> ORGANISM: Artificial Sequence
<220> FEATURE:
<223> OTHER INFORMATION: Amino acid sequence of PTP active domain pk1

<400> SEQUENCE: 165

```
Leu Ile Gly Asp Phe Ser Lys Gly Tyr Leu Phe His Thr Val Ala Gly
1               5                   10                  15

Lys His Gln Asp Leu Lys Tyr Ile Ser Pro Glu Ile Met Ala Ser Val
                20                  25                  30

Leu Asn Gly Lys Phe Ala Asn Leu Ile Lys Glu Phe Val Ile Asp
                35                  40                  45

Cys Arg Tyr Pro Tyr Glu Tyr Glu Gly Gly His Ile Lys Gly Ala Val
            50                  55                  60

Asn Leu His Met Glu Glu Glu Val Asp Phe Leu Leu Lys Lys Pro
65              70                  75                  80

Ile Val Pro Thr Asp Gly Lys Arg Val Ile Val Phe His Cys Glu
                    85                  90                  95

Phe Ser Ser Glu Arg Gly Pro Arg Met Cys Arg Tyr Val Arg Glu Arg
                100                 105                 110

Asp Arg Leu Gly Asn Glu Tyr Pro Lys Leu His Tyr Pro Glu Leu Tyr
            115                 120                 125

Val Leu Lys Gly Gly Tyr Lys Glu Phe Phe Met Lys Cys Gln Ser Tyr
            130                 135                 140

Cys Glu Pro Pro Ser Tyr Arg Pro Met His His Glu Asp Phe Lys Glu
145                 150                 155                 160

Asp Leu Lys Lys Phe Arg Thr Lys Ser Arg Thr Trp Ala Gly Glu Lys
                165                 170                 175

Ser Lys Arg Glu Met Tyr Ser Arg Leu Lys Lys Leu
            180                 185
```

<210> SEQ ID NO 166
<211> LENGTH: 189
<212> TYPE: PRT
<213> ORGANISM: Artificial Sequence
<220> FEATURE:
<223> OTHER INFORMATION: Amino acid sequence of PTP active domain T47

```
<400> SEQUENCE: 166

Leu Ile Gly Asp Tyr Ser Lys Ala Phe Leu Gln Thr Val Asp Gly
1               5                   10                  15

Lys His Gln Asp Leu Lys Tyr Ile Ser Pro Glu Thr Met Val Ala Leu
            20                  25                  30

Leu Thr Gly Lys Phe Ser Asn Ile Val Asp Lys Phe Val Ile Val Asp
            35                  40                  45

Cys Arg Tyr Pro Tyr Glu Tyr Glu Gly Gly His Ile Lys Thr Ala Val
50                  55                  60

Asn Leu Pro Leu Glu Arg Asp Ala Glu Ser Phe Leu Leu Lys Ser Pro
65                  70                  75                  80

Ile Ala Pro Cys Ser Leu Asp Lys Arg Val Ile Leu Ile Phe His Cys
                85                  90                  95

Glu Phe Ser Ser Glu Arg Gly Pro Arg Met Cys Arg Phe Ile Arg Glu
            100                 105                 110

Arg Asp Arg Ala Val Asn Asp Tyr Pro Ser Leu Tyr Tyr Pro Glu Met
            115                 120                 125

Tyr Ile Leu Lys Gly Gly Tyr Lys Glu Phe Phe Pro Gln His Pro Asn
130                 135                 140

Phe Cys Glu Pro Gln Asp Tyr Arg Pro Met Asn His Glu Ala Phe Lys
145                 150                 155                 160

Asp Glu Leu Lys Thr Phe Arg Leu Lys Thr Arg Ser Trp Ala Gly Glu
                165                 170                 175

Arg Ser Arg Arg Glu Leu Cys Ser Arg Leu Gln Asp Gln
            180                 185

<210> SEQ ID NO 167
<211> LENGTH: 194
<212> TYPE: PRT
<213> ORGANISM: Artificial Sequence
<220> FEATURE:
<223> OTHER INFORMATION: Amino acid sequence of PTP active domain T45

<400> SEQUENCE: 167

Gly His Leu Ile Gly Asp Phe Ser Lys Val Cys Ala Leu Pro Thr Val
1               5                   10                  15

Ser Gly Lys His Gln Asp Leu Lys Tyr Val Asn Pro Glu Thr Val Ala
            20                  25                  30

Ala Leu Leu Ser Gly Lys Phe Gln Gly Leu Ile Glu Lys Phe Tyr Val
            35                  40                  45

Ile Asp Cys Arg Tyr Pro Tyr Glu Tyr Leu Gly Gly His Ile Gln Gly
50                  55                  60

Ala Leu Asn Leu Tyr Ser Gln Glu Glu Leu Phe Asn Phe Phe Leu Lys
65                  70                  75                  80

Lys Pro Ile Val Pro Leu Asp Thr Gln Lys Arg Ile Ile Ile Val Phe
                85                  90                  95

His Cys Glu Phe Ser Ser Glu Arg Gly Pro Arg Met Cys Arg Cys Leu
            100                 105                 110

Arg Glu Glu Asp Arg Ser Leu Asn Gln Tyr Pro Ala Leu Tyr Tyr Pro
        115                 120                 125

Glu Leu Tyr Ile Leu Lys Gly Gly Tyr Arg Asp Phe Phe Pro Glu Tyr
            130                 135                 140

Met Glu Leu Cys Glu Pro Gln Ser Tyr Cys Pro Met His His Gln Asp
145                 150                 155                 160

His Lys Thr Glu Leu Leu Arg Cys Arg Ser Gln Ser Lys Val Gln Glu
```

```
            165                 170                 175
Gly Glu Arg Gln Leu Arg Glu Gln Ile Ala Leu Leu Val Lys Asp Met
            180                 185                 190

Ser Pro

<210> SEQ ID NO 168
<211> LENGTH: 271
<212> TYPE: PRT
<213> ORGANISM: Artificial Sequence
<220> FEATURE:
<223> OTHER INFORMATION: Amino acid sequence of PTP active domain Eya2

<400> SEQUENCE: 168

Glu Arg Val Phe Val Trp Asp Leu Asp Glu Thr Ile Ile Phe His
1               5                  10                  15

Ser Leu Leu Thr Gly Thr Phe Ala Ser Arg Tyr Gly Lys Asp Thr Thr
            20                  25                  30

Thr Ser Val Arg Ile Gly Leu Met Met Glu Glu Met Ile Phe Asn Leu
        35                  40                  45

Ala Asp Thr His Leu Phe Phe Asn Asp Leu Glu Asp Cys Asp Gln Ile
    50                  55                  60

His Val Asp Asp Val Ser Ser Asp Asp Asn Gly Gln Asp Leu Ser Thr
65                  70                  75                  80

Tyr Asn Phe Ser Ala Asp Gly Phe His Ser Ser Ala Pro Ala Ala Asn
                85                  90                  95

Leu Cys Leu Gly Ser Gly Val His Gly Gly Val Asp Trp Met Arg Lys
            100                 105                 110

Leu Ala Phe Arg Tyr Arg Arg Val Lys Glu Met Tyr Asn Thr Tyr Lys
        115                 120                 125

Asn Asn Val Gly Gly Leu Ile Gly Thr Pro Lys Arg Glu Thr Trp Leu
    130                 135                 140

Gln Leu Arg Ala Glu Leu Glu Ala Leu Thr Asp Leu Trp Leu Thr His
145                 150                 155                 160

Ser Leu Lys Ala Leu Asn Leu Ile Asn Ser Arg Pro Asn Cys Val Asn
                165                 170                 175

Val Leu Val Thr Thr Thr Gln Leu Ile Pro Ala Leu Ala Lys Val Leu
            180                 185                 190

Leu Tyr Gly Leu Gly Ser Val Phe Pro Ile Glu Asn Ile Tyr Ser Ala
        195                 200                 205

Thr Lys Thr Gly Lys Glu Ser Cys Phe Glu Arg Ile Met Gln Arg Phe
    210                 215                 220

Gly Arg Lys Ala Val Tyr Val Val Ile Gly Asp Gly Val Glu Glu Glu
225                 230                 235                 240

Gln Gly Ala Lys Lys His Asn Met Pro Phe Trp Arg Ile Ser Cys His
                245                 250                 255

Ala Asp Leu Glu Ala Leu Arg His Ala Leu Glu Leu Glu Tyr Leu
            260                 265                 270

<210> SEQ ID NO 169
<211> LENGTH: 17
<212> TYPE: PRT
<213> ORGANISM: Artificial Sequence
<220> FEATURE:
<223> OTHER INFORMATION: Synthetic peptide Eya2-1 3 3

<400> SEQUENCE: 169

Ala Val Tyr Val Val Ile Gly Asp Gly Val Glu Glu Glu Gln Gly Ala
1               5                  10                  15
```

Lys

<210> SEQ ID NO 170
<211> LENGTH: 21
<212> TYPE: PRT
<213> ORGANISM: Artificial Sequence
<220> FEATURE:
<223> OTHER INFORMATION: Synthetic peptide NE1-1

<400> SEQUENCE: 170

Thr His Ile Leu Asn Val Ala Tyr Gly Val Glu Asn Ala Phe Leu Ser
1               5                   10                  15

Asp Phe Thr Tyr Lys
            20

<210> SEQ ID NO 171
<211> LENGTH: 16
<212> TYPE: PRT
<213> ORGANISM: Artificial Sequence
<220> FEATURE:
<223> OTHER INFORMATION: Synthetic peptide NE3-1 3 3

<400> SEQUENCE: 171

Glu Ile Asp Asn Phe Phe Pro Gly Val Phe Glu Tyr His Asn Ile Arg
1               5                   10                  15

<210> SEQ ID NO 172
<211> LENGTH: 13
<212> TYPE: PRT
<213> ORGANISM: Artificial Sequence
<220> FEATURE:
<223> OTHER INFORMATION: Synthetic peptide p12-1

<400> SEQUENCE: 172

Ile Asp Pro Thr Val Leu Leu Gly Ala Leu Pro Leu Arg
1               5                   10

<210> SEQ ID NO 173
<211> LENGTH: 9
<212> TYPE: PRT
<213> ORGANISM: Artificial Sequence
<220> FEATURE:
<223> OTHER INFORMATION: Synthetic peptide p13-1

<400> SEQUENCE: 173

Val Pro Val Leu Ser Tyr Leu Tyr Lys
1               5

<210> SEQ ID NO 174
<211> LENGTH: 11
<212> TYPE: PRT
<213> ORGANISM: Artificial Sequence
<220> FEATURE:
<223> OTHER INFORMATION: Synthetic peptide p16-R*

<400> SEQUENCE: 174

Phe Val Gln Ile Val Asp Glu Ala Asn Ala Arg
1               5                   10

<210> SEQ ID NO 175
<211> LENGTH: 16
<212> TYPE: PRT
<213> ORGANISM: Artificial Sequence
<220> FEATURE:
<223> OTHER INFORMATION: Synthetic peptide p18-1

<400> SEQUENCE: 175

```
Glu Ile Asp Asn Phe Phe Pro Gly Leu Phe Ala Tyr His Asn Ile Arg
1               5                   10                  15

<210> SEQ ID NO 176
<211> LENGTH: 13
<212> TYPE: PRT
<213> ORGANISM: Artificial Sequence
<220> FEATURE:
<223> OTHER INFORMATION: Synthetic peptide p19-1

<400> SEQUENCE: 176

Ser Leu Phe Leu Ser Asn Gly Val Ala Ala Asn Asp Lys
1               5                   10

<210> SEQ ID NO 177
<211> LENGTH: 10
<212> TYPE: PRT
<213> ORGANISM: Artificial Sequence
<220> FEATURE:
<223> OTHER INFORMATION: Synthetic peptide p20-1

<400> SEQUENCE: 177

Ala Ala Gly Ala Glu Glu Gln Leu Ala Arg
1               5                   10

<210> SEQ ID NO 178
<211> LENGTH: 7
<212> TYPE: PRT
<213> ORGANISM: Artificial Sequence
<220> FEATURE:
<223> OTHER INFORMATION: Synthetic peptide p21-1

<400> SEQUENCE: 178

Asp Leu Asp Gln Leu Gly Arg
1               5

<210> SEQ ID NO 179
<211> LENGTH: 10
<212> TYPE: PRT
<213> ORGANISM: Artificial Sequence
<220> FEATURE:
<223> OTHER INFORMATION: Synthetic peptide p24-1

<400> SEQUENCE: 179

Val Ala Thr Glu Leu Gln Pro Ser Gln Arg
1               5                   10

<210> SEQ ID NO 180
<211> LENGTH: 8
<212> TYPE: PRT
<213> ORGANISM: Artificial Sequence
<220> FEATURE:
<223> OTHER INFORMATION: Synthetic peptide p44-1

<400> SEQUENCE: 180

Gln Leu Gln Val Leu Asp Asn Arg
1               5

<210> SEQ ID NO 181
<211> LENGTH: 16
<212> TYPE: PRT
<213> ORGANISM: Artificial Sequence
<220> FEATURE:
<223> OTHER INFORMATION: Synthetic peptide p45-1

<400> SEQUENCE: 181

Val Leu Glu Phe Gly Trp Pro Asp Leu His Thr Pro Ala Leu Glu Lys
```

<210> SEQ ID NO 182
<211> LENGTH: 15
<212> TYPE: PRT
<213> ORGANISM: Artificial Sequence
<220> FEATURE:
<223> OTHER INFORMATION: Synthetic peptide p46-1

<400> SEQUENCE: 182

Val Phe Leu Glu Asn Tyr Gln Ile Leu Gln Tyr Phe Ile Ile Arg
1               5                   10                  15

<210> SEQ ID NO 183
<211> LENGTH: 12
<212> TYPE: PRT
<213> ORGANISM: Artificial Sequence
<220> FEATURE:
<223> OTHER INFORMATION: Synthetic peptide p47-1

<400> SEQUENCE: 183

Ala Gln Glu Ala Leu Asp Phe Tyr Gly Glu Val Arg
1               5                   10

<210> SEQ ID NO 184
<211> LENGTH: 10
<212> TYPE: PRT
<213> ORGANISM: Artificial Sequence
<220> FEATURE:
<223> OTHER INFORMATION: Synthetic peptide pk10-1

<400> SEQUENCE: 184

Asp Ser Thr Asn Leu Asp Val Leu Gly Lys
1               5                   10

<210> SEQ ID NO 185
<211> LENGTH: 10
<212> TYPE: PRT
<213> ORGANISM: Artificial Sequence
<220> FEATURE:
<223> OTHER INFORMATION: Synthetic peptide pk1-1

<400> SEQUENCE: 185

Gly Tyr Leu Phe His Thr Val Ala Gly Lys
1               5                   10

<210> SEQ ID NO 186
<211> LENGTH: 10
<212> TYPE: PRT
<213> ORGANISM: Artificial Sequence
<220> FEATURE:
<223> OTHER INFORMATION: Synthetic peptide pk12-1

<400> SEQUENCE: 186

Asp Ser Ala Asn Leu Glu Ser Leu Ala Lys
1               5                   10

<210> SEQ ID NO 187
<211> LENGTH: 20
<212> TYPE: PRT
<213> ORGANISM: Artificial Sequence
<220> FEATURE:
<223> OTHER INFORMATION: Synthetic peptide pk13-1

<400> SEQUENCE: 187

Leu Asn Ile Gly Tyr Val Ile Asn Val Thr Thr His Leu Pro Leu Tyr
1               5                   10                  15

His Tyr Glu Lys
            20

<210> SEQ ID NO 188
<211> LENGTH: 16
<212> TYPE: PRT
<213> ORGANISM: Artificial Sequence
<220> FEATURE:
<223> OTHER INFORMATION: Synthetic peptide pk14-1

<400> SEQUENCE: 188

Ile Phe Thr Val Gly His Gln Val Pro Asp Asp Glu Thr Ile Phe Lys
1               5                   10                  15

<210> SEQ ID NO 189
<211> LENGTH: 8
<212> TYPE: PRT
<213> ORGANISM: Artificial Sequence
<220> FEATURE:
<223> OTHER INFORMATION: Synthetic peptide pk15-1

<400> SEQUENCE: 189

Ser Ser Ser Ile Leu Asp His Arg
1               5

<210> SEQ ID NO 190
<211> LENGTH: 12
<212> TYPE: PRT
<213> ORGANISM: Artificial Sequence
<220> FEATURE:
<223> OTHER INFORMATION: Synthetic peptide pk16-1

<400> SEQUENCE: 190

Gly Tyr Glu Asn Glu Asp Asn Tyr Ser Asn Ile Lys
1               5                   10

<210> SEQ ID NO 191
<211> LENGTH: 12
<212> TYPE: PRT
<213> ORGANISM: Artificial Sequence
<220> FEATURE:
<223> OTHER INFORMATION: Synthetic peptide pk17-1

<400> SEQUENCE: 191

Gly Thr Pro Glu Ala Tyr Glu Gly Leu Gly Ile Arg
1               5                   10

<210> SEQ ID NO 192
<211> LENGTH: 15
<212> TYPE: PRT
<213> ORGANISM: Artificial Sequence
<220> FEATURE:
<223> OTHER INFORMATION: Synthetic peptide pk18-1

<400> SEQUENCE: 192

Glu Glu Tyr Gly Glu Ser Pro Leu Gln Asp Ala Glu Glu Ala Lys
1               5                   10                  15

<210> SEQ ID NO 193
<211> LENGTH: 17
<212> TYPE: PRT
<213> ORGANISM: Artificial Sequence
<220> FEATURE:
<223> OTHER INFORMATION: Synthetic peptide pk19-1

<400> SEQUENCE: 193

Glu Pro Gly Gly Glu Leu Ser Trp Glu Gly Asn Gly Pro His His Asp
1               5                   10                  15

Arg

<210> SEQ ID NO 194
<211> LENGTH: 8
<212> TYPE: PRT
<213> ORGANISM: Artificial Sequence
<220> FEATURE:
<223> OTHER INFORMATION: Synthetic peptide pk2-1

<400> SEQUENCE: 194

Leu Ala Ala His Leu Ser Ser Arg
1               5

<210> SEQ ID NO 195
<211> LENGTH: 12
<212> TYPE: PRT
<213> ORGANISM: Artificial Sequence
<220> FEATURE:
<223> OTHER INFORMATION: Synthetic peptide pk28-1

<400> SEQUENCE: 195

Phe Asp Ser Leu Thr Asp Leu Val Glu His Tyr Lys
1               5                   10

<210> SEQ ID NO 196
<211> LENGTH: 15
<212> TYPE: PRT
<213> ORGANISM: Artificial Sequence
<220> FEATURE:
<223> OTHER INFORMATION: Synthetic peptide pk30-1

<400> SEQUENCE: 196

Met Val Gln Thr Pro Tyr Gly Ile Val Pro Asp Val Tyr Glu Lys
1               5                   10                  15

<210> SEQ ID NO 197
<211> LENGTH: 19
<212> TYPE: PRT
<213> ORGANISM: Artificial Sequence
<220> FEATURE:
<223> OTHER INFORMATION: Synthetic peptide pk32-1

<400> SEQUENCE: 197

Ile Pro Ser Asn Phe Val Ser Pro Glu Asp Leu Asp Ile Pro Gly His
1               5                   10                  15

Ala Ser Lys

<210> SEQ ID NO 198
<211> LENGTH: 19
<212> TYPE: PRT
<213> ORGANISM: Artificial Sequence
<220> FEATURE:
<223> OTHER INFORMATION: Synthetic peptide pk33-1

<400> SEQUENCE: 198

Val Asp Glu Val Trp Pro Asn Leu Phe Ile Gly Asp Ala Ala Thr Ala
1               5                   10                  15

Asn Asn Arg

<210> SEQ ID NO 199
<211> LENGTH: 12
<212> TYPE: PRT
<213> ORGANISM: Artificial Sequence
<220> FEATURE:
<223> OTHER INFORMATION: Synthetic peptide pk35-1

```
<400> SEQUENCE: 199

Gln Pro Ser Val Ser Gly Leu Ser Gln Ile Thr Lys
1               5                   10

<210> SEQ ID NO 200
<211> LENGTH: 7
<212> TYPE: PRT
<213> ORGANISM: Artificial Sequence
<220> FEATURE:
<223> OTHER INFORMATION: Synthetic peptide pk36-1

<400> SEQUENCE: 200

Phe Thr Tyr His Asn Val Arg
1               5

<210> SEQ ID NO 201
<211> LENGTH: 14
<212> TYPE: PRT
<213> ORGANISM: Artificial Sequence
<220> FEATURE:
<223> OTHER INFORMATION: Synthetic peptide pk38-1

<400> SEQUENCE: 201

Ile Glu Asp Ser Pro Glu Ala Gln Ile Leu Pro Phe Leu Arg
1               5                   10

<210> SEQ ID NO 202
<211> LENGTH: 9
<212> TYPE: PRT
<213> ORGANISM: Artificial Sequence
<220> FEATURE:
<223> OTHER INFORMATION: Synthetic peptide pk4-1

<400> SEQUENCE: 202

Leu Asp Glu Ala Phe Glu Phe Val Lys
1               5

<210> SEQ ID NO 203
<211> LENGTH: 9
<212> TYPE: PRT
<213> ORGANISM: Artificial Sequence
<220> FEATURE:
<223> OTHER INFORMATION: Synthetic peptide pk5-1

<400> SEQUENCE: 203

Leu Asp Glu Ala Phe Asp Phe Val Lys
1               5

<210> SEQ ID NO 204
<211> LENGTH: 13
<212> TYPE: PRT
<213> ORGANISM: Artificial Sequence
<220> FEATURE:
<223> OTHER INFORMATION: Synthetic peptide pk6-2

<400> SEQUENCE: 204

Leu Gly Ile Thr His Val Leu Asn Ala Ala Glu Gly Arg
1               5                   10

<210> SEQ ID NO 205
<211> LENGTH: 9
<212> TYPE: PRT
<213> ORGANISM: Artificial Sequence
<220> FEATURE:
<223> OTHER INFORMATION: Synthetic peptide pk7-1

<400> SEQUENCE: 205
```

Leu Glu Glu Ala Phe Glu Phe Val Lys
1               5

<210> SEQ ID NO 206
<211> LENGTH: 9
<212> TYPE: PRT
<213> ORGANISM: Artificial Sequence
<220> FEATURE:
<223> OTHER INFORMATION: Synthetic peptide pk8-1LK

<400> SEQUENCE: 206

Leu Lys Glu Ala Phe Asp Tyr Ile Lys
1               5

<210> SEQ ID NO 207
<211> LENGTH: 14
<212> TYPE: PRT
<213> ORGANISM: Artificial Sequence
<220> FEATURE:
<223> OTHER INFORMATION: Synthetic peptide pk9-1

<400> SEQUENCE: 207

Asp Ser Thr Asn Leu Asp Val Leu Glu Glu Phe Gly Ile Lys
1               5                   10

<210> SEQ ID NO 208
<211> LENGTH: 7
<212> TYPE: PRT
<213> ORGANISM: Artificial Sequence
<220> FEATURE:
<223> OTHER INFORMATION: Synthetic peptide PRL1-*KK

<400> SEQUENCE: 208

Phe Ile Glu Glu Leu Lys Lys
1               5

<210> SEQ ID NO 209
<211> LENGTH: 9
<212> TYPE: PRT
<213> ORGANISM: Artificial Sequence
<220> FEATURE:
<223> OTHER INFORMATION: Synthetic peptide PRL12-R*

<400> SEQUENCE: 209

Tyr Glu Asp Ala Val Gln Phe Ile Arg
1               5

<210> SEQ ID NO 210
<211> LENGTH: 7
<212> TYPE: PRT
<213> ORGANISM: Artificial Sequence
<220> FEATURE:
<223> OTHER INFORMATION: Synthetic peptide PRL2-*KK

<400> SEQUENCE: 210

Phe Thr Glu Glu Leu Lys Lys
1               5

<210> SEQ ID NO 211
<211> LENGTH: 21
<212> TYPE: PRT
<213> ORGANISM: Artificial Sequence
<220> FEATURE:
<223> OTHER INFORMATION: Synthetic peptide PRL3-F*KK

<400> SEQUENCE: 211

Phe Leu Ile Thr His Asn Pro Thr Asn Ala Thr Leu Ser Thr Phe Ile
1               5                   10                  15

```
Glu Asp Leu Lys Lys
            20

<210> SEQ ID NO 212
<211> LENGTH: 9
<212> TYPE: PRT
<213> ORGANISM: Artificial Sequence
<220> FEATURE:
<223> OTHER INFORMATION: Synthetic peptide PRL3-R*

<400> SEQUENCE: 212

Tyr Glu Asp Ala Ile Gln Phe Ile Arg
1               5

<210> SEQ ID NO 213
<211> LENGTH: 15
<212> TYPE: PRT
<213> ORGANISM: Artificial Sequence
<220> FEATURE:
<223> OTHER INFORMATION: Synthetic peptide PTP1B-1

<400> SEQUENCE: 213

Leu His Gln Glu Asp Asn Asp Tyr Ile Asn Ala Ser Leu Ile Lys
1               5                   10                  15

<210> SEQ ID NO 214
<211> LENGTH: 15
<212> TYPE: PRT
<213> ORGANISM: Artificial Sequence
<220> FEATURE:
<223> OTHER INFORMATION: Synthetic peptide PTPRT1

<400> SEQUENCE: 214

Val Thr Leu Ile Glu Thr Glu Pro Leu Ala Glu Tyr Val Ile Arg
1               5                   10                  15

<210> SEQ ID NO 215
<211> LENGTH: 14
<212> TYPE: PRT
<213> ORGANISM: Artificial Sequence
<220> FEATURE:
<223> OTHER INFORMATION: Synthetic peptide PTPRT2

<400> SEQUENCE: 215

Gly Ala Ser Thr Gln Asn Ser Asn Thr Val Glu Pro Glu Lys
1               5                   10

<210> SEQ ID NO 216
<211> LENGTH: 12
<212> TYPE: PRT
<213> ORGANISM: Artificial Sequence
<220> FEATURE:
<223> OTHER INFORMATION: Synthetic peptide SHP1-1

<400> SEQUENCE: 216

Asp Leu Ser Gly Leu Asp Ala Glu Thr Leu Leu Lys
1               5                   10

<210> SEQ ID NO 217
<211> LENGTH: 9
<212> TYPE: PRT
<213> ORGANISM: Artificial Sequence
<220> FEATURE:
<223> OTHER INFORMATION: Synthetic peptide SHP1-2

<400> SEQUENCE: 217

Gly Glu Pro Trp Thr Phe Leu Val Arg
```

```
<210> SEQ ID NO 218
<211> LENGTH: 11
<212> TYPE: PRT
<213> ORGANISM: Artificial Sequence
<220> FEATURE:
<223> OTHER INFORMATION: Synthetic peptide SHP1-3

<400> SEQUENCE: 218

Asn Gln Leu Leu Gly Pro Asp Glu Asn Ala Lys
1               5                   10

<210> SEQ ID NO 219
<211> LENGTH: 9
<212> TYPE: PRT
<213> ORGANISM: Artificial Sequence
<220> FEATURE:
<223> OTHER INFORMATION: Synthetic peptide T10-1

<400> SEQUENCE: 219

Thr Ile Leu Pro Asn Pro Leu Ser Arg
1               5

<210> SEQ ID NO 220
<211> LENGTH: 8
<212> TYPE: PRT
<213> ORGANISM: Artificial Sequence
<220> FEATURE:
<223> OTHER INFORMATION: Synthetic peptide T1-1

<400> SEQUENCE: 220

Glu Gln Tyr Glu Leu Val His Arg
1               5

<210> SEQ ID NO 221
<211> LENGTH: 11
<212> TYPE: PRT
<213> ORGANISM: Artificial Sequence
<220> FEATURE:
<223> OTHER INFORMATION: Synthetic peptide T12-1

<400> SEQUENCE: 221

Ser Leu Ala Val Leu Thr Tyr Asp His Ser Arg
1               5                   10

<210> SEQ ID NO 222
<211> LENGTH: 9
<212> TYPE: PRT
<213> ORGANISM: Artificial Sequence
<220> FEATURE:
<223> OTHER INFORMATION: Synthetic peptide T15-1

<400> SEQUENCE: 222

Phe Ser Leu Gln Phe Glu Glu Leu Lys
1               5

<210> SEQ ID NO 223
<211> LENGTH: 10
<212> TYPE: PRT
<213> ORGANISM: Artificial Sequence
<220> FEATURE:
<223> OTHER INFORMATION: Synthetic peptide T16-R*

<400> SEQUENCE: 223

Tyr Asp Ser Gln Val Ala Glu Glu Asn Arg
1               5                   10
```

<210> SEQ ID NO 224
<211> LENGTH: 8
<212> TYPE: PRT
<213> ORGANISM: Artificial Sequence
<220> FEATURE:
<223> OTHER INFORMATION: Synthetic peptide T17-1

<400> SEQUENCE: 224

Tyr Ile Ala Ala Gln Gly Pro Arg
1               5

<210> SEQ ID NO 225
<211> LENGTH: 13
<212> TYPE: PRT
<213> ORGANISM: Artificial Sequence
<220> FEATURE:
<223> OTHER INFORMATION: Synthetic peptide T19-1

<400> SEQUENCE: 225

Asn Ala Asp Asp Glu His Leu Val Gln Ser Val Ala Lys
1               5                   10

<210> SEQ ID NO 226
<211> LENGTH: 8
<212> TYPE: PRT
<213> ORGANISM: Artificial Sequence
<220> FEATURE:
<223> OTHER INFORMATION: Synthetic peptide T2-1

<400> SEQUENCE: 226

His Asn Thr Val Thr Tyr Gly Arg
1               5

<210> SEQ ID NO 227
<211> LENGTH: 9
<212> TYPE: PRT
<213> ORGANISM: Artificial Sequence
<220> FEATURE:
<223> OTHER INFORMATION: Synthetic peptide T21-1

<400> SEQUENCE: 227

Ser Tyr Thr Ala Ala Val Ala Asn Arg
1               5

<210> SEQ ID NO 228
<211> LENGTH: 12
<212> TYPE: PRT
<213> ORGANISM: Artificial Sequence
<220> FEATURE:
<223> OTHER INFORMATION: Synthetic peptide T22-1

<400> SEQUENCE: 228

Thr Val Asp Val Tyr Gly His Val Thr Leu Met Arg
1               5                   10

<210> SEQ ID NO 229
<211> LENGTH: 11
<212> TYPE: PRT
<213> ORGANISM: Artificial Sequence
<220> FEATURE:
<223> OTHER INFORMATION: Synthetic peptide T23-1

<400> SEQUENCE: 229

Asn Ile Gln Thr Ser Glu Ser His Pro Leu Arg
1               5                   10

<210> SEQ ID NO 230

<211> LENGTH: 9
<212> TYPE: PRT
<213> ORGANISM: Artificial Sequence
<220> FEATURE:
<223> OTHER INFORMATION: Synthetic peptide T24-1

<400> SEQUENCE: 230

Val Tyr Asp Pro Val Ser Glu Tyr Lys
1               5

<210> SEQ ID NO 231
<211> LENGTH: 9
<212> TYPE: PRT
<213> ORGANISM: Artificial Sequence
<220> FEATURE:
<223> OTHER INFORMATION: Synthetic peptide T25-1

<400> SEQUENCE: 231

Glu Phe Glu Glu Leu Asp Thr Gln Arg
1               5

<210> SEQ ID NO 232
<211> LENGTH: 14
<212> TYPE: PRT
<213> ORGANISM: Artificial Sequence
<220> FEATURE:
<223> OTHER INFORMATION: Synthetic peptide T26-1

<400> SEQUENCE: 232

Pro Ser Asp Thr Thr Lys Tyr Leu Leu Glu Gln Leu Glu Lys
1               5                   10

<210> SEQ ID NO 233
<211> LENGTH: 11
<212> TYPE: PRT
<213> ORGANISM: Artificial Sequence
<220> FEATURE:
<223> OTHER INFORMATION: Synthetic peptide T27-1

<400> SEQUENCE: 233

Ile Leu Pro Asn Leu Tyr Leu Gly Cys Gln Arg
1               5                   10

<210> SEQ ID NO 234
<211> LENGTH: 9
<212> TYPE: PRT
<213> ORGANISM: Artificial Sequence
<220> FEATURE:
<223> OTHER INFORMATION: Synthetic peptide T29-1

<400> SEQUENCE: 234

Asn His Asn Val Thr Thr Ile Ile Arg
1               5

<210> SEQ ID NO 235
<211> LENGTH: 7
<212> TYPE: PRT
<213> ORGANISM: Artificial Sequence
<220> FEATURE:
<223> OTHER INFORMATION: Synthetic peptide T30-1

<400> SEQUENCE: 235

Val Leu Ser Leu Gln Phe Arg
1               5

<210> SEQ ID NO 236
<211> LENGTH: 11
<212> TYPE: PRT

```
<213> ORGANISM: Artificial Sequence
<220> FEATURE:
<223> OTHER INFORMATION: Synthetic peptide T3-1

<400> SEQUENCE: 236

Tyr Lys Asp Val Leu Pro Tyr Asp Gln Thr Arg
1               5                   10

<210> SEQ ID NO 237
<211> LENGTH: 12
<212> TYPE: PRT
<213> ORGANISM: Artificial Sequence
<220> FEATURE:
<223> OTHER INFORMATION: Synthetic peptide T31-1

<400> SEQUENCE: 237

Val Ala Asp Leu Leu Gln His Ile Asn Gln Met Lys
1               5                   10

<210> SEQ ID NO 238
<211> LENGTH: 16
<212> TYPE: PRT
<213> ORGANISM: Artificial Sequence
<220> FEATURE:
<223> OTHER INFORMATION: Synthetic peptide T32-1

<400> SEQUENCE: 238

Val Pro Leu Gly Asp Glu Gly Gly Tyr Ile Asn Ala Ser Phe Ile Lys
1               5                   10                  15

<210> SEQ ID NO 239
<211> LENGTH: 11
<212> TYPE: PRT
<213> ORGANISM: Artificial Sequence
<220> FEATURE:
<223> OTHER INFORMATION: Synthetic peptide T33-1

<400> SEQUENCE: 239

Ile Leu Pro His Leu Tyr Leu Gly Ser Gln Lys
1               5                   10

<210> SEQ ID NO 240
<211> LENGTH: 15
<212> TYPE: PRT
<213> ORGANISM: Artificial Sequence
<220> FEATURE:
<223> OTHER INFORMATION: Synthetic peptide T35-1

<400> SEQUENCE: 240

Asp Gly Ile Ile Pro Glu Asn Phe Ser Val Phe Ser Leu Ile Arg
1               5                   10                  15

<210> SEQ ID NO 241
<211> LENGTH: 12
<212> TYPE: PRT
<213> ORGANISM: Artificial Sequence
<220> FEATURE:
<223> OTHER INFORMATION: Synthetic peptide T37-1

<400> SEQUENCE: 241

Asp Phe Leu Val Thr Leu Asn Gln Pro Gln Ala Arg
1               5                   10

<210> SEQ ID NO 242
<211> LENGTH: 12
<212> TYPE: PRT
<213> ORGANISM: Artificial Sequence
<220> FEATURE:
```

<223> OTHER INFORMATION: Synthetic peptide T38-1

<400> SEQUENCE: 242

Glu Ile Asp Ile Ala Ala Thr Leu Glu His Val Arg
1               5                   10

<210> SEQ ID NO 243
<211> LENGTH: 11
<212> TYPE: PRT
<213> ORGANISM: Artificial Sequence
<220> FEATURE:
<223> OTHER INFORMATION: Synthetic peptide T39-1

<400> SEQUENCE: 243

Gln Asn Val Val Asp Val Phe His Ala Val Lys
1               5                   10

<210> SEQ ID NO 244
<211> LENGTH: 16
<212> TYPE: PRT
<213> ORGANISM: Artificial Sequence
<220> FEATURE:
<223> OTHER INFORMATION: Synthetic peptide T40-1

<400> SEQUENCE: 244

Ala Asn Gly Ile Phe Ser Thr Ala Ala Leu Pro Glu Asn Ala Glu Arg
1               5                   10                  15

<210> SEQ ID NO 245
<211> LENGTH: 12
<212> TYPE: PRT
<213> ORGANISM: Artificial Sequence
<220> FEATURE:
<223> OTHER INFORMATION: Synthetic peptide T4-1

<400> SEQUENCE: 245

Ala Glu Gly Ile Leu Asp Val Phe Gln Thr Val Lys
1               5                   10

<210> SEQ ID NO 246
<211> LENGTH: 9
<212> TYPE: PRT
<213> ORGANISM: Artificial Sequence
<220> FEATURE:
<223> OTHER INFORMATION: Synthetic peptide T41-1

<400> SEQUENCE: 246

Ala Pro Pro Leu Leu His Leu Val Arg
1               5

<210> SEQ ID NO 247
<211> LENGTH: 14
<212> TYPE: PRT
<213> ORGANISM: Artificial Sequence
<220> FEATURE:
<223> OTHER INFORMATION: Synthetic peptide T45-1

<400> SEQUENCE: 247

Tyr Val Asn Pro Glu Thr Val Ala Ala Leu Leu Ser Gly Lys
1               5                   10

<210> SEQ ID NO 248
<211> LENGTH: 11
<212> TYPE: PRT
<213> ORGANISM: Artificial Sequence
<220> FEATURE:
<223> OTHER INFORMATION: Synthetic peptide T46-1

```
<400> SEQUENCE: 248

Ile Glu Leu Leu Gly Ser Tyr Asp Pro Gln Lys
1               5                   10

<210> SEQ ID NO 249
<211> LENGTH: 10
<212> TYPE: PRT
<213> ORGANISM: Artificial Sequence
<220> FEATURE:
<223> OTHER INFORMATION: Synthetic peptide T47-1

<400> SEQUENCE: 249

Ala Phe Leu Leu Gln Thr Val Asp Gly Lys
1               5                   10

<210> SEQ ID NO 250
<211> LENGTH: 8
<212> TYPE: PRT
<213> ORGANISM: Artificial Sequence
<220> FEATURE:
<223> OTHER INFORMATION: Synthetic peptide T48-1

<400> SEQUENCE: 250

Asn Leu Tyr Ala His Ile Gln Lys
1               5

<210> SEQ ID NO 251
<211> LENGTH: 9
<212> TYPE: PRT
<213> ORGANISM: Artificial Sequence
<220> FEATURE:
<223> OTHER INFORMATION: Synthetic peptide T5-1

<400> SEQUENCE: 251

Thr Val Asp Val Phe His Ala Val Lys
1               5

<210> SEQ ID NO 252
<211> LENGTH: 13
<212> TYPE: PRT
<213> ORGANISM: Artificial Sequence
<220> FEATURE:
<223> OTHER INFORMATION: Synthetic peptide T53-1

<400> SEQUENCE: 252

Ser Leu Ser Val His Ser Gly Thr Thr Gly Ser Leu Lys
1               5                   10

<210> SEQ ID NO 253
<211> LENGTH: 15
<212> TYPE: PRT
<213> ORGANISM: Artificial Sequence
<220> FEATURE:
<223> OTHER INFORMATION: Synthetic peptide T6-1

<400> SEQUENCE: 253

His Ser Asp Tyr Ile Asn Ala Asn Tyr Val Asp Gly Tyr Asn Lys
1               5                   10                  15

<210> SEQ ID NO 254
<211> LENGTH: 13
<212> TYPE: PRT
<213> ORGANISM: Artificial Sequence
<220> FEATURE:
<223> OTHER INFORMATION: Synthetic peptide T7-1 3 3

<400> SEQUENCE: 254
```

Asp Ser Val Asp Ile Tyr Gly Ala Val His Asp Leu Arg
1               5                   10

<210> SEQ ID NO 255
<211> LENGTH: 12
<212> TYPE: PRT
<213> ORGANISM: Artificial Sequence
<220> FEATURE:
<223> OTHER INFORMATION: Synthetic peptide T8-1

<400> SEQUENCE: 255

Thr Gly Thr Leu Ile Ala Leu Asp Val Leu Leu Arg
1               5                   10

<210> SEQ ID NO 256
<211> LENGTH: 295
<212> TYPE: PRT
<213> ORGANISM: Artificial Sequence
<220> FEATURE:
<223> OTHER INFORMATION: Amino acid sequence of PTP active domain  p45

<400> SEQUENCE: 256

Met Lys Asp Ser Glu Asn Lys Gly Ala Ser Pro Asp Met Glu Pro
1               5                   10                  15

Ser Tyr Gly Gly Gly Leu Phe Asp Met Val Lys Gly Ala Gly Arg
                20                  25                  30

Leu Phe Ser Asn Leu Lys Asp Asn Leu Lys Asp Thr Leu Lys Asp Thr
                35                  40                  45

Ser Ser Arg Val Ile Gln Ser Val Thr Ser Tyr Thr Lys Gly Asp Leu
            50                  55                  60

Asp Phe Thr Tyr Val Thr Ser Arg Ile Ile Val Met Ser Phe Pro Leu
65                  70                  75                  80

Asp Asn Val Asp Ile Gly Phe Arg Asn Gln Val Asp Ile Arg Ser
                    85                  90                  95

Phe Leu Asp Ser Arg His Leu Asp His Tyr Thr Val Tyr Asn Leu Ser
                    100                 105                 110

Pro Lys Ser Tyr Arg Thr Ala Lys Phe His Ser Arg Val Ser Glu Cys
                115                 120                 125

Ser Trp Pro Ile Arg Gln Ala Pro Ser Leu His Asn Leu Phe Ala Val
            130                 135                 140

Cys Arg Asn Met Tyr Asn Trp Leu Leu Gln Asn Pro Lys Asn Val Cys
145                 150                 155                 160

Val Val His Cys Leu Asp Gly Arg Ala Ala Ser Ser Ile Leu Val Gly
                    165                 170                 175

Ala Met Phe Ile Phe Cys Asn Leu Tyr Ser Thr Pro Gly Pro Ala Ile
                    180                 185                 190

Arg Leu Leu Tyr Ala Lys Arg Pro Gly Ile Gly Leu Ser Pro Ser His
                195                 200                 205

Arg Arg Tyr Leu Gly Tyr Met Cys Asp Leu Leu Ala Asp Lys Pro Tyr
            210                 215                 220

Arg Pro His Phe Lys Pro Leu Thr Ile Lys Ser Ile Thr Val Ser Pro
225                 230                 235                 240

Ile Pro Phe Phe Asn Lys Gln Arg Asn Gly Cys Arg Pro Tyr Cys Asp
                    245                 250                 255

Val Leu Ile Gly Glu Thr Lys Ile Tyr Ser Thr Cys Thr Asp Phe Glu
                260                 265                 270

Arg Met Lys Glu Tyr Arg Val Gln Asp Gly Lys Ile Phe Ile Pro Leu
            275                 280                 285

```
Asn Ile Thr Val Gln Gly Asp
    290                 295
```

<210> SEQ ID NO 257
<211> LENGTH: 272
<212> TYPE: PRT
<213> ORGANISM: Artificial Sequence
<220> FEATURE:
<223> OTHER INFORMATION: Amino acid sequence of PTP active domain p46

<400> SEQUENCE: 257

```
Ile Leu Glu Glu Lys Thr Ala Ala Tyr Asp Ile Met Gln Glu Phe Met
1               5                   10                  15

Ala Leu Glu Leu Lys Asn Leu Pro Gly Glu Phe Asn Ser Gly Asn Gln
            20                  25                  30

Pro Ser Asn Arg Glu Lys Asn Arg Tyr Arg Asp Ile Leu Pro Tyr Asp
        35                  40                  45

Ser Thr Arg Val Pro Leu Gly Lys Ser Lys Asp Tyr Ile Asn Ala Ser
    50                  55                  60

Tyr Ile Arg Ile Val Asn Cys Gly Glu Glu Tyr Phe Tyr Ile Ala Thr
65                  70                  75                  80

Gln Gly Pro Leu Leu Ser Thr Ile Asp Asp Phe Trp Gln Met Val Leu
                85                  90                  95

Glu Asn Asn Ser Asn Val Ile Ala Met Ile Thr Arg Glu Ile Glu Gly
            100                 105                 110

Gly Ile Ile Lys Cys Tyr His Tyr Trp Pro Ile Ser Leu Lys Lys Pro
        115                 120                 125

Leu Glu Leu Lys His Phe Arg Val Phe Leu Glu Asn Tyr Gln Ile Leu
    130                 135                 140

Gln Tyr Phe Ile Ile Arg Met Phe Gln Val Val Glu Lys Ser Thr Gly
145                 150                 155                 160

Thr Ser His Ser Val Lys Gln Leu Gln Phe Thr Lys Trp Pro Asp His
                165                 170                 175

Gly Thr Pro Ala Ser Ala Asp Ser Phe Ile Lys Tyr Ile Arg Tyr Ala
            180                 185                 190

Arg Lys Ser His Leu Thr Gly Pro Met Val Val His Cys Ser Ala Gly
        195                 200                 205

Ile Gly Arg Thr Gly Val Phe Leu Cys Val Asp Val Val Phe Cys Ala
    210                 215                 220

Ile Val Lys Asn Cys Ser Phe Asn Ile Met Asp Ile Val Ala Gln Met
225                 230                 235                 240

Arg Glu Gln Arg Ser Gly Met Val Gln Thr Lys Glu Gln Tyr His Phe
                245                 250                 255

Cys Tyr Asp Ile Val Leu Glu Val Leu Arg Lys Leu Leu Thr Leu Asp
            260                 265                 270
```

<210> SEQ ID NO 258
<211> LENGTH: 242
<212> TYPE: PRT
<213> ORGANISM: Artificial Sequence
<220> FEATURE:
<223> OTHER INFORMATION: Amino acid sequence of PTP active domain p47

<400> SEQUENCE: 258

```
Met Asp Thr Ser Asp Leu Phe Ala Ser Cys Arg Lys Gly Asp Val Gly
1               5                   10                  15

Arg Val Arg Tyr Leu Leu Glu Gln Arg Asp Val Glu Val Asn Val Arg
            20                  25                  30
```

```
Asp Lys Trp Asp Ser Thr Pro Leu Tyr Tyr Ala Cys Leu Cys Gly His
         35                  40                  45

Glu Glu Leu Val Leu Tyr Leu Leu Ala Asn Gly Ala Arg Cys Glu Ala
 50                  55                  60

Asn Thr Phe Asp Gly Glu Arg Cys Leu Tyr Gly Ala Leu Ser Asp Pro
 65                  70                  75                  80

Ile Arg Arg Ala Leu Arg Asp Tyr Lys Gln Val Thr Ala Ser Cys Arg
                 85                  90                  95

Arg Arg Asp Tyr Tyr Asp Phe Leu Gln Arg Leu Leu Glu Gln Gly
                100                 105                 110

Ile His Ser Asp Val Val Phe Val His Gly Lys Pro Phe Arg Val
                115                 120                 125

His Arg Cys Val Leu Gly Ala Arg Ser Ala Tyr Phe Ala Asn Met Leu
            130                 135                 140

Asp Thr Lys Trp Lys Gly Lys Ser Val Val Leu Arg His Pro Leu
145                 150                 155                 160

Ile Asn Pro Val Ala Phe Gly Ala Leu Leu Gln Tyr Leu Tyr Thr Gly
                    165                 170                 175

Arg Leu Asp Ile Gly Val Glu His Val Ser Asp Cys Glu Arg Leu Ala
                180                 185                 190

Lys Gln Cys Gln Leu Trp Asp Leu Leu Ser Asp Leu Glu Ala Lys Cys
            195                 200                 205

Glu Lys Val Ser Glu Phe Val Ala Ser Lys Pro Gly Thr Cys Val Lys
210                 215                 220

Val Leu Thr Ile Glu Pro Pro Ala Asp Pro Arg Leu Arg Glu Asp
225                 230                 235                 240

Met Ala

<210> SEQ ID NO 259
<211> LENGTH: 335
<212> TYPE: PRT
<213> ORGANISM: Artificial Sequence
<220> FEATURE:
<223> OTHER INFORMATION: Amino acid sequence of PTP active domain  T21

<400> SEQUENCE: 259

Met Gly Phe Asp Val Gln Asn Val Trp Arg Val Ser His Ile Asn Ser
 1               5                  10                  15

Asn Tyr Lys Leu Cys Pro Ser Tyr Pro Gln Lys Leu Leu Val Pro Val
                20                  25                  30

Trp Ile Thr Asp Lys Glu Leu Glu Asn Val Ala Ser Phe Arg Ser Trp
             35                  40                  45

Lys Arg Ile Pro Val Val Val Tyr Arg His Leu Arg Asn Gly Ala Ala
 50                  55                  60

Ile Ala Arg Cys Ser Gln Pro Glu Ile Ser Trp Trp Gly Trp Arg Asn
 65                  70                  75                  80

Ala Asp Asp Glu Tyr Leu Val Thr Ser Ile Ala Lys Ala Cys Ala Leu
                 85                  90                  95

Asp Pro Gly Thr Arg Ala Thr Gly Gly Ser Leu Ser Thr Gly Asn Asn
            100                 105                 110

Asp Thr Ser Glu Ala Cys Asp Ala Asp Phe Asp Ser Ser Leu Thr Ala
        115                 120                 125

Cys Ser Gly Val Glu Ser Thr Ala Ala Pro Gln Lys Leu Leu Ile Leu
    130                 135                 140

Asp Ala Arg Ser Tyr Thr Ala Ala Val Ala Asn Arg Ala Lys Gly Gly
145                 150                 155                 160
```

```
Gly Cys Glu Cys Glu Glu Tyr Tyr Pro Asn Cys Glu Val Val Phe Met
                165                 170                 175
Gly Met Ala Asn Ile His Ala Ile Arg Asn Ser Phe Gln Tyr Leu Arg
            180                 185                 190
Ala Val Cys Ser Gln Met Pro Asp Pro Ser Asn Trp Leu Ser Ala Leu
        195                 200                 205
Glu Ser Thr Lys Trp Leu Gln His Leu Ser Val Met Leu Lys Ala Ala
    210                 215                 220
Val Leu Val Ala Asn Thr Val Asp Arg Glu Gly Arg Pro Val Leu Val
225                 230                 235                 240
His Cys Ser Asp Gly Trp Asp Arg Thr Pro Gln Ile Val Ala Leu Ala
                245                 250                 255
Lys Ile Leu Leu Asp Pro Tyr Tyr Arg Thr Leu Glu Gly Phe Gln Val
                260                 265                 270
Leu Val Glu Ser Asp Trp Leu Asp Phe Gly His Lys Phe Gly Asp Arg
            275                 280                 285
Cys Gly His Gln Glu Asn Val Glu Asp Gln Asn Glu Gln Cys Pro Val
        290                 295                 300
Phe Leu Gln Trp Leu Asp Ser Val His Gln Leu Leu Lys Gln Phe Pro
305                 310                 315                 320
Cys Leu Phe Glu Phe Asn Glu Ala Phe Leu Val Lys Leu Val Gln
                325                 330                 335
```

<210> SEQ ID NO 260
<211> LENGTH: 223
<212> TYPE: PRT
<213> ORGANISM: Artificial Sequence
<220> FEATURE:
<223> OTHER INFORMATION: Amino acid sequence of PTP active domain T53

<400> SEQUENCE: 260

```
Met Glu Asp Val Lys Leu Glu Phe Pro Ser Leu Pro Gln Cys Lys Glu
1               5                   10                  15
Asp Ala Glu Glu Trp Thr Tyr Pro Met Arg Arg Glu Met Gln Glu Ile
                20                  25                  30
Leu Pro Gly Leu Phe Leu Gly Pro Tyr Ser Ser Ala Met Lys Ser Lys
            35                  40                  45
Leu Pro Val Leu Gln Lys His Gly Ile Thr His Ile Ile Cys Ile Arg
        50                  55                  60
Gln Asn Ile Glu Ala Asn Phe Ile Lys Pro Asn Phe Gln Gln Leu Phe
65                  70                  75                  80
Arg Tyr Leu Val Leu Asp Ile Ala Asp Asn Pro Val Glu Asn Ile Ile
                85                  90                  95
Arg Phe Phe Pro Met Thr Lys Glu Phe Ile Asp Gly Ser Leu Gln Met
                100                 105                 110
Gly Gly Lys Val Leu Val His Gly Asn Ala Gly Ile Ser Arg Ser Ala
            115                 120                 125
Ala Phe Val Ile Ala Tyr Ile Met Glu Thr Phe Gly Met Lys Tyr Arg
        130                 135                 140
Asp Ala Phe Ala Tyr Val Gln Glu Arg Arg Phe Cys Ile Asn Pro Asn
145                 150                 155                 160
Ala Gly Phe Val His Gln Leu Gln Glu Tyr Glu Ala Ile Tyr Leu Ala
                165                 170                 175
Lys Leu Thr Ile Gln Met Met Ser Pro Leu Gln Ile Glu Arg Ser Leu
                180                 185                 190
```

```
Ser Val His Ser Gly Thr Thr Gly Ser Leu Lys Arg Thr His Glu Glu
        195                 200                 205

Glu Asp Asp Phe Gly Thr Met Gln Val Ala Thr Ala Gln Asn Gly
    210                 215                 220
```

```
<210> SEQ ID NO 261
<211> LENGTH: 24
<212> TYPE: DNA
<213> ORGANISM: Artificial Sequence
<220> FEATURE:
<223> OTHER INFORMATION: p45 Forward primer

<400> SEQUENCE: 261
atgaggagaa cttccggagc aacc                                           24

<210> SEQ ID NO 262
<211> LENGTH: 27
<212> TYPE: DNA
<213> ORGANISM: Artificial Sequence
<220> FEATURE:
<223> OTHER INFORMATION: p45 Reverse primer

<400> SEQUENCE: 262
ctataggcac gatgatacaa aatataa                                        27

<210> SEQ ID NO 263
<211> LENGTH: 30
<212> TYPE: DNA
<213> ORGANISM: Artificial Sequence
<220> FEATURE:
<223> OTHER INFORMATION: p46 Forward primer

<400> SEQUENCE: 263
cctctagcta gcgatacgcg caaaattgtt                                     30

<210> SEQ ID NO 264
<211> LENGTH: 29
<212> TYPE: DNA
<213> ORGANISM: Artificial Sequence
<220> FEATURE:
<223> OTHER INFORMATION: p46 Reverse primer

<400> SEQUENCE: 264
ggatccttaa tccaaagtca gaagtttcc                                      29

<210> SEQ ID NO 265
<211> LENGTH: 32
<212> TYPE: DNA
<213> ORGANISM: Artificial Sequence
<220> FEATURE:
<223> OTHER INFORMATION: p47 Forward primer

<400> SEQUENCE: 265
cgcccacata tgacagccat catcaaagag at                                  32

<210> SEQ ID NO 266
<211> LENGTH: 32
<212> TYPE: DNA
<213> ORGANISM: Artificial Sequence
<220> FEATURE:
<223> OTHER INFORMATION: p47 Reverse primer

<400> SEQUENCE: 266
cgggatcctc aaagtacatg aacttgtctt cc                                  32

<210> SEQ ID NO 267
```

```
<211> LENGTH: 31
<212> TYPE: DNA
<213> ORGANISM: Artificial Sequence
<220> FEATURE:
<223> OTHER INFORMATION: T21 Forward primer

<400> SEQUENCE: 267
cttgcacata tgggctttga cgtgcagaac g                                    31

<210> SEQ ID NO 268
<211> LENGTH: 33
<212> TYPE: DNA
<213> ORGANISM: Artificial Sequence
<220> FEATURE:
<223> OTHER INFORMATION: T21 Reverse primer

<400> SEQUENCE: 268
ccgagatctt cattgcacca gttttaccag gaa                                  33

<210> SEQ ID NO 269
<211> LENGTH: 33
<212> TYPE: DNA
<213> ORGANISM: Artificial Sequence
<220> FEATURE:
<223> OTHER INFORMATION: T53 Forward primer

<400> SEQUENCE: 269
tcggcccata tgcctggttt gcttttatgt gaa                                  33

<210> SEQ ID NO 270
<211> LENGTH: 30
<212> TYPE: DNA
<213> ORGANISM: Artificial Sequence
<220> FEATURE:
<223> OTHER INFORMATION: T53 Reverse primer

<400> SEQUENCE: 270
cggaattctc agtagagcgg atccatgatg                                      30

<210> SEQ ID NO 271
<211> LENGTH: 583
<212> TYPE: PRT
<213> ORGANISM: Artificial Sequence
<220> FEATURE:
<223> OTHER INFORMATION: Amino acid sequence of PTP active domain  MTMR8

<400> SEQUENCE: 271

Met Arg Glu Ser Gly Trp Lys Leu Ile Asp Pro Ile Ser Asp Phe Gly
1               5                   10                  15

Arg Met Gly Ile Pro Asn Arg Asn Trp Thr Ile Thr Asp Ala Asn Arg
            20                  25                  30

Asn Tyr Glu Ile Cys Ser Thr Tyr Pro Pro Glu Ile Val Val Pro Lys
        35                  40                  45

Ser Val Thr Leu Gly Thr Val Gly Ser Ser Lys Phe Arg Ser Lys
    50                  55                  60

Glu Arg Val Pro Val Leu Ser Tyr Leu Tyr Lys Glu Asn Asn Ala Ala
65                  70                  75                  80

Ile Cys Arg Cys Ser Gln Pro Leu Ser Gly Phe Tyr Thr Arg Cys Val
                85                  90                  95

Asp Asp Glu Leu Leu Leu Glu Ala Ile Ser Gln Thr Asn Pro Gly Ser
            100                 105                 110

Gln Phe Met Tyr Val Val Asp Thr Arg Pro Lys Leu Asn Ala Met Ala
        115                 120                 125
```

```
Asn Arg Ala Ala Gly Lys Gly Tyr Glu Asn Glu Asp Asn Tyr Ala Asn
    130                 135                 140

Ile Arg Phe Arg Phe Met Gly Ile Glu Asn Ile His Val Met Arg Ser
145                 150                 155                 160

Ser Leu Gln Lys Leu Leu Glu Val Cys Glu Leu Lys Thr Pro Thr Met
                165                 170                 175

Ser Glu Phe Leu Ser Gly Leu Glu Ser Ser Gly Trp Leu Arg His Ile
            180                 185                 190

Lys Ala Ile Met Asp Ala Gly Ile Phe Ile Thr Lys Ala Val Lys Val
        195                 200                 205

Glu Lys Ala Ser Val Leu Val His Cys Ser Asp Gly Trp Asp Arg Thr
    210                 215                 220

Ala Gln Val Cys Ser Val Ala Ser Ile Leu Leu Asp Pro Phe Tyr Arg
225                 230                 235                 240

Thr Phe Lys Gly Leu Met Ile Leu Ile Glu Lys Glu Trp Ile Ser Met
                245                 250                 255

Gly His Lys Phe Ser Gln Arg Cys Gly His Leu Asp Gly Asp Ser Lys
            260                 265                 270

Glu Val Ser Pro Ile Phe Thr Gln Phe Leu Asp Cys Ile Trp Gln Leu
        275                 280                 285

Met Glu Gln Phe Pro Cys Ala Phe Glu Phe Asn Glu Asn Phe Leu Leu
    290                 295                 300

Glu Ile His Asp His Val Phe Ser Cys Gln Phe Gly Asn Phe Leu Gly
305                 310                 315                 320

Asn Cys Gln Lys Asp Arg Glu Asp Leu Arg Val Tyr Glu Lys Thr His
                325                 330                 335

Ser Val Trp Pro Phe Leu Val Gln Arg Lys Pro Asp Phe Arg Asn Pro
            340                 345                 350

Leu Tyr Lys Gly Phe Thr Met Tyr Gly Val Leu Asn Pro Ser Thr Val
        355                 360                 365

Pro Tyr Asn Ile Gln Phe Trp Cys Gly Met Tyr Asn Arg Phe Asp Lys
    370                 375                 380

Gly Leu Gln Pro Lys Gln Ser Met Leu Glu Ser Leu Leu Glu Ile Lys
385                 390                 395                 400

Lys Gln Arg Ala Met Leu Glu Thr Asp Val His Glu Leu Glu Lys Lys
                405                 410                 415

Leu Lys Val Arg Asp Glu Pro Pro Glu Glu Ile Cys Thr Cys Ser Gln
            420                 425                 430

Leu Gly Asn Ile Leu Ser Gln His Leu Gly Ser Pro Leu Thr Asn Pro
        435                 440                 445

Leu Gly Phe Met Gly Ile Asn Gly Asp Leu Asn Thr Leu Met Glu Asn
    450                 455                 460

Gly Thr Leu Ser Arg Glu Gly Gly Leu Arg Ala Gln Met Asp Gln Val
465                 470                 475                 480

Lys Ser Gln Gly Ala Asp Leu His His Asn Cys Cys Glu Ile Val Gly
                485                 490                 495

Ser Leu Arg Ala Ile Asn Ile Ser Gly Asp Val Gly Ile Ser Glu Ala
            500                 505                 510

Met Gly Ile Ser Gly Asp Met Cys Thr Phe Glu Ala Thr Gly Phe Ser
        515                 520                 525

Lys Asp Leu Gly Ile Cys Gly Ala Met Asp Ile Ser Glu Ala Thr Gly
    530                 535                 540

Ile Ser Gly Asn Leu Gly Ile Ser Glu Ala Arg Gly Phe Ser Gly Asp
545                 550                 555                 560
```

```
Met Gly Ile Leu Gly Asp Thr Gly Ile Ser Lys Ala Ser Thr Lys Glu
                565                 570                 575

Ala Asp Tyr Ser Lys His Gln
            580

<210> SEQ ID NO 272
<211> LENGTH: 176
<212> TYPE: PRT
<213> ORGANISM: Artificial Sequence
<220> FEATURE:
<223> OTHER INFORMATION: Amino acid sequence of PTP active domain  DUSP26

<400> SEQUENCE: 272

Met Gly Leu Glu Ala Ala Arg Glu Leu Glu Cys Ala Ala Leu Gly Thr
1               5                   10                  15

Leu Leu Arg Asp Pro Arg Glu Ala Glu Arg Thr Leu Leu Leu Asp Cys
                20                  25                  30

Arg Pro Phe Leu Ala Phe Cys Arg Arg His Val Arg Ala Ala Arg Pro
            35                  40                  45

Val Pro Trp Asn Ala Leu Leu Arg Arg Ala Arg Gly Pro Pro Ala
    50                  55                  60

Ala Val Leu Ala Cys Leu Leu Pro Asp Arg Ala Leu Arg Thr Arg Leu
65              70                  75                  80

Val Arg Gly Glu Leu Ala Arg Ala Val Val Leu Asp Glu Gly Ser Ala
                85                  90                  95

Ser Val Ala Glu Leu Arg Pro Asp Ser Pro Ala His Val Leu Leu Ala
                100                 105                 110

Ala Leu Leu His Glu Thr Arg Ala Gly Pro Thr Ala Val Tyr Phe Leu
            115                 120                 125

Arg Gly Gly Phe Asp Gly Phe Gln Gly Cys Cys Pro Asp Leu Cys Ser
    130                 135                 140

Glu Ala Pro Ala Pro Ala Leu Pro Pro Thr Gly Asp Lys Thr Ser Arg
145                 150                 155                 160

Ser Asp Ser Arg Ala Pro Val Tyr Asp Gln Gly Gly Pro Val Glu Ile
                165                 170                 175

<210> SEQ ID NO 273
<211> LENGTH: 196
<212> TYPE: PRT
<213> ORGANISM: Artificial Sequence
<220> FEATURE:
<223> OTHER INFORMATION: Amino acid sequence of PTP active domain  TENC1

<400> SEQUENCE: 273

Met Glu Arg Arg Trp Asp Leu Asp Leu Thr Tyr Val Thr Glu Arg Ile
1               5                   10                  15

Leu Ala Ala Ala Phe Pro Ala Arg Pro Asp Glu Gln Arg His Arg Gly
                20                  25                  30

His Leu Arg Glu Leu Ala His Val Leu Gln Ser Lys His Arg Asp Lys
            35                  40                  45

Tyr Leu Leu Phe Asn Leu Ser Glu Lys Arg His Asp Leu Thr Arg Leu
    50                  55                  60

Asn Pro Lys Val Gln Asp Phe Gly Trp Pro Glu Leu His Ala Pro Pro
65              70                  75                  80

Leu Asp Lys Leu Cys Ser Ile Cys Lys Ala Met Glu Thr Trp Leu Ser
                85                  90                  95

Ala Asp Pro Gln His Val Val Val Leu Tyr Cys Lys Gly Asn Lys Gly
                100                 105                 110
```

```
Lys Leu Gly Val Ile Val Ser Ala Tyr Met His Tyr Ser Lys Ile Ser
            115                 120                 125

Ala Gly Ala Asp Gln Ala Leu Ala Thr Leu Thr Met Arg Lys Phe Cys
    130                 135                 140

Glu Asp Lys Val Ala Thr Glu Leu Gln Pro Ser Gln Arg Arg Tyr Ile
145                 150                 155                 160

Ser Tyr Phe Ser Gly Leu Leu Ser Gly Ser Ile Arg Met Asn Ser Ser
                165                 170                 175

Pro Leu Phe Leu His Tyr Val Leu Ile Pro Met Leu Pro Ala Phe Glu
            180                 185                 190

Pro Gly Thr Gly
        195
```

<210> SEQ ID NO 274
<211> LENGTH: 334
<212> TYPE: PRT
<213> ORGANISM: Artificial Sequence
<220> FEATURE:
<223> OTHER INFORMATION: Amino acid sequence of PTP active domain MTMR7

<400> SEQUENCE: 274

```
Met Glu His Ile Arg Thr Pro Lys Val Glu Asn Val Arg Leu Val Asp
1               5                   10                  15

Arg Val Ser Pro Lys Lys Ala Ala Leu Gly Thr Leu Tyr Leu Thr Ala
            20                  25                  30

Thr His Val Ile Phe Val Glu Asn Ser Pro Asp Ala Arg Lys Glu Thr
        35                  40                  45

Trp Ile Leu His Ser Gln Ile Ser Thr Ile Glu Lys Gln Ala Thr Thr
    50                  55                  60

Ala Thr Gly Cys Pro Leu Leu Ile Arg Cys Lys Asn Phe Gln Ile Ile
65                  70                  75                  80

Gln Leu Ile Ile Pro Gln Glu Arg Asp Cys His Asp Val Tyr Ile Ser
                85                  90                  95

Leu Ile Arg Leu Ala Arg Pro Val Lys Tyr Glu Glu Leu Tyr Cys Phe
            100                 105                 110

Ser Phe Asn Pro Met Leu Asp Lys Glu Glu Arg Glu Gln Gly Trp Val
        115                 120                 125

Leu Ile Asp Leu Ser Glu Glu Tyr Thr Arg Met Gly Leu Pro Asn His
    130                 135                 140

Tyr Trp Gln Leu Ser Asp Val Asn Arg Asp Tyr Arg Val Cys Asp Ser
145                 150                 155                 160

Tyr Pro Thr Glu Leu Tyr Val Pro Lys Ser Ala Thr Ala His Ile Ile
                165                 170                 175

Val Gly Ser Ser Lys Phe Arg Ser Arg Arg Phe Pro Val Leu Ser
            180                 185                 190

Tyr Tyr Tyr Lys Asp Asn His Ala Ser Ile Cys Arg Ser Ser Gln Pro
        195                 200                 205

Leu Ser Gly Phe Ser Ala Arg Cys Leu Glu Asp Glu Gln Met Leu Gln
    210                 215                 220

Ala Ile Arg Lys Ala Asn Pro Gly Ser Asp Phe Val Tyr Val Val Asp
225                 230                 235                 240

Thr Arg Pro Lys Leu Asn Ala Met Ala Asn Arg Ala Ala Gly Lys Gly
                245                 250                 255

Tyr Glu Asn Glu Asp Asn Tyr Ser Asn Ile Lys Phe Gln Phe Ile Gly
            260                 265                 270
```

```
Ile Glu Asn Ile His Val Met Arg Asn Ser Leu Gln Lys Met Leu Glu
            275                 280                 285
Val Cys Glu Leu Lys Ser Pro Ser Met Ser Asp Phe Leu Trp Gly Leu
290                 295                 300
Glu Asn Ser Gly Trp Leu Arg His Ile Lys Ala Ile Met Asp Ala Gly
305                 310                 315                 320
Ile Phe Ile Ala Lys Ala Val Ser Glu Glu Gly Ala Ser Val
                325                 330

<210> SEQ ID NO 275
<211> LENGTH: 331
<212> TYPE: PRT
<213> ORGANISM: Artificial Sequence
<220> FEATURE:
<223> OTHER INFORMATION: Amino acid sequence of PTP active domain   EPM2A

<400> SEQUENCE: 275

Met Arg Phe Arg Phe Gly Val Val Val Pro Ala Val Ala Gly Ala
1                 5                   10                  15
Arg Pro Glu Leu Leu Val Val Gly Ser Arg Pro Glu Leu Gly Arg Trp
                20                  25                  30
Glu Pro Arg Gly Ala Val Arg Leu Arg Pro Ala Gly Thr Ala Ala Gly
            35                  40                  45
Asp Gly Ala Leu Ala Leu Gln Glu Pro Gly Leu Trp Leu Gly Glu Val
        50                  55                  60
Glu Leu Ala Ala Glu Glu Ala Ala Gln Asp Gly Ala Glu Pro Gly Arg
65                  70                  75                  80
Val Asp Thr Phe Trp Tyr Lys Phe Leu Lys Arg Glu Pro Gly Gly Glu
                85                  90                  95
Leu Ser Trp Glu Gly Asn Gly Pro His His Asp Arg Cys Cys Thr Tyr
            100                 105                 110
Asn Glu Asn Asn Leu Val Asp Gly Val Tyr Cys Leu Pro Ile Gly His
        115                 120                 125
Trp Ile Glu Ala Thr Gly His Thr Asn Glu Met Lys His Thr Thr Asp
130                 135                 140
Phe Tyr Phe Asn Ile Ala Gly His Gln Ala Met His Tyr Ser Arg Ile
145                 150                 155                 160
Leu Pro Asn Ile Trp Leu Gly Ser Cys Pro Arg Gln Val Glu His Val
                165                 170                 175
Thr Ile Lys Leu Lys His Glu Leu Gly Ile Thr Ala Val Met Asn Phe
            180                 185                 190
Gln Thr Glu Trp Asp Ile Val Gln Asn Ser Ser Gly Cys Asn Arg Tyr
        195                 200                 205
Pro Glu Pro Met Thr Pro Asp Thr Met Ile Lys Leu Tyr Arg Glu Glu
210                 215                 220
Gly Leu Ala Tyr Ile Trp Met Pro Thr Pro Asp Met Ser Thr Glu Gly
225                 230                 235                 240
Arg Val Gln Met Leu Pro Gln Ala Val Cys Leu Leu His Ala Leu Leu
                245                 250                 255
Glu Lys Gly His Ile Val Tyr Val His Cys Asn Ala Gly Val Gly Arg
            260                 265                 270
Ser Thr Ala Ala Val Cys Gly Trp Leu Gln Tyr Val Met Gly Trp Asn
        275                 280                 285
Leu Arg Lys Val Gln Tyr Phe Leu Met Ala Lys Arg Pro Ala Val Tyr
290                 295                 300
Ile Asp Glu Glu Ala Leu Ala Arg Ala Gln Glu Asp Phe Phe Gln Lys
```

Phe Gly Lys Val Arg Ser Ser Val Cys Ser Leu
        325                 330

<210> SEQ ID NO 276
<211> LENGTH: 198
<212> TYPE: PRT
<213> ORGANISM: Artificial Sequence
<220> FEATURE:
<223> OTHER INFORMATION: Amino acid sequence of PTP active domain
      DUSP14

<400> SEQUENCE: 276

Met Ser Ser Arg Gly His Ser Thr Leu Pro Arg Thr Leu Met Ala Pro
1               5                   10                  15

Arg Met Ile Ser Glu Gly Asp Ile Gly Gly Ile Ala Gln Ile Thr Ser
            20                  25                  30

Ser Leu Phe Leu Gly Arg Gly Ser Val Ala Ser Asn Arg His Leu Leu
        35                  40                  45

Gln Ala Arg Gly Ile Thr Cys Ile Val Asn Ala Thr Ile Glu Ile Pro
    50                  55                  60

Asn Phe Asn Trp Pro Gln Phe Glu Tyr Val Lys Val Pro Leu Ala Asp
65                  70                  75                  80

Met Pro His Ala Pro Ile Gly Leu Tyr Phe Asp Thr Val Ala Asp Lys
                85                  90                  95

Ile His Ser Val Ser Arg Lys His Gly Ala Thr Leu Val His Cys Ala
            100                 105                 110

Ala Gly Val Ser Arg Ser Ala Thr Leu Cys Ile Ala Tyr Leu Met Lys
        115                 120                 125

Phe His Asn Val Cys Leu Leu Glu Ala Tyr Asn Trp Val Lys Ala Arg
    130                 135                 140

Arg Pro Val Ile Arg Pro Asn Val Gly Phe Trp Arg Gln Leu Ile Asp
145                 150                 155                 160

Tyr Glu Arg Gln Leu Phe Gly Lys Ser Thr Val Lys Met Val Gln Thr
                165                 170                 175

Pro Tyr Gly Ile Val Pro Asp Val Tyr Glu Lys Glu Ser Arg His Leu
            180                 185                 190

Met Pro Tyr Trp Gly Ile
        195

<210> SEQ ID NO 277
<211> LENGTH: 140
<212> TYPE: PRT
<213> ORGANISM: Homo sapiens

<400> SEQUENCE: 277

Pro Gly Ser Gly Ala Ser Thr Pro Val Gly Pro Trp Asp Gln Ala Val
1               5                   10                  15

Gln Arg Arg Ser Arg Leu Gln Arg Gln Ser Phe Ala Val Leu Arg
            20                  25                  30

Gly Ala Val Leu Gly Leu Gln Asp Gly Asp Asn Asp Ala Ala
        35                  40                  45

Glu Ala Ser Ser Glu Pro Thr Glu Lys Ala Pro Ser Glu Glu Leu
    50                  55                  60

His Gly Asp Gln Thr Asp Phe Gly Gln Gly Ser Gln Ser Pro Gln Lys
65                  70                  75                  80

Gln Glu Glu Gln Arg Gln His Leu His Leu Met Val Gln Leu Leu Arg
                85                  90                  95

```
Pro Gln Asp Asp Ile Arg Leu Ala Ala Gln Leu Glu Ala Pro Arg Pro
        100                 105                 110

Pro Arg Leu Arg Tyr Leu Leu Val Val Ser Thr Arg Glu Gly Glu Gly
        115                 120                 125

Leu Ser Gln Asp Glu Thr Val Leu Leu Gly Val Asp
        130                 135                 140

<210> SEQ ID NO 278
<211> LENGTH: 313
<212> TYPE: PRT
<213> ORGANISM: Homo sapiens

<400> SEQUENCE: 278

Met Pro Gly Leu Leu Cys Glu Pro Thr Glu Leu Tyr Asn Ile Leu
1               5                   10                  15

Asn Gln Ala Thr Lys Leu Ser Arg Leu Thr Asp Pro Asn Tyr Leu Cys
            20                  25                  30

Leu Leu Asp Val Arg Ser Lys Trp Glu Tyr Asp Glu Ser His Val Ile
        35                  40                  45

Thr Ala Leu Arg Val Lys Lys Asn Glu Tyr Leu Leu Pro Glu
    50                  55                  60

Ser Val Asp Leu Glu Cys Val Lys Tyr Cys Val Val Tyr Asp Asn Asn
65                  70                  75                  80

Ser Ser Thr Leu Glu Ile Leu Lys Asp Asp Asp Ser Asp
            85                  90                  95

Ser Asp Gly Asp Gly Lys Asp Leu Val Pro Gln Ala Ala Ile Glu Tyr
            100                 105                 110

Gly Arg Ile Leu Thr Arg Leu Thr His His Pro Val Tyr Ile Leu Lys
            115                 120                 125

Gly Gly Tyr Glu Arg Phe Ser Gly Thr Tyr His Phe Leu Arg Thr Gln
        130                 135                 140

Lys Ile Ile Trp Met Pro Gln Glu Leu Asp Ala Phe Gln Pro Tyr Pro
145                 150                 155                 160

Ile Glu Ile Val Pro Gly Lys Val Phe Val Gly Asn Phe Ser Gln Ala
                165                 170                 175

Cys Asp Pro Lys Ile Gln Lys Asp Leu Lys Ile Lys Ala His Val Asn
            180                 185                 190

Val Ser Met Asp Thr Gly Pro Phe Phe Ala Gly Asp Ala Asp Lys Leu
        195                 200                 205

Leu His Ile Arg Ile Glu Asp Ser Pro Glu Ala Gln Ile Leu Pro Phe
    210                 215                 220

Leu Arg His Met Cys His Phe Ile Glu Ile His His Leu Gly Ser
225                 230                 235                 240

Val Ile Leu Ile Phe Ser Thr Gln Gly Ile Ser Arg Ser Cys Ala Ala
                245                 250                 255

Ile Ile Ala Tyr Leu Met His Ser Asn Glu Gln Thr Leu Gln Arg Ser
            260                 265                 270

Trp Ala Tyr Val Lys Lys Cys Lys Asn Asn Met Cys Pro Asn Arg Gly
        275                 280                 285

Leu Val Ser Gln Leu Leu Glu Trp Glu Lys Thr Ile Leu Gly Asp Ser
    290                 295                 300

Ile Thr Asn Ile Met Asp Pro Leu Tyr
305                 310

<210> SEQ ID NO 279
```

```
<211> LENGTH: 314
<212> TYPE: PRT
<213> ORGANISM: Homo sapiens

<400> SEQUENCE: 279

Met Gly Leu Glu Ala Ala Arg Glu Leu Glu Cys Ala Ala Leu Gly Thr
1               5                   10                  15

Leu Leu Arg Asp Pro Arg Glu Ala Glu Arg Thr Leu Leu Leu Asp Cys
            20                  25                  30

Arg Pro Phe Leu Ala Phe Cys Arg Arg His Val Arg Ala Ala Arg Pro
        35                  40                  45

Val Pro Trp Asn Ala Leu Leu Arg Arg Ala Arg Gly Pro Pro Ala
    50                  55                  60

Ala Val Leu Ala Cys Leu Leu Pro Asp Arg Ala Leu Arg Thr Arg Leu
65                  70                  75                  80

Val Arg Gly Glu Leu Ala Arg Ala Val Val Leu Asp Glu Gly Ser Ala
                85                  90                  95

Ser Val Ala Glu Leu Arg Pro Asp Ser Pro Ala His Val Leu Leu Ala
            100                 105                 110

Ala Leu Leu His Glu Thr Arg Ala Gly Pro Thr Ala Val Tyr Phe Leu
        115                 120                 125

Arg Gly Gly Phe Asp Gly Phe Gln Gly Cys Cys Pro Asp Leu Cys Ser
130                 135                 140

Glu Ala Pro Ala Pro Ala Leu Pro Pro Thr Gly Asp Lys Thr Ser Arg
145                 150                 155                 160

Ser Asp Ser Arg Ala Pro Val Tyr Asp Gln Gly Gly Pro Val Glu Ile
                165                 170                 175

Leu Pro Tyr Leu Phe Leu Gly Ser Cys Ser His Ser Ser Asp Leu Gln
            180                 185                 190

Gly Leu Gln Ala Cys Gly Ile Thr Ala Val Leu Asn Val Ser Ala Ser
        195                 200                 205

Cys Pro Asn His Phe Glu Gly Leu Phe Arg Tyr Lys Ser Ile Pro Val
    210                 215                 220

Glu Asp Asn Gln Met Val Glu Ile Ser Ala Trp Phe Gln Glu Ala Ile
225                 230                 235                 240

Gly Phe Ile Asp Trp Val Lys Asn Ser Gly Gly Arg Val Leu Val His
                245                 250                 255

Cys Gln Ala Gly Ile Ser Arg Ser Ala Thr Ile Cys Leu Ala Tyr Leu
            260                 265                 270

Met Gln Ser Arg Arg Val Arg Leu Asp Glu Ala Phe Asp Phe Val Lys
        275                 280                 285

Gln Arg Arg Gly Val Ile Ser Pro Asn Phe Ser Phe Met Gly Gln Leu
    290                 295                 300

Leu Gln Phe Glu Thr Gln Val Leu Cys His
305                 310

<210> SEQ ID NO 280
<211> LENGTH: 324
<212> TYPE: PRT
<213> ORGANISM: Homo sapiens

<400> SEQUENCE: 280

Met Glu Gln Val Glu Ile Leu Arg Lys Phe Ile Gln Arg Val Gln Ala
1               5                   10                  15

Met Lys Ser Pro Asp His Asn Gly Glu Asp Asn Phe Ala Arg Asp Phe
            20                  25                  30
```

-continued

```
Met Arg Leu Arg Arg Leu Ser Thr Lys Tyr Arg Thr Glu Lys Ile Tyr
             35                  40                  45
Pro Thr Ala Thr Gly Glu Lys Glu Glu Asn Val Lys Asn Arg Tyr
 50                  55                  60
Lys Asp Ile Leu Pro Phe Asp His Ser Arg Val Lys Leu Thr Leu Lys
 65                  70                  75                  80
Thr Pro Ser Gln Asp Ser Asp Tyr Ile Asn Ala Asn Phe Ile Lys Gly
                 85                  90                  95
Val Tyr Gly Pro Lys Ala Tyr Val Ala Thr Gln Gly Pro Leu Ala Asn
                100                 105                 110
Thr Val Ile Asp Phe Trp Arg Met Ile Trp Glu Tyr Asn Val Val Ile
            115                 120                 125
Ile Val Met Ala Cys Arg Glu Phe Glu Met Gly Arg Lys Lys Cys Glu
130                 135                 140
Arg Tyr Trp Pro Leu Tyr Gly Glu Asp Pro Ile Thr Phe Ala Pro Phe
145                 150                 155                 160
Lys Ile Ser Cys Glu Asp Glu Gln Ala Arg Thr Asp Tyr Phe Ile Arg
                165                 170                 175
Thr Leu Leu Leu Glu Phe Gln Asn Glu Ser Arg Arg Leu Tyr Gln Phe
            180                 185                 190
His Tyr Val Asn Trp Pro Asp His Asp Val Pro Ser Ser Phe Asp Ser
        195                 200                 205
Ile Leu Asp Met Ile Ser Leu Met Arg Lys Tyr Gln Glu His Glu Asp
210                 215                 220
Val Pro Ile Cys Ile His Cys Ser Ala Gly Cys Gly Arg Thr Gly Ala
225                 230                 235                 240
Ile Cys Ala Ile Asp Tyr Thr Trp Asn Leu Leu Lys Ala Gly Lys Ile
                245                 250                 255
Pro Glu Glu Phe Asn Val Phe Asn Leu Ile Gln Glu Met Arg Thr Gln
            260                 265                 270
Arg His Ser Ala Val Gln Thr Lys Glu Gln Tyr Glu Leu Val His Arg
        275                 280                 285
Ala Ile Ala Gln Leu Phe Glu Lys Gln Leu Gln Leu Tyr Glu Ile His
    290                 295                 300
Gly Ala Gln Lys Ile Ala Asp Gly Val Asn Glu Ile Asn Thr Glu Asn
305                 310                 315                 320
Met Ile Ser Ser
```

<210> SEQ ID NO 281
<211> LENGTH: 679
<212> TYPE: PRT
<213> ORGANISM: Homo sapiens

<400> SEQUENCE: 281

```
Gln Leu Met Asn Val Glu Pro Ile His Ala Asp Ile Leu Leu Glu Thr
 1               5                  10                  15
Tyr Lys Arg Lys Ile Ala Asp Glu Gly Arg Leu Phe Leu Ala Glu Phe
                20                  25                  30
Gln Ser Ile Pro Arg Val Phe Ser Lys Phe Pro Ile Lys Glu Ala Arg
            35                  40                  45
Lys Pro Phe Asn Gln Asn Lys Asn Arg Tyr Val Asp Ile Leu Pro Tyr
 50                  55                  60
Asp Tyr Asn Arg Val Glu Leu Ser Glu Ile Asn Gly Asp Ala Gly Ser
 65                  70                  75                  80
Asn Tyr Ile Asn Ala Ser Tyr Ile Asp Gly Phe Lys Glu Pro Arg Lys
```

```
                85                  90                  95
Tyr Ile Ala Ala Gln Gly Pro Arg Asp Glu Thr Val Asp Asp Phe Trp
            100                 105                 110

Arg Met Ile Trp Glu Gln Lys Ala Thr Val Ile Val Met Val Thr Arg
            115                 120                 125

Cys Glu Glu Gly Asn Arg Asn Lys Cys Ala Glu Tyr Trp Pro Ser Met
            130                 135                 140

Glu Glu Gly Thr Arg Ala Phe Gly Asp Val Val Lys Ile Asn Gln
145                 150                 155                 160

His Lys Arg Cys Pro Asp Tyr Ile Ile Gln Lys Leu Asn Ile Val Asn
                165                 170                 175

Lys Lys Glu Lys Ala Thr Gly Arg Glu Val Thr His Ile Gln Phe Thr
                180                 185                 190

Ser Trp Pro Asp His Gly Val Pro Glu Asp Pro His Leu Leu Leu Lys
                195                 200                 205

Leu Arg Arg Arg Val Asn Ala Phe Ser Asn Phe Ser Gly Pro Ile
210                 215                 220

Val Val His Cys Ser Ala Gly Val Gly Arg Thr Gly Thr Tyr Ile Gly
225                 230                 235                 240

Ile Asp Ala Met Leu Glu Gly Leu Glu Ala Glu Asn Lys Val Asp Val
                245                 250                 255

Tyr Gly Tyr Val Val Lys Leu Arg Arg Gln Arg Cys Leu Met Val Gln
                260                 265                 270

Val Glu Ala Gln Tyr Ile Leu Ile His Gln Ala Leu Val Glu Tyr Asn
                275                 280                 285

Gln Phe Gly Glu Thr Glu Val Asn Leu Ser Glu Leu His Pro Tyr Leu
                290                 295                 300

His Asn Met Lys Lys Arg Asp Pro Pro Ser Glu Pro Ser Pro Leu Glu
305                 310                 315                 320

Ala Glu Phe Gln Arg Leu Pro Ser Tyr Arg Ser Trp Arg Thr Gln His
                325                 330                 335

Ile Gly Asn Gln Glu Glu Asn Lys Ser Lys Asn Arg Asn Ser Asn Val
                340                 345                 350

Ile Pro Tyr Asp Tyr Asn Arg Val Pro Leu Lys His Glu Leu Glu Met
                355                 360                 365

Ser Lys Glu Ser Glu His Asp Ser Asp Glu Ser Ser Asp Asp Asp Ser
                370                 375                 380

Asp Ser Glu Glu Pro Ser Lys Tyr Ile Asn Ala Ser Phe Ile Met Ser
385                 390                 395                 400

Tyr Trp Lys Pro Glu Val Met Ile Ala Ala Gln Gly Pro Leu Lys Glu
                405                 410                 415

Thr Ile Gly Asp Phe Trp Gln Met Ile Phe Gln Arg Lys Val Lys Val
                420                 425                 430

Ile Val Met Leu Thr Glu Leu Lys His Gly Asp Gln Glu Ile Cys Ala
                435                 440                 445

Gln Tyr Trp Gly Glu Gly Lys Gln Thr Tyr Gly Asp Ile Glu Val Asp
450                 455                 460

Leu Lys Asp Thr Asp Lys Ser Ser Thr Tyr Thr Leu Arg Val Phe Glu
465                 470                 475                 480

Leu Arg His Ser Lys Arg Lys Asp Ser Arg Thr Val Tyr Gln Tyr Gln
                485                 490                 495

Tyr Thr Asn Trp Ser Val Glu Gln Leu Pro Ala Glu Pro Lys Glu Leu
                500                 505                 510
```

-continued

```
Ile Ser Met Ile Gln Val Val Lys Gln Lys Leu Pro Gln Lys Asn Ser
            515                 520                 525

Ser Glu Gly Asn Lys His His Lys Ser Thr Pro Leu Leu Ile His Cys
530                 535                 540

Arg Asp Gly Ser Gln Gln Thr Gly Ile Phe Cys Ala Leu Leu Asn Leu
545                 550                 555                 560

Leu Glu Ser Ala Glu Thr Glu Val Val Asp Ile Phe Gln Val Val
            565                 570                 575

Lys Ala Leu Arg Lys Ala Arg Pro Gly Met Val Ser Thr Phe Glu Gln
            580                 585                 590

Tyr Gln Phe Leu Tyr Asp Val Ile Ala Ser Thr Tyr Pro Ala Gln Asn
            595                 600                 605

Gly Gln Val Lys Lys Asn His Gln Glu Asp Lys Ile Glu Phe Asp
            610                 615                 620

Asn Glu Val Asp Lys Val Lys Gln Asp Ala Asn Cys Val Asn Pro Leu
625                 630                 635                 640

Gly Ala Pro Glu Lys Leu Pro Glu Ala Lys Glu Gln Ala Glu Gly Ser
            645                 650                 655

Glu Pro Thr Ser Gly Thr Glu Gly Pro Glu His Ser Val Asn Gly Pro
            660                 665                 670

Ala Ser Pro Ala Leu Asn Gln
            675

<210> SEQ ID NO 282
<211> LENGTH: 394
<212> TYPE: PRT
<213> ORGANISM: Homo sapiens

<400> SEQUENCE: 282

Met Glu Val Tyr Ala Ser Glu Lys Glu Gln His Gly Asp Leu Cys Arg
1               5                   10                  15

Pro Gly Glu His Val Thr Ser Arg Phe Lys Asn Glu Val Glu Arg Met
            20                  25                  30

Gly Phe Asp Met Asn Asn Ala Trp Arg Ile Ser Asn Ile Asn Glu Lys
        35                  40                  45

Tyr Lys Leu Cys Gly Ser Tyr Pro Gln Glu Leu Ile Val Pro Ala Trp
    50                  55                  60

Ile Thr Asp Lys Glu Leu Glu Ser Val Ser Ser Phe Arg Ser Trp Lys
65                  70                  75                  80

Arg Ile Pro Ala Val Ile Tyr Arg His Gln Ser Asn Gly Ala Val Ile
                85                  90                  95

Ala Arg Cys Gly Gln Pro Glu Val Ser Trp Trp Gly Trp Arg Asn Ala
            100                 105                 110

Asp Asp Glu His Leu Val Gln Ser Val Ala Lys Ala Cys Ala Ser Asp
        115                 120                 125

Ser Arg Ser Ser Gly Ser Lys Leu Ser Thr Arg Asn Thr Ser Arg Asp
    130                 135                 140

Phe Pro Asn Gly Gly Asp Leu Ser Asp Val Glu Phe Asp Ser Ser Leu
145                 150                 155                 160

Ser Asn Ala Ser Gly Ala Glu Ser Leu Ala Ile Gln Pro Gln Lys Leu
                165                 170                 175

Leu Ile Leu Asp Ala Arg Ser Tyr Ala Ala Val Ala Asn Arg Ala
            180                 185                 190

Lys Gly Gly Gly Cys Glu Cys Pro Glu Tyr Tyr Pro Asn Cys Glu Val
        195                 200                 205
```

Val Phe Met Gly Met Ala Asn Ile His Ser Ile Arg Arg Ser Phe Gln
210                 215                 220

Ser Leu Arg Leu Leu Cys Thr Gln Met Pro Asp Pro Gly Asn Trp Leu
225                 230                 235                 240

Ser Ala Leu Glu Ser Thr Lys Trp Leu His His Leu Ser Val Leu Leu
                245                 250                 255

Lys Ser Ala Leu Leu Val Val His Ala Val Asp Gln Asp Gln Arg Pro
            260                 265                 270

Val Leu Val His Cys Ser Asp Gly Trp Asp Arg Thr Pro Gln Ile Val
        275                 280                 285

Ala Leu Ala Lys Leu Leu Leu Asp Pro Tyr Tyr Arg Thr Ile Glu Gly
    290                 295                 300

Phe Gln Val Leu Val Glu Met Glu Trp Leu Asp Phe Gly His Lys Phe
305                 310                 315                 320

Ala Asp Arg Cys Gly His Gly Glu Asn Ser Asp Asp Leu Asn Glu Arg
                325                 330                 335

Cys Pro Val Phe Leu Gln Trp Leu Asp Cys Val His Gln Leu Gln Arg
            340                 345                 350

Gln Phe Pro Cys Ser Phe Glu Phe Asn Glu Ala Phe Leu Val Lys Leu
        355                 360                 365

Val Gln His Thr Tyr Ser Cys Leu Phe Gly Thr Phe Leu Cys Asn Asn
    370                 375                 380

Ala Lys Glu Arg Gly Glu Lys His Thr Gln
385                 390

<210> SEQ ID NO 283
<211> LENGTH: 571
<212> TYPE: PRT
<213> ORGANISM: Homo sapiens

<400> SEQUENCE: 283

Met Asp Arg Pro Ala Ala Ala Ala Gly Cys Glu Gly Gly Gly
1               5                   10                  15

Gly Pro Asn Pro Gly Pro Ala Gly Gly Arg Arg Pro Pro Arg Ala Ala
                20                  25                  30

Gly Gly Ala Thr Ala Gly Ser Arg Gln Pro Ser Val Glu Thr Leu Asp
            35                  40                  45

Ser Pro Thr Gly Ser His Val Glu Trp Cys Lys Gln Leu Ile Ala Ala
        50                  55                  60

Thr Ile Ser Ser Gln Ile Ser Gly Ser Val Thr Ser Glu Asn Val Ser
65                  70                  75                  80

Arg Asp Tyr Lys Ala Leu Arg Asp Gly Asn Lys Leu Ala Gln Met Glu
                85                  90                  95

Glu Ala Pro Leu Phe Pro Gly Glu Ser Ile Lys Ala Ile Val Lys Asp
                100                 105                 110

Val Met Tyr Ile Cys Pro Phe Met Gly Ala Val Ser Gly Thr Leu Thr
            115                 120                 125

Val Thr Asp Phe Lys Leu Tyr Phe Lys Asn Val Glu Arg Asp Pro His
        130                 135                 140

Phe Ile Leu Asp Val Pro Leu Gly Val Ile Ser Arg Val Glu Lys Ile
145                 150                 155                 160

Gly Ala Gln Ser His Gly Asp Asn Ser Cys Gly Ile Glu Ile Val Cys
                165                 170                 175

Lys Asp Met Arg Asn Leu Arg Leu Ala Tyr Lys Gln Glu Glu Gln Ser
                180                 185                 190

```
Lys Leu Gly Ile Phe Glu Asn Leu Asn Lys His Ala Phe Pro Leu Ser
        195                 200                 205

Asn Gly Gln Ala Leu Phe Ala Phe Ser Tyr Lys Glu Lys Phe Pro Ile
    210                 215                 220

Asn Gly Trp Lys Val Tyr Asp Pro Val Ser Glu Tyr Lys Arg Gln Gly
225                 230                 235                 240

Leu Pro Asn Glu Ser Trp Lys Ile Ser Lys Ile Asn Ser Asn Tyr Glu
            245                 250                 255

Phe Cys Asp Thr Tyr Pro Ala Ile Ile Val Pro Thr Ser Val Lys
                260                 265                 270

Asp Asp Asp Leu Ser Lys Val Ala Ala Phe Arg Ala Lys Gly Arg Val
            275                 280                 285

Pro Val Leu Ser Trp Ile His Pro Glu Ser Gln Ala Thr Ile Thr Arg
        290                 295                 300

Cys Ser Gln Pro Leu Val Gly Pro Asn Asp Lys Arg Cys Lys Glu Asp
305                 310                 315                 320

Glu Lys Tyr Leu Gln Thr Ile Met Asp Ala Asn Ala Gln Ser His Lys
                325                 330                 335

Leu Ile Ile Phe Asp Ala Arg Gln Asn Ser Val Ala Asp Thr Asn Lys
            340                 345                 350

Thr Lys Gly Gly Gly Tyr Glu Ser Glu Ser Ala Tyr Pro Asn Ala Glu
        355                 360                 365

Leu Val Phe Leu Glu Ile His Asn Ile His Val Met Arg Glu Ser Leu
    370                 375                 380

Arg Lys Leu Lys Glu Ile Val Tyr Pro Ser Ile Asp Glu Ala Arg Trp
385                 390                 395                 400

Leu Ser Asn Val Asp Gly Thr His Trp Leu Glu Tyr Ile Arg Met Leu
                405                 410                 415

Leu Ala Gly Ala Val Arg Ile Ala Asp Lys Ile Glu Ser Gly Lys Thr
            420                 425                 430

Ser Val Val Val His Cys Ser Asp Gly Trp Asp Arg Thr Ala Gln Leu
        435                 440                 445

Thr Ser Leu Ala Met Leu Met Leu Asp Ser Tyr Tyr Arg Thr Ile Lys
    450                 455                 460

Gly Phe Glu Thr Leu Val Glu Lys Glu Trp Ile Ser Phe Gly His Arg
465                 470                 475                 480

Phe Ala Leu Arg Val Gly His Gly Asn Asp Asn His Ala Asp Ala Asp
                485                 490                 495

Arg Ser Pro Ile Phe Leu Gln Phe Val Asp Cys Val Trp Gln Met Thr
            500                 505                 510

Arg Gln Phe Pro Ser Ala Phe Glu Phe Asn Glu Leu Phe Leu Ile Thr
        515                 520                 525

Ile Leu Asp His Leu Tyr Ser Cys Leu Phe Gly Thr Phe Leu Cys Asn
    530                 535                 540

Cys Glu Gln Gln Arg Phe Lys Glu Asp Val Tyr Thr Lys Thr Ile Ser
545                 550                 555                 560

Leu Trp Ser Tyr Ile Asn Ser Gln Leu Asp Glu
                565                 570

<210> SEQ ID NO 284
<211> LENGTH: 582
<212> TYPE: PRT
<213> ORGANISM: Homo sapiens

<400> SEQUENCE: 284
```

-continued

```
Met Ala Ser His Pro Pro Ile Pro Ile Leu Glu Leu Ala Asp His Ile
1               5                   10                  15

Glu Arg Leu Lys Ala Asn Asp Asn Leu Lys Phe Ser Gln Glu Tyr Glu
                20                  25                  30

Ser Ile Asp Pro Gly Gln Gln Phe Thr Trp Glu His Ser Asn Leu Glu
            35                  40                  45

Val Asn Lys Pro Lys Asn Arg Tyr Ala Asn Val Ile Ala Tyr Asp His
    50                  55                  60

Ser Arg Val Leu Leu Ser Ala Ile Glu Gly Ile Pro Gly Ser Asp Tyr
65                  70                  75                  80

Val Asn Ala Asn Tyr Ile Asp Gly Tyr Arg Lys Gln Asn Ala Tyr Ile
                85                  90                  95

Ala Thr Gln Gly Ser Leu Pro Glu Thr Phe Gly Asp Phe Trp Arg Met
            100                 105                 110

Ile Trp Glu Gln Arg Ser Ala Thr Val Val Met Met Thr Lys Leu Glu
        115                 120                 125

Glu Arg Ser Arg Val Lys Cys Asp Gln Tyr Trp Pro Ser Arg Gly Thr
    130                 135                 140

Glu Thr His Gly Leu Val Gln Val Thr Leu Leu Asp Thr Val Glu Leu
145                 150                 155                 160

Ala Thr Tyr Cys Val Arg Thr Phe Ala Leu Tyr Lys Asn Gly Ser Ser
                165                 170                 175

Glu Lys Arg Glu Val Arg Gln Phe Gln Phe Thr Ala Trp Pro Asp His
            180                 185                 190

Gly Val Pro Glu His Pro Thr Pro Phe Leu Ala Phe Leu Arg Arg Val
        195                 200                 205

Lys Thr Cys Asn Pro Pro Asp Ala Gly Pro Met Val Val His Cys Ser
    210                 215                 220

Ala Gly Val Gly Arg Thr Gly Cys Phe Ile Val Ile Asp Ala Met Leu
225                 230                 235                 240

Glu Arg Ile Lys His Glu Lys Thr Val Asp Ile Tyr Gly His Val Thr
                245                 250                 255

Leu Met Arg Ala Gln Arg Asn Tyr Met Val Gln Thr Glu Asp Gln Tyr
            260                 265                 270

Ile Phe Ile His Asp Ala Leu Leu Glu Ala Val Thr Cys Gly Asn Thr
        275                 280                 285

Glu Val Pro Ala Arg Asn Leu Tyr Ala Tyr Ile Gln Lys Leu Thr Gln
    290                 295                 300

Ile Glu Thr Gly Glu Asn Val Thr Gly Met Glu Leu Glu Phe Lys Arg
305                 310                 315                 320

Leu Ala Ser Ser Lys Ala His Thr Ser Arg Phe Ile Ser Ala Asn Leu
                325                 330                 335

Pro Cys Asn Lys Phe Lys Asn Arg Leu Val Asn Ile Met Pro Tyr Glu
            340                 345                 350

Ser Thr Arg Val Cys Leu Gln Pro Ile Arg Gly Val Glu Gly Ser Asp
        355                 360                 365

Tyr Ile Asn Ala Ser Phe Ile Asp Gly Tyr Arg Gln Gln Lys Ala Tyr
    370                 375                 380

Ile Ala Thr Gln Gly Pro Leu Ala Glu Thr Thr Glu Asp Phe Trp Arg
385                 390                 395                 400

Met Leu Trp Glu His Asn Ser Thr Ile Val Val Met Leu Thr Lys Leu
                405                 410                 415

Arg Glu Met Gly Arg Glu Lys Cys His Gln Tyr Trp Pro Ala Glu Arg
            420                 425                 430
```

Ser Ala Arg Tyr Gln Tyr Phe Val Val Asp Pro Met Ala Glu Tyr Asn
        435                 440                 445

Met Pro Gln Tyr Ile Leu Arg Glu Phe Lys Val Thr Asp Ala Arg Asp
        450                 455                 460

Gly Gln Ser Arg Thr Val Arg Gln Phe Gln Thr Asp Trp Pro Glu
465                 470                 475                 480

Gln Gly Val Pro Lys Ser Gly Glu Gly Phe Ile Asp Phe Ile Gly Gln
                    485                 490                 495

Val His Lys Thr Lys Glu Gln Phe Gly Gln Asp Gly Pro Ile Ser Val
                500                 505                 510

His Cys Ser Ala Gly Val Gly Arg Thr Gly Val Phe Ile Thr Leu Ser
            515                 520                 525

Ile Val Leu Glu Arg Met Arg Tyr Glu Gly Val Val Asp Ile Phe Gln
        530                 535                 540

Thr Val Lys Met Leu Arg Thr Gln Arg Pro Ala Met Val Gln Thr Glu
545                 550                 555                 560

Asp Gln Tyr Gln Phe Ser Tyr Arg Ala Ala Leu Glu Tyr Leu Gly Ser
                    565                 570                 575

Phe Asp His Tyr Ala Thr
            580

<210> SEQ ID NO 285
<211> LENGTH: 577
<212> TYPE: PRT
<213> ORGANISM: Homo sapiens

<400> SEQUENCE: 285

Met Gly Pro Gln Ala Ala Pro Leu Thr Ile Arg Gly Pro Ser Ser Ala
1               5                   10                  15

Gly Gln Ser Thr Pro Ser Pro His Leu Val Pro Ser Pro Ala Pro Ser
                20                  25                  30

Pro Gly Pro Gly Pro Val Pro Pro Arg Pro Pro Ala Ala Glu Pro Pro
            35                  40                  45

Pro Cys Leu Arg Arg Gly Ala Ala Ala Asp Leu Leu Ser Ser Ser
50                  55                  60

Pro Glu Ser Gln His Gly Gly Thr Gln Ser Pro Gly Gly Gly Gln Pro
65                  70                  75                  80

Leu Leu Gln Pro Thr Lys Val Asp Ala Ala Glu Gly Arg Arg Pro Gln
                85                  90                  95

Ala Leu Arg Leu Ile Glu Arg Asp Pro Tyr Glu His Pro Glu Arg Leu
            100                 105                 110

Arg Gln Leu Gln Gln Glu Leu Glu Ala Phe Arg Gly Gln Leu Gly Asp
        115                 120                 125

Val Gly Ala Leu Asp Thr Val Trp Arg Glu Leu Gln Asp Ala Gln Glu
130                 135                 140

His Asp Ala Arg Gly Arg Ser Ile Ala Ile Ala Arg Cys Tyr Ser Leu
145                 150                 155                 160

Lys Asn Arg His Gln Asp Val Met Pro Tyr Asp Ser Asn Arg Val Val
                165                 170                 175

Leu Arg Ser Gly Lys Asp Asp Tyr Ile Asn Ala Ser Cys Val Glu Gly
            180                 185                 190

Leu Ser Pro Tyr Cys Pro Pro Leu Val Ala Thr Gln Ala Pro Leu Pro
        195                 200                 205

Gly Thr Ala Ala Asp Phe Trp Leu Met Val His Glu Gln Lys Val Ser
210                 215                 220

```
Val Ile Val Met Leu Val Ser Glu Ala Glu Met Glu Lys Gln Lys Val
225                 230                 235                 240

Ala Arg Tyr Phe Pro Thr Glu Arg Gly Gln Pro Met Val His Gly Ala
            245                 250                 255

Leu Ser Leu Ala Leu Ser Ser Val Arg Ser Thr Glu Thr His Val Glu
                260                 265                 270

Arg Val Leu Ser Leu Gln Phe Arg Asp Gln Ser Leu Lys Arg Ser Leu
                275                 280                 285

Val His Leu His Phe Pro Thr Trp Pro Glu Leu Gly Leu Pro Asp Ser
290                 295                 300

Pro Ser Asn Leu Leu Arg Phe Ile Gln Glu Val His Ala His Tyr Leu
305                 310                 315                 320

His Gln Arg Pro Leu His Thr Pro Ile Ile Val His Cys Ser Ser Gly
                325                 330                 335

Val Gly Arg Thr Gly Ala Phe Ala Leu Leu Tyr Ala Ala Val Gln Glu
                340                 345                 350

Val Glu Ala Gly Asn Gly Ile Pro Glu Leu Pro Gln Leu Val Arg Arg
                355                 360                 365

Met Arg Gln Gln Arg Lys His Met Leu Gln Glu Lys Leu His Leu Arg
370                 375                 380

Phe Cys Tyr Glu Ala Val Val Arg His Val Glu Gln Val Leu Gln Arg
385                 390                 395                 400

His Gly Val Pro Pro Cys Lys Pro Leu Ala Ser Ala Ser Ile Ser
                405                 410                 415

Gln Lys Asn His Leu Pro Gln Asp Ser Gln Asp Leu Val Leu Gly Gly
                420                 425                 430

Asp Val Pro Ile Ser Ser Ile Gln Ala Thr Ile Ala Lys Leu Ser Ile
                435                 440                 445

Arg Pro Pro Gly Gly Leu Glu Ser Pro Val Ala Ser Leu Pro Gly Pro
450                 455                 460

Ala Glu Pro Pro Gly Leu Pro Pro Ala Ser Leu Pro Glu Ser Thr Pro
465                 470                 475                 480

Ile Pro Ser Ser Ser Pro Pro Leu Ser Ser Pro Leu Pro Glu Ala
                485                 490                 495

Pro Gln Pro Lys Glu Glu Pro Val Pro Glu Ala Pro Ser Ser Gly
                500                 505                 510

Pro Pro Ser Ser Ser Leu Glu Leu Leu Ala Ser Leu Thr Pro Glu Ala
                515                 520                 525

Phe Ser Leu Asp Ser Ser Leu Arg Gly Lys Gln Arg Met Ser Lys His
530                 535                 540

Asn Phe Leu Gln Ala His Asn Gly Gln Gly Leu Arg Ala Thr Arg Pro
545                 550                 555                 560

Ser Asp Asp Pro Leu Ser Leu Leu Asp Pro Leu Trp Thr Leu Asn Lys
                565                 570                 575

Thr

<210> SEQ ID NO 286
<211> LENGTH: 300
<212> TYPE: PRT
<213> ORGANISM: Homo sapiens

<400> SEQUENCE: 286

Met Ser Arg Ser Leu Asp Ser Ala Arg Ser Phe Leu Glu Arg Leu Glu
1               5                   10                  15
```

```
Ala Arg Gly Gly Arg Glu Gly Ala Val Leu Ala Gly Glu Phe Ser Asp
            20                  25                  30

Ile Gln Ala Cys Ser Ala Ala Trp Lys Ala Asp Gly Val Cys Ser Thr
        35                  40                  45

Val Ala Gly Ser Arg Pro Glu Asn Val Arg Lys Asn Arg Tyr Lys Asp
 50                  55                  60

Val Leu Pro Tyr Asp Gln Thr Arg Val Ile Leu Ser Leu Leu Gln Glu
 65                  70                  75                  80

Glu Gly His Ser Asp Tyr Ile Asn Gly Asn Phe Ile Arg Gly Val Asp
                85                  90                  95

Gly Ser Leu Ala Tyr Ile Ala Thr Gln Gly Pro Leu Pro His Thr Leu
            100                 105                 110

Leu Asp Phe Trp Arg Leu Val Trp Glu Phe Gly Val Lys Val Ile Leu
        115                 120                 125

Met Ala Cys Arg Glu Ile Glu Asn Gly Arg Lys Arg Cys Glu Arg Tyr
130                 135                 140

Trp Ala Gln Glu Gln Glu Pro Leu Gln Thr Gly Leu Phe Cys Ile Thr
145                 150                 155                 160

Leu Ile Lys Glu Lys Trp Leu Asn Glu Asp Ile Met Leu Arg Thr Leu
                165                 170                 175

Lys Val Thr Phe Gln Lys Glu Ser Arg Ser Val Tyr Gln Leu Gln Tyr
            180                 185                 190

Met Ser Trp Pro Asp Arg Gly Val Pro Ser Ser Pro Asp His Met Leu
        195                 200                 205

Ala Met Val Glu Glu Ala Arg Arg Leu Gln Gly Ser Gly Pro Glu Pro
210                 215                 220

Leu Cys Val His Cys Ser Ala Gly Cys Gly Arg Thr Gly Val Leu Cys
225                 230                 235                 240

Thr Val Asp Tyr Val Arg Gln Leu Leu Leu Thr Gln Met Ile Pro Pro
                245                 250                 255

Asp Phe Ser Leu Phe Asp Val Val Leu Lys Met Arg Lys Gln Arg Pro
            260                 265                 270

Ala Ala Val Gln Thr Glu Glu Gln Tyr Arg Phe Leu Tyr His Thr Val
        275                 280                 285

Ala Gln Met Phe Cys Ser Thr Leu Gln Asn Ala Ser
290                 295                 300

<210> SEQ ID NO 287
<211> LENGTH: 614
<212> TYPE: PRT
<213> ORGANISM: Homo sapiens

<400> SEQUENCE: 287

Ser Thr Arg Gly Asp Gln Arg Ser Gly Gly Val Thr Glu Ala Ser Ser
1               5                  10                  15

Leu Leu Gly Gly Ser Pro Arg Arg Pro Cys Gly Arg Lys Gly Ser Pro
            20                  25                  30

Tyr His Thr Gly Gln Leu His Pro Ala Val Arg Val Ala Asp Leu Leu
        35                  40                  45

Gln His Ile Asn Gln Met Lys Thr Ala Glu Gly Tyr Gly Phe Lys Gln
     50                  55                  60

Glu Tyr Glu Ser Phe Phe Glu Gly Trp Asp Ala Thr Lys Lys Lys Asp
65                  70                  75                  80

Lys Val Lys Gly Ser Arg Gln Glu Pro Met Pro Ala Tyr Asp Arg His
                85                  90                  95
```

```
Arg Val Lys Leu His Pro Met Leu Gly Asp Pro Asn Ala Asp Tyr Ile
            100                 105                 110

Asn Ala Asn Tyr Ile Asp Gly Tyr His Arg Ser Asn His Phe Ile Ala
            115                 120                 125

Thr Gln Gly Pro Lys Pro Glu Met Val Tyr Asp Phe Trp Arg Met Val
        130                 135                 140

Trp Gln Glu His Cys Ser Ser Ile Val Met Ile Thr Lys Leu Val Glu
145                 150                 155                 160

Val Gly Arg Val Lys Cys Ser Arg Tyr Trp Pro Glu Asp Ser Asp Thr
                165                 170                 175

Tyr Gly Asp Ile Lys Ile Met Leu Val Lys Thr Glu Thr Leu Ala Glu
            180                 185                 190

Tyr Val Val Arg Thr Phe Ala Leu Glu Arg Arg Gly Tyr Ser Ala Arg
        195                 200                 205

His Glu Val Arg Gln Ser His Phe Thr Ala Trp Pro Glu His Gly Val
210                 215                 220

Pro Tyr His Ala Thr Gly Leu Leu Ala Phe Ile Arg Arg Val Lys Ala
225                 230                 235                 240

Ser Thr Pro Pro Asp Ala Gly Pro Ile Val Ile His Cys Ser Ala Gly
                245                 250                 255

Thr Gly Arg Thr Gly Cys Tyr Ile Val Leu Asp Val Met Leu Asp Met
            260                 265                 270

Ala Glu Cys Glu Gly Val Val Asp Ile Tyr Asn Cys Val Lys Thr Leu
        275                 280                 285

Cys Ser Arg Arg Val Asn Met Ile Gln Thr Glu Glu Gln Tyr Ile Phe
290                 295                 300

Ile His Asp Ala Ile Leu Glu Ala Cys Leu Cys Gly Glu Thr Thr Ile
305                 310                 315                 320

Pro Val Ser Glu Phe Lys Ala Thr Tyr Lys Glu Met Ile Arg Ile Asp
                325                 330                 335

Pro Gln Ser Asn Ser Ser Gln Leu Arg Glu Glu Phe Gln Thr Leu Asn
            340                 345                 350

Ser Val Thr Pro Pro Leu Asp Val Glu Glu Cys Ser Ile Ala Leu Leu
        355                 360                 365

Pro Arg Asn Arg Asp Lys Asn Arg Ser Met Asp Val Leu Pro Pro Asp
370                 375                 380

Arg Cys Leu Pro Phe Leu Ile Ser Thr Asp Gly Asp Ser Asn Asn Tyr
385                 390                 395                 400

Ile Asn Ala Ala Leu Thr Asp Ser Tyr Thr Arg Arg Ser Ala Phe Met
                405                 410                 415

Val Thr Leu His Pro Leu Gln Ser Thr Thr Pro Asp Phe Trp Arg Leu
            420                 425                 430

Val Tyr Asp Tyr Gly Cys Thr Ser Ile Val Met Leu Asn Gln Leu Asn
        435                 440                 445

Gln Ser Asn Ser Ala Trp Pro Cys Leu Gln Tyr Trp Pro Glu Pro Gly
450                 455                 460

Arg Gln Gln Tyr Gly Leu Met Glu Val Glu Phe Met Ser Gly Thr Ala
465                 470                 475                 480

Asp Glu Asp Leu Val Ala Arg Val Phe Arg Val Gln Asn Ile Ser Arg
                485                 490                 495

Leu Gln Glu Gly Asp Leu Leu Val Arg His Phe Gln Phe Leu Arg Trp
            500                 505                 510

Ser Ala Tyr Arg Asp Thr Pro Asp Ser Lys Lys Ala Phe Leu His Leu
        515                 520                 525
```

```
Leu Ala Glu Val Asp Lys Trp Gln Ala Glu Ser Gly Asp Gly Arg Thr
    530                 535                 540
Ile Val His Cys Leu Asn Gly Gly Arg Ser Gly Thr Phe Cys Ala
545                 550                 555                 560
Cys Ala Thr Val Leu Glu Met Ile Arg Cys His Asn Leu Val Asp Val
                565                 570                 575
Phe Phe Ala Ala Gln Thr Leu Arg Asn Tyr Lys Pro Asn Met Val Glu
            580                 585                 590
Thr Met Asp Gln Tyr His Phe Cys Tyr Asp Val Ala Leu Glu Tyr Leu
        595                 600                 605
Glu Gly Leu Glu Ser Arg
    610
```

```
<210> SEQ ID NO 288
<211> LENGTH: 326
<212> TYPE: PRT
<213> ORGANISM: Homo sapiens

<400> SEQUENCE: 288

Met Asp Gln Arg Glu Ile Leu Gln Lys Phe Leu Asp Glu Ala Gln Ser
1               5                   10                  15
Lys Lys Ile Thr Lys Glu Glu Phe Ala Asn Glu Phe Leu Lys Leu Lys
            20                  25                  30
Arg Gln Ser Thr Lys Tyr Lys Ala Asp Lys Thr Tyr Pro Thr Thr Val
        35                  40                  45
Ala Glu Lys Pro Lys Asn Ile Lys Asn Arg Tyr Lys Asp Ile Leu
    50                  55                  60
Pro Tyr Asp Tyr Ser Arg Val Glu Leu Ser Leu Ile Thr Ser Asp Glu
65                  70                  75                  80
Asp Ser Ser Tyr Ile Asn Ala Asn Phe Ile Lys Gly Val Tyr Gly Pro
                85                  90                  95
Lys Ala Tyr Ile Ala Thr Gln Gly Pro Leu Ser Thr Thr Leu Leu Asp
            100                 105                 110
Phe Trp Arg Met Ile Trp Glu Tyr Ser Val Leu Ile Ile Val Met Ala
        115                 120                 125
Cys Met Glu Tyr Glu Met Gly Lys Lys Lys Cys Glu Arg Tyr Trp Ala
    130                 135                 140
Glu Pro Gly Glu Met Gln Leu Glu Phe Gly Pro Phe Ser Val Ser Cys
145                 150                 155                 160
Glu Ala Glu Lys Arg Lys Ser Asp Tyr Ile Ile Arg Thr Leu Lys Val
                165                 170                 175
Lys Phe Asn Ser Glu Thr Arg Thr Ile Tyr Gln Phe His Tyr Lys Asn
            180                 185                 190
Trp Pro Asp His Asp Val Pro Ser Ser Ile Asp Pro Ile Leu Glu Leu
        195                 200                 205
Ile Trp Asp Val Arg Cys Tyr Gln Glu Asp Asp Ser Val Pro Ile Cys
    210                 215                 220
Ile His Cys Ser Ala Gly Cys Gly Arg Thr Gly Val Ile Cys Ala Ile
225                 230                 235                 240
Asp Tyr Thr Trp Met Leu Leu Lys Asp Gly Ile Ile Pro Glu Asn Phe
                245                 250                 255
Ser Val Phe Ser Leu Ile Arg Glu Met Arg Thr Gln Arg Pro Ser Leu
            260                 265                 270
Val Gln Thr Gln Glu Gln Tyr Glu Leu Val Tyr Asn Ala Val Leu Glu
        275                 280                 285
```

Leu Phe Lys Arg Gln Met Asp Val Ile Arg Asp Lys His Ser Gly Thr
290                 295                 300

Glu Ser Gln Ala Lys His Cys Ile Pro Glu Lys Asn His Thr Leu Gln
305                 310                 315                 320

Ala Asp Ser Tyr Ser Pro
                325

<210> SEQ ID NO 289
<211> LENGTH: 601
<212> TYPE: PRT
<213> ORGANISM: Homo sapiens

<400> SEQUENCE: 289

Met Leu Leu Ser Arg Ser Pro Ser Gly Pro Lys Lys Tyr Phe Pro Ile
1               5                   10                  15

Pro Val Glu His Leu Glu Glu Ile Arg Ile Arg Ser Ala Asp Asp
            20                  25                  30

Cys Lys Gln Phe Arg Glu Glu Phe Asn Ser Leu Pro Ser Gly His Ile
            35                  40                  45

Gln Gly Thr Phe Glu Leu Ala Asn Lys Glu Glu Asn Arg Glu Lys Asn
    50                  55                  60

Arg Tyr Pro Asn Ile Leu Pro Asn Asp His Ser Arg Val Ile Leu Ser
65                  70                  75                  80

Gln Leu Asp Gly Ile Pro Cys Ser Asp Tyr Ile Asn Ala Ser Tyr Ile
                85                  90                  95

Asp Gly Tyr Lys Glu Lys Asn Lys Phe Ile Ala Ala Gln Gly Pro Lys
            100                 105                 110

Gln Glu Thr Val Asn Asp Phe Trp Arg Met Val Trp Glu Gln Lys Ser
        115                 120                 125

Ala Thr Ile Val Met Leu Thr Asn Leu Lys Glu Arg Lys Glu Glu Lys
130                 135                 140

Cys His Gln Tyr Trp Pro Asp Gln Gly Cys Trp Thr Tyr Gly Asn Ile
145                 150                 155                 160

Arg Val Cys Val Glu Asp Cys Val Val Leu Val Asp Tyr Thr Ile Arg
                165                 170                 175

Lys Phe Cys Ile Gln Pro Gln Leu Pro Asp Gly Cys Lys Ala Pro Arg
            180                 185                 190

Leu Val Ser Gln Leu His Phe Thr Ser Trp Pro Asp Phe Gly Val Pro
        195                 200                 205

Phe Thr Pro Ile Gly Met Leu Lys Phe Leu Lys Lys Val Lys Thr Leu
210                 215                 220

Asn Pro Val His Ala Gly Pro Ile Val Val His Cys Ser Ala Gly Val
225                 230                 235                 240

Gly Arg Thr Gly Thr Phe Ile Val Ile Asp Ala Met Met Ala Met Met
                245                 250                 255

His Ala Glu Gln Lys Val Asp Val Phe Glu Phe Val Ser Arg Ile Arg
            260                 265                 270

Asn Gln Arg Pro Gln Met Val Gln Thr Asp Met Gln Tyr Thr Phe Ile
        275                 280                 285

Tyr Gln Ala Leu Leu Glu Tyr Tyr Leu Tyr Gly Asp Thr Glu Leu Asp
290                 295                 300

Val Ser Ser Leu Glu Lys His Leu Gln Thr Met His Gly Thr Thr Thr
305                 310                 315                 320

His Phe Asp Lys Ile Gly Leu Glu Glu Glu Phe Arg Lys Leu Thr Asn
                325                 330                 335

```
Val Arg Ile Met Lys Glu Asn Met Arg Thr Gly Asn Leu Pro Ala Asn
            340                 345                 350

Met Lys Lys Ala Arg Val Ile Gln Ile Ile Pro Tyr Asp Phe Asn Arg
            355                 360                 365

Val Ile Leu Ser Met Lys Arg Gly Gln Glu Tyr Thr Asp Tyr Ile Asn
            370                 375                 380

Ala Ser Phe Ile Asp Gly Tyr Arg Gln Lys Asp Tyr Phe Ile Ala Thr
385                 390                 395                 400

Gln Gly Pro Leu Ala His Thr Val Glu Asp Phe Trp Arg Met Ile Trp
                405                 410                 415

Glu Trp Lys Ser His Thr Ile Val Met Leu Thr Glu Val Gln Glu Arg
            420                 425                 430

Glu Gln Asp Lys Cys Tyr Gln Tyr Trp Pro Thr Glu Gly Ser Val Thr
            435                 440                 445

His Gly Glu Ile Thr Ile Glu Ile Lys Asn Asp Thr Leu Ser Glu Ala
            450                 455                 460

Ile Ser Ile Arg Asp Phe Leu Val Thr Leu Asn Gln Pro Gln Ala Arg
465                 470                 475                 480

Gln Glu Glu Gln Val Arg Val Val Arg Gln Phe His Phe His Gly Trp
                485                 490                 495

Pro Glu Ile Gly Ile Pro Ala Glu Gly Lys Gly Met Ile Asp Leu Ile
            500                 505                 510

Ala Ala Val Gln Lys Gln Gln Gln Thr Gly Asn His Pro Ile Thr
            515                 520                 525

Val His Cys Ser Ala Gly Ala Gly Arg Thr Gly Thr Phe Ile Ala Leu
            530                 535                 540

Ser Asn Ile Leu Glu Arg Val Lys Ala Glu Gly Leu Leu Asp Val Phe
545                 550                 555                 560

Gln Ala Val Lys Ser Leu Arg Leu Gln Arg Pro His Met Val Gln Thr
                565                 570                 575

Leu Glu Gln Tyr Glu Phe Cys Tyr Lys Val Val Gln Asp Phe Ile Asp
            580                 585                 590

Ile Phe Ser Asp Tyr Ala Asn Phe Lys
            595                 600

<210> SEQ ID NO 290
<211> LENGTH: 590
<212> TYPE: PRT
<213> ORGANISM: Homo sapiens

<400> SEQUENCE: 290

Met Glu Ala Ile Pro Val Lys Gln Phe Val Lys His Ile Gly Glu Leu
1               5                   10                  15

Tyr Ser Asn Asn Gln His Gly Phe Ser Glu Asp Phe Glu Glu Val Gln
            20                  25                  30

Arg Cys Thr Ala Asp Met Asn Ile Thr Ala Glu His Ser Asn His Pro
            35                  40                  45

Glu Asn Lys His Lys Asn Arg Tyr Ile Asn Ile Leu Ala Tyr Asp His
            50                  55                  60

Ser Arg Val Lys Leu Arg Pro Leu Pro Gly Lys Asp Ser Lys His Ser
65                  70                  75                  80

Asp Tyr Ile Asn Ala Asn Tyr Val Asp Gly Tyr Asn Lys Ala Lys Ala
                85                  90                  95

Tyr Ile Ala Thr Gln Gly Pro Leu Lys Ser Thr Phe Glu Asp Phe Trp
            100                 105                 110
```

```
Arg Met Ile Trp Glu Gln Asn Thr Gly Ile Ile Val Met Ile Thr Asn
            115                 120                 125

Leu Val Glu Lys Gly Arg Arg Lys Cys Asp Gln Tyr Trp Pro Thr Glu
130                 135                 140

Asn Ser Glu Glu Tyr Gly Asn Ile Ile Val Thr Leu Lys Ser Thr Lys
145                 150                 155                 160

Ile His Ala Cys Tyr Thr Val Arg Arg Phe Ser Ile Arg Asn Thr Lys
                165                 170                 175

Val Lys Lys Gly Gln Lys Gly Asn Pro Lys Gly Arg Gln Asn Glu Arg
            180                 185                 190

Val Val Ile Gln Tyr His Tyr Thr Gln Trp Pro Asp Met Gly Val Pro
            195                 200                 205

Glu Tyr Ala Leu Pro Val Leu Thr Phe Val Arg Arg Ser Ser Ala Ala
            210                 215                 220

Arg Met Pro Glu Thr Gly Pro Val Leu Val His Cys Ser Ala Gly Val
225                 230                 235                 240

Gly Arg Thr Gly Thr Tyr Ile Val Ile Asp Ser Met Leu Gln Gln Ile
                245                 250                 255

Lys Asp Lys Ser Thr Val Asn Val Leu Gly Phe Leu Lys His Ile Arg
            260                 265                 270

Thr Gln Arg Asn Tyr Leu Val Gln Thr Glu Glu Gln Tyr Ile Phe Ile
            275                 280                 285

His Asp Ala Leu Leu Glu Ala Ile Leu Gly Lys Glu Thr Glu Val Ser
            290                 295                 300

Ser Asn Gln Leu His Ser Tyr Val Asn Ser Ile Leu Ile Pro Gly Val
305                 310                 315                 320

Gly Gly Lys Thr Arg Leu Glu Lys Gln Phe Lys Leu Val Thr Gln Cys
                325                 330                 335

Asn Ala Lys Tyr Val Glu Cys Phe Ser Ala Gln Lys Glu Cys Asn Lys
            340                 345                 350

Glu Lys Asn Arg Asn Ser Ser Val Val Pro Ser Glu Arg Ala Arg Val
            355                 360                 365

Gly Leu Ala Pro Leu Pro Gly Met Lys Gly Thr Asp Tyr Ile Asn Ala
            370                 375                 380

Ser Tyr Ile Met Gly Tyr Tyr Arg Ser Asn Glu Phe Ile Ile Thr Gln
385                 390                 395                 400

His Pro Leu Pro His Thr Thr Lys Asp Phe Trp Arg Met Ile Trp Asp
                405                 410                 415

His Asn Ala Gln Ile Ile Val Met Leu Pro Asp Asn Gln Ser Leu Ala
            420                 425                 430

Glu Asp Glu Phe Val Tyr Trp Pro Ser Arg Glu Ser Met Asn Cys
            435                 440                 445

Glu Ala Phe Thr Val Thr Leu Ile Ser Lys Asp Arg Leu Cys Leu Ser
450                 455                 460

Asn Glu Glu Gln Ile Ile Ile His Asp Phe Ile Leu Glu Ala Thr Gln
465                 470                 475                 480

Asp Asp Tyr Val Leu Glu Val Arg His Phe Gln Cys Pro Lys Trp Pro
                485                 490                 495

Asn Pro Asp Ala Pro Ile Ser Ser Thr Phe Glu Leu Ile Asn Val Ile
            500                 505                 510

Lys Glu Glu Ala Leu Thr Arg Asp Gly Pro Thr Ile Val His Asp Glu
515                 520                 525

Tyr Gly Ala Val Ser Ala Gly Met Leu Cys Ala Leu Thr Thr Leu Ser
```

-continued

```
                530             535             540
Gln Gln Leu Glu Asn Glu Asn Ala Val Asp Val Phe Gln Val Ala Lys
545                 550                 555                 560

Met Ile Asn Leu Met Arg Pro Gly Val Phe Thr Asp Ile Glu Gln Tyr
                565                 570                 575

Gln Phe Ile Tyr Lys Ala Arg Leu Ser Leu Val Ser Thr Lys
                580                 585                 590
```